(12) United States Patent
Bercovici et al.

(10) Patent No.: US 12,320,036 B2
(45) Date of Patent: Jun. 3, 2025

(54) DIRECT-TO-LIBRARY METHODS, SYSTEMS, AND COMPOSITIONS

(71) Applicant: KARIUS, INC., Redwood City, CA (US)

(72) Inventors: Sivan Bercovici, Redwood City, CA (US); Lily Blair, Redwood City, CA (US); Timothy A. Blauwkamp, Redwood City, CA (US); Peter J. Eugster, Redwood City, CA (US); David K. Hong, Redwood City, CA (US); Trupti Kawli, Redwood City, CA (US); Michael J. Rosen, Redwood City, CA (US); Damek Spacek, Redwood City, CA (US); Igor D. Vilfan, Redwood City, CA (US)

(73) Assignee: KARIUS, INC., Redwood City, CA (US)

( * ) Notice: Subject to any disclaimer, the term of this patent is extended or adjusted under 35 U.S.C. 154(b) by 997 days.

(21) Appl. No.: 17/323,843

(22) Filed: May 18, 2021

(65) Prior Publication Data

US 2022/0010303 A1 Jan. 13, 2022

Related U.S. Application Data

(63) Continuation of application No. PCT/US2019/062488, filed on Nov. 20, 2019.

(60) Provisional application No. 62/770,181, filed on Nov. 21, 2018.

(51) Int. Cl.
C40B 50/06 (2006.01)
C12N 15/10 (2006.01)
C12Q 1/6806 (2018.01)

(52) U.S. Cl.
CPC .......... C40B 50/06 (2013.01); C12N 15/1093 (2013.01); C12Q 1/6806 (2013.01)

(58) Field of Classification Search
None
See application file for complete search history.

(56) References Cited

U.S. PATENT DOCUMENTS

| | | |
|---|---|---|
| 6,753,137 B2 | 6/2004 | Lo et al. |
| RE39,920 E | 11/2007 | Umansky et al. |
| 7,803,929 B2 | 9/2010 | Melkonyan et al. |
| 7,914,982 B2 | 3/2011 | Melkonyan et al. |
| 7,973,154 B2 | 7/2011 | Melkonyan et al. |
| 8,682,592 B2 | 3/2014 | Rabinowitz et al. |
| 8,703,652 B2 | 4/2014 | Quake et al. |

(Continued)

FOREIGN PATENT DOCUMENTS

| | | |
|---|---|---|
| CA | 3030038 A1 | 1/2018 |
| EP | 1856295 A2 | 11/2007 |

(Continued)

OTHER PUBLICATIONS

Abbott et al., Design and use of signature primers to detect carry-over of amplified material. J Virol Methods 46(1):51-59 (1994).

(Continued)

*Primary Examiner* — Christian C Boesen
(74) *Attorney, Agent, or Firm* — Wilson Sonsini Goodrich & Rosati

(57) ABSTRACT

Provided herein are direct-to-library methods, systems, and compositions.

20 Claims, 52 Drawing Sheets

Specification includes a Sequence Listing.

(56) References Cited

U.S. PATENT DOCUMENTS

| | | |
|---|---|---|
| 8,715,967 B2 | 5/2014 | Casbon et al. |
| 8,877,442 B2 | 11/2014 | Quake et al. |
| 9,194,006 B2 | 11/2015 | Exner et al. |
| 9,353,414 B2 | 5/2016 | Fan et al. |
| 9,892,230 B2 | 2/2018 | Lo et al. |
| 9,976,181 B2 | 5/2018 | Christians et al. |
| 10,240,200 B2 | 3/2019 | Koh et al. |
| 10,450,620 B2 | 10/2019 | De Vlaminick et al. |
| 10,697,008 B2 | 6/2020 | Blauwkamp et al. |
| 11,078,532 B2 | 8/2021 | Christians et al. |
| 11,111,520 B2 | 9/2021 | Blauwkamp et al. |
| 2004/0209299 A1 | 10/2004 | Pinter et al. |
| 2005/0202414 A1 | 9/2005 | Jia et al. |
| 2006/0073506 A1 | 4/2006 | Christians et al. |
| 2007/0111233 A1 | 5/2007 | Bianchi et al. |
| 2010/0029498 A1 | 2/2010 | Gnirke et al. |
| 2010/0068711 A1 | 3/2010 | Umansky et al. |
| 2010/0209908 A1 | 8/2010 | Procop et al. |
| 2011/0160290 A1 | 6/2011 | Tewari |
| 2012/0021412 A1 | 1/2012 | Melkonyan et al. |
| 2012/0021919 A1 | 1/2012 | Scholl et al. |
| 2012/0058521 A1 | 3/2012 | Church et al. |
| 2012/0077185 A1 | 3/2012 | Oliphant et al. |
| 2012/0190663 A1 | 7/2012 | Gornik et al. |
| 2012/0283110 A1 | 11/2012 | Shendure et al. |
| 2013/0005585 A1 | 1/2013 | Anderson et al. |
| 2013/0024127 A1 | 1/2013 | Stuelpnagel et al. |
| 2013/0178544 A1 | 7/2013 | Melkonyan et al. |
| 2013/0245961 A1 | 9/2013 | Lo et al. |
| 2013/0252835 A1 | 9/2013 | Koh et al. |
| 2014/0066317 A1 | 3/2014 | Talasaz |
| 2014/0147851 A1 | 5/2014 | Qian et al. |
| 2014/0155274 A1 | 6/2014 | Xie et al. |
| 2014/0242582 A1 | 8/2014 | Oliphant et al. |
| 2014/0274740 A1 | 9/2014 | Srinivasan et al. |
| 2014/0336082 A1 | 11/2014 | Park et al. |
| 2014/0357528 A1 | 12/2014 | Robb et al. |
| 2015/0119257 A1 | 4/2015 | Fodor et al. |
| 2015/0133391 A1 | 5/2015 | De Vlaminick et al. |
| 2015/0211070 A1 | 7/2015 | Seligson et al. |
| 2015/0344977 A1 | 12/2015 | Rolfe |
| 2016/0177359 A1 | 6/2016 | Ukanis et al. |
| 2016/0251704 A1 | 9/2016 | Talasaz et al. |
| 2016/0289737 A1 | 10/2016 | Belyaev |
| 2016/0304953 A1 | 10/2016 | Chen et al. |
| 2016/0326572 A1 | 11/2016 | Schupp et al. |
| 2016/0326578 A1 | 11/2016 | Bielas |
| 2017/0145507 A1 | 5/2017 | Koh et al. |
| 2017/0145508 A1 | 5/2017 | Koh et al. |
| 2017/0145509 A1 | 5/2017 | Koh et al. |
| 2017/0247689 A1 | 8/2017 | Brown |
| 2017/0275691 A1 | 9/2017 | Christians et al. |
| 2018/0237851 A1 | 8/2018 | Christians et al. |
| 2019/0024127 A1* | 1/2019 | Yeh .................. C40B 40/06 |
| 2019/0256891 A1 | 8/2019 | Blauwkamp et al. |
| 2020/0291457 A1 | 9/2020 | Blauwkamp et al. |
| 2021/0324467 A1 | 10/2021 | Christians et al. |
| 2021/0403986 A1 | 12/2021 | Bercovici et al. |
| 2022/0195496 A1 | 6/2022 | Ahmed et al. |

FOREIGN PATENT DOCUMENTS

| | | |
|---|---|---|
| EP | 1885877 A2 | 2/2008 |
| EP | 2351857 A1 | 8/2011 |
| JP | 2015535431 A | 12/2015 |
| WO | WO-2011156795 A2 | 12/2011 |
| WO | WO-2012129363 A2 | 9/2012 |
| WO | WO-2012159023 A2 | 11/2012 |
| WO | WO-2012168815 A2 | 12/2012 |
| WO | WO-2013052907 A2 | 4/2013 |
| WO | WO-2013109981 A1 | 7/2013 |
| WO | WO-2013132305 A1 | 9/2013 |
| WO | WO-2013156627 A1 | 10/2013 |
| WO | WO-2013159035 A2 | 10/2013 |
| WO | WO-2013188846 A1 | 12/2013 |
| WO | WO-2014039556 A1 | 3/2014 |
| WO | WO-2014068075 A1 | 5/2014 |
| WO | WO-2014082032 A1 | 5/2014 |
| WO | WO-2014127484 A1 | 8/2014 |
| WO | WO-2014145078 A1 | 9/2014 |
| WO | WO-2014149134 A2 | 9/2014 |
| WO | WO-2014165596 A1 | 10/2014 |
| WO | WO-2015073080 A1 | 5/2015 |
| WO | WO-2015089333 A1 | 6/2015 |
| WO | WO-2015145133 A1 | 10/2015 |
| WO | WO-2016001736 A1 | 1/2016 |
| WO | WO-2016094947 A1 | 6/2016 |
| WO | WO-2017027835 A1 | 2/2017 |
| WO | WO-2017127741 A1 | 7/2017 |
| WO | WO-2017165864 A1 | 9/2017 |
| WO | WO-2018009723 A1 | 1/2018 |
| WO | WO-2018045359 A1 | 3/2018 |
| WO | WO-2018081130 A1 | 5/2018 |
| WO | WO-2018187521 A2 | 10/2018 |
| WO | WO-2018191563 A1 | 10/2018 |
| WO | WO-2018232598 A1 | 12/2018 |
| WO | WO-2019178157 A1 | 9/2019 |
| WO | WO-2020106893 A1 | 5/2020 |
| WO | WO-2020106987 A1 | 5/2020 |
| WO | WO-2022140302 A1 | 6/2022 |
| WO | WO-2022150725 A1 | 7/2022 |
| WO | WO-2022174117 A1 | 8/2022 |

OTHER PUBLICATIONS

Davis, et al., A DNA-Based Biological Sample Tracking Method. Cell Preservation Technology 54-60 (2005).

EP19887248.3 Extended European Search Report dated Aug. 1, 2022.

EP19888226.8 Extended European Search Report dated Aug. 8, 2022.

European partial search report dated Apr. 21, 2023 for EP Application No. 22199875.0.

European search report and opinion dated Feb. 28, 2022 for EP Application No. 21187675.0.

Fan H.C., et al., "Noninvasive Diagnosis of Fetal Aneuploidy by Shotgun Sequencing DNA from Maternal Blood,"Proceedings of the National Academy of Sciences of the United States of America, vol. 105:16266-16271 (2008).

Han et al., Liquid biopsy for infectious diseases: a focus on microbial cell-free DNA sequencing. Theranostics 10(12): 5501-5513 (2020).

PCT/US2019/062488 International Preliminary Report on Patentability dated Jun. 3, 2021.

PCT/US2019/062665 International Preliminary Report on Patentability dated Apr. 28, 2020.

U.S. Appl. No. 17/355,882 Office Action dated Apr. 6, 2023.
U.S. Appl. No. 17/355,882 Office Action dated Mar. 6, 2023.
U.S. Appl. No. 17/355,882 Office Action dated Mar. 30, 2023.
U.S. Appl. No. 17/355,882 Office Action dated May 4, 2023.

Wu et al., Facile single-stranded DNA sequencing of human plasma DNA via thermostable group II intron reverse transcriptase template switching. Nature Scientific Reports 7:8421 (2017).

Abril, et al. Diagnosis of Capnocytophaga canimorsus Sepsis by Whole-Genome Next-Generation Sequencing. Open Forum Infect Dis. Sep. 2016; 3(3): ofw144. Published online Jul. 12, 2016. DOI: 10.1093/ofid/ofw144.

Blauwkamp, et al. Analytical and clinical validation of a microbial cell-free DNA sequencing test for infectious disease. Nat Microbiol. Apr. 2019;4(4):663-674. doi: 10.1038/s41564-018-0349-6. Epub Feb. 11, 2019.

Burnham, et al. Single-stranded DNA library preparation uncovers the origin and diversity of ultrashort cell-free DNA in plasma. Sci Rep. Jun. 14, 2016;6:27859. doi: 10.1038/srep27859.

Chen, et al. Helicobacter pylori colonization is inversely associated with childhood asthma. J Infect Dis. Aug. 15, 2008; 198(4): 553-560.doi: 10.1086/590158.

Chen, et al. The overlooked fact: fundamental need of spike-in controls for virtually all genome-wide analyses. Manuscript posted

(56) References Cited

OTHER PUBLICATIONS online Dec. 28, 2015. Mol. Cell. Biol. American Society for Microbiology, doi:10.1128/MCB.00970-14. 20 pages.

Chey, et al. American College of Gastroenterology guideline on the management of Helicobacter pylori infection. Am J Gastroenterol. Aug. 2007; 102(8):1808-1825. doi: 10.1111/j.1572-0241.2007.01393.x. Epub Jun. 29, 2007.

Deveson, et al. Representing genetic variation with synthetic DNA standards. Nature Methods. vol. 13, pp. 784-791. Received Mar. 23, 2016. Accepted Jun. 28, 2016. Published online Aug. 8, 2016. DOI:doi: 10.1038/nmeth.3957.

Dixon, et al. Histological classification of gastritis and Helicobacter pylori infection: an agreement at last? The International Workshop on the Histopathology of Gastritis. Helicobacter. Jul. 1997;2 Suppl 1:S17-24. doi: 10.1111/j.1523-5378.1997.06b09.x.

Epigene, 5-methylcytosine (5mC), available at https://epigenie.com/key-epigenetic-players/important-dna-methylation-factors/5-v methylcytosine-5mc/, accessed Feb. 10, 2020.

European search report and opinion dated Aug. 29, 2019 for EP Application No. 17771302.1.

Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.

Fu, et al. Molecular indexing enables quantitative targeted RNA sequencing and reveals poor efficiencies in standard library preparations. Proc Natl Acad Sci U S A. Feb. 4, 2014;111(5):1891-6.

Gansauge, et al. Single-stranded DNA library preparation for the sequencing of ancient or damaged DNA. Nat Protoc. Apr. 2013;8(4):737-48. doi: 10.1038/nprot.2013.038. Epub Mar. 14, 2013.

Gansauge et al. Single-stranded DNA library preparation from highly degraded DNA using T4 DNA ligase. Nucleic Acids Research, vol. 45, No. 10, e79, 10 pages (2017). Published online Jan. 24, 2017.

Genelink, Degenerate Bases & Spiking—Introduction, available at http://www.genelink.com/oligo_modifications_reference/OMR_mod_category_intro.asp?mod_sp_cat_id=5, accessed Feb. 10, 2020.

Heger, Monica. Garvan Team Uses Synthetic DNA to Create Spike-In Method for NGS Assay Validation. Genomeweb. Aug. 8, 2016. 4 pages.

Highlander, Sarah K. High throughput sequencing methods for microbiome profiling: application to food animal systems. Anim Health Res Rev. Jun. 2012;13(1):40-53. doi: 10.1017/S1466252312000126.

IDT. Integrated DNA Technologies, Inc. Modifications. Accessed Oct. 12, 2021. 1 page. Available online at https://www.idtdna.com/site/Catalog/Modifications.

International search report with written opinion dated Mar. 10, 2020 for PCT/US2019/062488.

International search report with written opinion dated Apr. 28, 2020 for PCT/US2019/062665.

International search report with written opinion dated Jul. 26, 2017 for PCT/US2017/024176.

Islam, et al. Quantitative single-cell RNA-seq with unique molecular identifiers. Nat Methods. Feb. 2014;11(2):163-6.

Jiang, et al. Synthetic spike-in standards for RNA-seq experiments. Genome Res. Sep. 2011;21(9):1543-51. doi: 10.1101/gr.121095.111. Epub Aug. 4, 2011.

Kim et al., Characterizing noise structure in single-cell RNA-seq distinguishes genuine from technical stochastic allelic expression, Nat Commun. Oct. 22, 2015; 6: 8687.

Koh, W. et al., Noninvasive in vivo monitoring of tissue-specific global gene expression in humans, PNAS 111(20):7361-7366 (Jul. 29, 2014).

Kuipers, et al. The prevalence of Helicobacter pylori in peptic ulcer disease. Aliment Pharmacol Ther. 1995;9 Suppl 2:59-69.

Life Technologies Corporation. Ambion® ERCC RNA Spike-In Control Mixes. User Guide pp. 1-26 (2012) Accessed online at https://www.thermofisher.com/document-connect/document-connect.html?url=https%3A%2F%2Fassets.thermofisher.com%2FTFS-Assets%2FLSG%2Fmanuals%2Fcms_086340.pdf&title=VXNIciBH dWIKZTogRVJDQyBSTkEgU3Bpa2UtSW4gQ29udHJvbCBNaXhl IcyAoRW5%20nbGIzaCAp.

Lindner, et al. Metagenomic abundance estimation and diagnostic testing on species level. Nucleic Acids Res. Jan. 7, 2013;41(1):e10. doi: 10.1093/nar/gks803. Epub Aug. 31, 2012.

Locati, et al. Improving small RNA-seq by using a synthetic spike-in set for size-range quality control together with a set for data normalization. Nucleic Acids Res. Aug. 18, 2015;43(14):e89. doi: 10.1093/nar/gkv303. Epub Apr. 13, 2015.

Matranga, et al. Enhanced methods for unbiased deep sequencing of Lassa and Ebola RNA viruses from clinical and biological samples. Genome Biol. 2014; 15(11):519.

Merriam-Webster, definition of "or," available at https://www.merriam-webster.com/dictionary/or, accessed May 18, 2020.

Notice of Allowance dated Feb. 26, 2018 for U.S. Appl. No. 15/469,474.

Notice of Allowance dated Mar. 8, 2018 for U.S. Appl. No. 15/469,474.

Notice of Allowance dated Apr. 6, 2021 for U.S. Appl. No. 15/953,822.

Notice of Allowance dated May 5, 2021 for U.S. Appl. No. 15/953,822.

Notice of Allowance dated Jul. 9, 2021 for U.S. Appl. No. 15/953,822.

Office action dated Feb. 13, 2020 for U.S. Appl. No. 15/953,822.

Office action dated May 21, 2020 for U.S. Appl. No. 15/953,822.

Office action dated Oct. 26, 2017 for U.S. Appl. No. 15/469,474.

Office action dated Dec. 14, 2020 for U.S. Appl. No. 15/953,822.

Quail, et al. SASI-Seq: sample assurance Spike-Ins, and highly differentiating 384 barcoding for Illumina sequencing. BMC Genomics. Feb. 7, 2014;15:110. doi: 10.1186/1471-2164-15-110.

Risso, D., et al., Normalization of RNA-seq data using factor analysis of control genes or samples. Nat Biotechnol. Sep. 2014;32(9):896-902. doi: 10.1038/nbt.2931. Epub Aug. 24, 2014.

Saukkonen, et al. Cell-free plasma DNA as a predictor of outcome in severe sepsis and septic shock. Clin Chem. Jun. 2008;54(6):1000-7. doi: 10.1373/clinchem.2007.101030. Epub Apr. 17, 2008.

Stegle, O., Computational and analytical challenges in single-cell transcriptomics. Nat Rev Genet. Mar. 2015;16(3):133-45. doi: 10.1038/nrg3833. Epub Jan. 28, 2015.

Sung, et al. Systematic review: the global incidence and prevalence of peptic ulcer disease. Aliment Pharmacol Ther. May 1, 2009;29(9):938-946. doi: 10.1111/j.1365-2036.2009.03960.x.

Tong, et al. Evaluating the impact of sequencing error correction for RNA-seq data with ERCC RNA spike-in controls. IEEE EMBS Int Conf Biomed Health Inform. Feb. 2016;2016:74-77. doi: 10.1109/BHI.2016.7455838.

Xia, et al. Accurate genome relative abundance estimation based on shotgun metagenomic reads. PLoS One. 2011;6(12):e27992. doi: 10.1371/journal.pone.0027992. Epub Dec. 6, 2011.

Yu, et al. Normalization of human RNA-seq experiments using chimpanzee RNA as a spike-in standard. Sci Rep. Aug. 24, 2016;6:31923. doi: 10.1038/srep31923.

Zhu, et al. Reverse transcriptase template switching: a SMART approach for full-length cDNA library construction. Biotechniques. Apr. 2001;30(4):892-7.

Zook, et al. Synthetic spike-in standards improve run-specific systematic error analysis for DNA and RNA sequencing. PLoS One. 2012;7(7):e41356.

\* cited by examiner

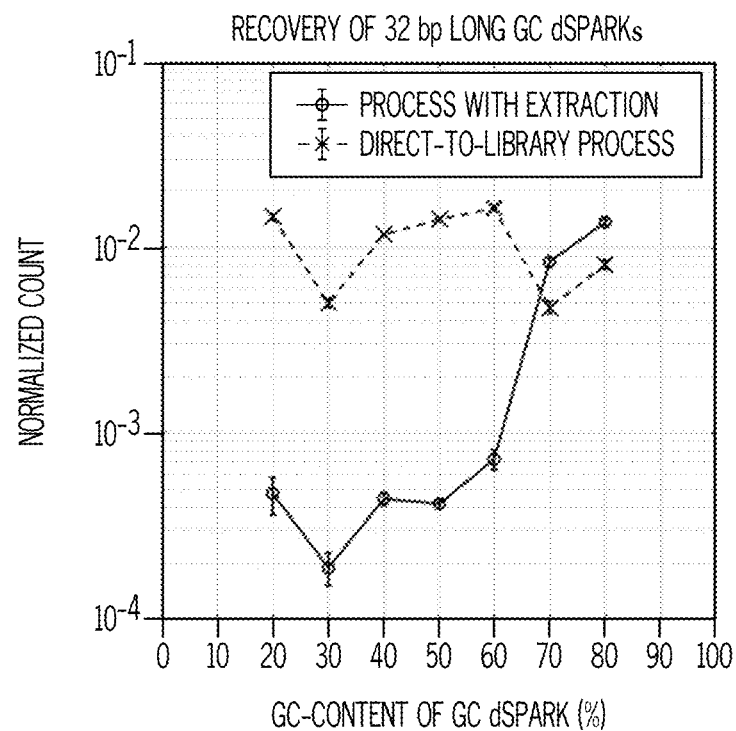
FIG. 4A1
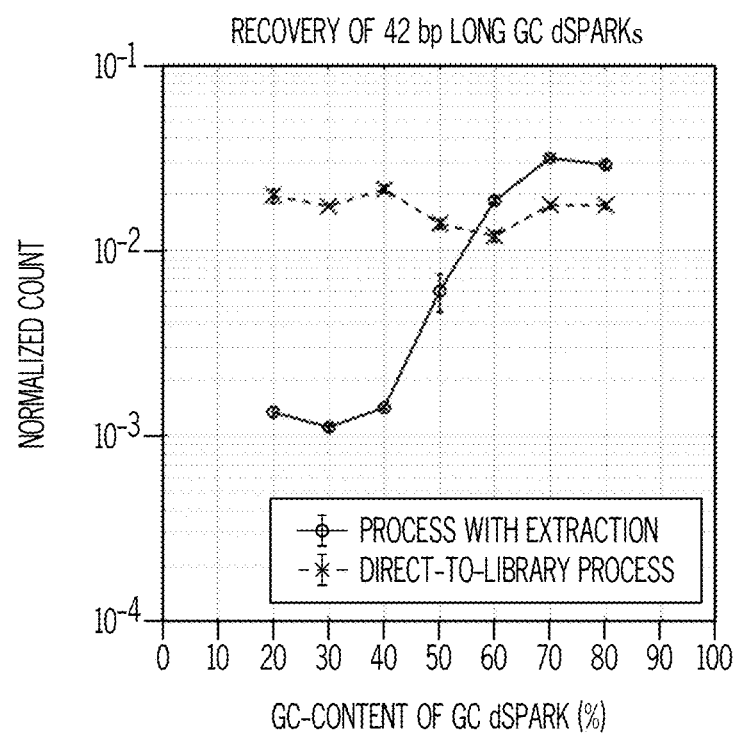
FIG. 4A2

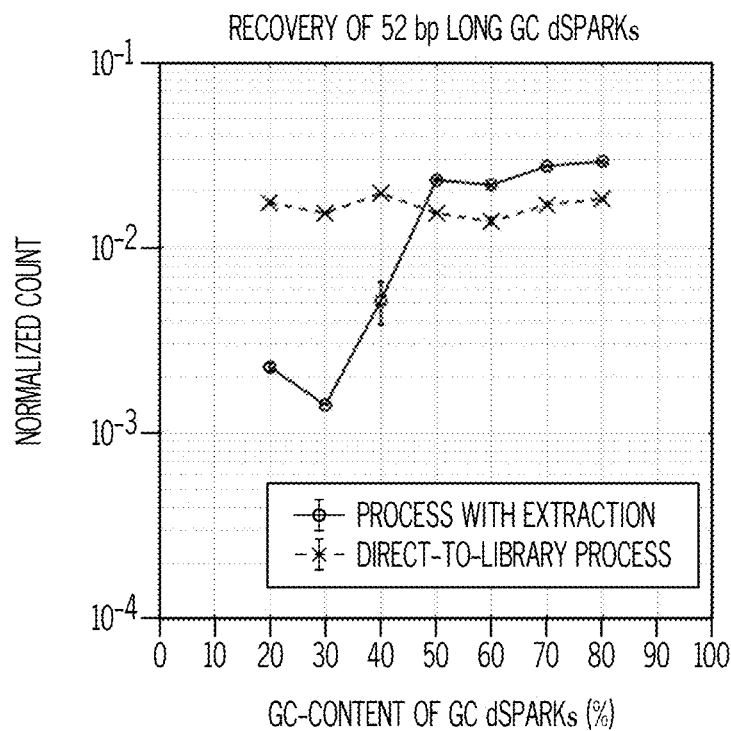
FIG. 4A3
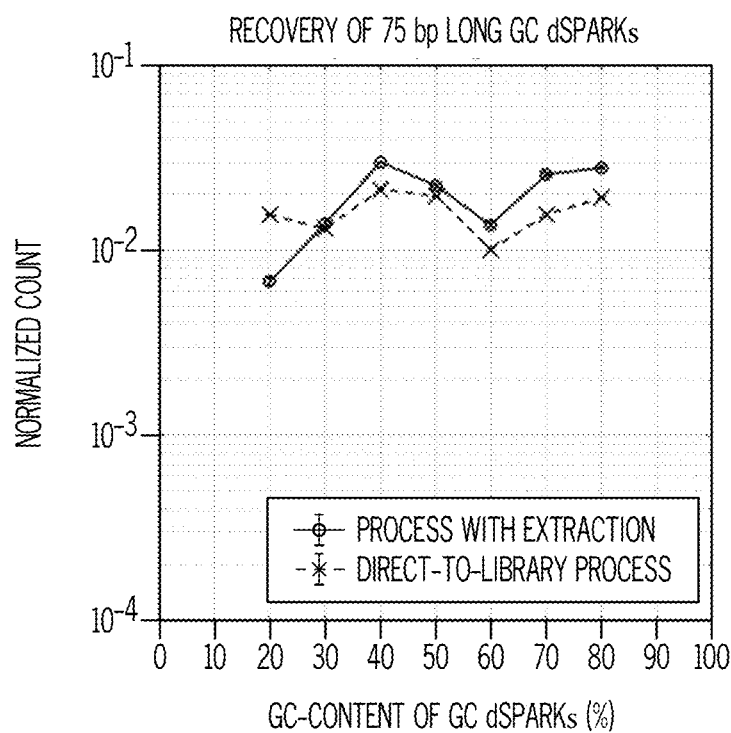
FIG. 4A4

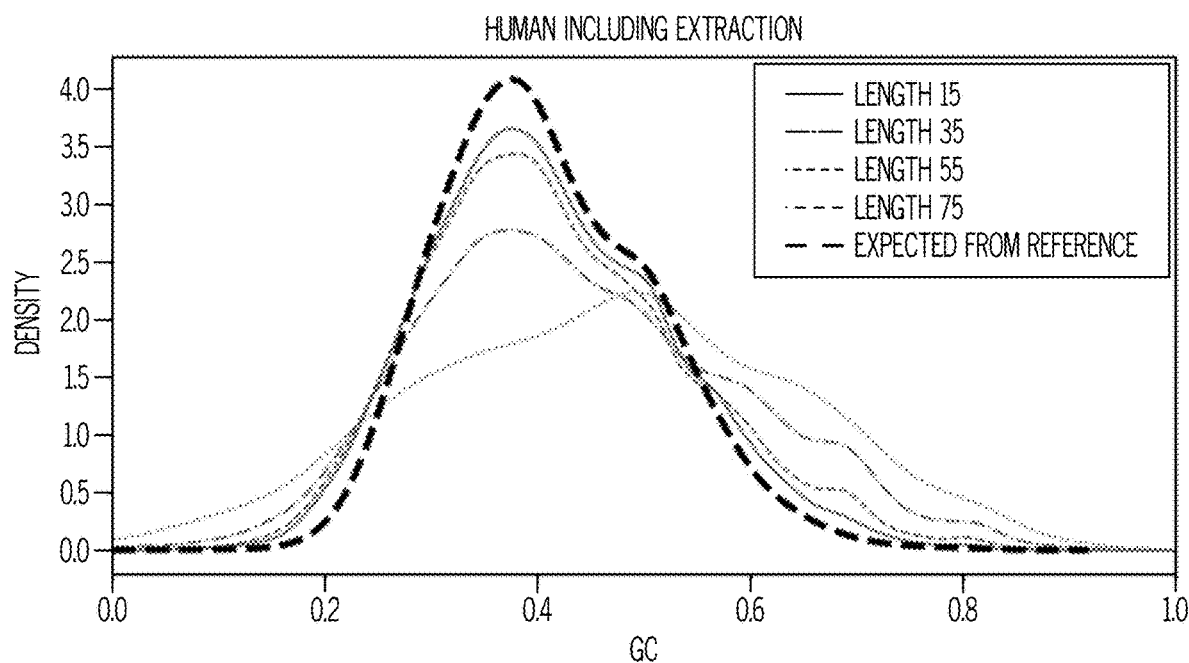
FIG. 4B1
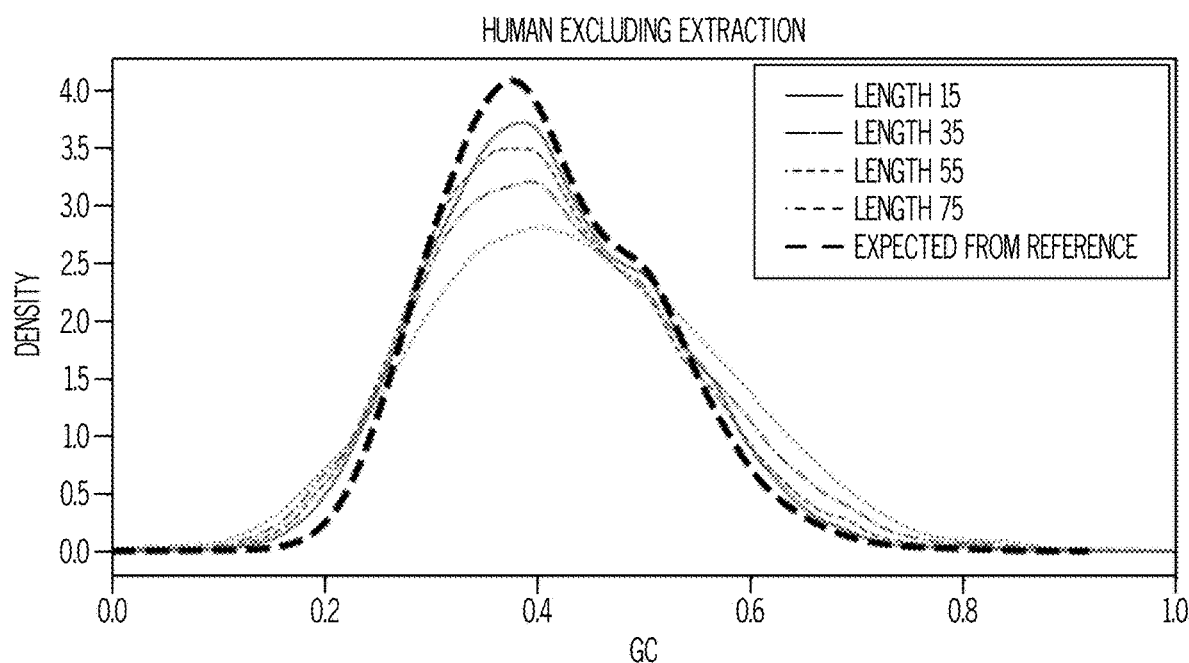
FIG. 4B2

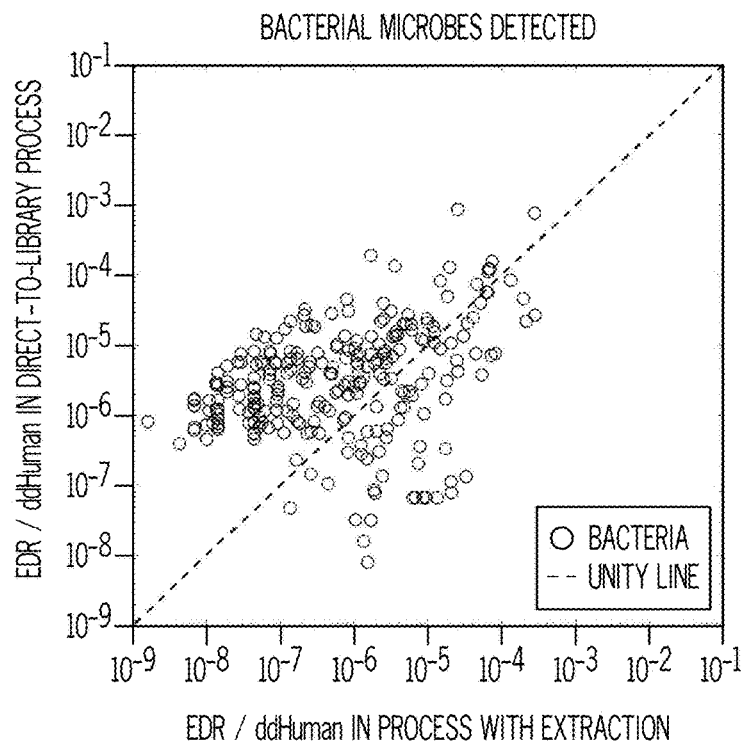
FIG. 6A1
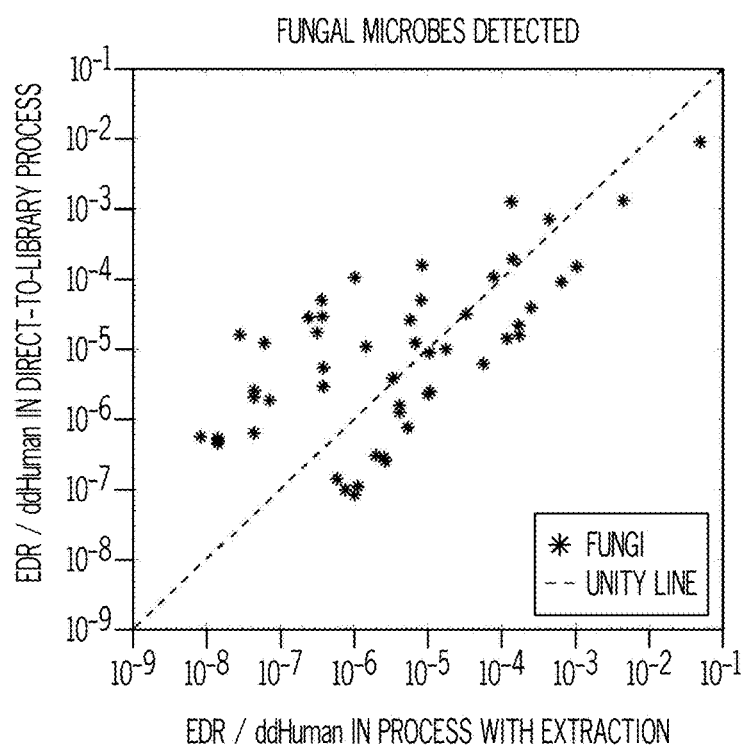
FIG. 6A2

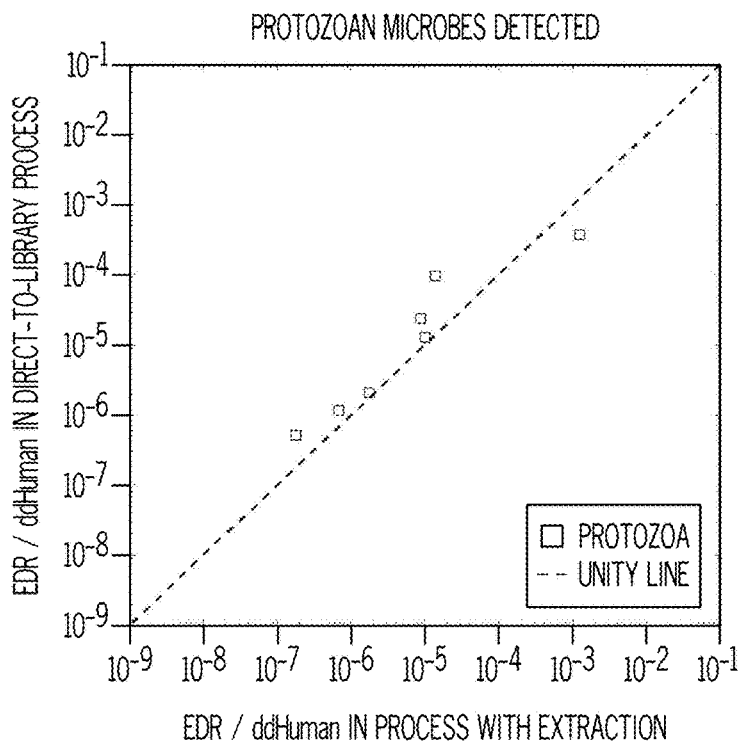
FIG. 6A3
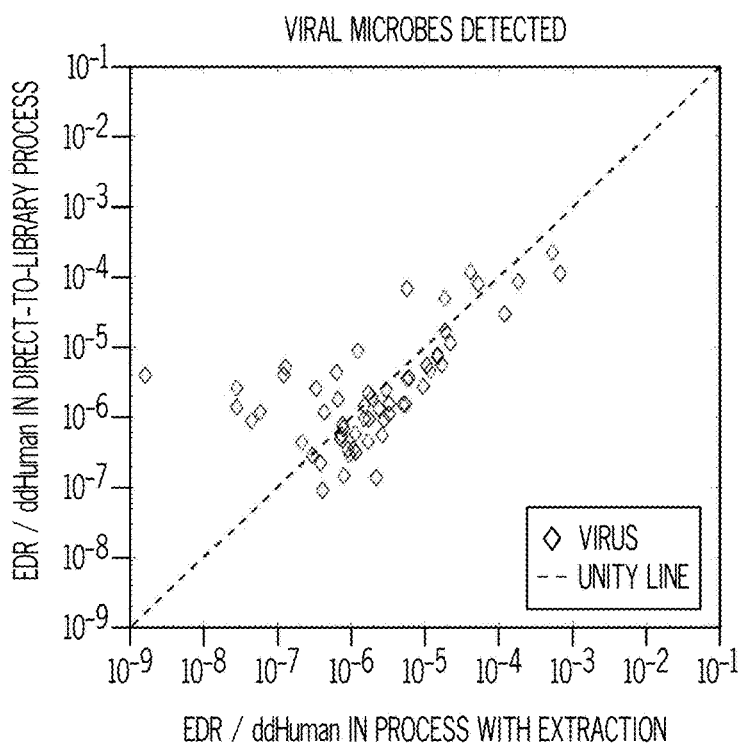
FIG. 6A4

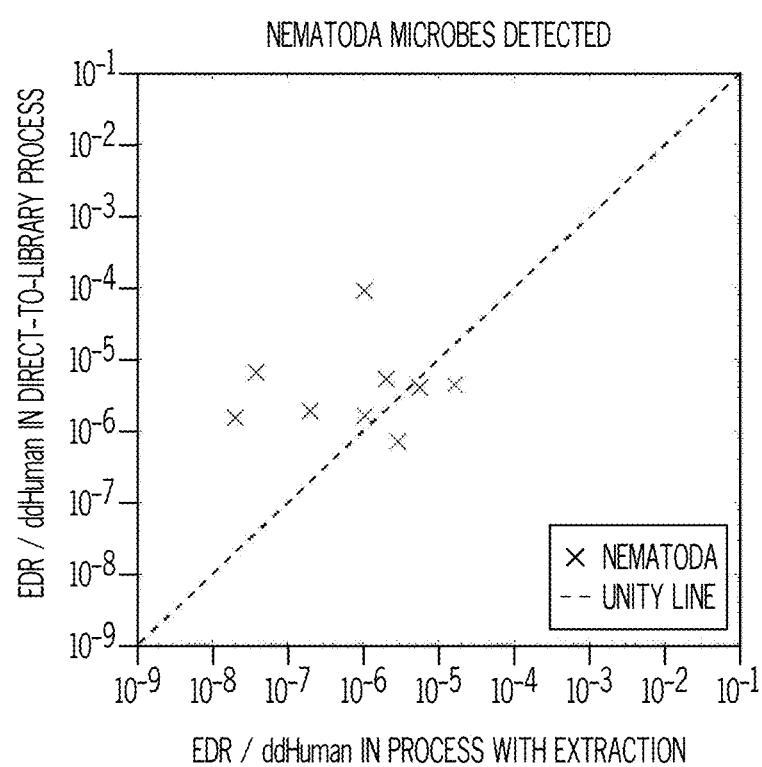
FIG. 6A5

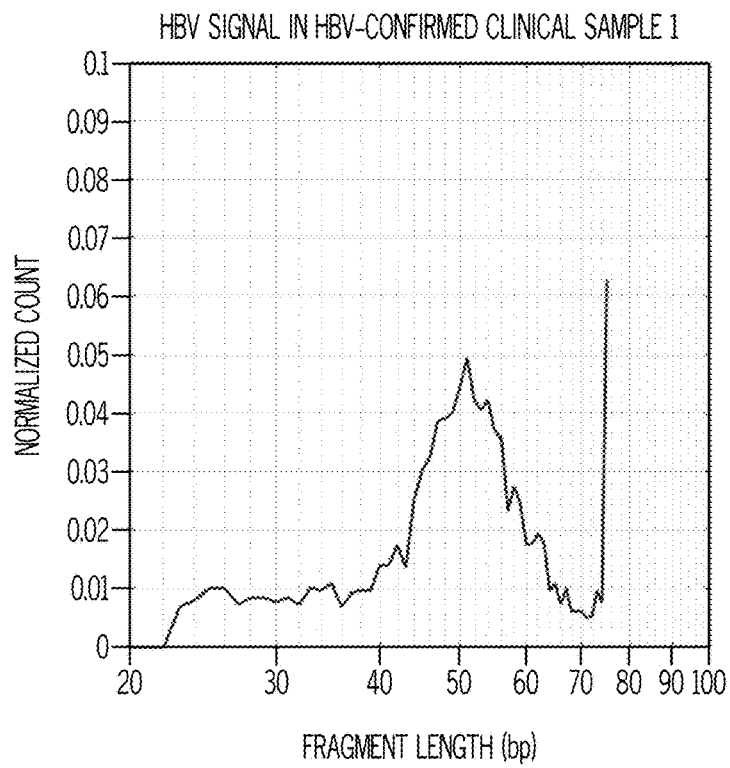
FIG. 7B1
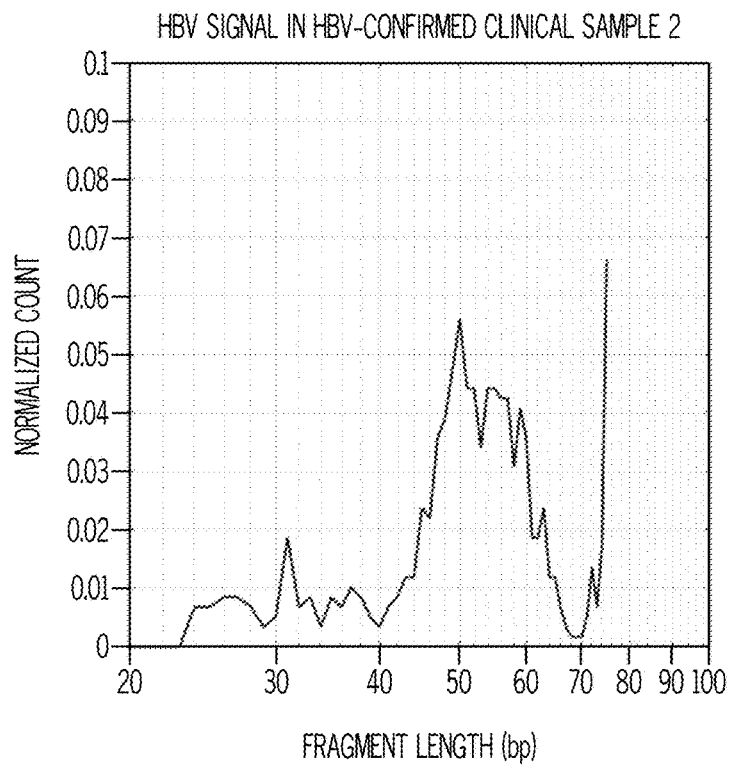
FIG. 7B2

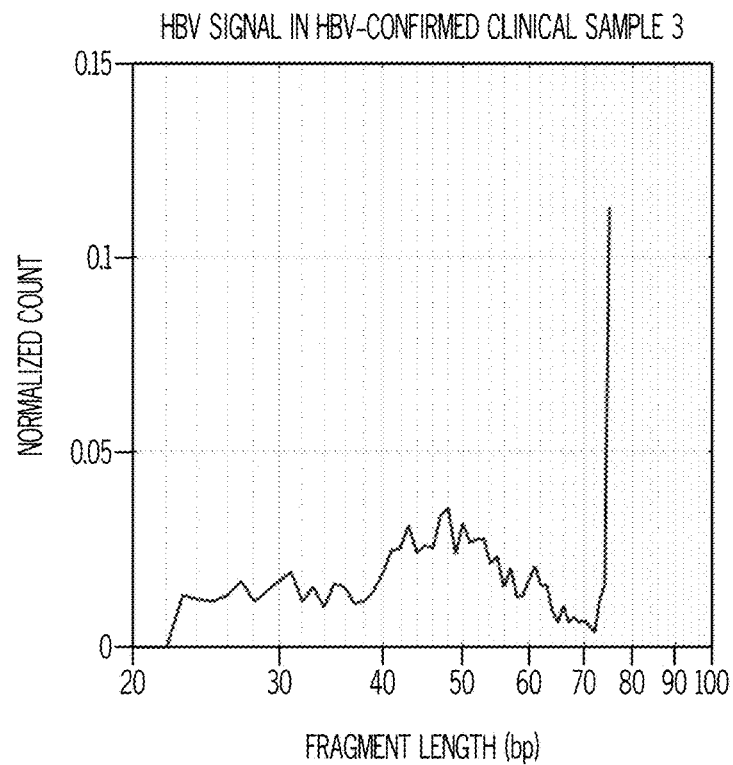
FIG. 7B3
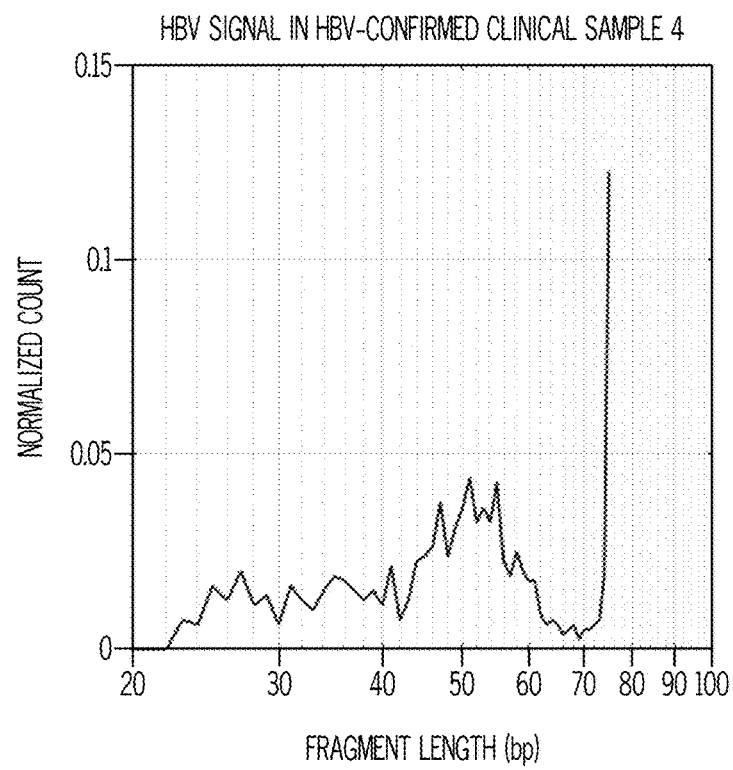
FIG. 7B4

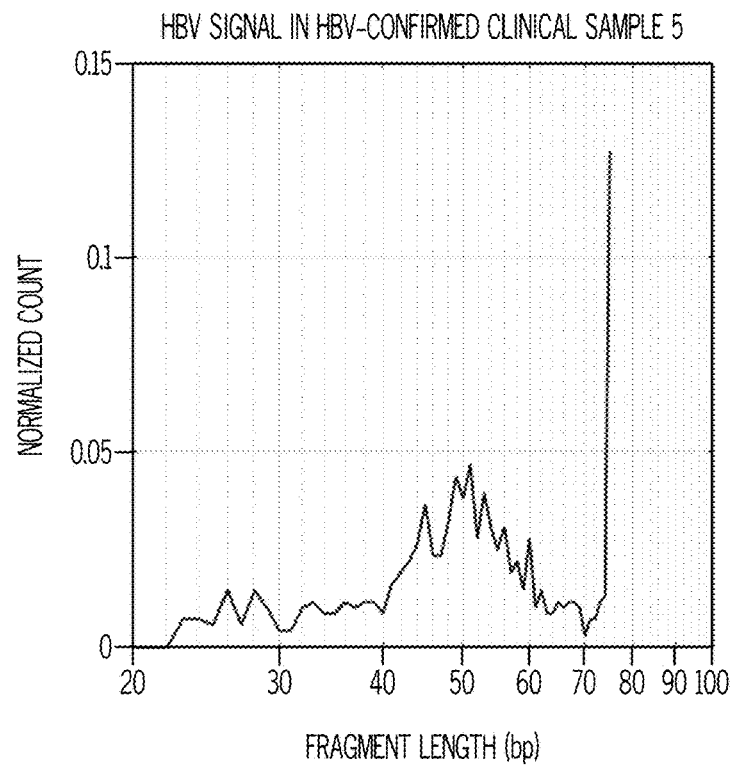
FIG. 7B5
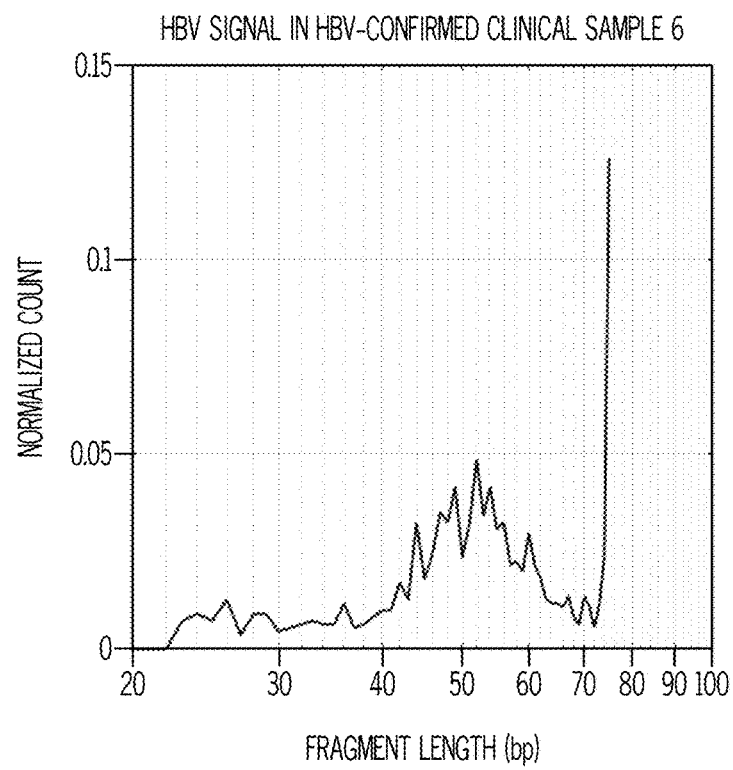
FIG. 7B6

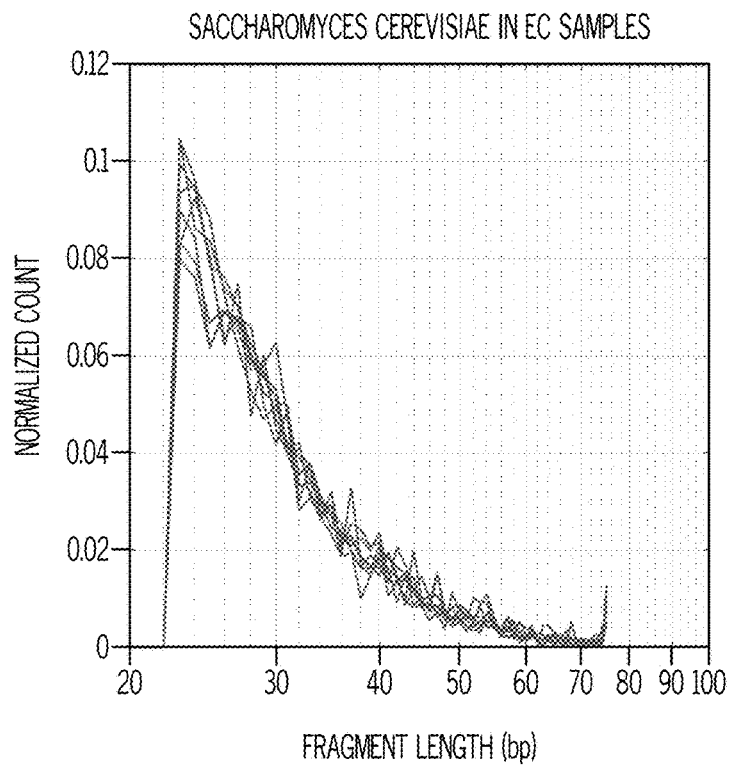
FIG. 7E1
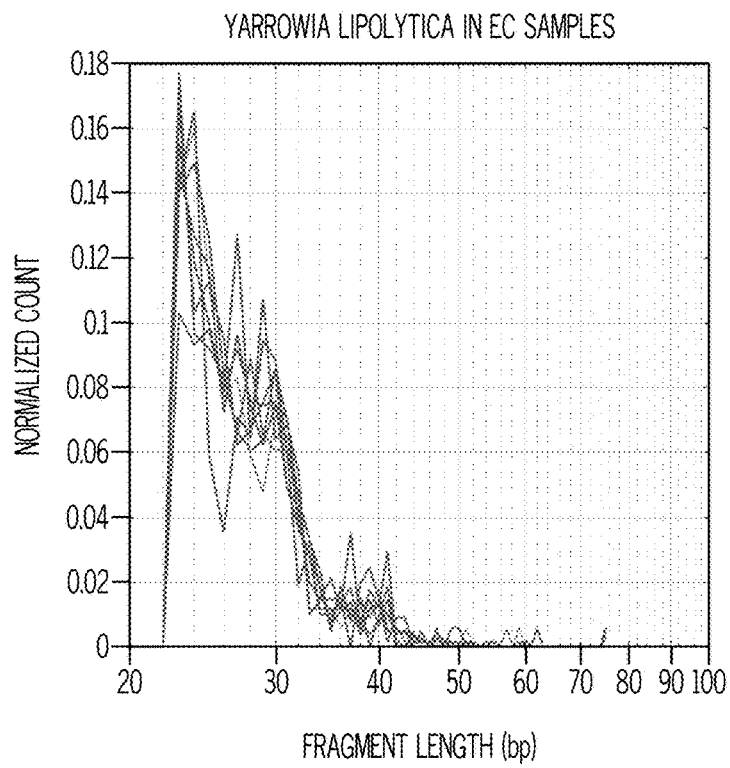
FIG. 7E2

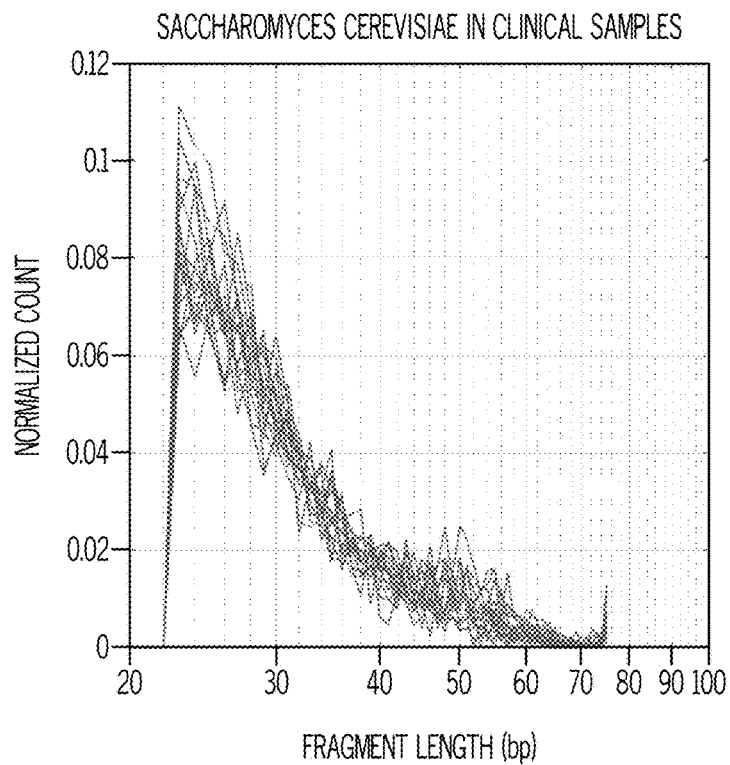
FIG. 7F1
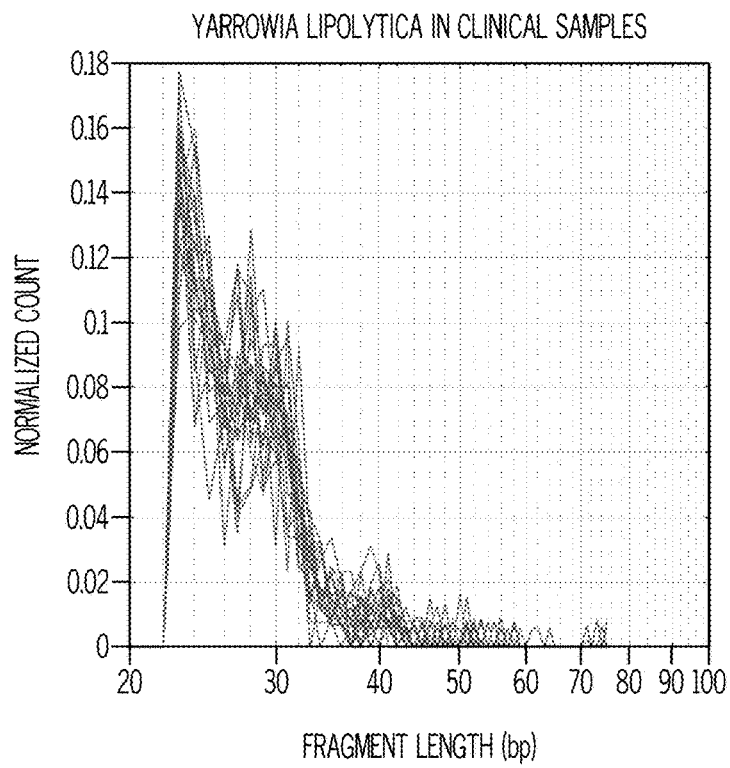
FIG. 7F2

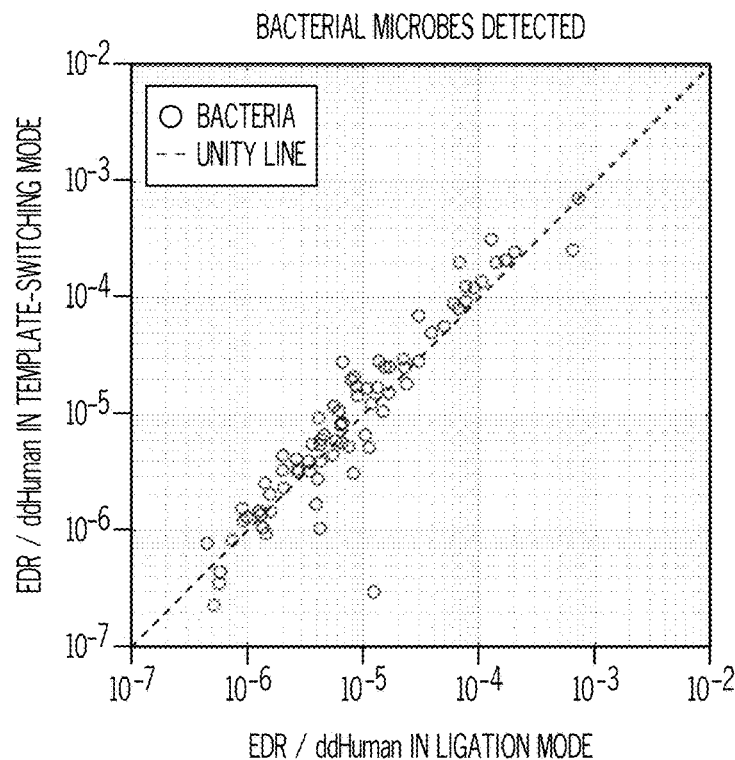
FIG. 11A1
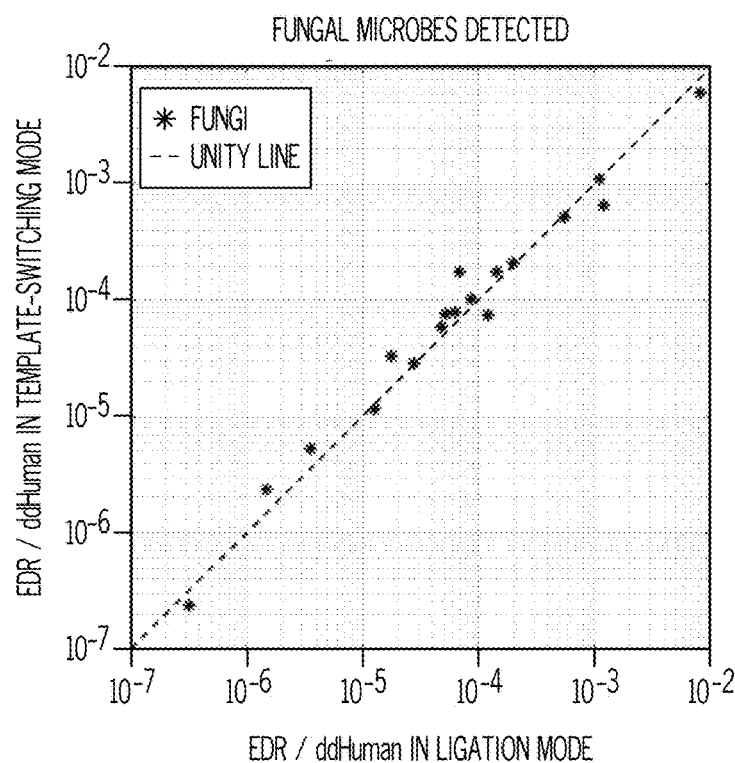
FIG. 11A2

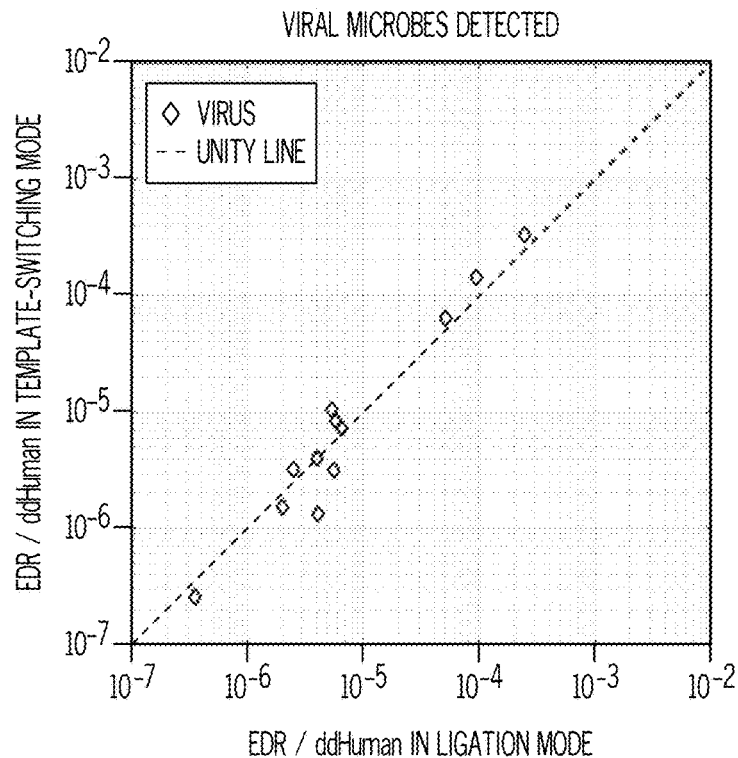
FIG. 11A3
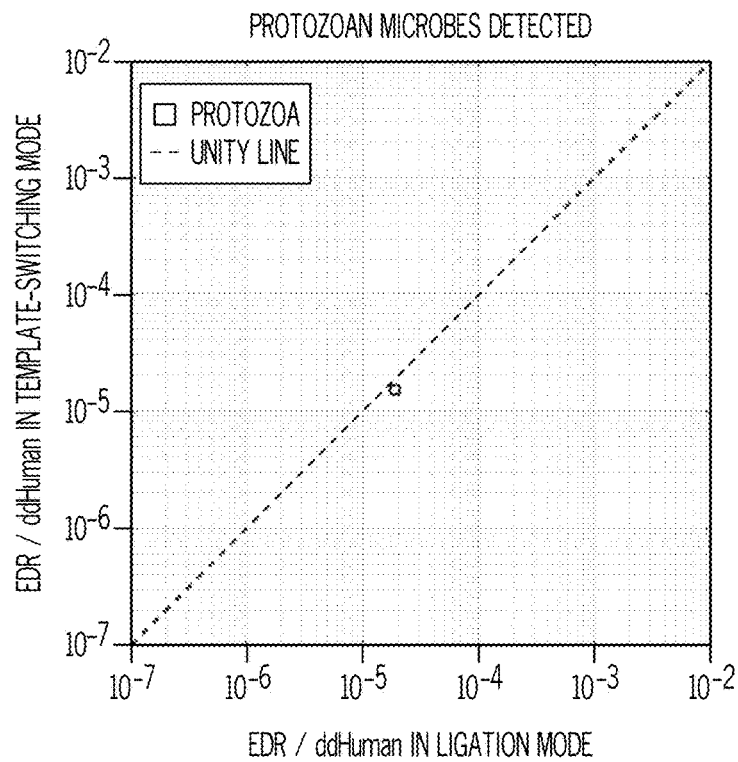
FIG. 11A4

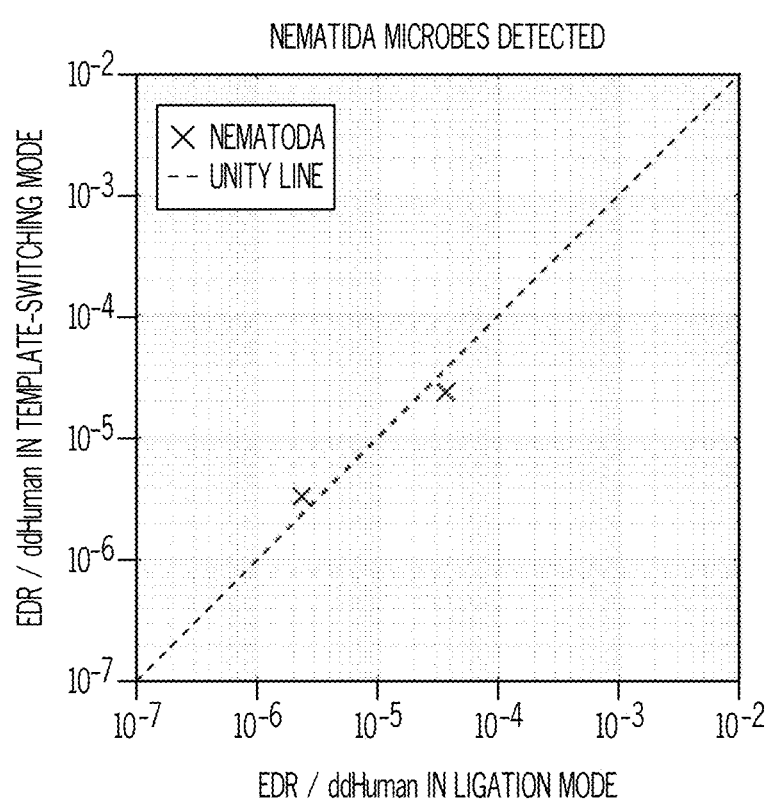
FIG. 11A5

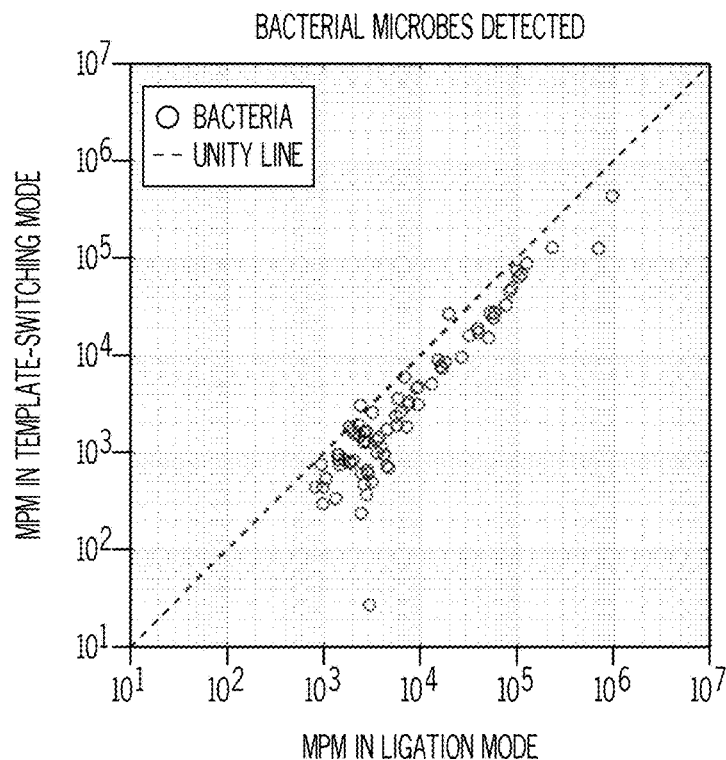
FIG. 11B1
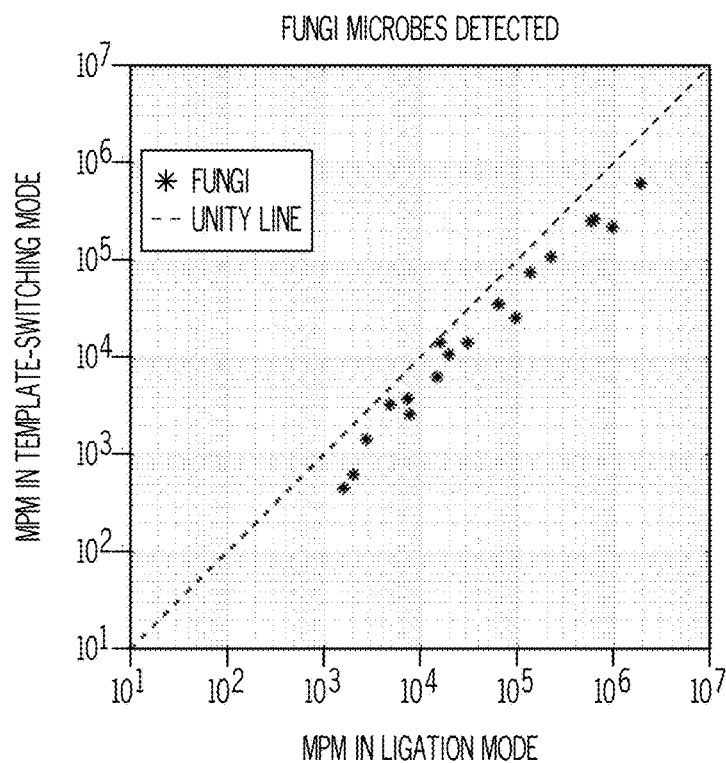
FIG. 11B2

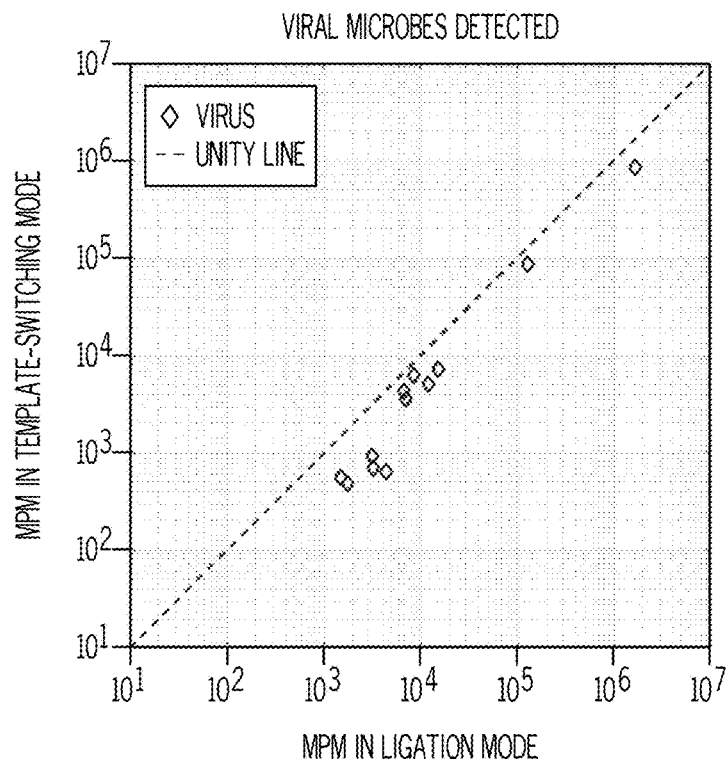
FIG. 11B3
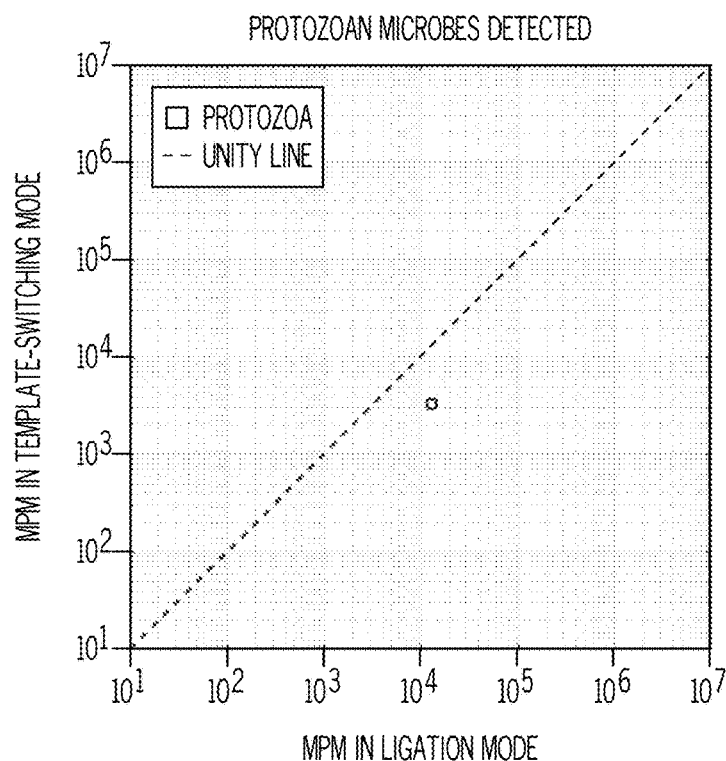
FIG. 11B4

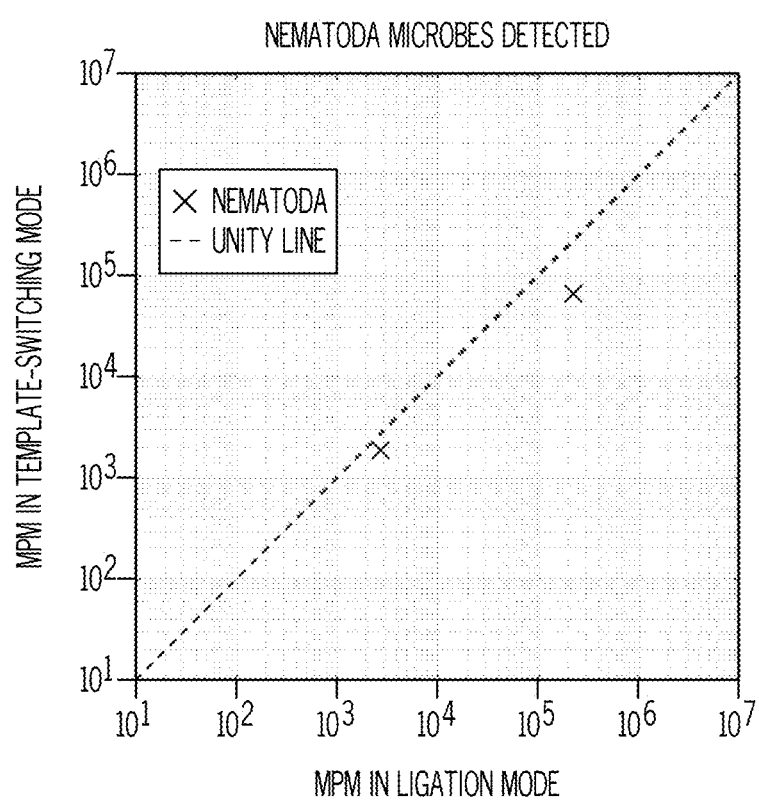
FIG. 11B5

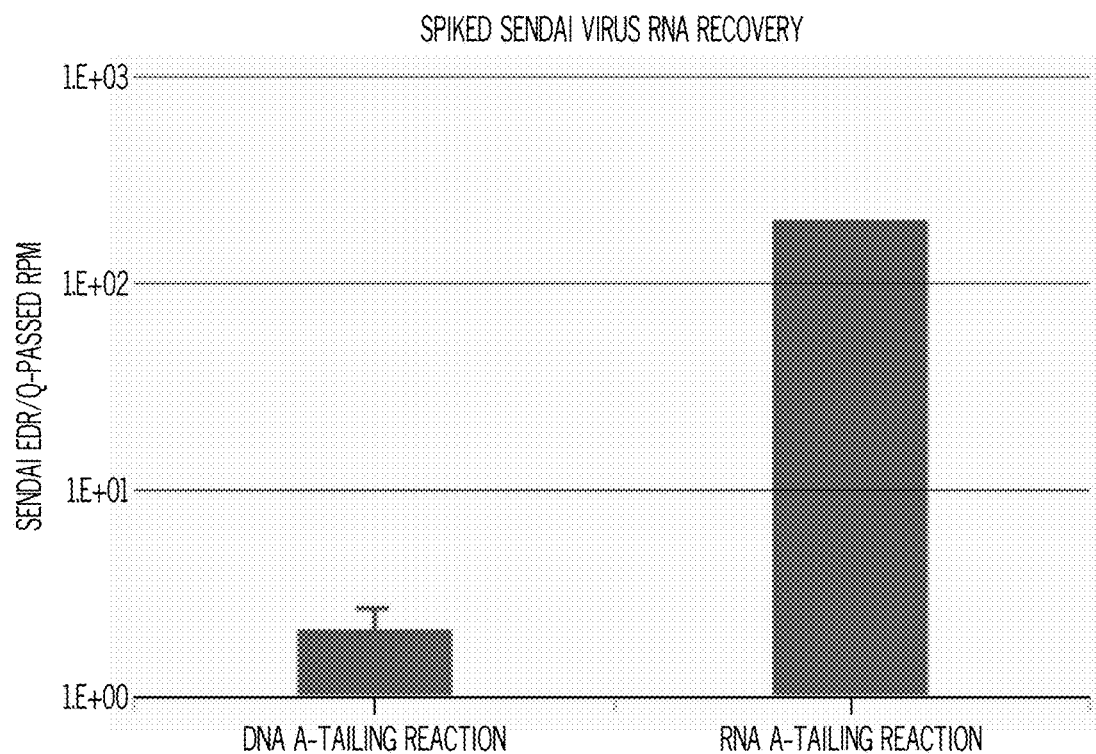
FIG. 22A1
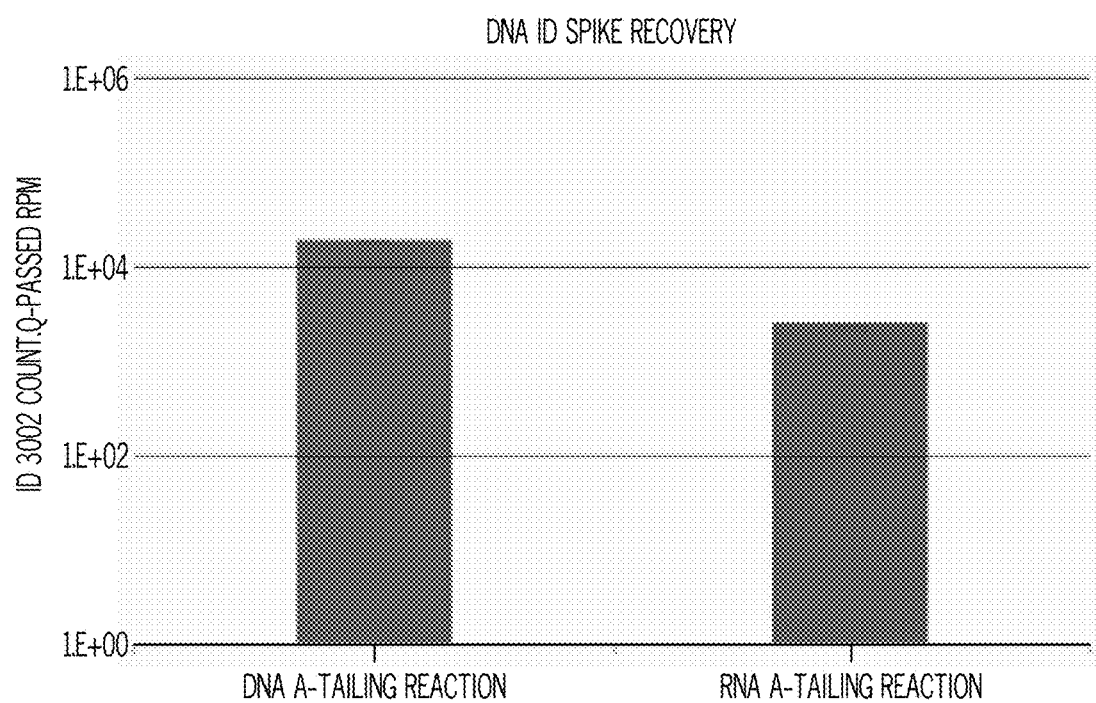
FIG. 22A2

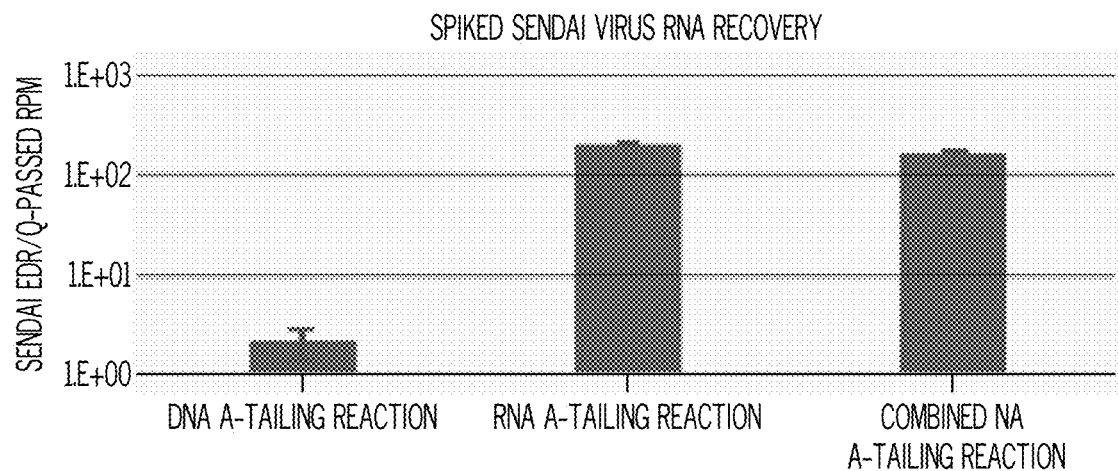
FIG. 22B1
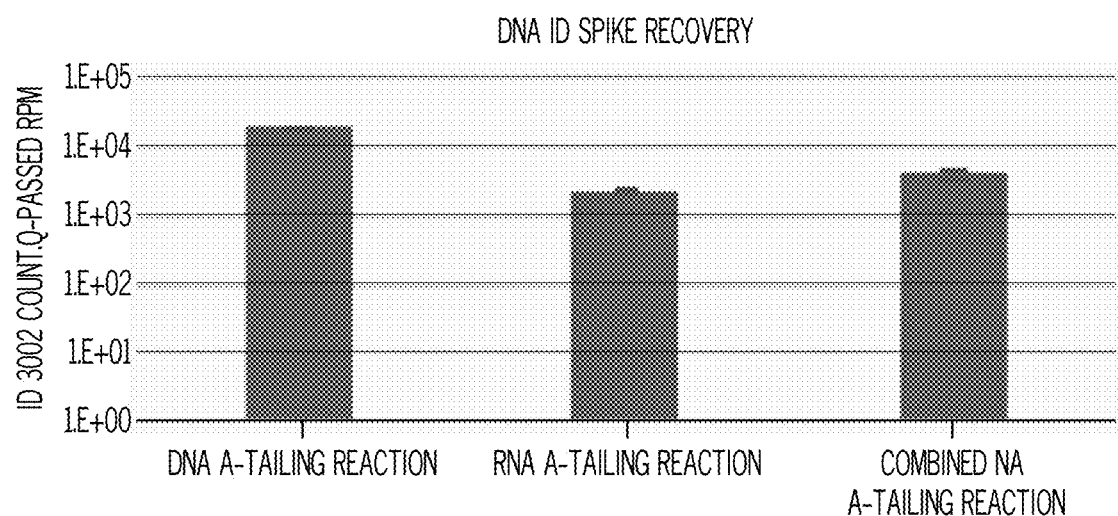
FIG. 22B2

DIRECT-TO-LIBRARY METHODS, SYSTEMS, AND COMPOSITIONS

CROSS REFERENCES TO RELATED APPLICATIONS

This application is a continuation of International Patent Application No. PCT/US2019/062488, titled "Direct-to Library Methods, Systems and Compositions", filed Nov. 20, 2019, which claims the benefit of U.S. Provisional Application No. 62/770,181, titled "Direct-to-Library Methods, Systems and Compositions", filed Nov. 21, 2018, each of which are hereby incorporated by reference in its entirety.

SEQUENCE LISTING

The instant application contains a Sequence Listing which has been submitted electronically in ASCII format and is hereby incorporated by reference in its entirety. Said ASCII copy, created on Dec. 27, 2019, is named 11043_713WO1_SL.txt and is 4,931 bytes in size.

BACKGROUND

Next generation sequencing (NGS) can be used to gather massive amounts of data about the nucleic acid content of a sample. It can be particularly useful for analyzing nucleic acids in complex samples, such as clinical samples. However, before using the NGS methods, a starting sample must often be extracted, which lowers nucleic acid recovery, delays sequencing, delays reporting of clinical calls, introduces errors, introduces bias, and often results in chemical waste requiring controlled handling. Errors and biases can affect results in many cases, such as when there are low abundance nucleic acids or target nucleic acids in patient samples. Furthermore processes for generating nucleic acid libraries from DNA and RNA simultaneously have been difficult to develop.

There is a need for more efficient and accurate methods for detecting and quantifying nucleic acids as well as preparing nucleic acid libraries. This need can be seen, for example, with respect to low abundance nucleic acids or target nucleic acids in patient samples.

SUMMARY

Current technologies for nucleic acid analysis often impede efficient sample processing. Many sample preparation methods introduce bias against certain GC-contents, fragment length, and/or structural form(s) of nucleic acids, which can decrease the efficiency of sample processing. Indeed, many have limited use in that they can only detect one nucleic acid form at a time. For example, with respect to DNA and RNA, most sample preparation methods require that a sample be divided so that DNA and RNA can be processed separately. Similarly, nucleic acids of different secondary or higher order structures require separate processing. In addition, sample preparation methods for nucleic acids (e.g., cell-free nucleic acids (cfNA)) require nucleic acids to be extracted before processing into a sequencing library because of concentration issues as well as inhibitory effects of the non-nucleic acid substances present in the biological samples containing these nucleic acids.

In the case of low quantity nucleic acids or low quality nucleic acids, treatment of nucleic acids before library generation can introduce yield losses and biases, and decreases the ability to recover nucleic acids for detection. Finally, samples containing low quantities of nucleic acids, or low quality nucleic acids, may not have sufficient material to permit detection of both RNA and DNA, or of any secondary or higher order structures, which could result in the possible loss of valuable information about the sample. Additionally processes such as improper handling of samples, nuclease treatment and other acts of human intervention may alter fragment length distribution profiles.

The present invention provides direct-to-library methods for generating a nucleic acid library that render a product incorporating such a nucleic acid library more specific and sensitive to low abundance, low quality nucleic acids, less sensitive to seasonal variation and sample shipping conditions. The present invention also provides greater ability to work with lower sample volumes, reduces sequence length bias, secondary structure bias, and GC biases, provides a reduced turnaround time, enables better quality control of materials, decreases the false positive rate of the target nucleic acid detection, and provides a lower cost of goods. The reduction in sequence length bias, secondary structure bias and GC bias allows insight into the actual distribution of these values in a sample. The present methods may eliminate the need for harmful and/or hazardous denaturing agents (e.g., guanidinium chloride, guanidinium thiocyanate). In addition, the present invention completely eliminates (e.g. phenol, chloroform, trizol, isopropanol) or lowers (e.g., ethanol) the quantities of harmful and/or hazardous chemicals required by all or some current processes of converting nucleic acids from the biological sample to a nucleic acid library. The present invention also allows better discrimination between the nucleic acid signal endogenous to a biological sample from that of a nucleic acid signal originating from environmental contamination during sample handling and processing.

A first aspect provides a method of generating a nucleic acid library from an initial sample, the method comprising, consisting of, or consisting essentially of:
  (a) optionally, adding one or more process control molecules to the initial sample to provide a spiked initial sample; and
  (b) generating the nucleic acid library from the initial sample.

The nucleic acid library is generated without extracting nucleic acids from the initial sample or spiked initial sample prior to generating the nucleic acid library from the initial sample. Thus, the method of generating the nucleic acid library from an initial sample comprises, consists of, or consists essentially of:
  (a) optionally, adding one or more process control molecules to the initial sample to provide a spiked initial sample; and
  (b) generating the nucleic acid library from the initial sample or spiked initial sample comprising the one or more process control molecules; wherein nucleic acids used to generate the nucleic library are not extracted prior to generating the library.

The nucleic acids from an initial sample can be single-stranded and/or double-stranded. In some embodiments, the nucleic acid library comprises, consists of, or consists essentially of a single-stranded nucleic acid library. In some embodiments, the nucleic acid library comprises, consists of, or consists essentially of a double-stranded nucleic acid library. In some embodiments, the nucleic acid library comprises, consists of, or consists essentially of a single-stranded nucleic acid library and double-stranded nucleic acid library.

In some embodiments, the one or more process control molecules comprises, consists of, or consists essentially of one or more of ID Spike(s), Spanks, and/or Sparks or GC Spike-in Panel (See, for example, U.S. Pat. No. 9,976,181, which is incorporated by reference in its entirety herein, including any drawings). In some embodiments, the one or more process control molecules comprises, consists of, or consists essentially of dephosphorylation control molecules, denaturation control molecules, nucleotide tailing control molecules, adapter attachment control molecules, degradation assessment molecules, and/or ligation control molecules. In some embodiments, the one or more process control molecules comprises, consists of, or consists essentially of one or more of ID Spike(s), Spanks, Sparks or GC Spike-in Panel, dephosphorylation control molecules, denaturation control molecules, and/or ligation control molecules.

In some embodiments, the one or more process control molecules comprises, consists of, or consists essentially of a plurality of synthetic nucleic acids. In some embodiments, the one or more process control molecules comprises, consists of, or consists essentially of synthetic nucleic acids with at least two different GC contents with a known input concentration. In some embodiments, the one or more process control molecules comprises, consists of, or consists essentially of synthetic nucleic acids with at least three different GC contents with a known input concentration.

In some embodiments, the at least two or at least three different GC contents each have GC-content between about 10% and about 50%. In some embodiments, the at least two or at least three different GC contents each have GC-content between about 5% and about 40%. In some embodiments, the at least two or at least three different GC contents each have GC-content between about 20% and about 80%, between about 30% and about 70%, between about 40% and about 60%, or between about 10% and about 90%.

In some embodiments, the at least three different GC contents comprise, consist of, or consist essentially of a first GC content that is between about 10% and about 40%, a second GC content that is between about 40% and about 60%, and a third GC content that is between about 60% and about 90%. In some embodiments, the at least three different GC contents comprise, consist of, or consist essentially of more than three GC contents, each GC content comprising, consisting of, or consisting essentially of a content that is between about 0% and 100%. Different GC contents may be uniformly distributed or non-uniformly distributed within respective ranges.

In some embodiments, generating the nucleic acid library from the initial sample further comprises, consists of, or consists essentially of:
(a) denaturing nucleic acids from the initial sample to produce denatured nucleic acids;
(b) annealing a primer to the denatured nucleic acids and extending the primer with a polymerase to generate complementary strands; and
(c) amplifying the complementary strands.

In some embodiments, generating the nucleic acid library from the initial sample further comprises, consists of, or consists essentially of:
(a) optionally, dephosphorylating the nucleic acids to produce nucleic acids;
(b) denaturing the nucleic acids to produce denatured nucleic acids;
(c) attaching an adapter to one or both ends of the denatured nucleic acids to produce adapted nucleic acids; and
(d) amplifying the adapted nucleic acids to generate the nucleic acid library.

The order of some of the steps may be reversed. For example, in some embodiments, generating the nucleic acid library from the initial sample further comprises, consists of, or consists essentially of:
(a) denaturing the nucleic acids to produce denatured nucleic acids;
(b) dephosphorylating the denatured nucleic acids to produce dephosphorylated nucleic acids;
(c) attaching an adapter to one or both ends of the dephosphorylated nucleic acids to produce adapted nucleic acids; and
(d) amplifying the adapted nucleic acids to generate the nucleic acid library.

In some embodiments, generating the nucleic acid library from the initial sample further comprises, consists of, or consists essentially of:
(a) optionally, dephosphorylating nucleic acids from the initial sample to produce dephosphorylated nucleic acids;
(b) denaturing the dephosphorylated nucleic acids to produce denatured nucleic acids;
(c) attaching a 3'-end adapter to the denatured nucleic acids to produce adapted nucleic acids;
(d) separating the adapted nucleic acids;
(e) annealing a primer to the adapted nucleic acids and extending the primer with a polymerase to generate complementary strands;
(f) attaching a 5'-end adapter;
(g) eluting the nucleic acid strands; and
(h) amplifying the complementary strands.

In some embodiments, a 5'-end adapter sequence is attached by the use in step (e) of a polymerase that has non-templated activity and, subsequently in step (f), using a template switching reaction to attach a 5'-end adapter sequence.

As above, the order of the steps may be reversed so that generating the nucleic acid library from the initial sample further comprises, consists of, or consists essentially of:
(a) denaturing nucleic acids from the initial sample to produce denatured nucleic acids;
(b) optionally, dephosphorylating the denatured nucleic acids to produce dephosphorylated nucleic acids;
(c) attaching a 3'-end adapter to the dephosphorylated nucleic acids to produce adapted nucleic acids;
(d) separating the adapted nucleic acids;
(e) annealing a primer to the adapted nucleic acids and extending the primer with a polymerase to generate complementary strands;
(f) attaching a 5'-end adapter;
(g) eluting the adapted nucleic acid strands; and
(h) amplifying the adapted nucleic acid strands.

In some embodiments, a 5'-end adapter sequence is attached by the use in step (e) of a polymerase that has non-templated activity and, subsequently in step (f), using a template switching reaction to attach a 5'-end adapter sequence.

In general, the steps set forth herein need not be in any particular order and some steps may be performed concurrently with others. For example, in some embodiments, attaching an adapter to one or both ends of the denatured nucleic acids to produce adapted nucleic acids can occur in the order of steps as set forth above. In some embodiments, attaching an adapter to one or both ends of the denatured nucleic acids to produce adapted nucleic acids can occur concurrently or concurrently with dephosphorylation when included in the method.

In some embodiments, separating the adapted nucleic acids comprises, consists of, or consists essentially of immobilizing the adapted nucleic acids. In some embodiments, immobilization occurs on magnetic beads. In some embodiments, immobilization occurs on a modified glass, beads with functionalized surface, modified capillary surfaces, and/or modified columns. In some embodiments, immobilization occurs on a column. In some embodiments, separating the adapted nucleic acids comprises, consists of, or consists essentially of purifying the adapted nucleic acids. In some embodiments, separating the adapted nucleic acids comprises, consists of, or consists essentially of precipitating the adapted nucleic acids.

In some embodiments, separating the adapted nucleic acids comprises, consists of, or consists essentially of using a 3'-end protected 3'-end adapter. In some embodiments, separating the adapted nucleic acids comprises, consists of, or consists essentially of separating adapted nucleic acids from unadapted nucleic acids by digesting unadapted nucleic acids with a 3' end exonuclease, the adapted nucleic acids comprising, consisting of, or consisting essentially of a 3'-end protected 3'-end adapter.

In some embodiments, attaching a 3'-end adapter comprises, consists of, or consists essentially of attaching with a splint oligonucleotide. In some embodiments, attaching a 3'-end adapter comprises, consists of, or consists essentially of ligating with a Splint-R ligase. In some embodiments, attaching a 3'-end adapter comprises, consists of, or consists essentially of adding a ligase. In some embodiments adding RNase inhibitor improves stability of splint oligonucleotides or endogenous RNA. In some embodiments, an adapter is attached through a primer extension reaction performed with a polymerase comprising, consisting of, or consisting essentially of a DNA-dependent or RNA-dependent polymerase. In some embodiments an adapter is attached by a polymerase that has a non-templated activity.

In some embodiments, the splint oligonucleotide comprises, consists of, or consists essentially of a single-stranded oligonucleotide. In some embodiments, the splint oligonucleotide comprises single-stranded and double-stranded portions. In some embodiments, the splint oligonucleotide comprises, consists of, or consists essentially of a random hexamer or a random hexamer with a UMI. In some embodiments, the single-stranded oligonucleotide comprises, consists of, or consists essentially of a sequencing adapter or a part of sequencing adapter. In some embodiments, the single-stranded oligonucleotide comprises, consists of, or consists essentially of a random hexamer and a sequencing adapter or random hexamer and a part of sequencing adapter.

In some embodiments, the nucleic acids comprise, consist of, or consist essentially of DNA and/or RNA. In some embodiments, the nucleic acids comprise, consist of, or consist essentially of DNA. In some embodiments, the nucleic acids comprise, consist of, or consist essentially of RNA. In some embodiments, the nucleic acids comprise, consist of, or consist essentially of a hybrid RNA-DNA complex.

Some embodiments further comprise, consist of, or consist essentially of enriching nucleic acids. Some embodiments further comprise, consist of, or consist essentially of enriching nucleic acids for fragments of a certain length. In some embodiments, denaturation is used to further enrich nucleic acids or target nucleic acids. In some embodiments, denaturation comprises, consists of, or consists essentially of selective denaturation. In some embodiments, selective denaturation comprises, consists of, or consists essentially of one or more denaturation steps effective for the selection of fragments of a certain length and/or GC-content. In some embodiments, enriching for fragments of a certain length or length range may occur through the use of proteinases, detergents, heparin, hemolysis and plasma concentration.

In some embodiments, selective denaturation comprises, consists of, or consists essentially of incubation at selected or elevated temperatures. In some embodiments, the selective denaturation step comprises, consists of, or consists essentially of incubation at a temperature of about 45° C., at a temperature of about 50° C., at a temperature of about 55° C., at a temperature of about 60° C., at a temperature of about 65° C., at a temperature of about 70° C., at a temperature of about 75° C., at a temperature of about 80° C., at a temperature of about 85° C., at a temperature of about 90° C., at a temperature of about 95° C., at a temperature of about 100° C., at a temperature of about 105° C., at a temperature of about 110° C. In some embodiments, setting the temperature occurs at any of the denaturation steps such as, for example, without limitation, following dephosphorylation, preceding 3'-end ligation, before or after primer extension, and/or during an elution step.

In some embodiments, selective denaturation comprises, consists of, or consists essentially of incubation for a selected time. In some embodiments, the selected time comprises, consists of, or consists essentially of about 1 second, about 2 seconds, about 3 seconds, about 4 seconds, about 5 seconds, about 10 seconds, about 15 seconds, about 20 seconds, about 25 seconds, about 30 seconds, about 35 seconds, about 40 seconds, about 45 seconds, about 50 seconds, about 55 seconds, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19, minutes about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, or about 60 minutes. In some embodiments, incubation occurs at any of the denaturation steps such as, for example, without limitation, following dephosphorylation, preceding 3'-end adapter attachment, primer extension and/or during an elution step.

In some embodiments, the initial sample comprises, consists of, or consists essentially of a reduced sample size. The initial sample size required for the method may be reduced in the respect that volume required for the reduced initial sample size may be reduced in comparison to the volume of a sample size required for a method that includes removal or extraction prior to generation of a nucleic acid library. In some embodiments, the initial sample size is below at least about 250 μL, or at least about 100 μL, about 90 μL, about 80 μL, about 70 μL, about 60 μL, about 50 μL, about 40 μL, about 30 μL, about 20 μL, about 15 μL, about 10 μL, about 5 μL, about 4 μL, about 3 μL, about 2 μL, about 1 μL, about 0.9 µL, about 0.8 µL, about 0.7 µL, about 0.6 µL, about 0.5 µL, about 0.4 µL, about 0.3 µL, about 0.2 µL, or about 0.1 µL.

A second aspect provides a method of determining abundance of nucleic acids in an initial sample comprising target nucleic acids, the method comprising, consisting of, or consisting essentially of:
  (a) generating a nucleic acid library from the initial sample by
    i) adding one or more process control molecules to the initial sample to provide a spiked initial sample and
    ii) generating the nucleic acid library from the spiked initial sample; and
  (b) calculating abundance of the target nucleic acids in the initial sample.

The nucleic acid library is generated without extracting nucleic acids prior to generating the nucleic acid library from the initial sample. Thus, the method of generating the nucleic acid library from an initial sample comprises, consists of, or consists essentially of:
  (a) adding one or more process control molecules to the initial sample to provide a spiked initial sample; and
  (b) generating the nucleic acid library from the spiked initial sample; wherein nucleic acids used to generate the nucleic library are not extracted prior to generating the library.

In some embodiments, generating the nucleic acid library from the spiked initial sample further comprises, consists of, or consists essentially of:
  (a) denaturing nucleic acids from the spiked initial sample to produce denatured nucleic acids;
  (b) annealing a primer to the denatured nucleic acids and extending the primer with a polymerase to generate complementary strands; and
  (c) amplifying the complementary strands.

In some embodiments, generating the nucleic acid library from the spiked initial sample further comprises, consists of, or consists essentially of:
  (a) (optionally) dephosphorylating the nucleic acids to produce nucleic acids;
  (b) denaturing the nucleic acids to produce denatured nucleic acids;
  (c) attaching an adapter to one or both ends of the denatured nucleic acids to produce adapted nucleic acids; and
  (d) amplifying the adapted nucleic acids to generate the nucleic acid library.

The order of some of the steps may be reversed. For example, in some embodiments, generating the nucleic acid library from the initial sample further comprises, consists of, or consists essentially of:
  (a) denaturing the nucleic acids to produce denatured nucleic acids;
  (b) dephosphorylating the denatured nucleic acids to produce dephosphorylated nucleic acids;
  (c) attaching an adapter to one or both ends of the dephosphorylated nucleic acids to produce adapted nucleic acids; and
  (d) amplifying the adapted nucleic acids to generate the nucleic acid library.

In some embodiments, generating the nucleic acid library from the spiked initial sample further comprises, consists of, or consists essentially of:
  (a) dephosphorylating nucleic acids from the initial sample to produce dephosphorylated nucleic acids;
  (b) denaturing the dephosphorylated nucleic acids to produce denatured nucleic acids;
  (c) attaching a 3'-end adapter to the denatured nucleic acids to produce adapted nucleic acids;
  (d) separating the adapted nucleic acids;
  (e) annealing a primer to the adapted nucleic acids and extending the primer with a polymerase to generate complementary strands;
  (f) attaching a 5'-end adapter;
  (g) eluting the nucleic acid strands; and
  (h) amplifying the complementary strands.

In some embodiments, a 5'-end adapter sequence is attached by the use in step (e) of a polymerase that has non-templated activity and, subsequently in step (f), using a template switching reaction to attach a 5'-end adapter sequence.

As above, the order of the steps may be reversed so that generating the nucleic acid library from the spiked initial sample further comprises, consists of, or consists essentially of:
  (a) denaturing nucleic acids from the spiked initial sample to produce denatured nucleic acids;
  (b) dephosphorylating the denatured nucleic acids to produce dephosphorylated nucleic acids;
  (c) attaching a 3'-end adapter to the dephosphorylated nucleic acids to produce adapted nucleic acids;
  (d) separating the adapted nucleic acids;
  (e) annealing a primer to the adapted nucleic acids and extending the primer with a polymerase to generate complementary strands;
  (f) attaching a 5'-end adapter sequence;
  (g) eluting the adapted nucleic acid strands; and
  (h) amplifying the adapted complementary strands.

In some embodiments, a 5'-end adapter sequence is attached by the use in step (e) of a polymerase that has non-templated activity and, subsequently in step (f), using a template switching reaction to attach a 5'-end adapter sequence.

In general, the steps set forth herein need not be in any particular order and some steps may be performed concurrently with others. For example, in some embodiments, attaching an adapter to one or both ends of the denatured nucleic acids to produce adapted nucleic acids can occur in the order of steps as set forth above. In some embodiments, attaching an adapter to one or both ends of the denatured nucleic acids to produce adapted nucleic acids can occur concurrently with dephosphorylation.

Some embodiments further comprise, consist of, or consist essentially of adding an anti-digoxigenin antibody. In some embodiments, the anti-digoxigenin antibody is added after the 3'-end adapter is attached to the denatured or dephosphorylated nucleic acids and before an adapter is attached to the 3'-end of the complementary strand or extension primer is hybridized. Some embodiments further comprise beads comprising, consisting of, or consisting essentially of an anti-digoxigenin antibody. Beads may be pulled down by, for example, pelleting on a magnet. In some embodiments, the anti-digoxigenin antibody is added during a separation step, annealing step, primary extension step, or second ligation step.

In some embodiments, the target nucleic acids comprise, consist of, or consist essentially of host nucleic acids and/or non-host nucleic acids, e.g., microbial and/or pathogen nucleic acids, fetal or organ donor nucleic acids, host nucleic acids, and/or nucleic acids that may be administered into a host as a therapeutic or for any other reason. In some embodiments, the target nucleic acids comprise, consist of, or consist essentially of microbial and/or pathogen nucleic acids. In some embodiments, the target nucleic acids comprise, consist of, or consist essentially of host nucleic acids.

In some embodiments, the target nucleic acids comprise, consist of, or consist essentially of microbial and/or pathogen nucleic acids from at least one microbe and/or pathogen. In some embodiments, the target nucleic acids comprise, consist of, or consist essentially of microbial and/or pathogen nucleic acids from at least two different microbes and/or pathogens. In some embodiments, the target nucleic acids comprise, consist of, or consist essentially of microbial and/or pathogen nucleic acids from at least five different microbes and/or pathogens. In some embodiments, non-host nucleic acids may have entered the host indirectly from the diet or in a drug; in such cases the non-host nucleic acid would not indicate the presence of a non-host organism harbored by a host. Without being limited by example, bovine DNA derived from food or porcine DNA from a medicine may be detected in a host.

In some embodiments, the microbes or pathogens comprise, consist of, or consist essentially of archaea, bacteria, yeast, fungi, molds, eukaryotes, viruses, protozoa and/or nematodes. In some embodiments, microbes comprise, consist of, or consist essentially of DNA viruses, RNA viruses, culturable bacteria, additional fastidious and unculturable bacteria, mycobacteria, and eukaryotic pathogens (See, Bennett J. E., D., R., Blaser, M. J. Mandell, Douglas, and Bennett's Principles and Practice of Infectious Diseases; Saunders, Philadelphia, PA, 2014; and Netter's Infectious Disease, 1st Edition, edited by Elaine C. Jong, M D and Dennis L. Stevens, M D, PhD (2015)), each of which is incorporated herein by reference in its entirety. In some embodiments, microbes comprise, consist of, or consist essentially of microbes set forth in https://www.ncbi.nlm.nih.gov/genome/microbes/or https://www.ncbi.nlm.nih.gov/biosample/, each of which is incorporated herein in its entirety.

In some embodiments, the target nucleic acids comprise, consist of, or consist essentially of microbial and/or pathogen nucleic acids from at least 1, at least 2, at least 3, at least 4, at least 5, or at least 10 different microbes and/or pathogens. In some embodiments, the target nucleic acids comprise, consist of, or consist essentially of microbial and/or pathogen nucleic acids from at least 20 different microbes and/or pathogens. In some embodiments, the target nucleic acids comprise, consist of, or consist essentially of microbial and/or pathogen nucleic acids from at least 30 different microbes and/or pathogens. In some embodiments, the target nucleic acids comprise, consist of, or consist essentially of microbial and/or pathogen nucleic acids from at least 40 different microbes and/or pathogens. In some embodiments, the target nucleic acids comprise, consist of, or consist essentially of microbial and/or pathogen nucleic acids from at least 50 different microbes and/or pathogens. In some embodiments, the target nucleic acids comprise, consist of, or consist essentially of microbial and/or pathogen nucleic acids from at least 60 different microbes and/or pathogens. In some embodiments, the target nucleic acids comprise, consist of, or consist essentially of microbial and/or pathogen nucleic acids from at least 70 different microbes and/or pathogens. In some embodiments, the target nucleic acids comprise, consist of, or consist essentially of microbial and/or pathogen nucleic acids from at least 80 different microbes and/or pathogens. In some embodiments, the target nucleic acids comprise, consist of, or consist essentially of microbial and/or pathogen nucleic acids from at least 90 different microbes and/or pathogens. In some embodiments, the target nucleic acids comprise, consist of, or consist essentially of microbial and/or pathogen nucleic acids from at least 100 different microbes and/or pathogens.

In some embodiments, the method further comprises, consists of, or consists essentially of:
  (a) performing a sequencing assay on the nucleic acid library derived from the initial sample, thereby determining an abundance of the one or more process control molecules and an abundance of microbial and/or pathogenic nucleic acids;
  (b) comparing an abundance of one or more process control molecules to a known input concentration of one or more process control molecules in order to produce a recovery profile; and
  (c) using the recovery profile to normalize the abundance of microbial and/or pathogen nucleic acids by comparing the microbial and/or pathogen nucleic acids to the one or more process control molecules.

A recovery profile may encompass any losses or biases including degradation loss. It is recognized that particularly with RNA, degradation may result in losses and changes in profile due to degradation.

In some embodiments, abundance comprises, consists of, or consists essentially of a relative abundance. In some embodiments, abundance comprises, consists of, or consists essentially of absolute abundance. Abundance may also be corrected for the process bias using various control molecules to obtain biased-corrected abundance.

In some embodiments, the method further comprises, consists of, or consists essentially of normalizing abundance of microbial or pathogen nucleic acid by using a weighting factor. In some embodiments, the weighting factor is obtained by analyzing a raw measurement of a first plurality of synthetic nucleic acids and a raw measurement of a second plurality of synthetic nucleic acids in comparison with a known concentration of the first plurality of synthetic nucleic acids and a known concentration of the second plurality of synthetic nucleic acids.

In some embodiments, determining abundance comprises, consists of, or consists essentially of methods excluding extraction and/or removal for some microbes or pathogens and methods which include extraction and/or removal for other pathogens. Any combination may be used as known by one skilled in the art. In some embodiments, the method is drawn to one or more combinations set forth in the drawings provided herein.

A third aspect provides a method of determining presence and/or abundance of microbial or pathogen nucleic acids in an initial sample, the method comprising, consisting of, or consisting essentially of:
  (a) obtaining the initial sample from a subject in a commensalistic relationship with, in a mutualistic relationship with, in an amensalistic relationship with, infected by, or suspected of being infected by, a microbe or pathogen, wherein the initial sample comprises, consists of, or consists essentially of a plurality of microbial or pathogen nucleic acids;
  (b) generating a nucleic acid library from the initial sample by
    i) optionally, adding one or more process control molecules to the initial sample to provide a spiked initial sample and
    ii) generating the nucleic acid library from the initial sample or spiked initial sample; and
  (c) determining presence and/or abundance of microbial or pathogen nucleic acids in the initial sample.

The nucleic acid library is generated without extracting nucleic acids prior to generating the nucleic acid library from the initial sample. Thus, the method of generating the nucleic acid library from an initial sample comprises, consists of, or consists essentially of:
  (a) optionally, adding one or more process control molecules to the initial sample to provide a spiked initial sample; and
  (b) generating the nucleic acid library from the initial sample or the spiked initial sample comprising the one or more process control molecules; wherein nucleic acids used to generate the nucleic library are not extracted from the initial sample prior to generating the library.

In some embodiments, the method further comprises, consists of, or consists essentially of partially or completely removing substances that may affect the library yield or inhibit library generation. In some embodiments, the nucleic acid library is generated from the initial sample without prior partial or complete removal of any substance that may affect the library yield or inhibit the library generation.

In some embodiments, generating the nucleic acid library from the initial sample further comprises, consists of, or consists essentially of:
  (a) denaturing nucleic acids from the initial sample to produce denatured nucleic acids;
  (b) annealing a primer to the denatured nucleic acids and extending the primer with a polymerase to generate complementary strands; and
  (c) amplifying the complementary strands.

In some embodiments, generating the nucleic acid library from the initial sample further comprises, consists of, or consists essentially of:
  (a) (optionally) dephosphorylating the nucleic acids to produce nucleic acids;
  (b) denaturing the nucleic acids to produce denatured nucleic acids;
  (c) attaching an adapter to one or both ends of the denatured nucleic acids to produce adapted nucleic acids; and
  (d) amplifying the adapted nucleic acids to generate the nucleic acid library.

The order of some of the steps may be reversed. For example, in some embodiments, generating the nucleic acid library from the initial sample further comprises, consists of, or consists essentially of:
  (a) denaturing the nucleic acids to produce denatured nucleic acids;
  (b) dephosphorylating the denatured nucleic acids to produce dephosphorylated nucleic acids;
  (c) attaching an adapter to one or both ends of the dephosphorylated nucleic acids to produce adapted nucleic acids; and
  (d) amplifying the adapted nucleic acids to generate the nucleic acid library.

In some embodiments, generating the nucleic acid library from the initial sample further comprises, consists of, or consists essentially of:
  (a) dephosphorylating nucleic acids from the initial sample to produce dephosphorylated nucleic acids;
  (b) denaturing the dephosphorylated nucleic acids to produce denatured nucleic acids;
  (c) attaching a 3'-end adapter to the denatured nucleic acids to produce adapted nucleic acids;
  (d) separating the adapted nucleic acids;
  (e) annealing a primer to the adapted nucleic acids and extending the primer with a polymerase to generate complementary strands;
  (f) attaching a 5'-end adapter sequence;
  (g) eluting the nucleic acid strands; and
  (h) amplifying the complementary strands.

In some embodiments, a 5'-end adapter sequence is attached by the use in step (e) of a polymerase that has non-templated activity and, subsequently in step (f), using a template switching reaction to attach a 5'-end adapter sequence.

As above, the order of the steps may be reversed so that generating the nucleic acid library from the initial sample further comprises, consists of, or consists essentially of:
  (a) denaturing nucleic acids from the initial sample to produce denatured nucleic acids;
  (b) dephosphorylating the denatured nucleic acids to produce dephosphorylated nucleic acids;
  (c) attaching a 3'-end adapter to the dephosphorylated nucleic acids to produce adapted nucleic acids;
  (d) separating the adapted nucleic acids;
  (e) annealing a primer to the adapted nucleic acids and extending the primer with a polymerase to generate complementary strands;
  (f) attaching an 5'-end adapter sequence adapted nucleic acid strands;
  (g) eluting the adapted nucleic acid strands; and
  (h) amplifying the adapted complementary strands.

In some embodiments, separating the adapted nucleic acids comprises, consists of, or consists essentially of immobilizing the adapted nucleic acids. In some embodiments, immobilization occurs on magnetic beads or functionalized magnetic beads. In some embodiments, immobilization occurs on a modified glass, modified capillary surfaces, and/or modified columns. In some embodiments, separating the adapted nucleic acids comprises, consists of, or consists essentially of purifying the adapted nucleic acids. In some embodiments, separating the adapted nucleic acids comprises, consists of, or consists essentially of precipitating the adapted nucleic acids.

In some embodiments, the method further comprises, consists of, or consists essentially of:
  (a) performing a sequencing assay on the initial sample, thereby determining an abundance of the one or more process control molecules and an abundance of microbial and/or pathogenic nucleic acids;
  (b) comparing an abundance of one or more process control molecules to a known input concentration of one or more process control molecules in order to produce a recovery profile; and
  (c) using the recovery profile to normalize the abundance of microbial and/or pathogen nucleic acids by comparing the microbial and/or pathogen nucleic acids to the one or more process control molecules.

In some embodiments, determining abundance of microbial or pathogenic nucleic acids comprises, consists of, or consists essentially of methods excluding extraction for some microbes or pathogens and methods which include extraction for other microbes or pathogens. Any combination may be used to suit particular microbes or pathogens or a combination of particular microbes or pathogens. In some embodiments, the method comprises, consists of, or consists essentially of one or more combinations set forth in the drawings provided herein.

A fourth aspect provides a method of reducing length bias, GC-bias, and/or secondary structure bias as compared to the biases introduced by an alternative process that generates a nucleic acid library from an initial sample or spiked initial sample where the alternative process includes a step that extracts nucleic acids prior to generation of the nucleic acid library from an initial sample or spiked initial sample, the method comprising, consisting of, or consisting essentially of:

(a) optionally, adding one or more process control molecules to the initial sample to provide a spiked initial sample and
(b) generating the nucleic acid library from the initial sample or spiked initial sample, wherein the nucleic acid library exhibits a decreased length bias, GC-bias, and/or secondary structure bias as compared to the alternative process. The nucleic acid library generated from the initial sample is generated without extracting nucleic acids prior to generating the nucleic acid library from the initial sample. Thus, the method of generating the nucleic acid library from an initial sample comprises, consists of, or consists essentially of:
(a) optionally, adding one or more process control molecules to the initial sample to provide a spiked initial sample; and
(b) generating the nucleic acid library from the initial sample or spiked initial sample comprising the one or more process control molecules; wherein nucleic acids used to generate the nucleic library are not extracted from the initial sample prior to generating the library.

In some embodiments, generating the nucleic acid library from the initial sample further comprises, consists of, or consists essentially of:
(a) dephosphorylating nucleic acids from the initial sample to produce dephosphorylated nucleic acids;
(b) denaturing the dephosphorylated nucleic acids to produce denatured nucleic acids;
(c) attaching a 3'-end adapter to the denatured nucleic acids to produce adapted nucleic acids;
(d) separating the adapted nucleic acids;
(e) annealing a primer to the adapted nucleic acids and extending the primer with a polymerase to generate complementary strands;
(f) attaching a 5'-end adapter sequence;
(g) eluting the nucleic acid strands; and
(h) amplifying the complementary strands.

In some embodiments, a 5'-end adapter sequence is attached by the use in step (e) of a polymerase that has non-templated activity and, subsequently in step (f), using a template switching reaction to attach a 5'-end adapter sequence.

As above, the order of the steps may be reversed so that generating the nucleic acid library from the initial sample further comprises, consists of, or consists essentially of:
(a) denaturing nucleic acids from the initial sample to produce denatured nucleic acids;
(b) dephosphorylating the denatured nucleic acids to produce dephosphorylated nucleic acids;
(c) attaching a 3'-end adapter to the dephosphorylated nucleic acids to produce adapted nucleic acids;
(d) separating the adapted nucleic acids;
(e) annealing a primer to the adapted nucleic acids and extending the primer with a polymerase to generate complementary strands;
(f) attaching a 5'-end adapter sequence to produce adapted complementary strands;
(g) eluting the adapted nucleic acid strands; and
(h) amplifying the adapted complementary strands.

In some embodiments, a 5'-end adapter sequence is attached by the use in step (e) of a polymerase that has non-templated activity and, subsequently in step (f), using a template switching reaction to attach a 5'-end adapter sequence.

In general, the steps set forth herein need not be in any particular order and some steps may be performed concurrently with others. For example, in some embodiments, attaching an adapter to one or both ends of the denatured nucleic acids to produce adapted nucleic acids can occur in the order of steps as set forth above. In some embodiments, attaching an adapter to one or both ends of the denatured nucleic acids to produce adapted nucleic acids can occur concurrently or concurrently with dephosphorylation.

A fifth aspect provides a method of recovering single-stranded nucleic acids from an initial sample for sequencing, the method comprising, consisting of, or consisting essentially of:
(a) optionally, adding one or more process control molecules to the initial sample to provide a spiked initial sample;
(b) generating a nucleic acid library from the initial sample or spiked initial sample; and
(c) recovering single-stranded nucleic acids from the initial sample or spiked initial sample for sequencing.

The nucleic acid library is generated without extracting nucleic acids prior to generating the nucleic acid library from the initial sample. Thus, the method of generating the nucleic acid library from an initial sample comprises, consists of, or consists essentially of:
(a) optionally, adding one or more process control molecules to the initial sample to provide a spiked initial sample; and
(b) recovering single-stranded nucleic acids from the initial sample or spiked initial sample comprising one or more process control molecules for sequencing; wherein nucleic acids used to generate the nucleic library are not extracted from the initial sample or spiked initial sample prior to generating the library.

A sixth aspect provides a method of lowering environmental contamination as compared to the environmental contamination introduced by a process that includes a step of extracting nucleic acids from an initial sample prior to generation of a nucleic acid library, the method comprising, consisting of, or consisting essentially of:
(a) optionally, adding one or more process control molecules to the initial sample to provide a spiked initial sample and
(b) generating the nucleic acid library from the initial sample or spiked initial sample, wherein environmental contamination is lowered compared to the process. The nucleic acid library is generated without extracting nucleic acids prior to generating the nucleic acid library from the initial sample. Thus, the method of generating the nucleic acid library from an initial sample comprises, consists of, or consists essentially of:
(a) optionally, adding one or more process control molecules to the initial sample to provide a spiked initial sample; and
(b) recovering single-stranded nucleic acids from the initial sample or spiked initial sample comprising the one or more process control molecules for sequencing; wherein nucleic acids used to generate the nucleic library are not extracted from the initial sample prior to generating the library.

Some embodiments further comprise, consist of, or consist essentially of using a protease to digest or fragment proteins in the initial sample or any protein introduced prior to the protease addition. In some embodiments, the protease comprises, consists of, or consists essentially of a serine protease. In some embodiments, the serine protease comprises, consists of, or consists essentially of Proteinase K. In some embodiments, the protease comprises, consists of, or consists essentially of one or more thermal labile or thermosensitive proteases.

In some embodiments, lowering environmental contamination reduces the need for a control. Lowering environmental contamination reduces the need for a negative control in particular. A negative control is eliminated in some embodiments.

A seventh aspect provides a method excluding extraction of nucleic acids which improves detection of microbial or pathogen nucleic acids compared to a method including extraction, the method excluding extraction comprising, consisting of, or consisting essentially of:
(a) generating a nucleic acid library from an initial sample by
  i) optionally, adding one or more process control molecules to the initial sample to provide a spiked initial sample;
  ii) generating the nucleic acid library from the initial sample or spiked initial sample; and
  iii) detecting microbial or pathogen nucleic acids,
(b) whereby detection of the microbial or pathogen nucleic acids is improved as compared to a method including extraction. The nucleic acid library is generated without extracting nucleic acids prior to generating the nucleic acid library from the initial sample. Thus, the method of generating the nucleic acid library from an initial sample comprises, consists of, or consists essentially of:
(a) optionally, adding one or more process control molecules to the initial sample to provide a spiked initial sample; and
(b) generating the nucleic acid library from the initial sample or spiked the initial sample comprising one or more process control molecules for sequencing; wherein nucleic acids used to generate the nucleic library are not extracted from the initial sample prior to generating the library.

An eighth aspect of the invention provides a method for correcting for environmental contamination from a process, the method comprising, consisting of, or consisting essentially of:
(a) optionally, adding one or more process control molecules to the initial sample to provide a spiked initial sample;
(b) generating the nucleic acid library from the initial sample or spiked initial sample; and
(c) correcting for environmental contamination from the process.

The nucleic acid library is generated without extracting nucleic acids prior to generating the nucleic acid library from the initial sample or spiked initial sample. Thus, the method of generating the nucleic acid library from an initial sample comprises, consists of, or consists essentially of:
(a) optionally, adding one or more process control molecules to the initial sample; and
(b) generating the nucleic acid library from the initial sample or spiked initial sample for sequencing; wherein nucleic acids used to generate the nucleic library are not extracted from the initial sample or spiked initial sample prior to generating the library.

In some embodiments, correcting for environmental contamination comprises, consists of, or consists essentially of subtracting or filtering at least one environmental contamination signal. In some embodiments, correcting for environmental contamination comprises, consists of, or consists essentially of subtracting or filtering at least one environmental contamination signal identified as having a fragment length distribution similar to a known fragment length distribution of an environmental contaminant or similar to a fragment length distribution typical of environmental contaminants. In some embodiments, correcting for environmental contamination comprises, consists of, or consists essentially of subtracting or filtering at least one environmental contamination signal identified as having a fragment length distribution that differs from a known fragment length distribution expected from an endogenous microbe.

In some embodiments, the known fragment length distribution comprises, consists of, or consists essentially of at least one environmental contamination fragment length distribution for a microbe that is present in at least one reagent lot. In some embodiments, the known fragment length distribution comprises, consists of, or consists essentially of at least one contamination fragment length distribution for a microbe that is present in a group of reagent lots. Additional sources of environmental contamination may include, but are not limited to, any aspect of the sample collection process, any aspect of the pre-analytical process, any aspect of the direct-to-library process, operators, instrumentation, tubes, surface areas such as benchtops and elements of the sample collecting system such as blood-collection tubes, needles and tubing. In some embodiments, the known fragment length distribution comprises, consists of, or consists essentially of at least one contamination fragment length distribution for each microbe obtained from at least one source of environmental contamination. In some embodiments, the known distribution comprises, consists of, or consists essentially of a fragment length distribution profile for different reagents and/or reagent lots. In some embodiments, reagent lots are compared to correct for environmental contamination.

In some embodiments, the correction is for identification of an environmental contaminant. In some embodiments, the correction is for identification of an endogenous microbe. In some embodiments, the correction is for identification of an environmental contaminant and/or an endogenous microbe.

In some embodiments, the correction is for quantification of an environmental contaminant. In some embodiments, the correction is for quantification of an endogenous microbe. In some embodiments, the correction is for quantification of the environmental contaminant and/or endogenous microbe.

In some embodiments, correcting for environmental contamination comprises, consists of, or consists essentially of deconvolving or separating the environmental contamination signal from the endogenous signal using a known distribution of the contribution of environmental contamination and/or an expected distribution of endogenous signal. Distributions could take the form of exponential decay, power law decay, and/or a peaked, multi-peak, and/or peaked-like function. In some embodiments, the peaked or peaked-like function comprises, consists of, or consists essentially of a Gaussian function or a polynomial function. In some embodiments, the peaked or peaked-like function comprises, consists of, or consists essentially of a function centered around about 300 base pairs, about 150 base pairs, about 100 base pairs, about 75 base pairs, about 70 base pairs, about 65 base pairs, about 60 base pairs, about 55 base pairs, about 50 base pairs, about 45 base pairs, about 40 base pairs, about 35 base pairs, about 30 base pairs, or about 25 base pairs. In some embodiments, the peaked or peaked-like function comprises, consists of, or consists essentially of a function centered around about fragment lengths higher than about 500 bp, about 1000 bp, about 10000 bp, about 50000 bp, about 100000 bp. In some embodiments, the peaked or peaked-like function comprises, consists of, or consists essentially of a function centered around about 50 base pairs.

In some embodiments, correcting for environmental contamination comprises, consists of, or consists essentially of controlling the properties of the distributions in the sources of environmental contamination and/or initial sample to improve a signal to noise ratio. In some embodiments, improvements in the signal to noise ratio can help distinguish between properties for endogenous signal and environmental contamination. Any property of nucleic acids of the environmental contamination from any source of the contamination may be controlled. For example, nucleic acid fragment length may be controlled to make a distribution distinct or more distinguishable from an endogenous fragment length distribution. Methods of controlling nucleic acid fragment length to make a distribution distinct or more distinguishable from an endogenous fragment length distribution may include but are not limited to mechanically shearing, enzymatically shearing, and/or depleting fractions of the contaminating nucleic acids in the reagents prior to use of the reagent in the generation of the nucleic acid library from initial sample. Reagents and consumables needed for processing the initial or raw biological sample may be selected among several alternatives based on their manufacturing process characteristics to make a contamination distribution profiles distinct or more distinguishable from an endogenous fragment length distribution. High energy irradiation may be used to change the fragment length distribution in the reagents or other elements of the pre-analytical and analytical process. In some embodiments, chemical modifications may be made to nucleic acids present in reagents to render them inaccessible or distinctly identifiable after downstream processing. A fragment length distribution of the nucleic acid fragments originating from the endogenous microbes can be controlled in order to make it distinct or more distinct from the fragment length distribution of the contaminating nucleic acids. Methods of controlling nucleic acid fragment length of the fragments originating from endogenous microbes to make a distribution distinct or more distinguishable from a fragment length distribution of the contaminating nucleic acids may include but are not limited to freeze/thaw cycling of the initial sample or raw biological sample, enzymatically fragmenting with nucleases in the initial sample or biological raw sample, exposing the initial sample or biological raw sample to shipping conditions prior to use of the reagent in the generation of the nucleic acid library from initial sample. A combination of methods to make both contaminating and endogenous fragment length distribution more distinct from each other can be used.

In some embodiments, the known fragment length distribution for the environmental contaminant is derived from negative control samples. In some embodiments, correcting for environmental contamination reduces the need for concurrent processing of control samples. Correcting for environmental contamination reduces the need for a negative control in particular. A negative control is eliminated in some embodiments. In some embodiments, a positive control is eliminated.

In some embodiments, the known fragment length distribution for the endogenous microbe is derived from at least one sample that contains at least one confirmed endogenous pathogen. In some embodiments, the known fragment length distribution for the endogenous microbe is derived from the features of the fragment length distribution for reads mapping to a human reference genome (e.g., hg38) in the same sample, at least one other test sample, or a positive control comprising human nucleic acids. In some embodiments, the known fragment length distribution for the endogenous microbe is derived from the fragment length distribution for reads mapping to a human mitochondrial reference genome in the same sample, at least one other test sample, or a positive control comprising human nucleic acids. In some embodiments, unique features of the fragment length distribution for endogenous signal (e.g., a presence of a peak, a width of a peak, an amplitude of a peak, a decay rate of an exponential distribution, scaling of a power law distribution) as compared to the features of the fragment length distribution for environmental contamination-derived signal are used to identify endogenous microbes.

A ninth aspect of the invention provides a method for correcting for environmental contamination from a process, the method comprising, consisting of, or consisting essentially of:
  (a) optionally, adding one or more process control molecules to the initial sample to provide a spiked initial sample;
  (b) generating the nucleic acid library from the initial sample or spiked initial sample; and
  (c) correcting for environmental contamination from the process.

As opposed to the eighth aspect, the nucleic acid library is generated with a step including extracting nucleic acids prior to or isolating during the generation of the nucleic acid library from the initial sample or spiked initial sample. In some embodiments, the method further comprises, consists of, or consists essentially of partially or completely removing substances that may affect the library yield or inhibit library generation. In some embodiments, the nucleic acid library is generated from the initial sample without prior partial or complete removal of any substance that may affect the library yield or inhibit the library generation.

Some embodiments further comprise, consist of, or consist essentially of adding an antibody, for example, an anti-digoxigenin antibody. In some embodiments, the anti-digoxigenin antibody is added after the 3'-end adapter is attached to the denatured and/or dephosphorylated nucleic acids and before an adapter is attached to the 3'-end of the complementary strand. Some embodiments further comprise beads comprising, consisting of, or consisting essentially of an antibody, such as an anti-digoxigenin antibody. Beads may be removed by, for example, pelleting on a magnet. In some embodiments, the antibody, such as the anti-digoxigenin antibody, is added during a separation step, annealing step, primary extension step, or second attachment step.

In some embodiments, attaching a 3'-end adapter to nucleic acids, for example, denatured or dephosphorylated nucleic acids, and/or attaching an adapter to the 3'-end of the complementary strands comprises, consists of, or consists essentially of ligating with an enzyme comprising, consisting of, or consisting essentially of a ligase, e.g., a T4 DNA ligase, CircLigase II. In some embodiments, the ligase is a single-stranded ligase. In some embodiments, the method further comprises, consists of, or consists essentially of utilizing a DNA polymerase, e.g., Klenow fragment, SuperScript IV reverse transcriptase, SMART MMLV Reverse Transcriptase, Tth polymerase, etc. to extend a primer hybridized to adapted nucleic acids and to generate complementary strands with an attached adapter.

Some embodiments further comprise, consist of, or consist essentially of using a protease to digest or fragment proteins in the initial sample or any protein introduced prior to the protease addition. In some embodiments, the protease comprises, consists of, or consists essentially of a serine protease. In some embodiments, the serine protease comprises, consists of, or consists essentially of Proteinase K. In some embodiments, the protease comprises, consists of, or consists essentially of one or more thermal labile or thermosensitive proteases.

In some embodiments, correcting for environmental contamination is discussed elsewhere herein. Correcting for environmental contamination may involve the use of fragment length distribution as discussed above herein.

A tenth aspect provides a kit for generating a sequencing library, the kit comprising one or more components useful for generating a sequencing library, wherein the kit excludes alcohol based materials for extraction and/or removal of nucleic acids prior to generating the nucleic acid library from the initial sample. Kits for generating a sequencing library may include one or more components selected from the group consisting of functionalized beads or columns, adapter attachment reaction components, amplification reaction components and optionally primer extension and template switching component systems.

An eleventh aspect provides methods of preparing a nucleic acid library from an initial sample comprising adding one or more process control molecules to the initial sample to provide a spiked initial sample, generating a nucleic acid library from the spiked initial sample, wherein the nucleic acids used to generate the nucleic acid library are not extracted from the initial sample before preparing the nucleic acid library, wherein generating a nucleic acid library comprises the step of attaching an adapter. In embodiments of the method, the attaching step comprises the steps of incubating with a polymerase and subsequently using a template switching reaction to attach an adapter. Polymerases suitable for use may include polymerases having non-templated activity, DNA-dependent polymerases and RNA-dependent polymerases. In embodiments of the method, the attaching step comprises ligating with an enzyme.

A twelfth aspect provides methods of preparing a nucleic acid library from an initial sample comprising generating a nucleic acid library from the initial sample, wherein nucleic acids used to generate the nucleic acid library are not extracted from the initial sample before preparing the library. In various embodiments the methods may further comprise one or more steps selected from the group of steps consisting of isolating nucleic acids during or after generating the nucleic acid library, adding one or more process control molecules and dephosphorylating nucleic acids from the initial sample to produce group of dephosphorylated nucleic acids. In various embodiments, the one or more process control molecules are added to the initial sample to provide a spike initial sample. In other embodiments, one or more process control molecules are added during or after generating the nucleic acid library. In certain embodiments, the step of dephosphorylating nucleic acids from the initial sample is selected when a target nucleic acid is RNA. It is further recognized that any of the above steps may be combined with any of the below steps.

In various embodiments, the methods further comprise the steps of denaturing the nucleic acids to produce denatured nucleic acids, attaching a 3'-end adapter, enriching adapted nucleic acids, performing a primer extension reaction, attaching a 5'-end adapter and eluting the adapted nucleic acid. The method may further comprise one or two steps selected from the group consisting of incubating with a protease prior to denaturing the nucleic acids and amplifying the adapted nucleic acid. Encompassed configurations may include the steps of incubating with a protease, denaturing, attaching a 3'-end adapter, enriching adapted nucleic acids, performing a primer extension reaction, attaching a 5'-end adapter, eluting the adapted nucleic acid strands and amplification; denaturing, attaching a 3'-end adapter, enriching adapted nucleic acids, performing a primer extension reaction, attaching a 5'-end adapter, eluting the adapted nucleic acid strands and amplification; incubating with a protease, denaturing, attaching a 3'-end adapter, enriching adapted nucleic acids, performing a primer extension reaction, attaching a 5'-end adapter, and eluting the adapted nucleic acid strands; and denaturing, attaching a 3'-end adapter, enriching adapted nucleic acids, performing a primer extension reaction, attaching a 5'-end adapter, and eluting the adapted nucleic acid strands.

In various embodiments, the methods further comprise the steps of denaturing the nucleic acids to produce denatured nucleic acids, attaching a 3'- and 5'-end adapter concurrently or in succession, enriching adapted nucleic acids, and eluting the adapted nucleic acid strands. The method may further comprise one or two steps selected from the group consisting of incubating with a protease prior to denaturing the nucleic acids and amplifying the adapted nucleic acids. Encompassed configurations may include a single step adapter attachment configuration. Single step adapter attachment configurations may include configurations with the steps of incubating with protease, denaturing the nucleic acids to produce denatured nucleic acids, attaching 3'- and 5'-end adapter concurrently, enriching adapted nucleic acids, eluting the adapted nucleic acid strands, and amplifying the adapted nucleic acid; the steps of denaturing the nucleic acids to produce denatured nucleic acids, attaching 3'- and 5'-end adapter concurrently, enriching adapted nucleic acids, eluting the adapted nucleic acids, and amplifying the adapted nucleic acid; the steps of incubating with protease, denaturing the nucleic acids to produce denatured nucleic acids, attaching 3'- and 5'-end adapters concurrently, enriching adapted nucleic acids, and eluting the adapted nucleic acids; and the steps of denaturing the nucleic acids to produce denatured nucleic acids, attaching a 3'- and 5'-end adapter concurrently, enriching adapted nucleic acids, and eluting the adapted nucleic acids.

In various embodiments, the methods further comprise the steps of denaturing the nucleic acids to produce denatured nucleic acids, attaching a 3' end adapter, enriching adapted nucleic acids, eluting the adapted nucleic acids, performing a primer extension reaction, and attaching a 5'-end adapter. The method may further comprise one or two steps selected from the group consisting of incubating with a protease prior to denaturing the nucleic acids and amplifying the adapted nucleic acids. Encompassed configurations may include configurations with elution immediately after enriching. Immediate elution configurations may include configurations with the steps of incubating with a protease, denaturing the nucleic acids to produce denatured nucleic acids, attaching a 3'-end adapter, enriching adapted nucleic acids, eluting the strands, performing a primer extension reaction, attaching an 5'-end adapter and amplification; the steps of denaturing the nucleic acids to produce denatured nucleic acids, attaching a 3'-end adapter, enriching adapted nucleic acids, eluting the strands, performing a primer extension reaction, attaching a 5'-end adapter and amplification; the steps of incubating with a protease, denaturing the nucleic acids to produce denatured nucleic acids, attaching a 3'-end adapter, enriching adapted nucleic acids, eluting the strands, performing a primer extension reaction, and attaching a 5'-end adapter; and the steps of denaturing the nucleic acids to produce denatured nucleic acids, attaching a 3'-end adapter, enriching adapted nucleic acids, eluting the strands, performing a primer extension reaction, and attaching a 5'-end adapter.

In various embodiments, the methods further comprise the steps of denaturing the nucleic acids to produce denatured nucleic acids, attaching a 3' end adapter, enriching adapted nucleic acids, performing a primer extension reaction, and attaching a 5'-end adapter. The method may further comprise one or two steps selected from the group consisting of incubating with a protease prior to denaturing the nucleic acids and amplifying the adapted nucleic acids after attaching a 5'-end adapter. Encompassed configurations may include configurations with no elution. No elution configurations may include configurations with the steps of incubating with a protease, denaturing the nucleic acids to produce denatured nucleic acids, attaching a 3' end adapter, enriching adapted nucleic acids, performing a primer extension reaction, attaching a 5' end adapter, and amplifying; the steps of denaturing the nucleic acids to produce denatured nucleic acids, attaching a 3' end adapter, enriching adapted nucleic acids, performing a primer extension reaction, attaching a 5'-end adapter, and amplifying; the steps of incubating with a protease, denaturing the nucleic acids to produce denatured nucleic acids, attaching a 3' end adapter, enriching adapted nucleic acids, performing a primer extension reaction, and attaching a 5'-end adapter; the steps of denaturing the nucleic acids to produce denatured nucleic acids, attaching a 3' end adapter, enriching adapted nucleic acids, performing a primer extension reaction and attaching a 5'-end adapter.

In various embodiments, the methods further comprise the steps of denaturing the nucleic acids to produce denatured nucleic acids, attaching a 3' end adapter, performing a primer extension reaction, and attaching a 5'-end adapter. The method may further comprise one or two steps selected from the group consisting of incubating with a protease prior to denaturing the nucleic acids and amplifying the adapted nucleic acids. Encompassed configurations may include configurations with no enrichment. No enrichment configurations may include configurations with the steps of incubating with a protease, denaturing the nucleic acids to produce denatured nucleic acids, attaching a 3' end adapter, performing a primer extension reaction, attaching a 5'-end adapter, and amplifying; the steps of denaturing the nucleic acids to produce denatured nucleic acids, attaching a 3' end adapter, performing a primer extension reaction, attaching a 5'-end adapter, and amplifying; the steps of denaturing the nucleic acids to produce denatured nucleic acids, attaching a 3' end adapter, performing a primer extension reaction, and attaching a 5'-end adapter.

In various embodiments, the methods further comprise the steps of denaturing the nucleic acids to produce denatured nucleic acids and attaching a 3'- and 5'-end adapters concurrently or in succession, The method may further comprise one or two steps selected from the group consisting of incubating with a protease prior to denaturing the nucleic acids and amplifying the adapted nucleic acids. Encompassed configurations may include configurations with single step adapter attachment and no enrichment. No enrichment configurations with single-step adapter attachment may include configurations with the steps of incubating with a protease, denaturing the nucleic acids to produce denatured nucleic acids, attaching a 3' adapter to both strands and amplifying the strands after attaching a 3' end adapter to both strands; the steps of denaturing the nucleic acids to produce denatured nucleic acids, attaching a 3' adapter to both strands and amplifying the strands after attaching a 3' end adapter to both strands; the steps of incubating with a protease, denaturing the nucleic acids to produce denatured nucleic acids, and attaching a 3' adapter to both strands; and the steps of denaturing the nucleic acids to produce denatured nucleic acids and attaching a 3' adapter to both strands.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A1-4A4 depict GC-content bias as measured by the GC dSPARK subset of the process control molecules resulting from a process with extraction (solid lines and circles) and without extraction (dashed lines and crosses). FIG. 4A1 and FIG. 4A2 summarize results obtained from 32 and 42 base pair long dsSPARKS, respectively. FIG. 4A3 and FIG. 4A4 summarize results obtained from 52 and 75 base pair long dsSPARKs respectively. FIG. 4B1-4B2 depict GC-content of the sequencing reads that mapped to the human reference genome with extraction (FIG. 4B1) and without extraction (FIG. 4B2).

FIG. 5A discloses SEQ ID NOS 1-4 and 2, respectively, in order of appearance.

FIG. 6A1-6A5 The panels depict the ratio of the number of unique sequencing reads mapping to a microbial species (EDR) to the number of unique sequencing reads mapping to the human reference (ddHuman) for process with extraction on x-axis and for process without extraction on y-axis. Each symbol represents one microbial species detected. FIG. 6A1 summarizes bacterial microbes; FIG. 6A2 summarizes fungal microbes; FIG. 6A3 summarizes protozoan microbes; FIG. 6A4 summarizes viral microbes; FIG. 6A5 summarizes nematodes.

FIG. 7B1-7B6 depict fragment length distributions of sequencing reads mapping to Hepatitis B Virus (HBV) detected in six clinical samples with orthogonally confirmed HBV infections (FIGS. 7B1-7B6). FIG. 7E1-7E2 depict fragment length distributions for sequencing reads mapping to *Saccharomyces cerevisiae* (FIG. 7E1) and *Yarrowia lipolytica* (FIG. 7E2) references in libraries obtained from EC samples using process without extraction. FIG. 7F1-7F2 depict fragment length distributions for sequencing reads mapping to *Saccharomyces cerevisiae* (FIG. 7F1) and *Yarrowia lipolytica* (FIG. 7F2) references in libraries obtained from clinical samples using process without extraction.

(FIG. 8A—Hepatitis B virus and *Bacillus lichenfromis*; FIG. 8B—Hepatitis B virus; FIG. 8C—Hepatitis B virus; FIG. 8D Wu polyomavirus; FIG. 8E—*Propionibacterium acnes*; FIG. 8F—*Saccharomyces cerevisiae*; FIG. 8G—*Balamuthia mandrillaris*; FIG. 8H—*Enterococcus cecorum*).

FIG. 11A1-11A5 depict a comparison of the relative concentration of the unique sequencing reads mapping to significant microbes (i.e., EDR/ddHuman) obtained with the process without extraction utilizing the ligation reaction on the x-axis and obtained with the process without extraction utilizing the template-switching reaction on the y-axis. FIG. 11A1 summarizes unique sequencing reads mapping to bacteria. FIG. 11A2 summarizes unique sequencing reads mapping to fungi. FIG. 11A3 summarizes unique sequence reads mapping to viruses. FIG. 11A4 summarizes unique sequence reads mapping to protozoans. FIG. 11A5 summarizes unique sequence reads mapping to nematodes. FIG. 11B1-11B5 depicts a comparison of the MPMs obtained with the process without extraction utilizing the ligation reaction on the x-axis and obtained with the process without extraction utilizing the template-switching reaction on the y-axis. FIG. 11B1 depicts a comparison of MPMs from bacteria. FIG. 11B2 depicts a comparison of the MPMs from fungi. FIG. 11B3 depicts a comparison of the MPMs from viruses. FIG. 11B4 depicts a comparison of the MPMs from protozoans. FIG. 11B5 depicts a comparison of the MPM's from nematodes.

FIG. 13A is an exemplary library generation method, wherein a denaturation step follows a dephosphorylation step in a method wherein adapter attachment is via ligation. As noted elsewhere, those denaturation and dephosphorylation steps may be performed in the reverse order, or, in the case of dephosphorylation, not done at all. FIG. 13B is an exemplary library generation method, wherein adapter attachment is via hybridization and template-switching reaction. Note that the dephosphorylation step is not shown in this figure but could be added either before or after the denaturation step.

FIG. 22A1-22A2 depict the specificity of capture RNA as assessed using spiked Sendai Virus in a direct to library (without extraction configuration, FIG. 22A1) or DNA as assessed using spiked synthetic oligonucleotide (DNA ID Spike Recovery, FIG. 22A2). The DNA and RNA A-tailing reaction show specific recovery of the DNA or RNA analyte in the two reaction conditions. The relative cross-reactivity of the two analytes is apparent. FIG. 22B1-22B2 show the relative recovery of the spiked Sendai Virus (RNA, FIG. 22B1) and DNA synthetic oligonucleotides (DNA ID Spike recovery, FIG. 22B2) in a combined DNA+RNA A-tailing reaction (combined NA A-tailing reaction).

DETAILED DESCRIPTION

Figure 1:
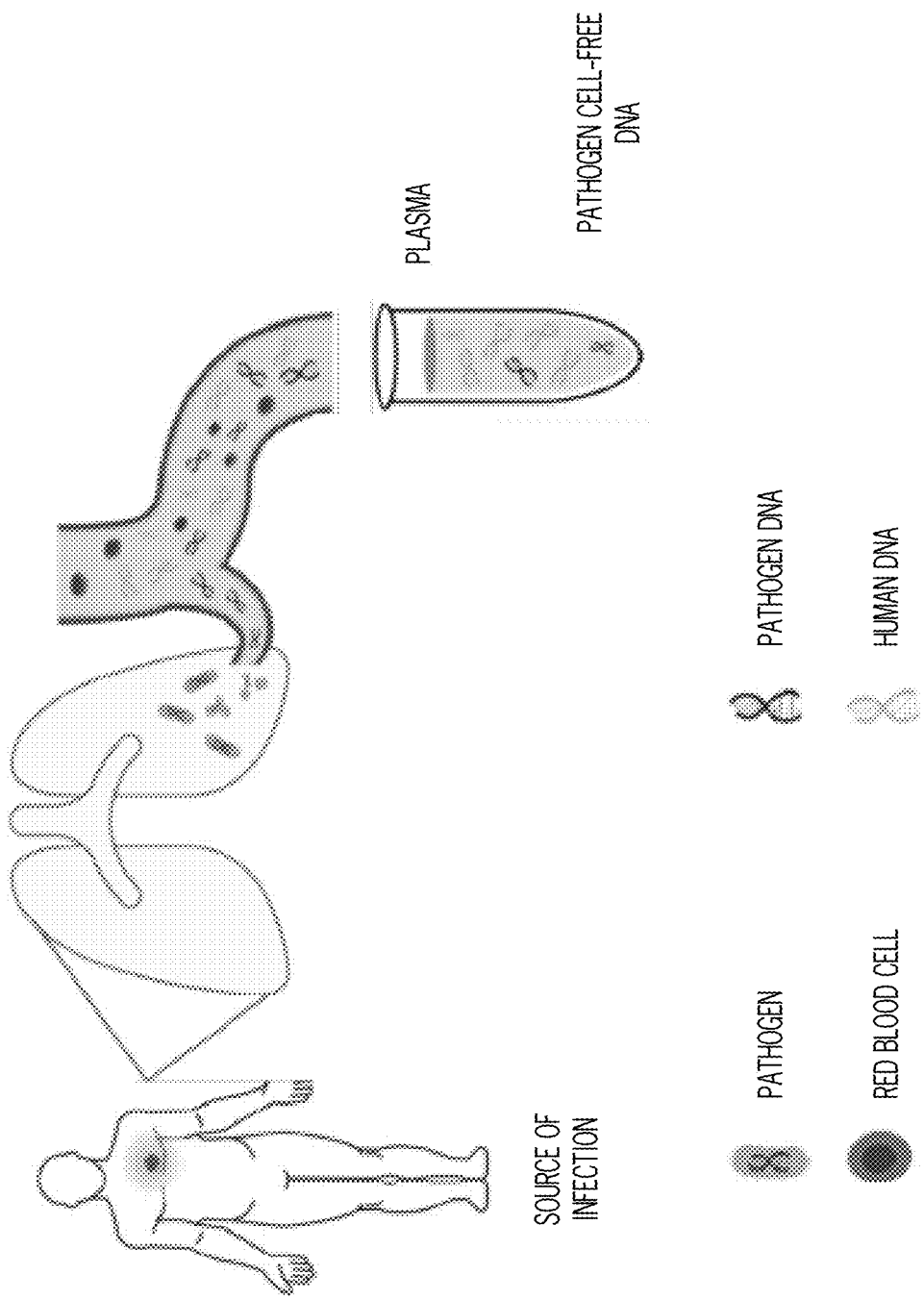
FIG. 1 depicts a schematic of an exemplary infection.

The following passages describe different aspects of the invention in greater detail. Each aspect, embodiment, or feature of the invention may be combined with any other aspect, embodiment, or feature the invention unless clearly indicated to the contrary.

I. Definitions

Unless defined otherwise, all technical and scientific terms used herein have the meaning commonly understood by a person skilled in the art to which this invention belongs.

"A," "an," and "the", as used herein, can include plural referents unless expressly and unequivocally limited to one referent.

As used herein, the term "or" is used to refer to a nonexclusive "or"; as such, "A or B" includes "A but not B," "B but not A," and "A and B," unless otherwise indicated.

As used throughout the specification herein, the term "about" when referring to a number or a numerical range means that the number or numerical range referred to is an approximation within experimental variability (or within statistical experimental error), and the number or numerical range may vary from, for example, from 10% to 25% of the stated number or numerical range. In examples, the term "about" refers to ±20% of a stated number or value. In other examples, the departure from equimolarity in the case of mixes intended to be equimolar, such as but not limited to, some control molecules in the spike-in mixes, is no more than a ten fold disparity, an eight fold disparity, a six fold disparity, a four fold disparity or a two fold disparity.

As used herein, "abundance" refers to the quantity of something, such as, for example, the quantity or number of molecules, such as nucleic acids. As used herein, "relative abundance" is the abundance of a molecule or molecules of interest per abundance of a reference molecule or molecules of interest. For example, relative abundance of target nucleic acid molecules (e.g., pathogen nucleic acid molecules, fetal nucleic acid molecules, tumor-derived nucleic acid molecules, etc.) refers to abundance per reference nucleic acids (e.g., human nucleic acids, synthetic nucleic acid added to the sample, etc.). As used herein, "absolute abundance" is the abundance of molecules per a defined unit of initial sample or sample quantity. For example, absolute abundance of target nucleic acid molecules (e.g., microbe or pathogen molecules, fetal nucleic acid molecules, tumor-derived nucleic acid molecules, etc.) refers to the abundance per defined unit of sample quantity (e.g., sample volume, sample mass etc.).

As used herein, "antibody" refers to a type of immunoglobulin molecule and is used in the broadest sense to include intact antibodies as well as antibody fragments. Antibodies comprise, consist of, or consist essentially of at least one antigen-binding domain. For example, an antibody as described herein may have an antigen binding domain or antigen binding region, the antigen binding domain or antigen binding region being specific for an antigen. In some embodiments, the antigen is a bulky moiety, such as digoxigenin.

As used herein, "adapter" or "portions of an adapter" refers to a chemically synthesized, single-stranded, or double-stranded oligonucleotide that can be attached, e.g., covalently (e.g., ligation) or non-covalently (e.g., hybridization), to the ends of nucleic acid molecules, such as DNA or RNA molecules. Adapter may refer to either a full-length adapter or a portion of the adapter, e.g., partial adapters may be attached in some embodiments before the full-lengths are introduced by e.g. indexing primers in amplification steps. 3'-end adapters and 5'-end adapters may be full-length or a portion of an adapter sequence that are attached to the opposite ends of a target nucleic acid, a copy of a target nucleic acid, or a target nucleic acid complement. 3'-end adapters and 5'-end adapters sequences end up being attached to the opposite ends of e.g. a sequenceable template that comprises target nucleic acid, a copy of a target nucleic acid, and/or a target nucleic acid complement. The 3'-end adapter and 5'-end adapter sequences can be the same or they can be different. Adapter sequences may be of any length.

As used herein, "bulky moiety" refers to a molecule that takes up more space than is conventionally required or a molecule that forms a complex that takes up more space than is conventionally required. A bulky moiety may comprise, consist of, or consist essentially of any reactive group capable of forming covalent, non-covalent, or coordinating chemical bonds. In some embodiments, the bulky moiety comprises, consists of, or consists essentially of one or more azide groups and products of reactions with azide groups, one or more small molecules, one or more polyhistidine tags, one or more antigens, and/or one or more proteins. In some embodiments, the bulky moiety comprises, consists of, or consists essentially of digoxigenin. In some embodiments, the splint oligonucleotide with a bulky moiety comprises, consists of, or consists essentially of 5Sp9/A/iDiGN/A/iSp9/CTTCCGATCT/3AmMO (SEQ ID NO: 5) (designations for oligomer modifications adopted from designation convention used by IDT (Coralville, IA; https://www.idtdna.com/site/Catalog/Modifications). A bulky moiety for example, can include a functional group that is sterically hindering and can prevent certain enzymatic or chemical reactions from occurring. A bulky group can block a position. A bulky group can also affect a molecule's shape and reactivity and so prevent a reaction from occurring through the steric hindrance. Moieties attached to the groups by covalent, non-covalent or coordinating bonds may provide the bulkiness of the groups. For example a bulky molecule such as a protein or polymer can be attached covalently to an azide group; a bulky entity such as a bead, protein or polymer can be attached to a histag through coordinating bonds using Ni ions; or an antigen antibody can be attached to an antigen attached to an adapter such as an anti-digoxigenin antibody can be attached to digoxigenin. Examples of bulky moieties may also include, but are not limited to, complexes between any of the molecules disclosed herein and their respective binding and reaction partners including, for example, without limitation, complexes between digoxigenin and an anti-digoxigenin antibody; polyhistidine tag and a Ni-NTA-containing polymer; a protein and a binding partner; an azide group and a covalently bound large molecule; and the biotin and streptavidin complex. Additional examples of bulky molecules include, for example, without limitation, biotin, azide groups and products of reactions with azide groups, one or more small molecules, one or more polyhistidine tags, and/or one or more proteins. Some embodiments further comprise, consist of, or consist essentially of introducing a bulky moiety into the splint oligonucleotide. Some embodiments further comprise, consist of, or consist essentially of introducing a bulky moiety on the template switching oligos; such bulky moieties may reduce concatemer formation. The bulky moiety may be introduced at a position that has the lowest effect on adapter attachment efficiency, such as the 5'-end region of the splint oligonucleotide, close to the 5'-end region of the splint oligonucleotide, or away from the ligation junction in ligation-based adapter attachment reactions.

As used herein, "control" refers to a standard of comparison. A "negative control" refers to a standard of comparison that is used to identify contaminants from samples or to identify the nature of a signal in the absence of a sample. A "positive control" refers to a standard of comparison that is used to identify normal substances from an initial sample or a sample. Some embodiments of the invention comprise, consist of, or consist essentially of a positive and/or negative control. Some embodiments of the invention comprise, consist of, or consist essentially of an initial sample or samples without a positive and/or negative control. Some embodiments of the invention comprise, consist of, or consist essentially of an initial sample or samples without a positive control. Some embodiments of the invention comprise, consist of, or consist essentially of an initial sample or samples without a negative control.

As used herein, "denaturing" refers to a process in which biomolecules, such as proteins or nucleic acids, lose their native or higher order structure. Native and higher order structure may include, for example, without limitation, quarternary structure, tertiary structure, or secondary structure. For example, a double-stranded nucleic acid molecule can be denatured into two single-stranded molecules.

As used herein, the term "dephosphorylation" or "dephosphorylating" refers to removal of a terminal phosphate group, such as the 5'- and/or 3'-end phosphate, from a nucleic acid, such as DNA to generate 5'- and/or 3'-hydroxyl groups. It is recognized that 3' dephosphorylation with polynucleotide kinase (PNK) improves subsequent 3' RNA adenylation.

As used herein, "detect" refers to quantitative or qualitative detection, including, without limitation, detection by identifying the presence, absence, quantity, frequency, concentration, sequence, form, structure, origin, or amount of an analyte.

As used herein, "digoxigenin" refers to a bulky molecule or its complex comprising, consisting of, or consisting essentially of the structure:

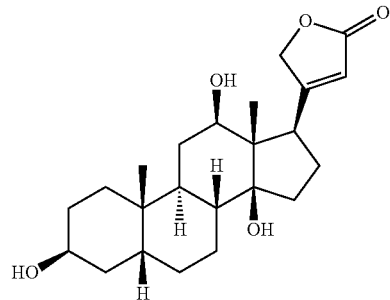

As used herein, "isolation" or "purification," and their cognates, of nucleic acids refers to steps (e.g., elution) after the start of and in the generation of a nucleic acid library that separate the nucleic acid from at least one component with which it is normally associated (e.g., a ligase or a polymerase). Isolation or purification is not used to create an initial sample from a raw biological sample.

As used herein, "removal" or "extraction," and their cognates, of nucleic acids refers to steps prior to the start of generating or preparing a nucleic acid library that separate nucleic acids from at least one component with which they are normally associated. Removal or extraction of nucleic acids may refer to the process of creating an initial sample from a raw biological sample. For example, without limitation, the fractionation of whole blood into its component parts, such as plasma, may be considered to involve removal or extraction. In the current methods, alcohol based extraction of nucleic acid is not performed prior to the start of generating or preparing a nucleic acid library.

As used herein, "GC-bias" refers to differential performance or treatment of nucleic acids of different GC content but having identical length.

As used herein, "GC-content" or "guanine-cytosine content" refer to the percentage of nitrogenous bases in a nucleic acid, such as a DNA or RNA molecule, that are either guanine or cytosine or their chemical modifications.

As used herein, "host" refers to an organism that harbors another organism. The latter is defined as "non-host" organism. For example, a human can be a host that harbors a microbe or pathogen, the microbe or pathogen being the non-host. Additionally, a host may harbor non-host nucleic acids introduced from a food or medical source where the non-host organism is not present in the host organism. For example, a human sample may include bovine nucleic acids.

As used herein, the turn of phrase "identifying sequence element" or "identifying tag" refers to an element of a sequence that identifies an index, a code, a barcode, a random sequence, an adapter, an overhang of non-templated nucleic acids, a tag comprising one or more non-templated nucleotides, a priming sequence, unique molecular identifiers or any combination thereof.

As used herein, "Klenow fragment" refers to a large protein fragment of DNA polymerase I that retains the 5'→3' polymerase activity and the 3'→5' exonuclease activity for removal of precoding nucleotides and proofreading, but loses its 5'→3' exonuclease activity.

As used herein, "ligating" or "ligation" refers to the joining of two ends of nucleic acid fragments through the action of an enzyme. DNA molecules and RNA molecules may be ligated. There are many methods of ligation and one skilled in the art would readily understand methods of ligation other than those disclosed herein.

As used herein, "length bias" refers to a bias with respect to length of a particular nucleic acid size or fragment length created by a sequencing library generation process as opposed to another size or fragment length. It may be preferable to reduce length bias for consistent or more accurate results. In some aspects, it may be preferable to increase a length bias for a certain range or against a certain range.

As used herein, "microbe," "microbial," or "microorganism" refers to an organism, such as, for example, a microscopic or macroscopic organism, which may exist as a single cell or as a colony of cells, capsids, spores, filaments, or multicellular organisms. Microbes include all unicellular organisms and multicellular organisms, such as, for example, those from archaea, bacteria, protozoa, nematodes, viruses, and eukaryotes. Microbes are often pathogens responsible for disease, but may also exist in a non-pathogenic, symbiotic, commensalistic, mutualistic, or amensalistic relationship with a host, such as a human.

Examples of microbes are one or more of the species or strains from one or more of the following genera: *Coniosporium, Hantavirus, Talaromyces, Machlomovirus, Betatetravirus, Raoultella, Aeromonas, Ephemerovirus, Empedobacter, Loa, Macluravirus, Stenotrophomonas, Alfamovirus, Rosavirus, Emmonsia, Aggregatibacter, Orthopneumovirus, Weeksella, Nairovirus, Salivirus, Weissella, Mosavirus, Gammapartitivirus, Strongyloides, Passerivirus, Erysipelatoclostridium, Bacillarnavirus, Iotatorquevirus, Taenia, Trypanosoma, Olsenella, Cladosporium, Rhizobium, Prevotella, Leclercia, Paracoccus, Ilarvirus, Lagovirus, Rasamsonia, Plasmodium, Acremonium, Chlamydia, Clonorchis, Vibrio, Bartonella, Nakazawaea, Franconibacter, Anisakis, Norovirus, Nocardia, Solobacterium, Parechovirus, Avenavirus, Orthohepevirus, Aphthovirus, Hepandensovirus, Microbacterium, Lichtheimia, Lomentospora, Achromobacter, Ipomovirus, Tsukamurella, Elizabethkingia, Hepevirus, Seadornavirus, Alternaria, Trueperella, Gammatorquevirus, Bifidobacterium, Chrysosporium, Thogotovirus, Curtovirus, Deltatorquevirus, Balamuthia, Mastrevirus, Bdellomicrovirus, Mupapillomavirus, Pseudozyma, Wickerhamiella, Aquamavirus, Alloscardovia, Thielavia, Idaeovirus, Henipavirus, Coxiella, Haemophilus, Gammacoronavirus, Negevirus, Brevibacterium, Peptoniphilus, Alphacarmotetravirus, Nosema, Trichovirus, Arenavirus, Thermomyces, Necator, Waikavirus, Blosnavirus, Jonesia, Tetraparvovirus, Emaravirus, Plectrovirus, Sclerodarnavirus, Toxocara, Umbravirus, Burkholderia, Chromobacterium, Paracoccidioides, Brugia, Eragrovirus, Macrococcus, Absidia, Colletotrichum, Inovirus, Phycomyces, Wickerhamyces, Acidaminococcus, Moraxella, Rothia, Phlebovirus, Slackia, Purpureocillium, Betapapillomavirus, Tupavirus, Cryspovirus, Saksenaea, Erysipelothrix, Kobuvirus, Mimoreovirus, Echinococcus, Mannheimia, Bergeyella, Cyclospora, Xylanimonas, Leptospira, Finegoldia, Curvularia, Cryptosporidium, Babuvirus, Pecluvirus, Lambdatorquevirus, Pythium, Carlavirus, Entomobirnavirus, Kocuria, Anaplasma, Ampelovirus, Avihepatovirus, Nepovirus, Rhodococcus, Bordetella, Mischivirus, Scedosporium, Gardnerella, Maculavirus, Trichoderma, Aveparvovirus, Salmonella, Avastrovirus, Copiparvovirus, Trachipleistophora, Clostridioides, Nanovirus, Siccibacter, Leptotrichia, Citrivirus, Odoribacter, Sanguibacter, Novirhabdovirus, Acremonium, Hafnia, Chaetomium, Tenuivirus, Yokenella, Rubulavirus, Varicellovirus, Alphamesonivirus, Sicinivirus, Leuconostoc, Microvirus, Gallantivirus, Morbillivirus, Lolavirus, Pantoea, Hepatovirus, Nupapillomavirus, Metschnikowia, Barnavirus, Kytococcus, Tritimovirus, Tannerella, Respirovirus, Pneumocystis, Dirofilaria, Pediococcus, Lactococcus, Blastomyces, Dianthovirus, Actinobacillus, Teschovirus, Oscivirus, Begomovirus, Potyvirus, Byssochlamys, Alphacoronavirus, Molluscipoxvirus, Lymphocryptovirus, Sapelovirus, Parabacteroides, Pyrenochaeta, Listeria, Senecavirus, Brevidensovirus, Potexvirus, Parvimonas, Flavivirus, Recovirus, Toxoplasma, Yatapoxvirus, Opisthorchis, Trichuris, Cyphellophora, Morganella, Perhabdovirus, Micrococcus, Pequenovirus, Mastadenovirus, Anaeroglobus, Tropheryma, Dolosigranulum, Wolbachia, Lelliottia, Mycoplasma, Tobravirus, Shewanella, Paeniclostridium, Erythroparvovirus, Sutterella, Sporopachydermia, Narnavirus, Nyavirus, Francisella, Arthroderma, Epsilontorquevirus, Sigmavirus, Amdoparvovirus, Actinomyces, Alphapermutotetravirus, Cardiobacterium, Influenzavirus C, Orthopoxvirus, Poacevirus, Phialophora, Lactobacillus, Polyomavirus, Debaryomyces, Foveavirus, Bymovirus, Mycoflexivirus, Grimontia, Mucor, Rhytidhysteron, Quadrivirus, Thermoascus, Aureusvirus, Trichosporon, Myceliophthora, Dermacoccus, Dysgonomonas, Pseudoramibacter, Becurtovirus, Gordonia, Sapovirus, Orthobunyavirus, Spiromicrovirus, Pomovirus, Exophiala, Sneathia, Helicobacter, Photorhabdus, Mogibacterium, Betapartitivirus, Avibirnavirus, Ambidensovirus, Oleavirus, Orientia, Deltacoronavirus, Anulavirus, Trichomonasvirus, Budvicia, Geotrichum, Enamovirus, Lachnoclostridium, Schistosoma, Paecilomyces, Panicovirus, Rhizoctonia, Brevibacillus, Beauveria, Pestivirus, Tombusvirus, Cilevirus, Cokeromyces, Peptostreptococcus, Phanerochaete, Proteus, Idnoreovirus, Aspergillus, Pasteurella, Malassezia, Hanseniaspora, Endornavirus, Azospiril-*

*lum, Velarivirus, Cystovirus, Avisivirus, Bacteroides, Picobirnavirus, Myroides, Circovirus, Arterivirus, Aquaparamyxovirus, Onchocerca, Cosavirus, Kluyveromyces, Fijivirus, Candida, Hepacivirus, Dermabacter, Ourmiavirus, Allexivirus, Enterobacter, Acidovorax, Bracorhabdovirus, Carmovirus, Pluralibacter, Coltivirus, Fonsecaea, Streptobacillus, Corynebacterium, Macrophomina, Marburgvirus, Comovirus, Fabavirus, Alphanodavirus, Cellulomonas, Enterobius, Catabacter, Moellerella, Nakaseomyces, Cucumovirus, Valsa, Deltapartitivirus, Plesiomonas, Pseudomonas, Torovirus, Cuevavirus, Hypovirus, Trichomonas, Influenzavirus D, Giardiavirus, Crinivirus, Tepovirus, Sakobuvirus, Cyberlindnera, Paenalcaligenes, Bafinivirus, Rymovirus, Pegivirus, Yarrowia, Treponema, Borreliella, Rubivirus, Aureobasidium, Angiostrongylus, Filobasidium, Photobacterium, Rhizopus, Orthoreovirus, Ustilago, Simplexvirus, Aquareovirus, Protoparvovirus, Propionibacterium, Sprivivirus, Hunnivirus, Apophysomyces, Meyerozyma, Alphapapillomavirus, Candida, Brucella, Gallivirus, Dinovernavirus, Anaerobiospirillum, Eubacterium, Tatlockia, Terrisporobacter, Quaranjavirus, Sobemovirus, Dicipivirus, Arcanobacterium, Macanavirus, Atopobium, Vesivirus, Lodderomyces, Dinornavirus, Betatorquevirus, Kerstersia, Aparavirus, Neisseria, Agrobacterium, Edwardsiella, Labyrnavirus, Totivirus, Actinomadura, Tobamovirus, Influenzavirus B, Mandarivirus, Anaerococcus, Kunsagivirus, Naegleria, Campylobacter, Veillonella, Yamadazyma, Filobasidiella, Oerskovia, Penicillium, Anncaliia, Leptosphaeria, Pneumovirus, Psychrobacter, Isavirus, Granulicatella, Torradovirus, Cladophialophora, Influenzavirus A, Ophiostoma, Aerococcus, Ureaplasma, Etatorquevirus, Bocaparvovirus, Megasphaera, Reptarenavirus, Comamonas, Capnocytophaga, Alphatorquevirus, Syncephalastrum, Wallemia, Betacoronavirus, Hyphopichia, Nocardiopsis, Legionella, Trichinella, Paraburkholderia, Mammarenavirus, Echinostoma, Sphingobacterium, Enterovirus, Methanobrevibacter, Ochroconis, Cheravirus, Pasivirus, Enterococcus, Mycoreovirus, Tospovirus, Betanodavirus, Phytoreovirus, Enterocytozoon, Ferlavirus, Stemphylium, Filifactor, Leishmaniavirus, Gemella, Bromovirus, Alloiococcus, Cunninghamella, Cronobacter, Oribacterium, Orbivirus, Chrysovirus, Cripavirus, Tatumella, Pandoraea, Ogataea, Dracunculus, Volvariella, Iflavirus, Benyvirus, Rhadinovirus, Histoplasma, Rahnella, Morococcus, Verticillium, Janibacter, Gyrovirus, Alphapartitivirus, Mycobacterium, Roseomonas, Varicosavirus, Chryseobacterium, Parapoxvirus, Rhizomucor, Aureimonas, Levivirus, Leishmania, Luteovirus, Cypovirus, Ochrobactrum, Microsporum, Piscihepevirus, Ceratocystis, Sporothrix, Vesiculovirus, Cupriavidus, Cryptococcus, Metapneumovirus, Alphanecrovirus, Eikenella, Brevundimonas, Escherichia, Leifsonia, Schizophyllum, Granulibacter, Gordonibacter, Lachancea, Madurella, Ophiovirus, Phellinus, Nebovirus, Acanthamoeba, Fusobacterium, Pichia, Verruconis, Ehrlichia, Tibrovirus, Higrevirus, Wohlfahrtiimonas, Rhinocladiella, Neorickettsia, Sadwavirus, Roseobacter, Sequivirus, Pannonibacter, Rotavirus, Turicella, Cardiovirus, Propionimicrobium, Furovirus, Naumovozyma, Closterovirus, Fluoribacter, Zeavirus, Clavispora, Megrivirus, Gammapapillomavirus, Rickettsia, Polemovirus, Corynespora, Encephalitozoon, Shimwellia, Fusarium, Yersinia, Capronia, Delftia, Victorivirus, Marafivirus, Kluyvera, Iteradensovirus, Isoptericola, Vitivirus, Roseolovirus, Conidiobolus, Abiotrophia, Babesia, Phoma, Sanguibacteroides, Staphylococcus, Rhodotorula, Zetatorquevirus, Hymenolepis, Fasciola, Cytorhabdovirus, Cardoreovirus, Memnoniella, Trichophyton, Mitovirus, Phaeoacremonium, Providencia, Lysinibacillus, Giardia, Oligella, Streptomyces, Paraclostridium, Ralstonia, Coccidioides, Brambyvirus, Biatriospora, Allolevivirus, Acinetobacter, Starmerella, Omegatetravirus, Porphyromonas, Avulavirus, Streptococcus, Arcobacter, Topocuvirus, Mamastrovirus, Ancylostoma, Bornavirus, Capillovirus, Alphavirus, Tymovirus, Nucleorhabdovirus, Diaporthe, Chlamydiamicrovirus, Turncurtovirus, Saccharomyces, Riemerella, Betanecrovirus, Clostridium, Mobiluncus, Cercospora, Marnavirus, Mortierella, Aquabirnavirus, Xanthomonas, Dependoparvovirus, Ebolavirus, Neofusicoccum, Borrelia, Leminorella, Klebsiella, Blastocystis, Alcaligenes, Citrobacter, Eggerthella, Cedecea, Serratia, Penstyldensovirus, Bacillus, Laribacter, Wuchereria, Hordeivirus, Cytomegalovirus, Actinomucor, Ascaris, Shigella, Vittaforma, Torulaspora, Kingella, Oryzavirus, Polerovirus, Tremovirus, Erbovirus, Entamoeba, Lyssavirus, Paenibacillus, Facklamia, Kappatorquevirus, Metarhizium, Stachybotrys, Okavirus, Botrexvirus, Thetatorquevirus,* and *Basidiobolus.*

Microbes or pathogens may include archaea, bacteria, yeast, fungi, molds, protozoans, nematodes, eukaryotes, and/or viruses. Microbes or pathogens may also include DNA viruses, RNA viruses, culturable bacteria, additional fastidious and unculturable bacteria, mycobacteria, and eukaryotic pathogens (See, Bennett J. E., D., R., Blaser, M. J. Mandell, Douglas, and Bennett's Principles and Practice of Infectious Diseases; Saunders, Philadelphia, PA, 2014; and Netter's Infectious Disease, 1st Edition, edited by Elaine C. Jong, M D and Dennis L. Stevens, M D, PhD (2015)). Microbes or pathogens may also include any of the microbes set forth in https://www.ncbi.nlm.nih.gov/genome/microbes/or https://www.ncbi.nlm.nih.gov/biosample/.

As used herein, "nucleic acid" refers to a polymer or oligomer of nucleotides and is generally synonymous with the term "polynucleotide" or "oligonucleotide." Nucleic acids may comprise, consist of, or consist essentially of a deoxyribonucleotide, a ribonucleotide, a deoxyribonucleotide analog, chemically modified canonical deoxyribonucleotides, ribonucleotides, and/or ribonucleotide analog, nucleic acids with modified backbones, or any combination thereof.

Nucleic acids can be of any length. Nucleic acids may perform any function, known or unknown, or may even be present as an inert entity. The following are non-limiting examples of nucleic acids: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), long non coding RNA (lnc RNA), small non coding RNAs such as but not restricted to piwi RNAs and enhancer RNAs, circ RNA (circular RNA), ribozymes, cDNA, recombinant polynucleotides, branched polynucleotides, plasmids, vectors, isolated DNA of any sequence, isolated RNA of any sequence, nucleic acid probes, primers, mitochondrial DNA, circulating nucleic acids, cell-free nucleic acids, cfDNA, cfna, CFNA, host cfNA, non-host cfNA, circulating cfNA, microbial cell free nucleic acids, viral nucleic acid, bacterial nucleic acid, genomic DNA, pathogen nucleic acids, fungal nucleic acid, parasitic nucleic acid, exosomal nucleic acid, intercellular signal nucleic acid, exogenous nucleic acids, nucleic acid therapeutics, and DNA enzymes. A nucleic acid may comprise, consist of, or consist essentially of one or more modified nucleotides, such as methylated nucleotides or methylated nucleotide analogs. If present, modifications to the nucleotide structure may be imparted before or after assembly of the polymer. The sequence of nucleotides may be interrupted by non-nucleotide components. A nucleic acid may be further modified after polymerization, such as by conjugation with a labeling component. A nucleic acid may be single-stranded, double-stranded, have higher numbers of strands (e.g., triple-stranded), and/or have a higher order of structure (e.g., tertiary or quaternary structure). A target nucleic acid may be any type, category or subcategory of nucleic acids.

As used herein, a "nucleic acid library" refers to a collection of nucleic acid fragments. The collection of nucleic acid fragments may be used, for example, for sequencing.

As used herein, "pathogen" refers to a microorganism that causes, or can cause, disease.

As used herein, "plasma" or "blood plasma" refers to the liquid component or fraction of blood that normally holds human blood cells in whole blood in suspension. Holding blood cells in whole blood makes plasma the extracellular matrix of blood cells.

As used herein, the phrase "process control molecules" refers to molecules that are added to a sample before or during nucleic acid library generation to aid in the identification or quantification of nucleic acids in a sample. Process control molecules are separate from and not integrated in the target molecules, such as nucleic acids. Process control molecules may have special features such as specific sequences, lengths, GC content, degrees of degeneracy, degrees of diversity, different secondary, tertiary, or quaternary structures, and/or known starting concentrations. Process control molecules may be used for normalizing the signal in a sample in order to account for variations in sample processing or to control process performance. Process control molecules may include, for example, without limitation, ID Spike(s), Spanks, and/or Sparks or GC Spike-in Panel molecules. Process control molecules may additionally include dephosphorylation control molecules, denaturation control molecules, and/or ligation control molecules. Examples of dephosphorylation control molecules include, without limitation:

```
                                    (SEQ ID NO: 6)
GGCCTCGCGGAGGCATGCGTCATGCTAGCGT

GCGGGGTACTCTTGCTATC;

(SEQ ID NO: 7)
GAGAATTATTCGGGGGCAGTGACAACCAACA

TCTCGGGTCCTGCCCAACC-3' Phosph;

(SEQ ID NO: 8)
5' Phosph-GGTCTACACGCTAATATAGCG

AATCACCGAGAACCCGGCGCCACGCAATG-

3' Phosph;
and (SEQ ID NO: 9)
5' Phosph-GAACGTCCTTAACTCCGGCAG

GCAATTAAAGGGAACGTATGTATAACGCA,
``` where "5' Phosph" and "3' Phosph" indicate that the 5'-end and 3'-end of the control molecule is phosphorylated, respectively. By "adapter attachment control molecule" is intended a control molecule that allows monitoring of the efficiency of an adapter attachment reaction be it ligation-based, TdT-based, template-switching-based, primer-extension-based, or amplification-based. By "degradation assessment molecules" is intended a control molecule used to evaluate sample and spiked sample integrity during processing.

The term "sequencing," as used herein, generally refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA). Sequencing may involve basic methods including Maxam-Gilbert sequencing and chain-termination methods, or de novo sequencing methods including shotgun sequencing and bridge PCR, or next-generation methods including but not limited to polony sequencing, 454 pyrosequencing, Illumina sequencing, SOLiD sequencing, Ion Torrent semiconductor sequencing, HeliScope single molecule sequencing, SMRT® sequencing, nanopore sequencing and others. Sequencing can be performed by various systems currently available, such as, without limitation, a sequencing system by Illumina, Pacific Biosciences, Oxford Nanopore, Genia Technologies, or Life Technologies (Ion Torrent) and others. Such devices may provide a plurality of raw genetic data corresponding to the genetic information of a host (e.g., human), a non-host (e.g., a pathogen, an organ donor), a host-derived variant genetic sequence (e.g., a single nucleotide polymorphism), and/or combinations thereof as generated by the device from a sample provided by the subject.

As used herein, "Spanks" refers to degenerate pools, or pools of nucleic acids with diverse sequences, which degenerate pools may often be used for diversity assessment, abundance calculation, and/or determination of information transfer efficiency (See, for example, U.S. Pat. No. 9,976,181).

As used herein, "Sparks" "GC Spike-in Panel" or "GC dSPARKS" refers to nucleic acids that are size or length or GC-content markers, which may be used for abundance normalization, development, and/or analysis purposes and other purposes (See, for example, U.S. Pat. No. 9,976,181).

As used herein, "ID Spike(s)" refers to identification spikes that can be used, for example without limitation, for sample identification tracking, cross-contamination detection, reagent tracking, and/or reagent lot tracking (See, for example, U.S. Pat. No. 9,976,181).

As used herein, the phrase "raw biological sample" refers to an unmanipulated sample obtained from a subject, e.g., host, containing or presumed to contain target nucleic acids. In other words, a raw biological sample, once obtained from the subject, has not been subjected to any extraction methods, e.g., alcohol-based extraction, size separation, etc., needed to generate an initial sample. Exemplary raw biological samples include whole blood, cerebrospinal fluid, synovial fluid, bronchoalveolar lavage, urine, stool, saliva, abdominal fluid, ascites fluid, peritoneal lavage, gastric fluid, interstitial fluid, lymph fluid, bile, abscess fluid, tissue, amniotic fluid, meconium, sinus aspirate, lymph node, bone marrow, hair, nails, cheek swab, skin swab, urethral swab, cervical swab, nasopharyngeal swab, nasopharyngeal aspirate, vaginal swab, epithelial cells, semen, vaginal discharge, intercellular fluid, pericardial fluid, rectal swab, bone, skin tissue, soft tissue, tears, and/or a nasal sample. The raw biological sample may be an initial sample if no manipulation of the raw biological sample is needed, e.g., whole blood, to obtain the target nucleic acids. A raw biological sample may also be manipulated, such as, for example to create a fraction of whole blood (e.g. plasma, serum, etc.) to yield an initial sample.

As used herein, the term "initial sample" refers to a sample comprising nucleic acids derived from a raw biological sample. An initial sample, for example, may comprise target or desired nucleic acids extracted from a raw biological sample.

As used herein, the phrase "spiked initial sample" refers to an initial sample to which process control molecules have been added prior to the start of generating a sequencing library.

The term "derived from" encompasses the terms "originated from," "obtained from," "obtainable from" and "created from," and generally indicates that one specified material finds its origin in another specified material or has features that can be described with reference to the specified material. For example, an initial sample may be derived from a raw biological sample.

As used herein, the turn of phrase "uniformly distributed" refers to a distribution that is continuous or uniform between members of a family such that for each member of a family there is a predictable or symmetric interval between them. The term "non-uniformly distributed" refers to a distribution of members of a family that does not have a predictable or symmetric interval between them.

II. General Overview

The current invention provides for methods of generating a nucleic acid library from an initial sample without extracting the nucleic acids before starting the nucleic acid library generation process from the initial sample. In some embodiments, substances that may decrease yield or inhibit generation of a nucleic acid library, themselves, may be extracted or removed, but the nucleic acids are not extracted from the initial sample before the start of nucleic acid library generation.

The method comprises, consists of, or consists essentially of adding one or more process control molecules to an initial sample and generating the nucleic acid library from the initial sample. The method comprises, consists of, or consists essentially of generating the nucleic acid library from the initial sample. Nucleic acid libraries may utilize single-stranded and/or double-stranded nucleic acids.

Process control molecules can be one or more of ID Spike(s), Spanks, Sparks or GC Spike-in Panel, dephosphorylation control molecules, denaturation control molecules, ligation control molecules and/or other process control molecules described elsewhere herein.

The method offers several advantages. The method is more specific and sensitive to low abundance, low quality nucleic acids, less sensitive to seasonal variation, and less sensitive to sample shipping conditions. Chemical waste requiring controlled handling is reduced by the method. The method provides a greater ability to work with lower sample volumes, reduces sequence length, secondary structure and GC-content biases, recovers a higher fraction of nucleic acids present in the sample, provides a reduced turnaround time, enables better quality control of materials, and provides a lower cost of goods and services. The method also allows better discrimination between the nucleic acid signal endogenous to an initial sample from that of a nucleic acid signal originating from process contamination.

III. Initial Samples and Raw Biological Samples

A. Samples

The disclosed methods, systems, compositions, and kits can be used for the analysis of a wide range of different sample types. The disclosure may be particularly useful in the evaluation of initial samples in which the level of nucleic acids are of low quality or quantity by allowing analysis of a larger fraction of the nucleic acids present in the initial sample, regardless of purification efficiencies or biases or chemical type or structure.

In some embodiments, the initial sample comprises, consists of, or consists essentially of a raw biological sample.

In some embodiments, the initial sample comprises, consists of, or consists essentially of a solid or a body fluid such as blood, plasma, serum, cerebrospinal fluid, synovial fluid, bronchoalveolar lavage, urine, stool, saliva, abdominal fluid, ascites fluid, peritoneal lavage, gastric fluid, interstitial fluid, lymph fluid, bile, abscess fluid, tissue, amniotic fluid, meconium, sinus aspirate, lymph node, bone marrow, hair, nails, cheek swab, skin swab, urethral swab, cervical swab, nasopharyngeal swab, nasopharyngeal aspirate, vaginal swab, epithelial cells, semen, vaginal discharge, intercellular fluid, pericardial fluid, rectal swab, bone, skin tissue, soft tissue, tears, and/or a nasal sample. In some embodiments, the initial sample comprises, consists or consists essentially of a solid or a body fluid selected from the group consisting of plasma, cerebrospinal fluid, bronchoalveolar lavage, urine, and synovial fluid. In some embodiments, the initial sample comprises, consists of, or consists essentially of plasma. In some embodiments, the initial sample comprises, consists of, or consists essentially of urine. In some embodiments, the initial sample comprises, consists of, or consists essentially of cerebrospinal fluid. In some embodiments, the initial sample is from a human subject.

Cell-free nucleic acids may be present in any biological sample, including raw biological samples, raw samples and initial samples. In some embodiments, an initial sample can be made up of, in whole or in part, cells and/or tissue. The initial sample may be cell-free or cell-depleted. The initial cell-free sample or initial sample may comprise, consist of, or consist essentially of nucleic acids that originated from a different site in the body, such as a site of pathogenic infection. In the case of blood, serum, lymph, or plasma, the initial sample may contain "circulating" cell-free nucleic acids that originated at anatomic locations other than the site of bodily fluid collection of the fluid in question. In the case of urine, the cell-free nucleic acids may be cell-free nucleic acids that originated in a different site in the body. The cell-free samples or cell-depleted initial samples can be obtained by depleting or removing cells, cell fragments, or exosomes by a known technique such as by centrifugation or filtration.

In some embodiments, an initial sample comprises, consists of, or consists essentially of circulating tumor or fetal nucleic acids. (See, for example, Analysis of serum or blood borne nucleic acids, such as circulating tumor or fetal nucleic acids, e.g., as described in U.S. Pat. Nos. 8,877,442 and 9,353,414, or in pathogen identification through, e.g., analysis of circulating microbial or viral nucleic acids, e.g., as described in Published U.S. Patent Application No. 2015-0133391 and Published U.S. Patent Application No. 2017-0016048, the full disclosures of each is incorporated herein by reference in its entirety for all purposes). In some embodiments, the initial sample comprises, consists of, or consists essentially of circulating donor nucleic acids (See, for example, US 20150211070, which is incorporated by reference herein in its entirety, including any drawings).

In some embodiments, substances that may affect library generation are partially or completely removed. In some embodiments, the nucleic acid library is generated from the initial sample without prior partial or complete removal of any substance that may affect the library yield or inhibit the library generation. Examples of substances that may affect library generation that can be completely or partially removed include, but are not limited to, heparin or other oligo-/poly-saccharides, EDTA, fat, lipids, fatty acids, urea, haemoglobin and other products of hemolysis, immunoglobulin, lactoferrin, buffy coat, components of the buffy coat, calcium, collagen, haematin, tannic acid, melanin, humic acids, antiviral substances (e.g., acyclovir), therapeutic drugs, human serum albumin, lipoproteins, triglyceride-rich lipoproteins, hemolysate, protein, conjugated bilirubin, unconjugated bilirubin, antibody, acetylcysteine, ampicillin, cefoxitin, doxycycline, theophylline, levodopa, methyldopa, metronidazole, acetylsalicylic acid, ibuprofen, phenylbutazone, rifampicin, cyclosporine, acetaminophen, creatinine, glucose, glycerol, lactate, pyruvate, uric acid, and/or biotin.

B. Subjects

An initial sample can be derived from any subject (e.g., a human subject, a non-human subject, etc.). The subject can be healthy. In some embodiments, the subject is a human patient having, suspected of having, or at risk of having, a disease or infection.

The initial sample can be from a subject who has a specific disease, condition, or infection, or is suspected of having (or at risk of having) a specific disease, condition, or infection. For example, the initial sample can be from a cancer patient, a patient suspected of having cancer or a patient at risk of having cancer. In some embodiments, the initial sample can be from a patient with an infection, a patient suspected of an infection, or a patient at risk of having an infection. In some embodiments, the initial sample is from a subject who has undergone, or will undergo, an organ transplant.

A human subject can be a male or female. In some embodiments, the sample can be from a human embryo or a human fetus. In some embodiments, the human can be an infant, child, teenager, adult, or elderly person. In some embodiments, the subject is a female subject who is pregnant, suspected of being pregnant, or planning to become pregnant.

In some embodiments, the subject is a human subject who has undergone an organ transplant or who is planning to undergo organ transplant.

In some embodiments, the subject is a farm animal, a lab animal, or a domestic pet. In some embodiments, the animal can be an insect, a dog, a cat, a horse, a cow, a mouse, a rat, a pig, a fish, a bird, a chicken, or a monkey.

The subject can be an organism, such as a single-celled or multicellular organism. In some embodiments, the sample may be obtained from a plant, fungi, eubacteria, archaebacteria, protist, or any multicellular organism. The subject may be cultured cells, which may be primary cells or cells from an established cell line.

In some embodiments, the subject has a genetic disease or disorder, is affected by a genetic disease or disorder, or is at risk of having a genetic disease or disorder. A genetic disease or disorder can be linked to a genetic variation such as mutations, insertions, additions, deletions, translocations, point mutations, trinucleotide repeat disorders, single nucleotide polymorphisms (SNPs), or a combination of genetic variations.

C. Nucleic Acids

The disclosure provides for the detection, and genetic analysis of various chemical and structural forms of nucleic acid found in a biological sample. Detection of various chemical and structural forms of nucleic acid found in a biological sample may be concurrent, consecutive or independent. Nucleic acids can include various chemical forms of a DNA molecule as well as various chemical forms of an RNA molecule. Nucleic acids can also include different structural forms of DNA and RNA found in a sample. In some embodiments, the nucleic acids can be located outside of cells, viral particles or spores (e.g., such as cell-free nucleic acids).

Nucleic acids may be any type of nucleic acid including but not limited to: double-stranded (ds) nucleic acids, single stranded (ss) nucleic acids, DNA, RNA, cDNA, mRNA, cRNA, tRNA, ribosomal RNA, dsDNA, ssDNA, miRNA, siRNA, circulating nucleic acids, circulating cell-free nucleic acids, circulating DNA, circulating RNA, cell-free nucleic acids, cell-free DNA, cell-free RNA, circulating cell-free DNA, cell-free dsDNA, cell-free ssDNA, circulating cell-free RNA, genomic DNA, exosomes, cell-free pathogen nucleic acids, circulating microbe or pathogen nucleic acids, mitochondrial nucleic acids, non-mitochondrial nucleic acids, nuclear DNA, nuclear RNA, chromosomal DNA, circulating tumor DNA, circulating tumor RNA, circular nucleic acids, circular DNA, circular RNA, circular single-stranded DNA, circular double-stranded DNA, plasmids, bacterial nucleic acids, fungal nucleic acids, parasite nucleic acids, viral nucleic acids, cell-free bacterial nucleic acids, cell-free fungal nucleic acids, cell-free parasite nucleic acids, viral particle-associated nucleic acids, mitochondrial DNA, intercellular signal nucleic acids, exogenous nucleic acids, DNA enzymes, RNA enzymes, food-derived nucleic acids, any metabolic form of nucleic acid-based therapeutics, or any combination thereof. Nucleic acids may be nucleic acids derived from microbes or pathogens including but not limited to viruses, bacteria, fungi, parasites and any other microbe, particularly an infectious microbe or potentially infectious microbe. Nucleic acids may derive from archaea, bacteria, fungi, molds, eukaryotes, and/or viruses. In some embodiments, nucleic acids may be derived directly from the subject, as opposed to a microbe or pathogen.

In some embodiments, the present disclosure provides for generation of a single-stranded nucleic acid library. The single-stranded methods provided by the present disclosure can be applied for more efficient processing of shorter nucleic acid fragments as well as less biased processing of nucleic acids in respect to any of their properties (e.g., nucleic acid length, sequence, GC content, secondary and/or any higher order structure, degree of damage, such as nicking and/or the presence of gaps, and/or degree of chemical damage). In some embodiments, the single-stranded nucleic acid methods, composition, systems, and kits can be applied for a microbe or pathogen identification in samples that contain circulating or cell-free nucleic acids or highly degraded or low-quality samples such as ancient, formalin-fixed paraffin-embedded (FFPE) samples, or samples which have undergone many freeze-thaw cycles. In some embodiments, the present disclosure provides for analysis of both double-stranded and single-stranded nucleic acids in a sample. In some embodiments, double-stranded nucleic acids are denatured to form single-stranded nucleic acids.

Previous efforts had indicated heat denaturation of samples reduced RNA fragment recovery in the library generation process. Heat in the presence of divalent cations ($Ca^{2+}$ or $Mg^{2+}$) causes strand cleavage of RNA molecules. Previous efforts to solve this problem by chelating the divalent cations have been attempted, but chelating the divalent cations is difficult to achieve given the reaction buffer requirements or variable concentration of anticoagulants in the input samples. In some embodiments, a sample comprising cell free or viral particle protected RNA is incubated with reverse transcriptase. The cell free RNA is converted to cDNA which is stable in subsequent heat denaturation steps. The heat denaturation step releases particle protected RNA. A second incubation with reverse transcriptase converts the released nucleic acids to cDNA. In some aspects of the method, a polyadenylation process occurs before incubation with the reverse transcriptase. In some aspects of the method a thermolabile or deactivatable proteinase K is used. In some aspects, salts are removed or reduced to destabilize dsDNA.

In addition to reducing environmental contamination protease incubation may reduce inhibitors of the direct to library process. Incubating with a protease may include any protease known in art including but not limited to proteinase K. In the presence of detergents and shearing forces proteases such as proteinase K may release nucleic acids present in viral capsids, bacterial and eukaryotic cells. The released nucleic acids may be accessible for utilization in downstream library preparation. If the target nucleic acid is cell free RNA, the method will need a variation to convert cfRNA to cDNA prior to incubation with protease, particularly proteinase K, and heat denaturation. The protease and denaturation step should be followed by additional steps to capture the newly released RNA along with cfDNA and cDNA present in the sample. The additional step may be A-tailing of the nucleic acid or a second round of cDNA synthesis. The additional step enables capture of particle protected and cell-free RNA in the same protocol.

In some embodiments, the subject may have, or is suspected of having, a pathogenic infection. In some embodiments, the sample from the host subject comprises, consists of, or consists essentially of the host DNA and RNA, as well as DNA and RNA from a pathogen or microbe which can be in the chemical or structural form of ssRNA, ssDNA, dsRNA, or dsDNA.

IV. Nucleic Acid Enrichment

In some embodiments, nucleic acids are enriched for fragments of a certain length and/or GC-content. In some embodiments, fragments of a certain length and/or GC-content comprise, consist of, or consist essentially of fragments having a length less than about 10,000 base pairs, less than about 5,000 base pairs, less than about 4,000 base pairs, less than about 3,000 base pairs, less than about 2,000 base pairs, less than about 1,000 base pairs, less than about 500 base pairs, less than about 450 base pairs, less than about 400 base pairs, less than about 350 base pairs, less than about 300 base pairs, less than about 250 base pairs, less than about 200 base pairs, less than about 180 base pairs, less than about 160 base pairs, less than about 140 base pairs, less than about 120 base pairs, less than about 115 base pairs, less than about 110 base pairs, less than about 105 base pairs, less than about 100 base pairs, less than about 95 base pairs, less than about 90 base pairs, less than about 85 base pairs, less than about 80 base pairs, less than about 75 base pairs, less than about 70 base pairs, less than about 65 base pairs, less than about 60 base pairs, less than about 55 base pairs, less than about 50 base pairs, less than about 45 base pairs, less than about 40 base pairs, less than about 35 base pairs, less than about 30 base pairs, less than about 25 base pairs, less than about 20 base pairs, or less than about 15 base pairs.

Nucleic acid enrichment may occur through any means known in the art including but not limited to, electrophoresis, chromatography immobilizing agents, and removal of unwanted sequences. In addition, selective denaturation, inclusion of protease treatment, and the addition of certain detergents (e.g. Tween-20, Triton 100X) can be used to enrich for certain length and/or GC content. It is recognized that certain nucleic acid enrichment means are better suited for use with certain reagents or at certain steps. By way of example, not limitation, methods of generating a nucleic acid library that involve a ligation step may involve a proteinase K treatment enrichment step. Nucleic acids can also be enriched with denaturation, which can happen at any step in the process set forth herein. In some embodiments, denaturation comprises, consists of, or consists essentially of selective denaturation. In some embodiments, selective denaturation comprises, consists of, or consists essentially of one or more denaturation steps effective for the selection of fragments of a certain length and/or GC-content.

In some embodiments, the denaturation step comprises, consists of, or consists essentially of adding one or more denaturing agents. In some embodiments, the one or more denaturing agents comprises, consists of, or consists essentially of, for example, without limitation, one or more of formamide, urea, guanidinium chloride, salts, betaine, detergents, surfactants, and/or DMSO. Salts may comprise, consist of, or consist essentially of, for example, without limitation, NaCl and $MgCl_2$.

A nucleic acid sample can be enriched for target nucleic acids associated with a condition, disease, infection, drug resistance or activity, indicia of transplant rejection, and/or a target tissue type. Target enrichment can be by any means known in the art. For example, the nucleic acid sample may be enriched by amplifying target sequences using target-specific primers (e.g., primers specific for pathogen or microbe nucleic acids). The target amplification can occur in a digital PCR format, using any methods or systems known in the art.

A nucleic acid sample may be enriched by capture of target sequences onto an array immobilized thereon for target-selective oligonucleotides. The nucleic acid sample may be enriched by hybridizing to target-selective oligonucleotides free in solution or on a solid support. The oligonucleotides comprise, consist of, or consist essentially of a capture moiety that enables capture by a capture reagent. In some embodiments, the nucleic acid sample is not enriched for target polynucleotides, e.g., represents a whole genome.

In some embodiments, nucleic acids are enriched by separating unwanted nucleic acids. Enrichment can occur at any point in the process. In some embodiments, enrichment comprises, consists of, or consists essentially of a pull-down method. In some embodiments, enrichment comprises, consists of, or consists essentially of hybridization to complementary oligonucleotides conjugated to a label such as a biotin tag and using, for example, avidin or streptavidin attached to a solid support), targeted PCR, or other methods. Examples of enrichment techniques that can be used include but are not limited to: (a) self-hybridization techniques in which the major population in a sample of nucleic acids self-hybridizes more rapidly than the minor population in the sample; (b) depletion of nucleosome-associated DNA from free DNA; (c) exosome depletion or enrichment; and/or (d) strategic capture of regions of interest.

V. Denaturation

The invention may include the step of denaturing nucleic acids. Denaturation may cause all, most, part, or a sufficient part for detection, of the double-stranded nucleic acids to become single-stranded. Denaturation may occur at any step in the process. In some embodiments, denaturation may remove all, most, or part of the secondary, tertiary, or quaternary structure of double-stranded or single-stranded nucleic acids. As such, any type of initial sample may be subjected to the denaturation step, including samples that contain, or are suspected to contain, only double-stranded nucleic acids, only single-stranded nucleic acids, a mixture of double-stranded and single-stranded nucleic acids, or any higher order nucleic acid structure.

The nucleic acids may be denatured using any method known in the art. In some embodiments, single-stranded nucleic acids in the sample arise as a result of being subjected to denaturation. In some embodiments, however, the nucleic acids in the sample are single-stranded because they were originally single-stranded when they were obtained from the subject, e.g., without limitation, single-stranded viral genomic RNA or single-stranded DNA or as a result of shipping and handling conditions.

A. Heat and Time

In some embodiments, denaturation is accomplished by applying heat to the sample for an amount of time sufficient to denature double-stranded nucleic acids of interest or to denature secondary, tertiary, or quaternary structures of double-stranded or single-stranded nucleic acids. In general, the sample may be denatured by heating at 95° C., or within a range from about 65 to about 110° C., such as from about 85 to about 100° C. Similarly, the sample may be heated at any temperature between about 50° C. and about 110° C. for any length of time sufficient to effectuate the denaturation, e.g., from about 1 second to about 60 minutes. In some embodiments, long nucleic acids such as intact dsRNA viruses may require longer denaturation times. In general, denaturation is performed in order to ensure that all, most, or part of the nucleic acids or nucleic acids of interest within a sample are present in single-stranded form.

In some embodiments, denaturation comprises, consists of, or consists essentially of selective denaturation to enrich certain nucleic acids. In some embodiments, selective denaturation comprises, consists of, or consists essentially of one or more denaturation steps effective for the selection of fragments of a certain length and/or GC-content. In some embodiments, selective denaturation comprises, consists of, or consists essentially of incubation at selected or elevated temperatures. In some embodiments, the selective denaturation step comprises, consists of, or consists essentially of incubation at a temperature of about 45° C., at a temperature of about 50° C., at a temperature of about 55° C., at a temperature of about 60° C., at a temperature of about 65° C., at a temperature of about 70° C., at a temperature of about 75° C., at a temperature of about 80° C., at a temperature of about 85° C., at a temperature of about 90° C., at a temperature of about 95° C., at a temperature of about 100° C., at a temperature of about 105° C., at a temperature of about 110° C. In some embodiments, setting the temperature occurs at any of the denaturation steps such as, for example, without limitation, following dephosphorylation, preceding 3'-end adapter attachment, and/or during an elution step.

In some embodiments, denaturation may remove all, most, part, or a sufficient part for detection of the secondary, tertiary, or quaternary structures in single-stranded DNA and/or RNA molecules. Non-limiting examples of domains of secondary structure that may be removed during the denaturation step include hairpin loops, hairpin stems, bulges, internal loops, and complexes of complementary nucleic acid sequences and any element contributing to folding of the molecule or complexes. In some embodiments, denaturation may not need to be performed, for example when the sample is known to contain only single-stranded nucleic acids or when there is a desire to restrict the ultimate analysis to only the single-stranded and not the double-stranded nucleic acids in the sample.

B. Chemical and Mechanical Denaturation

In some embodiments, denaturation comprises, consists of, or consists essentially of adding one or more denaturing agents for a selective or controlled denaturation. In some embodiments, denaturation comprises, consists of, or consists essentially of a selective or controlled denaturation. Depending on the application, chemical or mechanical denaturation can be used (e.g., sonication, mechanical force applied by magnetic field (e.g. magnetic tweezers) or optical traps (e.g. optical tweezers) or the like) with the methods.

Chemical denaturation agents that can be used with the methods of the disclosure include but are not limited to, alkaline agents (e.g., NaOH), formamide, guanidinium chloride, guanidine, sodium salicylate, dimethyl sulfoxide (DMSO), propylene glycol, betaine, or urea. In some embodiments, the one or more denaturing agents comprises, consists of, or consists essentially of, for example, without limitation, one or more of formamide, urea, guanidinium chloride, salts, betaine, detergents, surfactants, and/or DMSO. Salts may comprise, consist of, or consist essentially of, for example, without limitation, NaCl and $MgCl_2$.

C. Pathogen Signal Enrichment by Selective Denaturation

The concentration of the pathogen or microbe signal in the cell-free nucleic acid fraction is minuscule and requires enrichment of its signal or depletion of human signal in order to be detectable with current sequencing techniques at acceptable cost. Short fragments (<110 base pairs) where pathogen or microbe fragments are present at higher molar fraction can be enriched using approaches such as an electrophoretic-based size-selection or methods described in U.S. patent application Ser. No. 15/157,374. Such an approach, however, can be time-consuming and hard to miniaturize.

The human fraction in cell-free nucleic acid pool is partially derived from the fragments initially wrapped around the nucleosomal core particle. These fragments are mostly 150-175 base pairs long. The vast majority of the microbial cell-free nucleic acids on the other hand are shorter than 110 base pairs with average lengths about and less than 50 base pairs.

Depletion of the human fragments can be performed by selective denaturation where a controlled amount of heat is introduced into the system that allows the shorter, and thermally less stable cell-free nucleic acids fragments that are enriched for the microbial fraction to denature, but leaves intact the longer fragments that are thermally more stable and enriched for human fraction.

In some embodiments, denaturation is used to further enrich pathogen or microbe nucleic acids. In some embodiments, denaturation comprises, consists of, or consists essentially of selective denaturation. In some embodiments, selective denaturation comprises, consists of, or consists essentially of one or more denaturation steps effective for the selection of pathogen or microbe fragments of a certain length and/or GC-content.

In some embodiments, selective denaturation comprises, consists of, or consists essentially of incubation at a selected time. In some embodiments, the selected time comprises, consists of, or consists essentially of about 1 second, about 2 seconds, about 3 seconds, about 4 seconds, about 5 seconds, about 10 seconds, about 15 seconds, about 20 seconds, about 25 seconds, about 30 seconds, about 35 seconds, about 40 seconds, about 45 seconds, about 50 seconds, about 55 seconds, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19, minutes about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, or about 60 minutes. In some embodiments, incubation occurs at any of the denaturation steps such as, for example, without limitation, following a dephosphorylation, preceding 3'-end adapter attachment, and/or during an elution step.

In some embodiments setting the temperature selects for fragments of a certain length and/or GC-content. In some embodiments, fragments of a certain length and/or GC-content comprise, consist of, or consist essentially of fragments having a length less than about 10,000 base pairs, less than about 5,000 base pairs, less than about 4,000 base pairs, less than about 3,000 base pairs, less than about 2,000 base pairs, less than about 1,000 base pairs, less than about 500 base pairs, less than about 450 base pairs, less than about 400 base pairs, less than about 350 base pairs, less than about 300 base pairs, less than about 250 base pairs, less than about 200 base pairs, less than about 180 base pairs, less than about 160 base pairs, less than about 140 base pairs, less than about 120 base pairs, less than about 115 base pairs, less than about 110 base pairs, less than about 105 base pairs, less than about 100 base pairs, less than about 95 base pairs, less than about 90 base pairs, less than about 85 base pairs, less than about 80 base pairs, less than about 75 base pairs, less than about 70 base pairs, less than about 65 base pairs, less than about 60 base pairs, less than about 55 base pairs, less than about 50 base pairs, less than about 45 base pairs, less than about 40 base pairs, less than about 35 base pairs, less than about 30 base pairs, less than about 25 base pairs, less than about 20 base pairs, or less than about 15 base pairs.

VI. Modification

In some embodiments, an adapter is used with nucleic acids. Adapters, full length or partial, may be attached to the nucleic acids in a sample at one or more points during the sample preparation process. In some embodiments, adapters may be attached by ligation, by primer extension, by non-templated extension, by template switching, by the addition of nucleotides to the 3' terminus of a nucleic acid molecule, by hybridization, by amplification (e.g., PCR) or a combination of any of these reaction types. In some embodiments, adapters are attached by a ligation reaction method using a ligase enzyme that recognizes a particular nucleic acid form. In some embodiments, adapters are attached by a primer extension reaction method using, e.g., a PCR reaction, where the adapter also acts as a primer for a polymerase which acts on a particular nucleic acid form. In some embodiments, adapters are attached with a combination of a non-templated nucleic acid polymerase and primer extension off of non-templated sequences (e.g., template switching or template switching PCR).

Depending on the type of nucleic molecule in the sample, the adapter attached can be either double-stranded or single-stranded such that the adapter is compatible with the nucleic acid molecules in the sample. For example, in some embodiments a double-stranded adapter is attached to a double-stranded nucleic acid. In some embodiments, it is desirable to protect adapter ends, for example by adding 5'-end and/or 3'-end protective groups, such as amino modifiers, C3 spacers, dideoxy nucleotides, and/or inverted nucleotides or by providing an adapter that is duplexed on one end (or double-stranded) and single-stranded on the other end. Any combination of protective methods and/or groups set forth herein may be used.

Primer extension reactions can be carried out with a DNA-dependent polymerase, an RNA-dependent polymerase, polymerase with non-templated activity, a reverse transcriptase or a combination thereof. In some embodiments, the primer extension reaction can be carried out by a DNA or RNA polymerase having strand displacing activity. In some embodiments, the primer extension reaction is carried out by a DNA or RNA polymerase that has non-templated activity. In some other embodiments, the primer extension reaction can be carried out by a DNA or RNA polymerase having strand displacing activity and a DNA or RNA polymerase that has non-templated activity. In some embodiments, primer extension is carried out with a Klenow fragment.

A. Adapter Compositions

Particular adapters may be used with the present invention. In general, the adapter compositions allow for the detection of different nucleic acid forms in a sample.

Depending on the starting sample type, what nucleic acid(s) are being analyzed, the method, and what detection system is being used, an appropriate adapter can be employed (e.g., particular functional elements or modifications).

In general, an adapter can comprise, consist of, or consist essentially of a polymerase priming sequence, a sequence required to initiate reading of a nucleic acid sequence in sequencing, a sequence required to initiate reading of identifying sequences, and/or one or more identifying sequences (e.g., such as an index, a barcode, a non-templated overhang, a random sequence, unique molecular identifiers, or a combination thereof). For other applications, an adapter can comprise, consist of, or consist essentially of at least one functional element selected from polymerase priming sequence, a sequencing priming sequence, binding sites for amplification primers, a recognition sequence or structural elements required by the sequencing method utilized, one or more identifying sequences, and a label (e.g., radioactive phosphates, biotin, fluorophores, or enzymes). Labels can be added to an adapter if a purification step or particular detection system is desired (e.g., digital PCR, ddPCR, quantitative PCR, microfluidic device, microarray).

The adapter may be single-stranded or double-stranded or can have both single-stranded and double-stranded regions. In some embodiments, the adapter comprises, consists of, or consists essentially of an RNA molecule, a DNA molecule, or a molecule that contains both DNA and RNA sections and/or strands, and/or a single strand that has both RNA and DNA components. In some embodiments, a double-stranded adapter may be blunt-ended. In some embodiments, a double-stranded adapter may contain nucleic acid residue overhang(s).

Such nucleic acid residue overhangs (or tails) may be used to mark a molecule as originating from DNA or RNA in the starting sample, particularly when the overhangs are complementary to an overhang sequence deposited by a DNA nucleotidylexotransferase (e.g. TdT), Poly(A) Polymerase, a RT (e.g., SMARTer RT, HIV RT), RNA-dependent polymerase (e.g. RdRP from turnip crinkle virus), and/or a DNA-dependent polymerase (e.g., Bst 2.0 DNA polymerase). For example, the adapter overhang may contain one or more T residues in order to hybridize to one or more overhang residues deposited by a DNA polymerase (e.g., Bst 2.0 DNA polymerase, TdT or the like). Similarly, the adapter overhang may contain one or more C residues in order to hybridize to one or more overhang residues deposited by an RT (e.g., SMARTer RT, Reverse transcriptases derived from Moloney Murine Leukemia Virus, or the like). HIV reverse transcriptase and the long terminal repeat retrotransposon also have non-templated activity but may add a different nucleotide other than C.

B. Amplification Element

An adapter can comprise, consist of, or consist essentially of an amplification primer that is a primer used to carry out a polymerase chain reaction (PCR). In some embodiments, the amplification primer comprises, consists of, or consists essentially of a random primer. In some embodiments, the amplification primer comprises, consists of, or consists essentially of a template-specific primer. In some embodiments, the amplification primer comprises, consists of, or consists essentially of a primer complementary to a known non-templated overhang known to be added by the polymerase. In some embodiments, the amplification primer comprises a standardized flow cell adapter sequence or a part thereof; standardized flow cell adapter sequences are known in the art and include, but are not limited to P5 and P7. In some embodiments, the amplification primer comprises, consists of, or consists essentially of a P5 primer. In some embodiments, the amplification primer comprises, consists of, or consists essentially of a P7 primer. In some embodiments, the amplification primer comprises, consists of, or consists essentially of only part of a P5 or P7 primer. In some embodiments, depending on the method of detection, the amplification primer comprises, consists of, or consists essentially of one or more additional functional elements.

C. Identifying Sequence Element

Identifying sequences (e.g., barcode, index, or a combination thereof) can comprise a unique sequence. The identifying sequences can be added to a particular nucleic acid form by the methods provided herein (e.g., ligation, primer extension, amplification, non-templated extension, template switching, template switching PCR or a combination thereof) allowing the identification of each nucleic acid form in a sample or after sequencing. In some embodiments, the identifying sequences may also contain additional functional elements such as primer amplification sites, sequencing priming sites, or sample indexes.

The identifying sequences can be completely scrambled (e.g., randomers of A, C, G, and T for DNA or A, C, G, and U for RNA) or they can have some regions of shared sequence. For example, a shared region on each end may reduce sequence biases in ligation events. In some embodiments, the adapter comprises, consists of, or consists essentially of a shared region and the shared region comprises, consists of, or consists essentially of about or at least about 1, 2, 3, 4, 5, 6, 7, 8, 9, 10, 11, 12, 13, 14, 15, 16, 17, 18, 19, or 20 common base pairs.

Combinations of barcodes and/or indexes can be added to increase diversity. For example, barcodes and/or indexes can be used as identifiers for well position in a microtiter plate, array, or the like (e.g., 96 different barcodes for a 96-well plate), and another barcode can be used as an identifier for a plate number (e.g., 24 different barcodes for 24 different plates), giving 96×24=2,304 combinations using 96+24=120 sequences. Using three or more barcodes per sample can further increase achievable diversity.

In some embodiments, the adapter comprises, consists of, or consists essentially of barcodes and/or indexes. In some embodiments, the barcodes and/or indexes are linked to sequencing reads. In some embodiments, particular barcodes and/or indexes may be linked to particular sequencing reads. In some embodiments, particular barcodes and/or indexes may be linked to particular initial sample. In some embodiments, barcodes comprise, consist of, or consist essentially of about 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150, 160, 170, 200, 250, 300, 350, or 400, 500, or 1000 nucleotides (or base pairs) in length.

D. Label Element and Other Components

In some embodiments, the adapter comprises, consists of, or consists essentially of one or more labels. Labels can be added to an adapter when purification is desired or for using particular detection. Examples of labels that can be used with the disclosure include, but are not limited to, any of those known in the art, such as enzymes, fluorophores, radioisotopes, stable free radicals, luminescers, such as chemluminescers, bioluminescers, dyes, pigments, enzyme substrates, biotin, digoxigenin, antigens, antibodies, a His-tag, and other labels. One skilled in the art will choose a label that is compatible with the chosen detection method.

E. Attaching Adapters & Ligase Enzymes

In some embodiments, attaching comprises, consists of, or consists essentially of using a ligase; in other embodiments attaching comprises, consists of, or consists essentially of using a polymerase. In some embodiments, attaching an adapter comprises, consists of, or consists essentially of attaching an adapter to both DNA and RNA target molecules. When multiple different ligases are used (e.g., a dual ligase system), the ligases may each be specific for a target (e.g., DNA-specific or RNA-specific). In some embodiments, attaching comprises, consists of, or consists essentially of using a dual ligase system. In some embodiments, the dual ligase system comprises, consists of, or consists essentially of DNA-specific, RNA-specific, and/or ligases that ligate both DNA and RNA templates in any combination.

In some embodiments, the ligase comprises, consists of, or consists essentially of a ligase specific for double-stranded nucleic acids (e.g., dsDNA, dsRNA, RNA/DNA duplex). An example of a ligase specific for double-stranded DNA and DNA/RNA hybrids is T4 DNA ligase. In some embodiments, the ligase is specific for single-stranded nucleic acids (e.g., ssDNA, ssRNA). An example of such ligase is CircLigase II. In some embodiments, the ligase comprises, consists of, or consists essentially of a ligase specific for RNA/DNA duplexes. In some embodiments, the ligase comprises, consists of, or consists essentially of a ligase that is able to work on single-stranded, double-stranded, and/or RNA/DNA nucleic acids in any combination.

Both DNA or/and RNA ligases may be used with the disclosure. Ligases that may be used in the methods provided herein may include, but are not limited to, T4 DNA Ligase, T3 DNA Ligase, T7 DNA Ligase, *E. coli* DNA Ligase, HiFi Taq DNA Ligase, 9° N™ DNA Ligase, Taq DNA Ligase, SplintR® Ligase (also known as Splint-R ligase or PBCV-1 DNA Ligase or *Chlorella* virus DNA Ligase), Thermostable 5' AppDNA/RNA Ligase, T4 RNA Ligase, T4 RNA Ligase 2, T4 RNA Ligase 2 Truncated, T4 RNA Ligase 2 Truncated K227Q, T4 RNA Ligase 2, Truncated KQ, RtcB Ligase, CircLigase II, CircLigase ssDNA Ligase, CircLigase RNA Ligase, Ampligase® Thermostable DNA Ligase, T4 RNA ligase II and its modified or truncated derivatives, or a combination thereof.

In some embodiments, the adapters are attached to nucleic acids, such as, for example, without limitation, a single-stranded RNA, comprise, consist of, or consist essentially of a 5'-end modification such as App (e.g., pre-adenylation). The presence of the 5' App modification can enable oligonucleotides to act as direct substrates for certain ligases and remove the need for ATP. Adapters to single-stranded RNA can contain a 5' adenylation (5' App) modification and/or an RNA-identifying code.

Alternatively or additionally, DNA and RNA in a sample can be specifically marked during an adapter attachment step. In some embodiments the adapter attachment step may involve template switching or ligation. In some embodiments, the ligase comprises, consists of, or consists essentially of a ligase specific for one type of nucleic acids. For example, a DNA-specific ligase may be used so that adapters are only ligated to the DNA molecules in the sample. In another example, an RNA-specific ligase may be used so that adapters are only ligated to the RNA molecules in the sample. In some embodiments, ligation comprises, consists of, or consists essentially of successive ligation with a first ligase specific to one type of nucleic acid and a second ligase not discriminating between nucleic acids types. For example, successive ligation first with a DNA-specific ligase (e.g., CircLigase ssDNA ligase) followed by a ligase that can act on a DNA or RNA template (e.g., CircLigase II) may be used. Sequential or concurrent first adapter attachment and/or sequential or concurrent second adapter attachment may provide the ability to distinguish between chemical forms of nucleic acids (e.g., DNA and RNA). The choice of ligation method may depend on the ligase specificities and reaction conditions for each ligase used.

In some embodiments, the ligase comprises, consists of, or consists essentially of ligase selected with an appropriate profile of contaminating nucleic acids so that the profile deters sufficiently from an expected signal of interest (e.g., endogenous microbe signal in cell-free nucleic acid pool) in order to recognize and filter contamination signal originating from ligase. In some embodiments, an appropriate profile of contaminating components (e.g., buffers, buffer components, oligonucleotides, enzymes, water, beads, etc.) is selected so that the profile deters sufficiently from an expected signal of interest in order to recognize and filter contamination signal originating from components.

F. Successive Mode of Attachment

The methods provided by the present disclosure can be applied in a successive mode, that is more than one enzymatic step can be applied at separate steps in the process. In some embodiments when successive ligation is used, a wash step can be performed between the two ligation reactions to remove the first ligase and excess adapters. For example, successive ligation can be used in the first adapter ligation step. Biotinylated first adapters with a code for DNA (1a adapters) can be added to the sample nucleic acids and ligated to ssDNA using a DNA ligase. Ligation products can be immobilized on streptavidin beads. Excess 1a adapters can be washed off. First adapters with a code for RNA (1b adapters) can be added and ligated to ssRNA using an RNA ligase.

In general, for each ligation step (e.g., first ligation, second ligation, pre-denaturation ligation), a single general adapter or specific adapters can be used. In some embodiments, a single adapter is added to all nucleic acids in a ligation step. In some embodiments, a single adapter is added to a specific group of nucleic acids (e.g., only single-stranded or only double-stranded for a pre-denaturation ligation) in a ligation step. In some embodiments, different adapters can be added to specific groups of nucleic acids (e.g., ssDNA, ssRNA, dsDNA, or dsRNA). In some embodiments, selectivity can be achieved through enzymatic selectivity with a wash step in between sequential enzymatic steps to remove excess unadapted adapters. In some embodiments, selectivity can be achieved through sequence-specific hybridization to different overhangs added by polymerases in the primer extension step. In some embodiments, a polymerase attaches the adapter sequence with the splint wherein the splint binds anywhere on the original strand and the polymerase performs the primer extension reaction, thus doing multiple steps concurrently.

G. Fragmentation & End Modification

In some embodiments, the methods do not include fragmenting the nucleic acids, such as, in application with low quality samples or samples containing short fragments such as certain samples containing cell-free nucleic acids.

In some embodiments, nucleic acids are fragmented. Fragmenting of the nucleic acids may be performed by e.g., mechanical shearing, passing the sample through a syringe, sonication, heat treatment, or a combination thereof. In some embodiments, shearing may be performed by mechanical shearing (e.g., ultrasound, hydrodynamic shearing forces), enzymatic shearing (e.g., endonuclease), thermal fragmentation (e.g., incubation at high temperatures), chemical fragmentation (e.g., alkaline solutions, divalent ions). In some embodiments, fragmenting can be performed by using an enzyme, including a nuclease, or a transposase. Nucleases used for fragmenting comprise, consist of, or consist essentially of restriction endonucleases, homing endonucleases, nicking endonucleases, high fidelity restriction enzymes, or any enzyme disclosed herein.

The ends of dsDNA fragments can be polished (e.g., blunt-ended). The ends of DNA fragments can be polished by treatment with a polymerase. Polishing can involve removal of 3' overhangs, fill-in of 5' overhangs, or a combination thereof. The polymerase can be a proofreading polymerase (e.g., comprising 3' to 5' exonuclease activity). The proofreading polymerase can be, e.g., a T4 DNA polymerase, Pol 1 Klenow fragment, or Pfu polymerase. Polishing can comprise removal of damaged nucleotides (e.g., abasic sites), using any means known in the art.

VII. Reduction of Adapter Dimers and Adapter by-Products

Some methods may produce adapter dimers and adapter-derived by-products. Adapter dimers and adapter-derived by-products are two classes of unwanted products of a single-stranded library protocol that are generated by two distinct mechanisms.

For example, the single-stranded nucleic acid library protocol developed by Gansauge et al. generates high concentration of adapter dimers and adapter-derived by-products, especially with input samples characterized by low nucleic acid concentration (See, Gansauge, M T and Meyer, M., Single-stranded DNA library preparation for the sequencing of ancient or damaged DNA, Nat Protoc. 2013 April; 8(4):737-48 and Gansauge M T, Gerber T, Glocke I, Korlevic P, Lippik L, Nagel S, Riehl L M, Schmidt A, and Meyer M., Single-stranded DNA library preparation from highly degraded DNA using T4 DNA ligase, Nucleic Acids Res. 2017 Jun. 2; 45 (10), each of which is incorporated by reference in their entirety herein, including any drawings).

One way to decrease adapter-derived by-products according to an embodiment of the invention comprises, consists of, or consists essentially of using an RNA splint oligonucleotide. In some embodiments, attaching a 3'-end adapter to the denatured nucleic acids and/or single-stranded nucleic acids comprises, consists of, or consists essentially of attaching with a splint oligonucleotide. In some embodiments, the splint oligonucleotide comprises, consists of, or consists essentially of a DNA splint oligonucleotide. In some embodiments, the splint oligonucleotide comprises, consists of, or consists essentially of an RNA splint oligonucleotide or a partial RNA splint oligonucleotide. In some embodiments, attaching a 3'-end adapter to the denatured nucleic acids and/or single-stranded nucleic acids comprises, consists of, or consists essentially of ligating with a Splint-R ligase. In some embodiments, attaching a 3'-end adapter to the denatured nucleic acids further comprises, consists of, or consists essentially of adding an Rnase inhibitor. In some embodiments, an adapter is attached through a primer extension reaction performed with a polymerase comprising, consisting of, or consisting essentially of DNA-dependent RNA-dependent polymerase, or a polymerase having non-templated activity.

Some embodiments comprise, consist of, or consist essentially of preventing ligation of the 5'-end adapter to a complement synthesized during the primer extension reaction set forth above during a second ligation step. Some embodiments comprise, consist of, or consist essentially of preventing ligation of the 5'-end adapter to an adapter-derived side product. Digoxigenin may be introduced to the 5'-end of the splint oligo and an anti-digoxigenin antibody may be added to the bead-binding buffer during immobilization of adapted products. An anti-digoxigenin antibody can be added at any point prior to the second ligation. This will produce a bulky moiety at the 5'-end of any splint oligo attached to the biotinylated 3'-end adapter. This moiety will reduce the ability of T4 DNA ligase in a second ligation step to ligate 5'-end adapter to splint oligo hybrid rendering it un-amplifiable in the final PCR step. It may also reduce the efficiency of primer-extension.

Some embodiments comprise, consist of, or consist essentially of adding an antibody, such as an anti-digoxigenin antibody. In some embodiments, the anti-digoxigenin antibody is added after the 3'-end adapter is attached to the denatured nucleic acids and before a 5'-end adapter is attached. Some embodiments further comprise, consist of, or consist essentially of using beads comprising, or consisting, or consisting essentially of the anti-digoxigenin antibody. Beads may be removed by, for example, without limitation, pelleting on a magnet. For example, an anti-digoxigenin antibody-coated magnetic bead can be added to deplete digoxiginated splint oligos as well as any unhybridized digoxiginated splint oligos. This can be followed by strepta-vidin-coated magnetic bead. In some embodiments, the anti-digoxigenin antibody is added during a separation step, annealing step, primary extension step, or second ligation step.

VIII. Detection, Abundance, Bias, and Contamination

Libraries of the invention may be used for detection. Non-limiting examples of detection which can be used with the nucleic acid libraries set forth herein include various forms of sequencing, qPCR, ddPCR, microfluidic device, or microarray.

A. Process Control Molecules

One or more process control molecules may be added to the initial sample and the process molecules can be used in detection. Process control molecules may have special features such as specific sequences, lengths, GC content, degrees of degeneracy, degrees of diversity, secondary, tertiary, and quaternary structure, and/or known starting concentrations. Process control molecules may be used for normalizing signal in an initial sample in order to account for variations in sample processing. Process control molecules can be added during the library process itself, e.g., without limitation, dephosphorylation controls may be added before and after dephosphorylation or attachment control before and/or after the 3'-end adapter attachment step. Process control molecules include, but are not limited to, ID Spike(s), Spanks, and/or Sparks or GC Spike-in Panel molecules. In some embodiments, process control molecules comprise, consist of, or consist essentially of ID Spike(s), Spanks, and/or Sparks or GC Spike-in Panel molecules.

ID Spike(s) refers to identification spikes used for sample identification tracking, cross-contamination detection, reagent tracking, and/or reagent lot tracking (See, for example, U.S. Pat. No. 9,976,181). Spanks are degenerate pools of nucleic acids, or pools of nucleic acids with diverse sequences, used for diversity assessment and abundance calculation (See, for example, U.S. Pat. No. 9,976,181). Sparks, "GC Spike-in Panel," or "GC dSPARKS" are size or length markers which may be used for abundance normalization, development and/or analysis purposes, process performance monitoring, and other purposes (See, for example, U.S. Pat. No. 9,976,181).

Process control molecules may additionally include molecules designed to monitor individual steps of the process. Process control molecules may additionally include dephosphorylation control molecules, denaturation control molecules, ligation control molecules, and/or control molecules for non-templated extension or template switching. Partially or fully phosphorylated control molecules (i.e., phosphorylated 5'-end and/or 3'-ends of the control nucleic acids), control molecules with adapter sequences pre-attached (i.e., an example of a control molecule that is added after 3'-end adapter attachment step) may be added during the library process itself, e.g., dephosphorylation control post dephosphorylation step or adapter attachment control post 3'-end adapter attachment step. In some embodiments, process control molecules comprise, consist of, or consist essentially of dephosphorylation control molecules, denaturation control molecules, and/or ligation control molecules.

An example of a ligation process control molecule that can be added after the 3'-end ligation step is (SEQ ID NO: 10)
ATGACGCGCTTTCAAGCGTGGCGAGTATGTGAACCAAGGCTTCGGAC AGGAGATCGGAAG/iSpC3/iSpC3/iSpC3/iSpC3/iSpC3/ iSpC3/iSpC3/iSpC3/iSpC3/iSpC3/3BioTEG/.

Exemplary denaturation control molecules: Two nucleic acid sequences, the first one added in single-stranded form (e.g., (SEQ ID NO: 11))
ACTATATACTTAGGTTTGATCTCGCC

CCGAGAACTGTAAACCTCAACATT, and the second one, a close sequence relative to the first one, but added in a double-stranded form (e.g., (SEQ ID NO: 12))
TGAAATATCTTAGGTTTGATCTCGCC

CCGAGAACTGTAAACCTCAACATT.

Examples of dephosphorylation control molecules include, without limitation:

(SEQ ID NO: 6)
GGCCTCGCGGAGGCATGCGTCATGCTAGCGT

GCGGGGTACTCTTGCTATC;

(SEQ ID NO: 7)
GAGAATTATTCGGGGGCAGTGACAACCAACA

TCTCGGGTCCTGCCCAACC-3' Phosph;

(SEQ ID NO: 8)
5' Phosph-GGTCTACACGCTAATATAGCG

AATCACCGAGAACCCGGCGCCACGCAATG-

3' Phosph;
and (SEQ ID NO: 9)
5' Phosph-GAACGTCCTTAACTCCGGCAG

GCAATTAAAGGGAACGTATGTATAACGCA, where "5' Phosph" and "3' Phosph" indicate that the 5'-end and 3'-end of the control molecule is phosphorylated, respectively. The dephosphorylation control molecules are represented in single-stranded form, but the dephosphorylation control molecules may be double-stranded, RNA and/or any other form of modified nucleic acids.

B. Sequencing

Some embodiments comprise, consist of, or consist essentially of sequencing the nucleic acid libraries of the current invention to generate sequencing information. Some embodiments further comprise, consist of, or consist essentially of a computer comprising software that performs bioinformatics analysis on the sequence information. Bioinformatics analysis comprises, consists of, or consists essentially of, without limitation, assembling sequence data, detecting and quantifying genetic variants in a sample, including germline variants and somatic cell variants (e.g., a genetic variation associated with cancer or a pre-cancerous condition, a genetic variation associated with infection), detecting species or strain of microbes, detecting presence and measuring the abundance of microbe nucleic acids, detecting presence and measuring the abundance of therapeutic nucleic acids, detecting site of infection, detecting risk of transplant rejection, detecting state of infection, and/or detecting potential for drug resistance. One skilled in the art would appreciate other bioinformatics analysis.

Sequencing may be used to analyze nucleic acids, particularly different forms of nucleic acids present in the same sample. Such analytical methods include sequencing the nucleic acids as well as bioinformatics analysis of the sequencing results. Sequencing results may be analyzed to obtain various types of information including genomic and RNA expression. Generally, analyses provided herein allow for simultaneous analysis of DNA and RNA in a sample, as well as both single- and double-stranded nucleic acids in a sample.

In some embodiments, the analysis detects both DNA and RNA yet does not distinguish between the two. In some embodiments, the analysis detects both DNA and RNA (or double- and single-stranded nucleic acids) and also identifies whether the originating molecules are DNA, RNA, ssDNA, dsDNA, ssRNA, dsRNA, or any combination of the molecules. Often, distinguishing is accomplished by detecting markers added by using a combination of adapters specific to a molecule type of interest and/or appropriate enzyme that facilitate and enhance discrimination between different nucleic acid types (RNA vs DNA, single- vs double-stranded).

Sequencing may be by any method known in the art. Sequencing methods include, but are not limited to, Maxam-Gilbert sequencing-based techniques, chain-termination-based techniques, shotgun sequencing, bridge PCR sequencing, single-molecule real-time sequencing, ion semiconductor sequencing (e.g., Ion Torrent sequencing), nanopore sequencing, pyrosequencing (454), sequencing by synthesis, sequencing by ligation (SOLiD sequencing), sequencing by electron microscopy, dideoxy sequencing reactions (Sanger method), massively parallel sequencing, polony sequencing, and DNA nanoball sequencing. The term "Next Generation Sequencing (NGS)" herein refers to sequencing methods that allow for massively parallel sequencing of nucleic acid molecules during which a plurality, e.g., millions, of nucleic acid fragments from a single sample or from multiple different samples are sequenced simultaneously. Non-limiting examples of NGS include sequencing-by-synthesis, sequencing-by-ligation, real-time sequencing, and nanopore sequencing. In some embodiments, sequencing involves hybridizing a primer to the template to form a template/primer duplex, contacting the duplex with a polymerase enzyme in the presence of detectably labeled or unlabeled nucleotides under conditions that permit the polymerase to add labeled or unlabeled nucleotides to the primer in a template-dependent manner, detecting a signal from the incorporated labeled nucleotide or detecting a signal resulting from the process of incorporating labeled or unlabeled nucleotide (e.g., proton release), and sequentially repeating the contacting and/or detecting steps at least once, wherein sequential detection of incorporated labeled or unlabeled nucleotide determines the sequence of the nucleic acid.

Exemplary detectable labels include radiolabels, fluorescent labels, protein labels, dye labels, enzymatic labels, etc. In some embodiments, the detectable label may be an optically detectable label, such as a fluorescent label. Exemplary fluorescent labels include cyanine, rhodamine, fluorescein, coumarin, BODIPY, alexa, or conjugated multi-dyes.

In some embodiments, the sequencing comprises, consists of, or consists essentially of obtaining paired end reads. In some embodiments, the sequencing comprises, consists of, or consists essentially of obtaining consensus reads.

The accuracy or average accuracy of the sequence information may be greater than about 80%, about 90%, about 95%, about 99%, about 99.98%, or about 99.99%. The sequence accuracy or average accuracy may be greater than about 95% or about 99%. The sequence coverage may be greater than about 0.00001 fold, 0.0001 fold, 0.001 fold, about 0.01 fold, about 0.1 fold, about 0.5 fold, about 0.7 fold, or about 0.9 fold. The sequence coverage may be less than about 200,000 fold, about 100,000 fold, about 10,000 fold, about 1,000 fold, or about 500 fold.

In some embodiments, the sequence information obtained per nucleic acid template is more than about 10 base pairs, about 15 base pairs, about 20 base pairs, about 50 base pairs, about 100 base pairs, or about 200 base pairs. The sequence information may be obtained in less than 1 month, 2 weeks, 1 week, 2 days, 1 day, 14 hours, 10 hours, 3 hours, 1 hour, 30 minutes, 10 minutes, or 5 minutes.

Although the Examples (below) use specific sequences (see Table 1 in Example 1) for certain sequencing systems, e.g., Illumina systems, it will be understood that the reference to these sequences is for illustration purposes only, and the methods described herein may be configured for use with other sequencing systems incorporating specific priming, attachment, index, and other operational sequences used in those systems, e.g., systems available from Ion Torrent, Oxford Nanopore, Genia Technologies, Pacific Biosciences, Complete Genomics, and the like.

IX. Applications

Nucleic acid libraries set forth herein can be used for a variety of applications including personalized medicine. Specifically, the nucleic acid libraries can be used to detect, monitor, diagnose, prognose, guide treatment, or predict the risk of disease. Exemplary applications are provided below.

A. Cancer

The nucleic acid libraries can be used for detecting cancer in a subject or for cancer diagnosis. Initial samples may be either somatic, germline, or a combination thereof. Initial samples can be from blood, tissue, or any sample known to harbor the cancer mutation. Cancer cells in the blood can be cell-free nucleic acids or circulating cancer cells. In some embodiments, the nucleic acid library from the initial sample is sequenced and assessed for the detection or diagnosing cancer in a subject.

B. Fetal Health

The nucleic acid libraries can be used for detection, diagnosis, or prognosis of fetal health (e.g., a IVF embryo or a fetus) in a subject. In some embodiments, the nucleic acid libraries can be used to determine or assess the risk of infection status of an embryo or fetus. In some embodiments, nucleic acid libraries can be used for the genetic assessment for chromosomal aberrations, an inherited condition including but not limited to, autosomal-recessive, dominant, X-linked, or SNP-based genetic conditions in a subject. In some embodiments, the nucleic acid library from the initial sample is sequenced and assessed for the detection, diagnosis, or prognosis of fetal health in a subject.

C. Organ Transplant

The nucleic acid libraries can be used for the detection, diagnosis, or prognosis of organ transplant acceptance or rejection in a subject. Transplant rejection occurs when transplanted tissue is rejected by a recipient's immune system. Incompatibility across key HLA alleles has traditionally been considered the main factor influencing rejection in stem cell and solid organ transplants. The effect of specific FHA mismatches in kidney, transplantation are known in the art. Even in HLA identically matched kidney transplantation, some degree of rejection is still evident. Non-HLA or minor histocompatibility antigens (mHAs) resulting from a range of functional polymorphisms in the genome have been suggested to be capable of inducing strong cellular immune responses. In some embodiments, the nucleic acid library from the initial sample is sequenced and assessed for the detection, diagnosis, or prognosis of organ transplant acceptance or rejection in a subject.

D. Microbe or Pathogen Detection and Quantification

The methods can be used for detecting a pathogenic infection in a subject, as well as the symbiotic presence of microbes in a host, such as commensals and a normal host microbiome. In some embodiments, the methods may provide a more comprehensive view of the state and diversity of the infection or symbiotic microbes in a subject. For example, the identification of both RNA and DNA in a sample may be useful to detect both RNA and DNA type viruses, as well as bacterial or fungal genomic DNA and transcriptomic RNA. Such process may also be able to differentiate between latent infection (e.g., which might be indicated by the presence of integrated retroviral DNA) versus active infection (e.g., which might be indicated by the presence of viral RNA from intact viral particles). Such processes may also be able to detect drug resistance and origin of infection and analyze host response. Such analyses may include analysis of cell-free, circulating nucleic acids, or degraded nucleic acids e.g., for microbial or viral infection identification.

In an infected sample, nucleic acid forms within a given sample may include a variety of different structural forms and hybrids of those forms, including DNA and RNA, single and double-stranded forms of these, and structured and unstructured forms of these. By way of example, in the case of pathogen identification, it will be appreciated that pathogenic organisms may include a variety of chemical and/or structural forms of nucleic acids that may be used in their identification. As another example, pathogenic organisms may also include chemical modifications of DNA and RNA, some which may confer pathogenicity or make a pathogenic microbe harmless.

In some embodiments, the nucleic acid library from the initial sample is sequenced and assessed for detecting a pathogenic infection in a subject, as well as the symbiotic presence of microbes in a host, such as commensals and a normal host microbiome.

In some embodiments, pathogens are one or more of the species or strains of microbes described elsewhere herein.

IX. Kits and Systems

A. Kits or Systems

The methods of the disclosure can include a kit or system. The kit or system of the current invention comprises one or more process control molecules, wherein the kit or system excludes materials for extraction of the nucleic acids prior to generating the nucleic acid library from the initial sample. The subject reagents and kits thereof may vary greatly. Reagents of interest include reagents specifically designed for use in identification, detection, and/or quantitation of one or more pathogen or microbe nucleic acids in a sample obtained from a subject infected with a pathogen or microbe or at risk of infection. The kit or system may further comprise a software package for data analysis, which may include reference profiles for comparison with the test profile from a clinical sample, and in particular may include reference databases. The kits or systems may also comprise reagents such as buffers and water.

Such kits or systems may also include information, such as scientific literature references, package insert materials, clinical trial results, and/or summaries of these and the like. Such kits or systems may also include instructions to access a database. Kits or systems described herein can be provided, marketed and/or promoted to health providers, including physicians, nurses, pharmacists, formulary officials, and the like. Kits or system may also be marketed directly to the consumer.

The kit or system can further comprise an apparatus for detection and/or computer control systems with machine-executable instructions to implement the methods. In some embodiments, computer control systems are further programmed for conducting genetic analysis. Detection systems that can be used including, but are not limited to, sequencing, digital PCR, ddPCR, quantitative PCR (e.g., real-time PCR), or by a microfluidic device, microarray, or the like.

B. Hardware Systems

A kit or system can include a nucleic acid sequencer (e.g., DNA sequencer, RNA sequencer) for generating DNA or RNA sequence information. The kit or system may further include a computer comprising software that performs bioinformatics analysis on the DNA or RNA sequence information. Bioinformatics analysis can include, without limitation, assembling sequence data, detecting and quantifying genetic variants in a sample, including germline variants and somatic cell variants (e.g., a genetic variation associated with cancer or pre-cancerous condition, a genetic variation associated with infection), detecting presence and measuring the abundance of microbe nucleic acids, detecting site of infection, detecting the state of infection, detecting the risk of organ rejection in a transplant patient, and/or detecting potential for drug resistance. One skilled in the art would appreciate other bioinformatics analysis.

Sequencing data may be used to determine genetic sequence information, such as, for example, without limitation, species information, ploidy states, the identity of one or more genetic variants, as well as a quantitative measure of the variants, including relative and absolute relative measures. The sequencing may be unbiased and may involve sequencing all, substantially all, or some (e.g., greater than about 0.01%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 20%, about 30%, about 40%, about 50%, about 60%, about 70%, about 80%, or about 90%) of the nucleic acids in a sample. Sequencing can be selective, e.g., directed to portions of the genome of interest. For example, many select genes (and mutant forms of these genes) are known to be associated with antibiotic resistance, drug resistance, genetic disorders, and various cancers. Many select genes (and mutant forms of these genes) associated with antibiotic resistance, drug resistance, genetic disorders, and various cancers are also known to be amplified. Sequencing of the select genes, portions of genes, or non-genes along with other genes or sequences may suffice for the analysis desired. Polynucleotides mapping to specific loci in the genome that are the subject of interest can be isolated for sequencing by, for example, sequence capture or site-specific amplification.

C. Computer Control Systems

Figure 12:
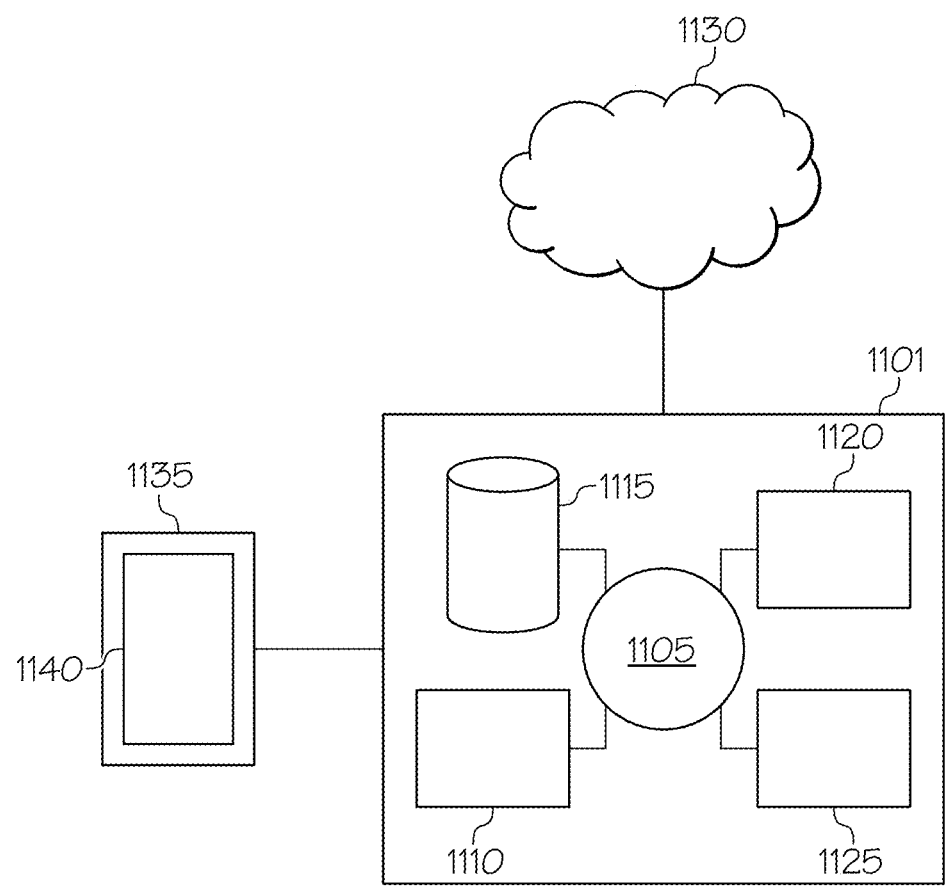
FIG. 12 depicts a computer control system that is programmed or otherwise configured to implement the methods and systems provided herein.
Figure 13A:
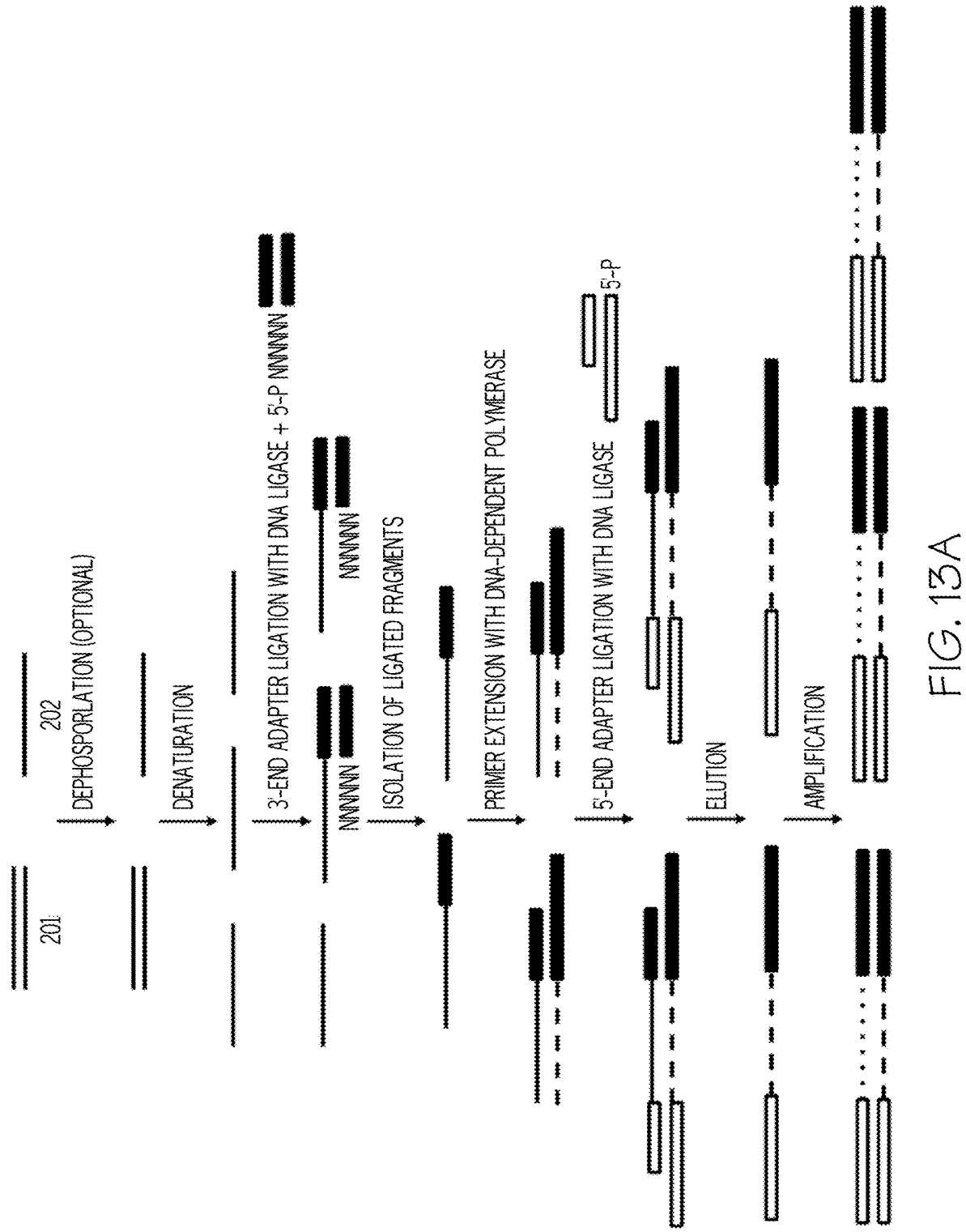
FIG. 13A and FIG. 13B are schematics of exemplary methods for sequencing library generation from either double-stranded nucleic acids (201) and/or single-stranded nucleic acids (202).
Figure 13B:
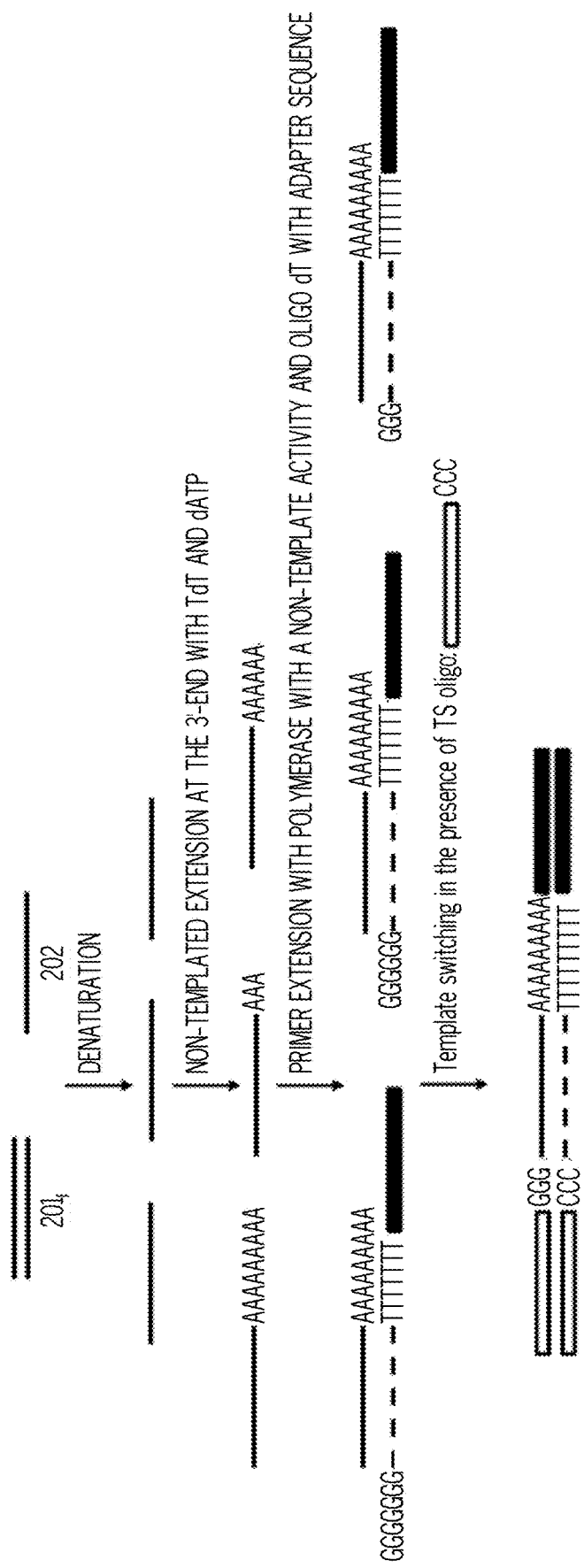

The kit or system can also include computer control systems with machine-executable instructions to implement the methods. FIG. 12 shows a computer system 1201 that is programmed or otherwise configured to implement methods of the present disclosure.

The computer system 1201 includes a central processing unit (CPU, also "processor" and "computer processor" herein) 1205, which can be a single core or multi core processor, or a plurality of processors for parallel processing. The computer system 1201 also includes memory or memory location 1210 (e.g., random-access memory, read-only memory, flash memory), electronic storage unit 1212 (e.g., hard disk), communication interface 1220 (e.g., network adapter) for communicating with one or more other systems, and peripheral devices 1225, such as cache, other memory, data storage and/or electronic display adapters. The memory 1210, storage unit 1212, interface 1220, and peripheral devices 1225 are in communication with the CPU 1205 through a communication bus (solid lines), such as a motherboard. The storage unit 1212 can be a data storage unit (or data repository) for storing data. The computer system 1201 can be operatively coupled to a computer network ("network") 1230 with the aid of the communication interface 1220.

The network 1230 can be the Internet, an internet and/or extranet, or an intranet and/or extranet that is in communication with the Internet. The network 1230 in some embodiments is a telecommunication and/or data network. The network 1230 can include one or more computer servers, which can enable distributed computing, such as cloud computing. The network 1230, in some embodiments with the aid of the computer system 1201, can implement a peer-to-peer network, which may enable devices coupled to the computer system 1201 to behave as a client or a server.

The CPU 1205 can execute a sequence of machine-readable instructions, which can be embodied in a program or software. The instructions may be stored in a memory location, such as the memory 1210. The instructions can be directed to the CPU 1205, which can subsequently program or otherwise configure the CPU 1205 to implement methods of the present disclosure. Examples of operations performed by the CPU 1205 can include fetch, decode, execute, and writeback.

The CPU 1205 can be part of a circuit, such as an integrated circuit. One or more other components of the system 1201 can be included in the circuit. In some embodiments, the circuit is an application specific integrated circuit (ASIC).

The storage unit 1212 can store files, such as drivers, libraries and saved programs. The storage unit 1212 can store user data, e.g., user preferences and user programs. The computer system 1201 in some embodiments can include one or more additional data storage units that are external to the computer system 1201, such as located on a remote server that is in communication with the computer system 1201 through an intranet or the Internet.

The computer system 1201 can communicate with one or more remote computer systems through the network 1230. For instance, the computer system 1201 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1201 via the network 1230.

The kit or system can be implemented by way of machine (e.g., computer processor) executable code stored on an electronic storage location of the computer system 1201, such as, for example, on the memory 1210 or electronic storage unit 1212. The machine executable or machine readable code can be provided in the form of software. During use, the code can be executed by the processor 1205. In some embodiments, the code can be retrieved from the storage unit 1212 and stored on the memory 1210 for ready access by the processor 1205. In some situations, the electronic storage unit 1212 can be precluded, and machine-executable instructions are stored on memory 1210.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Parts of the kits and systems, such as the computer system 1201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1201 can include or be in communication with an electronic display 1235 that comprises a user interface (UI) 1240 for providing, an output of a report, which may include a diagnosis of a subject or a therapeutic intervention for the subject. Examples of UI's include, without limitation, a graphical user interface (GUI) and web-based user interface. The analysis can be provided as a report. The report may be provided to a subject, to a health care professional, a lab-worker, or other individual.

Methods and systems of the present disclosure can be implemented by way of one or more algorithms. An algorithm can be implemented by way of software upon execution by the central processing unit 1205. The algorithm can, for example, facilitate the enrichment, sequencing and/or detection of pathogen or microbe or other target nucleic acids.

Information about a patient or subject can be entered into a computer system, for example, patient background, patient medical history, or medical scans. The computer system can be used to analyze results from a method described herein, report results to a patient or doctor, or come up with a treatment plan.

EXAMPLES

Example 1: Improved Recovery of Host and Microbial Cell-Free Nucleic Acid Fragments A proof of concept study was conducted to determine if a library made directly from plasma could detect pathogens at a similar or better level than a process that uses extraction prior to the start of library generation. An asymptomatic plasma sample spiked with enzymatically sheared genomic DNA isolated from *Escherichia coli, Aspergillus fumigatus, Staphylococcus epidermidis*, and *Pseudomonas aeruginosa* were processed into sequencing libraries using either the direct-to-library protocol (i.e., excluding extraction, the right side of FIG. 2A) or one that uses extraction (i.e., including extraction, the left side of FIG. 2A).

Asymptomatic plasma was thawed and 10 mL of the plasma was spiked with enzymatically sheared genomes of human pathogens, purchased in purified form from ATCC (American Type Culture Collection, Manassas Historic District, VA). Selected human pathogens were *Aspergillus fumigatus, Escherichia coli, Pseudomonas aeruginosa*, and *Staphylococcus epidermidis*. Purified genomes of selected human pathogens were sheared to the average lengths typical for microbial cell-free nucleic acids (see e.g., Burnham P., et al., (2016) *Scientific Reports* 6, Article number: 27859, which is incorporated by reference herein in its entirety, including any drawings) and added in 1:10:1:1 molar ratio, respectively. Six 1 mL aliquots of asymptomatic plasma with sheared human pathogens were prepared and each aliquot spiked with 10 µL of Spike-in master mix containing a unique Spike ID (see below). Also, a dilution series (See, for example, U.S. Ser. No. 62/644,357, which is incorporated by reference herein in its entirety, including any drawings) of asymptomatic plasma without sheared human pathogens was performed to determine the endogenous human microbes in the asymptomatic plasma used in this Example. In addition, eight 1 mL aliquots of Negative Control Buffer (10 mM Tris-HCl (pH 8.0), 0.1 mM EDTA) were spiked with 10 µL of Spike-in master mix containing a unique Spike ID (see below). After the addition of enzymatically sheared human pathogens and spike-in master mix, three 1 mL aliquots of spiked plasma and four Negative Control Buffer aliquots were centrifuged at 16000 g's for 10 min at 20° C. to obtain cell-free plasma fraction that was used in the process utilizing extraction (FIG. 2A, left) only. The remaining three aliquots of spiked asymptomatic plasma and four aliquots of Negative Control Buffer were not centrifuged, and used in direct-to-library process (FIG. 2A, right) only.

Spike-in Master Mix:

A set of process control molecules were pre-mixed together in a single Spike-in Master Mix, with each Spike-in Master Mix containing a unique "ID Spike" process control molecule, See, for example, U.S. Pat. No. 9,976,181. Spike-in Master Mix contained three classes of molecules: ID Spike molecules, SPANK molecules, and SPARK molecules. The latter group of molecules was composed of two classes of SPARKs: GC dSPARKs and Long SPARKs. The molar concentration of the ID Spike, SPANK molecules, and long SPARK molecules in Spike-in Master Mix was 10 pM per molecule while GC dSPARK molecules were present at 1 pM per molecule.

"ID Spike" Molecules

Each sample received a unique ID Spike double-stranded DNA molecule characterized by a 100 base pairs long unique sequence that was not present in any reference genome available in public databases at the time of processing.

SPANK Molecules

SPANK molecules used were a pool of double-stranded DNA molecules, each 75 base pairs long with identical 3'-end and 5'-end sequences that were not present in any reference genome available in public databases at the time of processing. In addition, two stretches of 8 base pairs nested between the constant 3'-end and 5' end sequences were present and fully degenerate within the pool. The pool of SPANK molecules contained $4^{16}$ unique SPANK molecules. The two degenerate stretches were separated by a stretch of four non-degenerate bases.

SPARK Molecules

A GC Spike-in Panel was a set of molecules 32, 42, 52, and 75 base pairs long where 7 different sequences with GC content 20%, 30%, 40%, 50%, 60%, 70%, and 80% were included for each length. Like some of the other molecules provided above, GC dSPARK sequences did not occur in the available reference genomes. A Long SPARK sequence set was a group of 4 non-natural sequences, each with 50% GC content and lengths of 100 base pairs, 125 base pairs, 150 base pairs, and 175 base pairs. A complete set of SPARK molecules contained 32 different sequences.

Extraction of Cell-Free DNA (cfDNA) from Cell-Free Plasma

For the process which included an extraction step (as set forth in the left process in FIG. 2A), cell-free DNA was extracted from cell-free plasma samples of spiked asymptomatic plasma and negative controls using the MagBind® Circulating DNA (Omega Bio-tek, Norcross, GA) according to the manufacturer's protocol. Briefly, four 250 µL aliquots of spiked cell-free asymptomatic plasma containing enzymatically sheared human pathogens and four 250 µL aliquots of spiked negative controls were each mixed with Proteinase K, followed by the addition of DCL Buffer (Omega Bio-tek, Norcross, GA). Briefly, the process was performed according to the manufacturer's recommended protocol. Finally, the pelleted magnetic beads were resuspended in Elution Buffer (Omega Bio-tek, Norcross, GA) to elute the extracted cell-free nucleic acids.

Sequencing Library Generation

Sequencing libraries were prepared following the process outlined below. For the process that included extraction (FIG. 2A, left), 5 µL of extracted cell-free DNA from above was used as the library input. For the direct-to-library process (FIG. 2A, right), 5 µL of spiked asymptomatic plasma was used as the library input.

Step 2.1: Manufacturing 3'-end adapter hybrid. Oligomers A and B (Table 1) were purchased from IDT (Coralville, IA) and separately dissolved in 1×IDTE (IDT, Coralville, IA) at final concentration of 100 µM. Before use, the oligomers were enzymatically purified in separate reactions by mixing 200 µL of 100 µM oligomer A or B, 100 µL 10×NEBuffer 2 (NEB, Ipswich, MA), 10 µL Klenow fragment (50 u/µL, NEB, Ipswich, MA), 50 µL T4 PNK (10 u/µL, Thermo-Fisher Scientific, Waltham, MA), and 640 µL Nuclease-free water, followed by incubation at 37° C. for 20 min, and thermal deactivation at 95° C. for 1 min. After thermal deactivation, the enzymatically purified oligos A and B were mixed in an equimolar ratio without prior purification, and hybridized with the following thermal program: 95° C. for 10 s, cooling to 14° C. at 0.1° C./s, 5 min 14° C., cool down to 4° C. The 3'-end adapter hybrid was stored at −20° C. before use.

Step 2.2: Manufacturing 5'-end adapters. Oligomers C and D (Table 1) were purchased from IDT (Coralville, IA) and individually dissolved in 1×IDTE (IDT, Coralville, IA) at final concentration of 500 µM. In order to obtain 5'-end adapter hybrid, 200 µL of 500 µM oligomer C and 200 µL of 500 µM oligomer D were mixed together and supplemented with 80 µL of Hybridization Buffer (0.95× TE, 250 mM NaCl). The oligomer annealing was then performed with the following temperature reaction: 95° C. for 10 s, cooling to 14° C. at 0.1° C./s, 5 min 14° C., cool down to 4° C. The resulting 5'-end adapter hybrid solution was then diluted with equal volume of 1×IDTE and stored at −20° C. before use. 5'-end adapters may be attached to a 3'-end of a complementary nucleic acid sequence.

TABLE 1

List of oligomers used in the Examples. All oligomers were purchased from IDT (Coralville, IA); nucleotide and all modification annotations are adopted from IDT.

| Name of the oligomer | Sequence (annotation adopted from IDT) |
|---|---|
| A | /5Phos/AGATCGGAAG/iSpC3/iSpC3/iSpC3/iSpC3/iSpc3/iSpC3/iSpC3/iSpC3/iSpC3/iSpC3/3BioTEG/ (SEQ ID NO: 1) |
| B | /5Sp9/AA/iSp9/CTTCCGATCTNNNNNN/3AmMO/ (SEQ ID NO: 2) |
| C | CGACGCTCTTC/3ddC/ (SEQ ID NO: 14) |
| D | /5Phos/GGAAGAGCGTCGTGTAGGGAAAGAG*T*G*T*A (SEQ ID NO: 15) |

TABLE 1-continued

List of oligomers used in the Examples.
All oligomers were purchased from IDT
(Coralville, IA); nucleotide and all modification annotations are adopted from IDT.

| Name of the oligomer | Sequence (annotation adopted from IDT) |
|---|---|
| Extension Primer | GTGACTGGAGTTCAGACGTGTGCTCTTCC*GA*TC*T (SEQ ID NO: 16) |
| Sequencing Primer | ACACTCTTTCCCTACACGACGCTCTTCC (SEQ ID NO: 17) |
| RNA splint oligo | /5Sp9/AA/iSp9/rCrUrUrCrCrGrArUrCrUrNrNrNrNrNrN/3AmMO/ (SEQ ID NO: 18) |

Figure 2A:
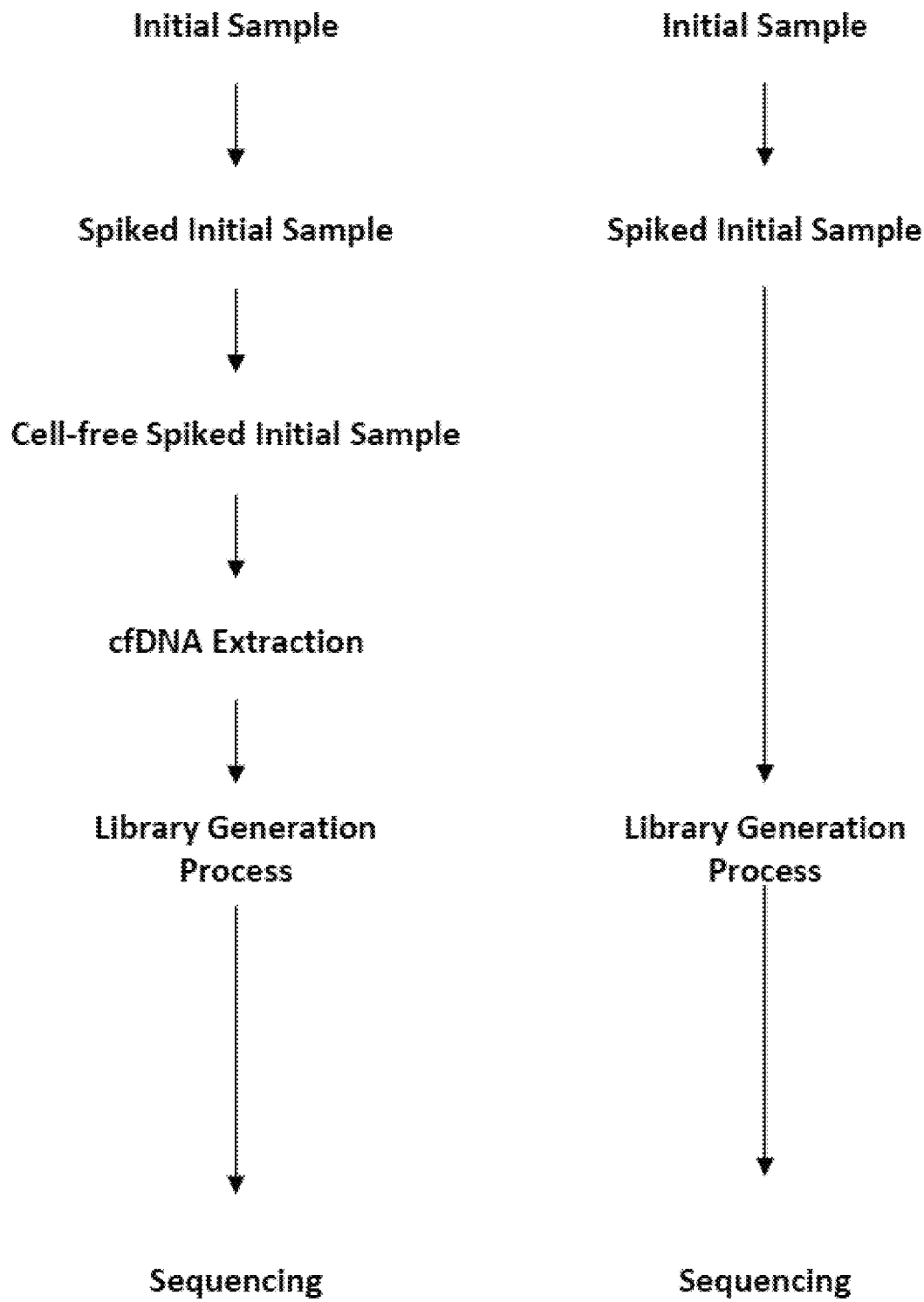
FIG. 2A depicts two processes, one that excludes extraction and one that includes extraction. The process flow schematic on the left includes the steps of obtaining the cell free spiked initial sample and cfDNA extraction; process flow schematic on the right shows the direct to library process that does not include an extraction step.

Step 2.3: Dephosphorylation and denaturation. 5 µL of spiked plasma sample (direct-to-library process; FIG. 2A, right) or 5 µL of cell-free DNA extract (process with extraction; FIG. 2A, left) was mixed with 41.5 µL of Dephosphorylation Master Mix (8.0 µL 10× T4 RNA Ligase Reaction Buffer (NEB, Ipswich, MA), 0.2 µL 10% Tween-20, 1.0 µL FastAP (1 u/µL, Thermo-Fisher Scientific, Waltham, MA), 31.4 µL Nuclease-free water), mixed well, and incubated at 37° C. for 10 min, followed by 2 min incubation at 95° C. to denature the molecules in the samples. While still at 95° C. the reaction mixture was transferred immediately on ice to prevent renaturation of the nucleic acids. The library reactions using unprocessed spiked asymptomatic plasma as their inputs (direct-to-library process; FIG. 2A, right) were centrifuged at 1600 g's, and 4° C. for 5 min to pellet the precipitate. Supernatant was collected and used in the next reaction step. The library reactions using extracted cell-free DNA as their inputs were not centrifuged and were instead directly taken into Step 2.4.

Step 2.4: 3'-end adapter ligation. 32 µL 50% PEG-8000, 0.4 µL 100 mM ATP, 1 µL 10 µM 3'-end adapter hybrid, and 1 µL T4 DNA Ligase (30 u/µL, Thermo-Fisher Scientific, Waltham, MA) were added to the reaction mixture resulting from the previous step. The mixture was mixed well, and incubated at 37° C. for 30 min, followed by denaturation and inactivation step at 95° C. for 1 min.

Step 2.5: Magnetic bead immobilization. Per library reaction, 20 µL of Dynabeads™ MyOne™ Streptavidin C1 magnetic beads were pre-washed with Bead-binding buffer (1 M NaCl, 10 mM Tris-HCl (pH 8.0), 1 mM EDTA (pH 8.0), 0.05% Tween-20 and 0.5% SDS) and resuspended in 250 µL of Bead-binding buffer. The resuspended magnetic beads were added to the final reaction mix from Step 2.2. The resulting mixture was incubated at ambient temperature for 20 min while constantly keeping the beads homogeneously dispersed in the mix. After a 20 min incubation, the tube with the sample was placed on a magnet stand to pellet the beads. The supernatant was collected and discarded. The remaining magnetic beads were washed with 200 µL Buffer A (0.1 M NaCl, 10 mM Tris-HCl (pH 8.0), 1 mM EDTA (pH 8.0), 0.05% Tween-20 and 0.5% SDS), the magnetic beads were pelleted and the supernatant discarded. The remaining magnetic beads were resuspended in 100 µL Stringency Buffer (0.1×SSC and 0.1% SDS), and the suspension was incubated at 45° C. for 4 min, when it was placed on the magnet stand to pellet the beads. The supernatant was discarded, the remaining beads were resuspended in 200 µL Buffer B (0.1 M NaCl, 10 mM Tris-HCl (pH 8.0), 1 mM EDTA (pH 8.0) and 0.05% Tween-20) and pelleted on the stand. The supernatant was discarded, and the remaining beads were resuspended in the Primer Extension Master Mix (see Step 2.4).

Step 2.6: Primer Extension. The pelleted magnetic beads were resuspended in Primer Extension Master Mix (5 µL 10×10X REact® 2 Buffer (Thermo-Fisher Scientific, Waltham, MA), 0.4 µL 25 mM per each dNTP mix (Thermo-Fisher Scientific, Waltham, MA), 0.25 µL 10% Tween-20 and 1 µL 100 µM Extension Primer (Table 1), 41.35 µL Nuclease-free water). The resulting suspension was incubated at 65° C. for 2 min, and immediately placed on ice. 2 µL Klenow fragment (4 u/µL, Thermo-Fisher Scientific, Waltham, MA) was added to the mixture, mixed well, and placed at 25° C. for 5 min, while keeping the suspension homogeneous. After 5 min, the temperature was raised to 35° C., and incubated for 25 min, while keeping the suspension homogeneous. After, the suspension was placed on the magnet stand to pellet the beads. The supernatant was collected and discarded. The remaining magnetic beads were washed with Buffer A (0.1 M NaCl, 10 mM Tris-HCl (pH 8.0), 1 mM EDTA (pH 8.0), 0.05% Tween-20 and 0.5% SDS), the magnetic beads were pelleted and the supernatant was discarded. The remaining magnetic beads were resuspended in Stringency Buffer (0.1×SSC and 0.1% SDS), and the suspension was incubated at 45° C. for 4 min, when it was placed on the magnet to pellet the beads. The supernatant was discarded, the remaining magnetic beads were resuspended in Buffer B (0.1 M NaCl, 10 mM Tris-HCl (pH 8.0), 1 mM EDTA (pH 8.0) and 0.05% Tween-20) and pelleted on a magnet. The supernatant was discarded, and the remaining magnetic beads were resuspended in the 5'-end Ligation Master Mix (see Step 2.5).

Step 2.7: 5'-end adapter ligation. The pelleted beads were resuspended in 5'-end Ligation Master Mix (10 µL 10× T4 DNA Ligase Buffer (Thermo-Fisher Scientific, Waltham, MA), 10 µL 50% PEG-4000 (Thermo-Fisher Scientific, Waltham, MA), 2 µL 100 µM 5'-end adapter hybrid, 0.25 10% Tween-20, 0.332 µL T4 DNA Ligase (30 u/µL, Thermo-Fisher Scientific, Waltham, MA), 75.9 µL Nuclease-free water), and incubated at 25° C., while keeping the suspension homogeneous. After incubation, the suspension was placed on a magnet stand to pellet the beads. The supernatant was collected and discarded. The remaining beads were washed with Buffer A (0.1 M NaCl, 10 mM Tris-HCl (pH 8.0), 1 mM EDTA (pH 8.0), 0.05% Tween-20 and 0.5% SDS), pelleted, and the supernatant was discarded. The remaining magnetic beads were resuspended in Stringency Buffer (0.1×SSC and 0.1% SDS) and the suspension was incubated at 45° C. for 4 min, then placed on the magnet to pellet the beads. The supernatant was discarded, the remaining magnetic beads were resuspended in Buffer B (0.1 M NaCl, 10 mM Tris-HCl (pH 8.0), 1 mM EDTA (pH 8.0) and 0.05% Tween-20), and pelleted on a magnet. The supernatant was discarded and the remaining magnetic beads were resuspended in the Library Elution Buffer (see Step 2.8).

Step 2.8: Library Elution. The pelleted magnetic beads were resuspended in 50 µL Library Elution Buffer (10 mM Tris-HCl (pH 8.0), 0.1 mM EDTA, and 0.05% Tween-20), and incubated at 95° C. for 1 min to elute the library fragments off the beads. Next, the solution was placed immediately on a magnet to pellet the beads. 48 µL of the supernatant was then collected and placed in a new tube for amplification (see Step 2.9).

Step 2.9: Library Amplification. The library fragments in the eluate were amplified using AccuPrime™ Pfx DNA Polymerase (Thermo-Fisher Scientific, Waltham, MA) according to the manufacturer's recommendations, supplemented with indexing P5 and P7 primers purchased from IDT (Coralville, IA). Then the products were amplified using a thermocycler with the following temperature cycling program: Initial denaturation at 95° C. for 2 min, followed by 12 (direct-to-library process; FIG. 2A, right) or 10 (process with extraction; FIG. 2A, left) PCR cycles composed of cycle denaturation at 95° C. for 15 sec, cycle primer annealing at primer annealing at 60° C. for 30 sec, and primer extension at 68° C. for 1 min. In the final cycle, an extended primer extension step of 2 min was applied before cooling down to 4° C. Finally, the samples were purified using Agencourt® RNAClean® XP magnetic beads per the manufacturer's recommendations and quantified using HS D1000 ScreenTape System (Agilent Technologies, Santa Clara, CA) before running on a sequencer.

Sequencing and Attribution of Reads

The samples were sequenced to obtain sequence reads using a NextSeq™ 500 sequencer by Illumina. Sequencing was conducted following the manufacturer's instructions using Sequencing Primer (Table 1) as a custom Read 1 primer.

Primary sequencing output was demultiplexed by bcl2fastq v2.17.1.14 (with default parameters). Reads were aligned against human and synthetic (including process control molecules and sequencing adapter) references using Bowtie v2.2.4. Reads with alignments to either were set aside. Reads potentially representing human satellite DNA were also filtered via a k-mer based method. The remaining reads were aligned against a microorganism reference database using BLAST v2.2.30. Reads with alignments that exhibited both high percent identity and high query coverage were retained, with the exception of reads that aligned against any mitochondrial or plasmid reference sequences. PCR duplicates were removed based on their alignments.

Relative abundances were assigned to each taxon in a sample based on the sequencing reads and their alignments. For each combination of read and taxon, a read-sequence probability was defined that accounted for the divergence between the microorganism present in the sample and reference assemblies in the database. A mixture model was used to assign a likelihood to the complete collection of sequencing reads that included the read sequence probabilities and the (unknown) abundances of each taxon in the sample. An expectation-maximization algorithm was applied to compute the maximum likelihood estimate of each taxon abundance. From these abundances, the number of reads arising from each taxon were aggregated up the taxonomic tree.

A set of libraries was prepared from the respective Negative Control Buffers and processed and sequenced within each batch. Estimated taxon abundances from the negative control samples within the batch were combined to parameterize a model of read abundance arising from the environment with variations driven by counting noise. Statistical significance values was computed for each estimated taxon abundance and those within the CRR at high significance levels comprised candidate calls (i.e., significant calls). Final calls (i.e., reportable calls) were made after additional filtering is applied, accounting for read location uniformity, read percent identity, and cross-reactivity originating from higher abundance calls.

Figure 2B:
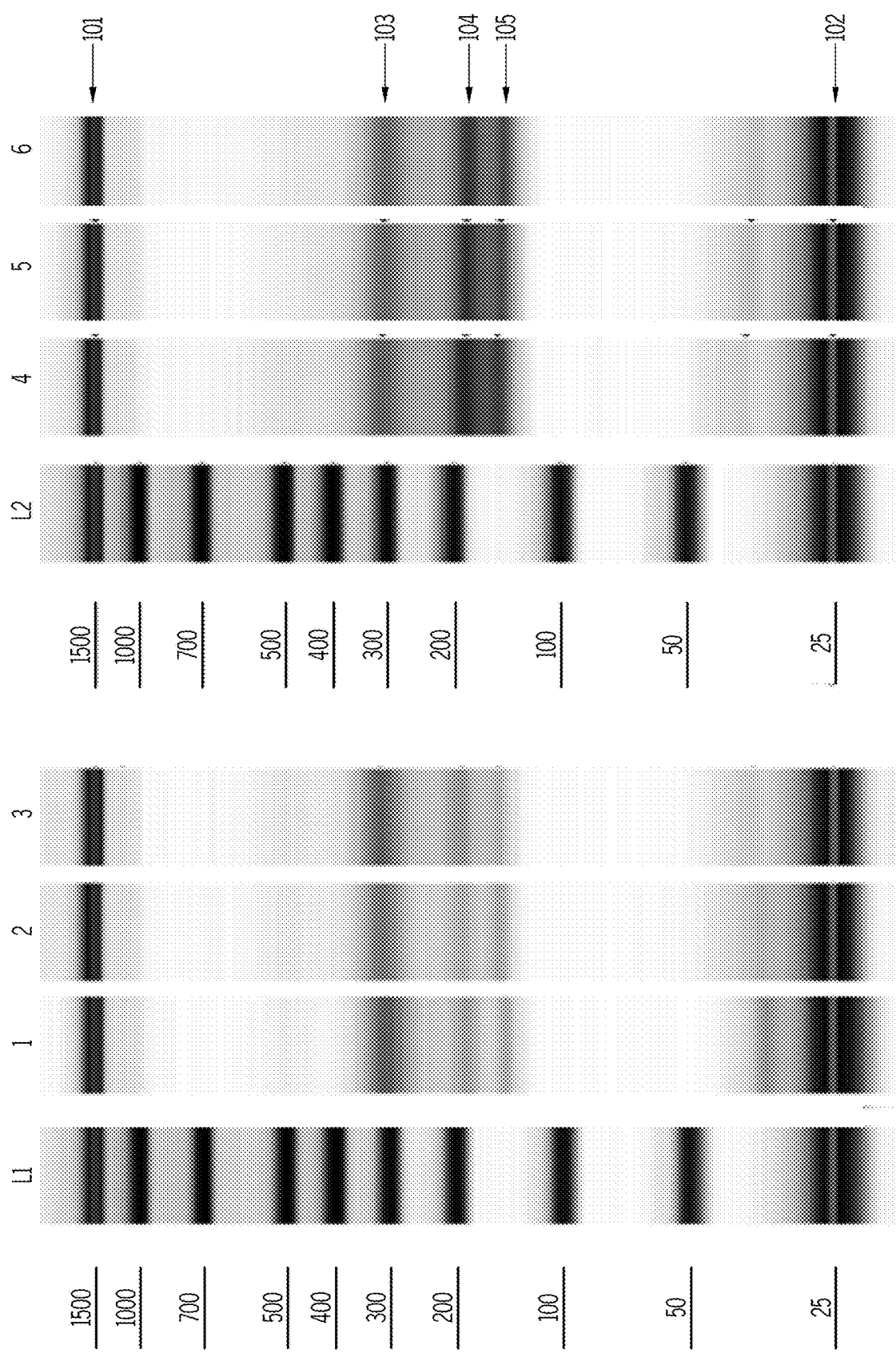
FIG. 2B depicts electrophoretic profiles of the library obtained with extraction (lanes 1, 2, and 3) and library obtained without extraction (lanes 4, 5, and 6). Lanes L1 and L2 contain electrophoretic size markers for double-stranded DNA.

FIG. 2B shows electropherograms of all six purified libraries obtained from spiked asymptomatic plasma samples using either the process with extraction (Lanes 1, 2, and 3) or direct-to-library process (Lanes 4, 5, and 6). Quantification of electrophoretic signal revealed a mean library yield of 0.42±0.07 ng per 1 µL of plasma, and 3.9±0.6 ng per 1 µL of plasma for the process with extraction, and direct-to-library process, respectively. Direct-to-library process resulted in approximately ten times higher yield per unit volume of plasma as compared to a process with extraction, demonstrating that the direct-to-library process prevented losses of nucleic acids, and therefore better recovery of the analyte. Furthermore, direct-to-library process recovered higher fraction of the nucleic acids shorter than 100 base pairs as determined from the electropherogram. Nucleic acids shorter than 100 base pairs represented, on average 40%±3%, and 69%±2% of the libraries obtained with the process including the extraction, and direct-to-library process, respectively.

Figure 2C:
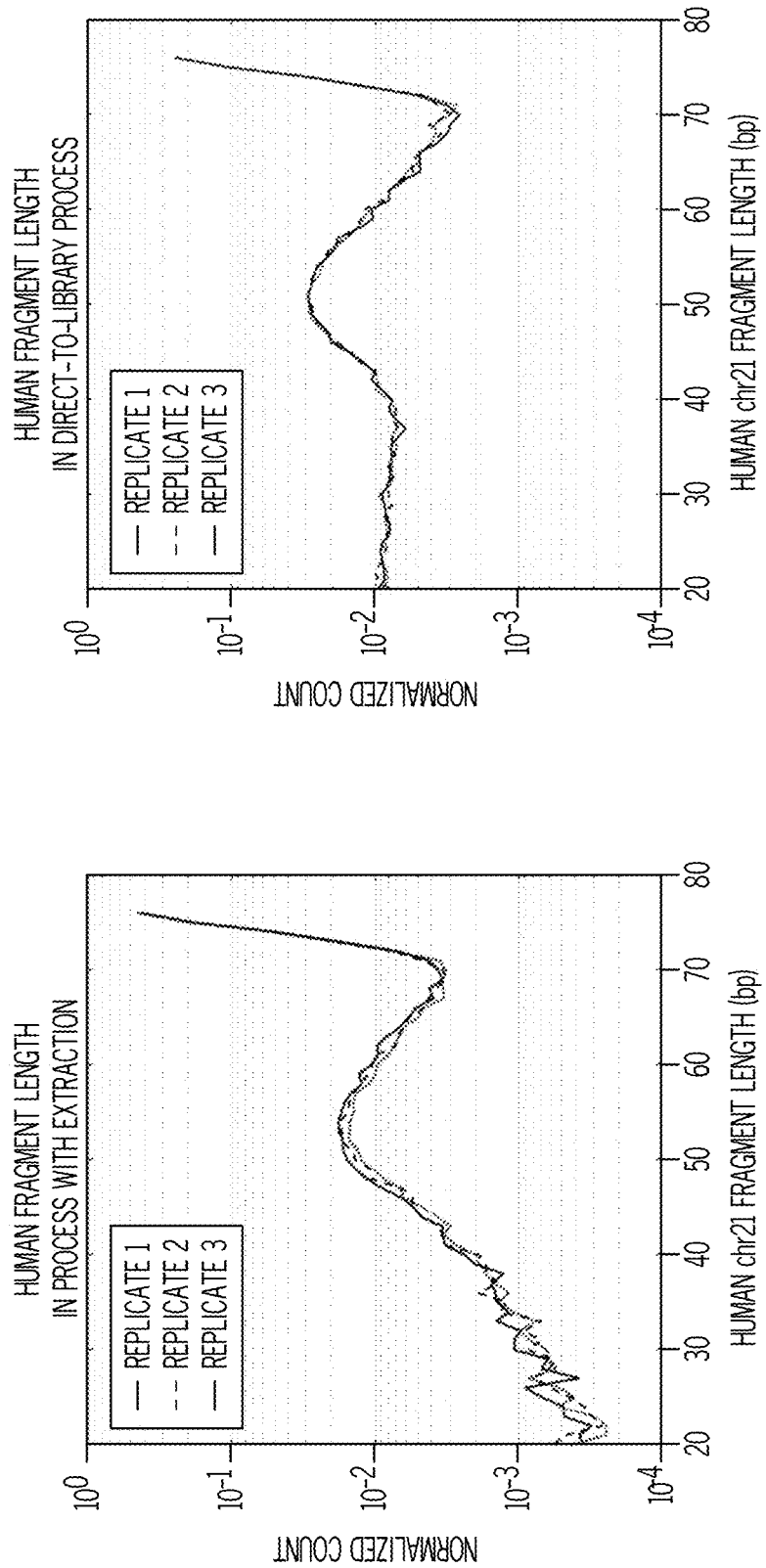
FIG. 2C depicts fragment length distributions of sequence reads mapping to human chromosome 21 reference sequence for process with extraction (left panel) and process without extraction (right panel)

The improved recovery of the short nucleic acid fragments by the direct-to-library process was confirmed by the analysis of sequencing reads mapping to human chromosome 21 reference sequence (FIG. 2C). FIG. 2B depicts electrophoretic profiles of the library obtained with extraction (Lane 1) and library obtained without extraction (Lane 2). Lane M contains double-stranded DNA ladder standard with fragment lengths noted to the left of the ladder in units of base pairs. 101 indicates a fully adapted nucleosomal fragment fraction; 102 indicates fully adapted short fragment fraction; 103 indicates adapter side-product of the library process employed; 104 indicates HS D1000 TapeStation Upper Marker; and 105 indicates HS D1000 TapeStation Lower Marker.

The comparison of the normalized fragment length distributions obtained with the process that included extraction (FIG. 2C, left panel) and direct-to-library process (FIG. 2C, right panel) demonstrated a better recovery of nucleic acid fragments shorter than 55 base pairs by the later process. The improvement was as high as an order of magnitude at the shorter edge of the mapped fragments.

In addition to efficiency of the short nucleic acid fragment recovery, the obtained sequencing data was analyzed for the efficiency of sheared human microbe fragment recovery. Table 2 shows the concentration of the sheared human microbe molecules in the libraries obtained from the spiked asymptomatic plasma using either the process with extraction or direct-to-library process. The concentration of the human microbe molecules is given in units of Molecules Per Microliter (MPM) of sample, a normalized quantity that gives the estimated number of unique nucleic acid fragments for an organism in 1 microliter of the initial sample. This calculation was derived from the number of unique or deduped sequences present for each organism normalized to the known quantity of synthetic spiked-in the initial plasma sample before the extraction (See U.S. Pat. No. 9,976,181). All human microbial nucleic acids added in a sheared form to the asymptomatic plasma were detected at higher MPM values in the libraries obtained with a direct-to-library process, demonstrating the superior ability of the direct-to-library process to recover the nucleic acid fragments with the properties of microbial cell-free nucleic acids. In addition, a microbe determined to be endogenous to the asymptomatic plasma used in this Example (i.e., *Helicobacter pylori*) also increased its MPM in the direct-to-library process as compared to the process with extraction.

TABLE 2

Human Pathogens detected by the processes utilizing extraction and direct-to-library process.

| Process with extraction | | Direct-to-Library Process | |
|---|---|---|---|
| Species Name | MPM | Species Name | MPM |
| Aspergillus fumigatus | 1759 ± 98 | Aspergillus fumigatus | 6310 ± 177 |
| Escherichia. Coli | 19223 ± 1270 | Escherichia. coli | 61052 ± 1245 |
| Pseudomonas aeruginosa | 2616 ± 86 | Pseudomonas aeruginosa | 2599 ± 102 |
| Staphylococcus epidermidis | 2027 ± 46 | Staphylococcus epidermidis | 6768 ± 156 |
| Helicobacter pylori(*) | 317 ± 65 | Helicobacter pylori(*) | 1176 ± 133 |

MPM's are given in mean MPM ± standard deviation, based on three libraries per condition.
(*)Microbes detected as endogenous microbes by the dilution series of the asymptomatic plasma Taken together, these results indicate that the omission of extraction step in the direct-to-library protocol resulted in an improved recovery of cell-free nucleic acids from plasma, in particular the fragments shorter than 100 base pairs. This was true for the host fraction of the cell-free nucleic acid pool as well as the sheared human microbial nucleic acids that were added as imitation of the microbial fraction of the cell-free nucleic acid pool.

Example 2: Direct-to-Library Protocol Reduces Environmental Contamination

Environmental contamination can result in performance bias and lower sensitivity for non-host species that are also present in the process reagents, process environment, process equipment, introduced by sample handling and operators, or non-host species that share sequence similarities with the contaminating non-host species. Environmental contamination is an inevitable phenomenon in lab processing of samples. Environmental contamination can include any contamination from the environment including, for example, without limitation, reagents, environmental factors, and even biological material such as skin from those processing sample. Reducing it leads to an improved sensitivity and specificity. This study was conducted to determine if direct-to-library process can reduce the amount of environmental contamination in the final library as compared to a process that uses nucleic acid extraction prior to starting the library synthesis. Eliminating the extraction step was found to reduce the environmental contamination in the final library.

The process with extraction and direct-to-library library process and subsequent sequencing as described in Example 1 were followed for negative control types of samples in order to assess and compare the levels of the contamination in both types of processes. Negative controls consisted of 500 µL of Negative Control Buffer (10 mM Tris-HCl (pH 8.0), 0.1 mM EDTA, 0.05 v/v % Tween-20) spiked with 5 µL of Spike-in master mix (see Example 1 for details). Four replicates of Negative control were converted to the libraries per each process under investigation here. The libraries were sequenced and the resulting data analyzed as described above.

Figure 3:
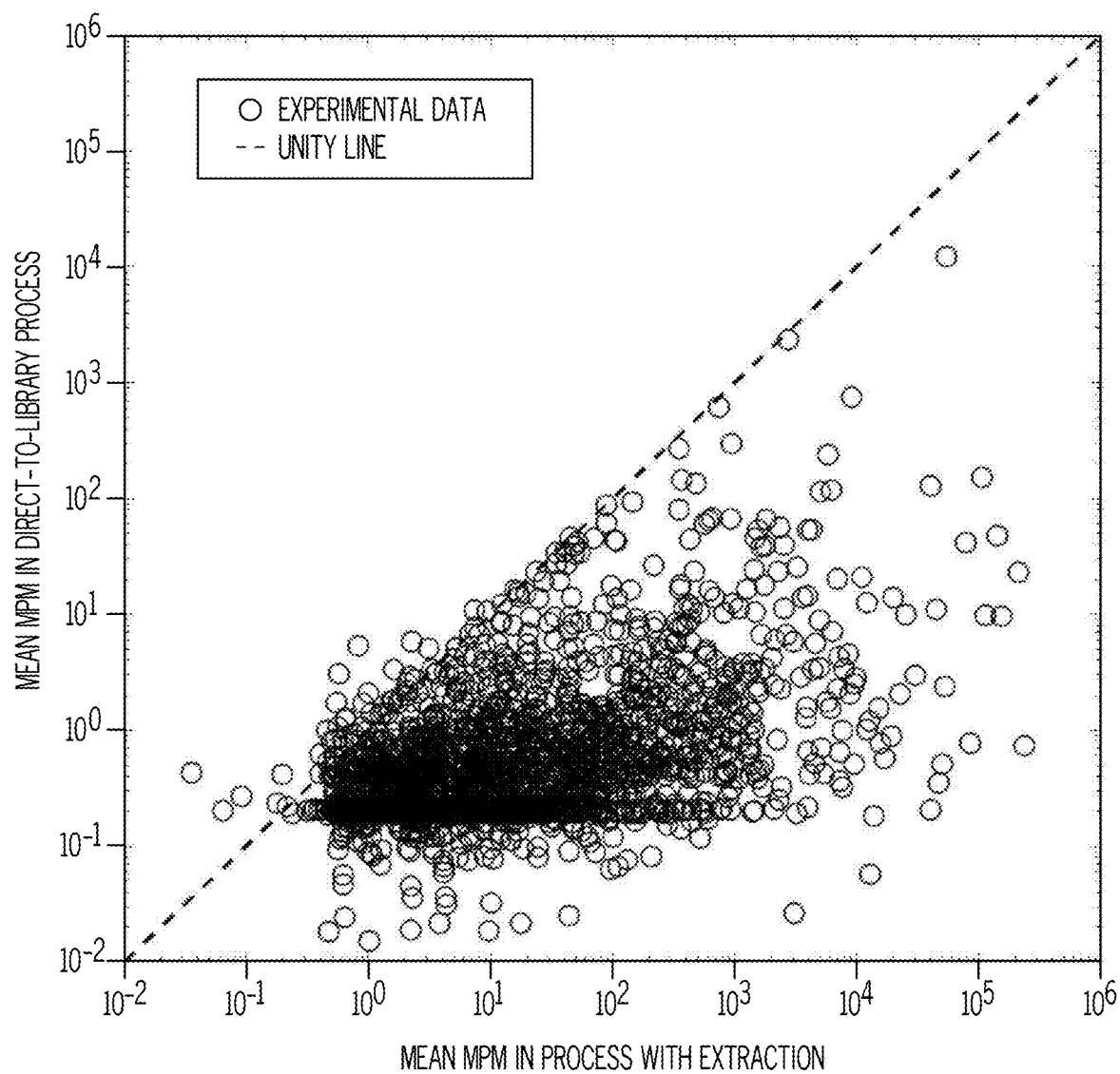
FIG. 3 depicts mean MPMs (Molecules Per Microliter, i.e., normalized per unique SPANK molecule or process control molecule) for environmental contaminants detected in the libraries obtained from negative controls using the process with extraction on the x-axis and without extraction on the y-axis.

The magnitude of the environmental contamination in each process was compared by contrasting the MPM values of the microbial species found in the Negative controls of each process. FIG. 3 plots the mean MPM detected from the process with extraction on the x-axis and the mean MPM detected from the direct-to-library process (i.e., without extraction) on the y-axis with the dotted diagonal line representing the unity line where y=x. Experimentally measured MPM values in the direct-to-library process were corrected by multiplying with a factor of 0.1, as the direct-to-library process utilized 10% of the sample volume of the process with extraction, resulting in ten times lower maximum unique SPANK count in the final library. Each point on the plot represents a single microbial species detected in either of the processes.

The process with extraction resulted in a higher environmental contamination (e.g., signal originating from the environment, process reagents, sample handling, and processing etc.) as revealed by higher MPMs of the process as compared to the direct-to-library process for almost all contaminating microbial species (FIG. 3). The reduction in the contamination signal as measured with MPMs can be as high as approximately five orders of magnitude. These observations suggested that the environmental contamination was considerably lower in the direct-to-library process when compared to the process with extraction.

Example 3: Reduced Length Bias and GC Bias and Increased Recovery of Single-Stranded Nucleic Acids Potential sources of performance bias can include bias in the form of length bias, bias from GC-content, and differential recovery of various structural forms of nucleic acids (e.g., differential recovery of single-stranded vs. double-stranded nucleic acids of the same length and GC-content). This study was conducted to determine if a library made by a direct-to-library process can reduce the amount of GC-content and length bias introduced during processing compared to a process that uses extraction. In addition, the two processes were evaluated for the extent of the differential recovery of single-stranded vs. double-stranded nucleic acids.

10 mL of frozen asymptomatic plasma was thawed, homogenized by gently inverting the tube ten times. Next, six 500 µL aliquots were transferred to six clean 1.5 mL LoBind tubes, and each aliquot was spiked with 5 µL of Spike-in master mix containing a unique ID Spike molecule (see Example 1 for details). In addition, six 500 µL aliquots of the same asymptomatic plasma were transferred to six clean 1.5 mL LoBind tubes, and spiked with 5 µL of a mixture containing only the sense single-strands of all GC dSPARKs and Long SPARKs at the same molar concentrations as in the Spike-in master mix. In addition to the asymptomatic samples, eight negative controls were prepared by aliquoting eight times 500 µL of Negative Control Buffer A (10 mM Tris-HCl (pH 8.0), 0.1 mM EDTA, 0.05 v/v % Tween-20), and spiking them individually with 5 µL of Spike-in master mix containing a unique ID Spike molecule (see Example 1 for details). Four replicates of spiked negative control, three asymptomatic plasma samples spiked with Spike-in master mix, and three asymptomatic plasma samples spiked with a mixture of sense single-stranded GC dSPARKs, and Long SPARKs were converted to the libraries per each process under investigation here. The process with extraction and direct-to-library process and subsequent sequencing and data analysis outlined in Example 1 were followed as set forth above.

GC dSPARK process control molecules can be used to monitor GC and length bias of each process. FIG. 4A1-4A4 contrasts GC-content bias as measured by GC dSPARK set resulting from a process with extraction (solid line and circles) and direct-to-library process (dashed lines and crosses). The results showed that direct-to-library process resulted in considerably reduced GC-content bias, in particular for the shorter GC dSPARK molecules (<75 base pairs) where process with extraction resulted in almost two orders of magnitude lower efficiency in recovery of the low GC-content GC dSPARKs as compared to GC dSPARK with high GC-content and the same length.

Figure 4C:
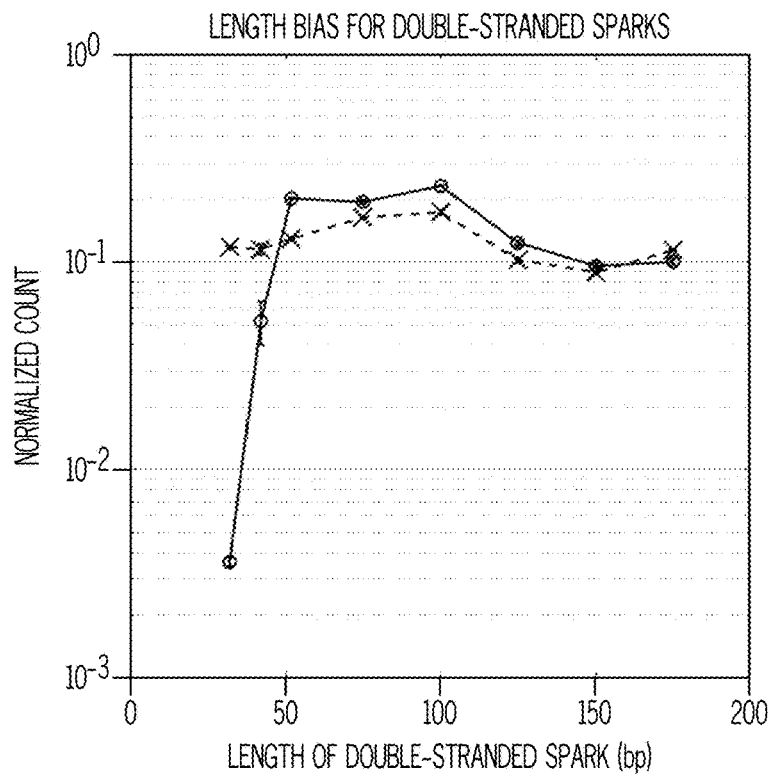
FIG. 4C depicts length bias for double-stranded SPARKs in the process with extraction (empty circles and solid line) and the process without extraction (crosses and dashed line).

GC-content bias of each process can be analyzed also by investigating GC-content distribution of sequencing reads that mapped to the human reference. (FIG. 4B1-4B2). FIG. 4C shows normalized counts for Long SPARKs and GC dSPARKs with 50% GC-content in order to visualize the length bias characteristic for a process with extraction (solid line, circles), and direct-to-library process (dashed line, crosses). Similarly as with human fragments in Example 1, here the process control molecules indicated a substantial improvement in the recovery of short nucleic acid fragments in the direct-to-library process as compared to the process with extraction.

Figure 4D:
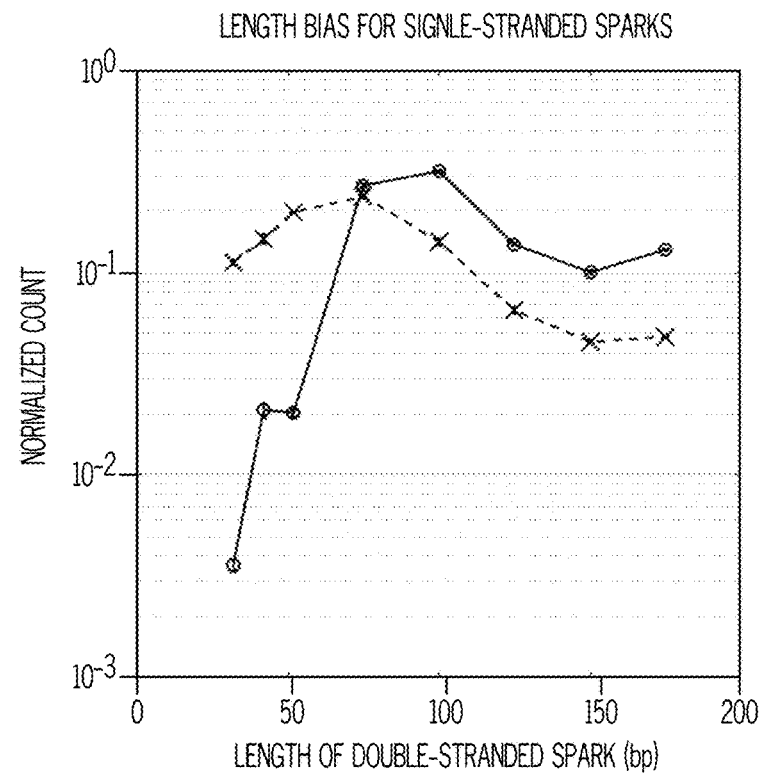
FIG. 4D depicts length bias for single-stranded SPARKs in the process with extraction (empty circles and solid line) and the process without extraction (crosses and dashed line).

Finally, length bias in the recovery of shorter single-stranded nucleic acids (e.g., <75 base pairs) was steeper than for shorter double-stranded nucleic acids in the process with extraction (solid lines with circles in FIG. 4C vs 4D). Here, direct-to-library process again helped to dramatically reduce this bias (FIG. 4D). The count of Long SPARK molecules was divided by a factor of 10 before normalizing the counts for FIGS. 4C and 4D as the Long SPARK molecules were added to the plasma sample at 10× molar concentration as compared to the individual GC dSPARK molecules.

Example 4: Reduction of Adapter Side-Product Fraction

Figure 5A:
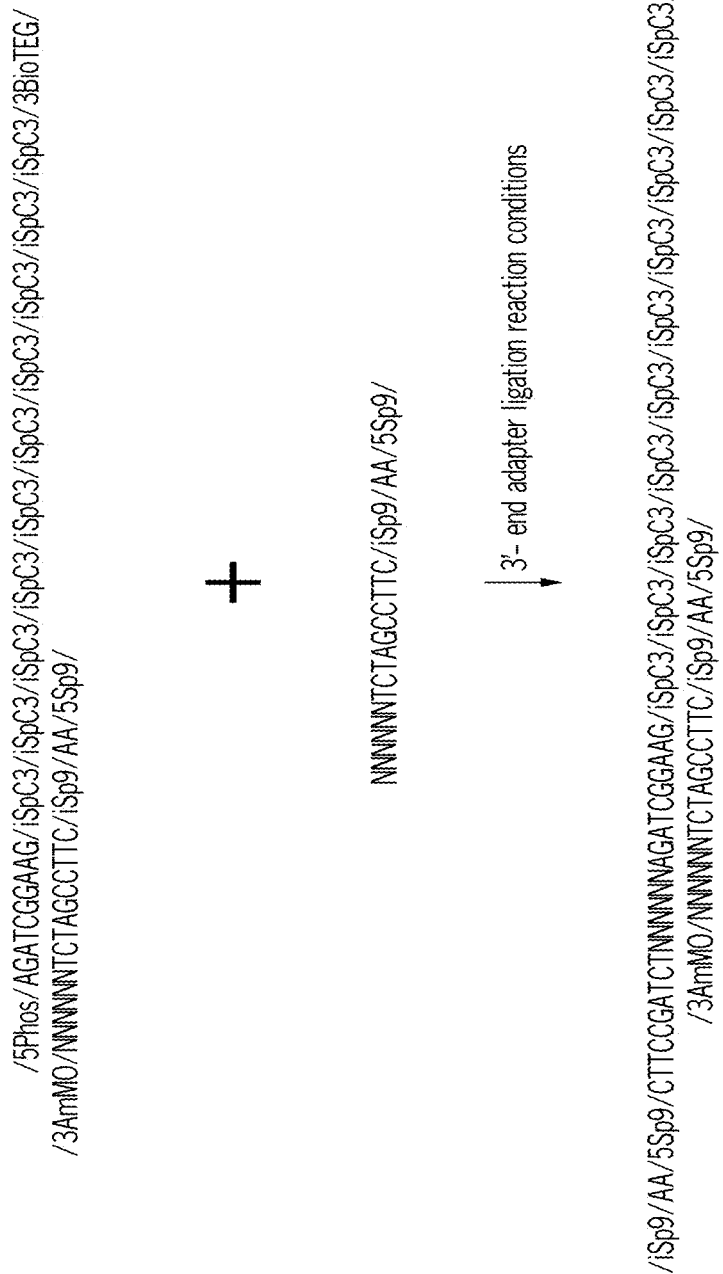
FIG. 5A depicts possible mechanisms of adapter side-product formation.

Adapter-side product is a group of products resulting from the library generation process described in Example 1. It can typically be detected in the electropherogram of the final library as a band at approximately 150 base pairs, if using the library generation process outlined in Example 1. For example, the band 105 in the electropherograms in FIG. 2B represents such products. The analysis of sequencing data obtained from the libraries generated by the library generation process described in Example 1 revealed possible mechanisms of adapter side-product formation (FIG. 5A). Briefly, if 3'-end unprotected DNA splint oligo (Oligo B in Table 1) hybridizes to an intact 3'-end adapter hybrid and forms a ligation product in 3'-end adapter hybrid ligation step of the library process of Example 1 then, its ligation products can be immobilized on the streptavidin-coated magnetic beads in a subsequent step which can result in a sequenceable product within the final library. Such sequenceable adapter side-product is an unwanted product that reduces the available sequencing space for targeted nucleic acids.

A potential way to reduce the yield of sequenceable side-products of 3'-end ligation is to replace DNA splint oligo (Oligo B in Table 1) with an RNA splint oligo (Table 1) in 3'-end adapter hybrid in order to inhibit primer extension reaction on adapter side-product when a DNA-dependent polymerase is used in the primer extension step. To test this hypothesis, RNA splint oligo (Table 1) was purchased from IDT (Coralville, IA) and dissolved in 1×IDTE at 100 µM concentration. Oligomer A (Table 1) were purchased from IDT (Coralville, IA) and separately dissolved in 1×IDTE (IDT, Coralville, IA) at a final concentration of 100 µM. Oligomer A was then enzymatically purified by mixing 20 µL of 100 µM oligomer A, 10 µL 10× T4 RNA Ligase Reaction Buffer (NEB, Ipswich, MA), 5 µL Klenow fragment (50 u/µL, Invitrogen, Carlsbad, CA), 5 µL T4 PNK (10 u/µL, Thermo-Fisher Scientific, Waltham, MA), and 60 µL Nuclease-free water, followed by incubation at 37° C. for 20 min, and thermal deactivation at 95° C. for 1 min. After thermal deactivation, the modified 3'-end adapter hybrid was prepared by mixing 25 µL of enzymatically purified oligomer A, 10 µL of 100 µM RNA splint oligo, 0.6 µL 5 M NaCl, 1 µL EDTA pH 8, and 10.9 µL Nuclease-free water. A hybridization reaction was performed with the following thermal program: 95° C. for 10 s, cooling to 14° C. at 0.1° C./s, 5 min 14° C., cool down to 4° C. The modified 3'-end adapter hybrid was stored at −20° C. until use in the library generation process. In order to generate a nucleic acid library using the modified 3'-end adapter hybrid, four 500 µL aliquots of 1×TET (10 mM Tris pH 8, 0.1 mM EDTA, 0.05 v/v % Tween-20) were first individually spiked with Spike-in master mix. Two aliquots were processed with a modified library process from Example 1, and the remaining two aliquots were processes according to an unmodified library process from Example 1. In the modified library process, modified 3'-end adapter hybrid and SplintR Ligase (NEB, Ipswich, MA) were used in place of 3'-end adapter hybrid, and T4 DNA Ligase in Step 2.4 in order to facilitate successful ligation of DNA fragments splinted by an RNA oligo. In addition, RNase inhibitor, SUPERase In™ RNase Inhibitor (Invitrogen, Carlsbad, CA) was added in Step 2.4 in order to minimize Rnase activity in the system. Finally, the use of a DNA-dependent polymerase in the primer extension step is critical to the efficient reduction in adapter side-product as it is incapable of translocating along an/the RNA template presented by the adapter side-product in primer extension step of the modified library process. Specifically, Klenow fragment was successfully used as such DNA-dependent polymerase in the primer extension step. The rest of the protocol followed the library steps outlined in Example 1.

Figure 5B:
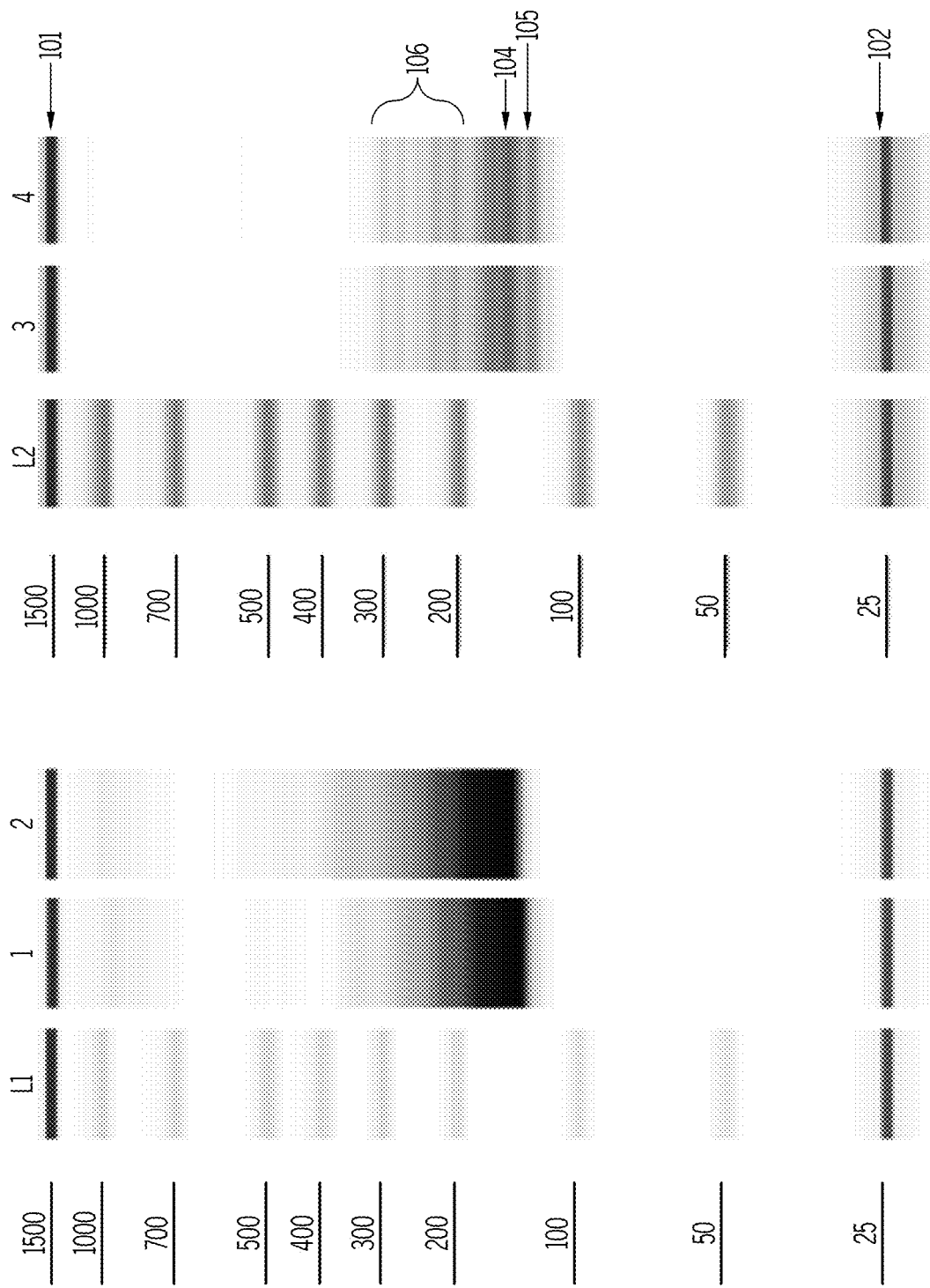
FIG. 5B depicts an electropherogram of nucleic acid libraries obtained with DNA splint oligo (two independent replicates in lanes 1 and 2) or with RNA splint oligo (two independent replicates in lanes 3 and 4).

FIG. 5B shows the electropherogram of the resulting nucleic acid libraries. The two libraries obtained with the library process utilizing RNA splint oligo (FIG. 5B, Lanes 4 and 5) showed substantial reduction in the adapter side-product (band 104 in FIG. 5B) as compared to the two libraries obtained with an unmodified library process (FIG. 5B, Lanes 1 and 2). The reduction in the adapter side-product was so efficient that the ladder pattern of the molecules forming the Spike-in master mix is detectable in the libraries obtained with the modified process (106 in FIG. 5B).

Example 5: Reduction of by-Product Formation

More reliable ways of suppressing the formation of the adapter dimer and adapter side-product are needed for a successful commercialization of a single-stranded nucleic acid library protocol. An approach was tested that is not based on preventing the unprotected fraction of the splint oligo from attaching to the biotinylated 3'-end adapter during the first ligation step but rather on preventing successful ligation of the 5'-end adapter to the same molecule during the second ligation step. A bulky moiety, a digoxigenin, is introduced to the 5'-end of the splint oligo, and adding anti-digoxigenin antibody to the bead-binding buffer during the immobilization of the successfully adapted products of the first ligation step on the surface of streptavidin-coated magnetic beads. This bulky moiety reduces the ability of T4 DNA ligase in the second ligation step to ligate 5'-end adapter to splint oligo hybrid rendering it un-amplifiable in the final PCR step.

Example 6: Detection of Microbial Signal in Clinical Samples

A proof of concept study was conducted to determine if a library made directly from plasma (i.e. direct-to-library) could detect pathogens at a similar or better level than a process that uses extraction. Clinical, assay control, and negative control samples were processed in parallel and in an identical manner, using either the direct-to-library protocol (i.e., excluding extraction, the right side of FIG. 2A) or one that uses extraction (i.e., the left side of FIG. 2A).
Clinical Samples:
21 plasma samples were collected from human subjects. Plasma was extracted from whole blood samples within 24 hours of sample collection. A modified version of the Fan H C et al., PNAS 2008; 105(42): 16266-16271 protocol was used, with only one centrifugation step, and stored at −80° C. until use. (Fan et al is incorporated by reference in its entirety herein, including any drawings).

Samples were thawed, and 1 mL of each plasma, assay control, and negative control sample was spiked with 10 µL of Spike-in Master Mix (see Example 1). If smaller volumes were received, a proportionally smaller volume of Spike-in Master Mix was added to maintain a constant concentration of the process control molecules in all of the initial samples and control samples.
Positive Assay Control Samples:
Two or one positive control, referred to as assay control samples (AC) were processed for each group of 18 or 21 clinical samples, respectively. AC samples were prepared from human asymptomatic plasma spiked with enzymatically sheared genomes of human pathogens, purchased in purified form from ATCC (American Type Culture Collection). Selected human pathogens were *Aspergillus fumigatus, Escherichia coli, Pseudomonas aeruginosa*, and *Staphylococcus epidermidis*. 10 µL of Spike-in Master Mix (see Example 1) were added per 1 mL of AC sample.
Negative Control Samples:
Four 500 µL negative control samples (EC) per 18 or 21 plasma samples were made from aqueous buffer (10 mM Tris pH 8, 0.1 mM EDTA, 0.05 v/v % Tween-20) with 5 µL of Spiked-in Master Mix and served as control for environmental contamination (i.e., microbe and pathogen nucleic acid contamination introduced by either the reagents, instrumentation, consumables, operators, and/or air during processing). These synthetic nucleic acids are later used for normalizing the signal in the samples in order to account for variations in sample processing.
Process with Extraction
Extraction of nucleic acids from clinical samples, positive assay control samples, and negative control samples, and subsequent conversion of the extracted nucleic acids to nucleic acid libraries is performed according to the process described above in Example 1.
Library Generation without Extraction (i.e., Direct-to-Library Process)
A sequencing library can be prepared without an extraction step using an unprocessed plasma sample by performing the procedure outlined in the section "Sequencing Library Generation" in Example 1.
Sequencing and Attribution of Reads
The obtained libraries were purified, sequenced and the resulting data analyzed as described in Example 1.

Similarly to the spiked asymptomatic plasma samples of Example 1, all purified libraries obtained from the clinical plasma samples were quantified using TapeStation 2200 and High Sensitivity D1000 Screen Tape system (Agilent Technologies, Santa Clara. CA). A comparison of the concentration of the library obtained with the direct-to-library process to the concentration of the library obtained using the process with extraction for each clinical sample included in the study reveals that, on average direct-to-library process yields 9.9× more library material per unit volume of plasma as compared to the process that includes an extraction step.

Figure 19:
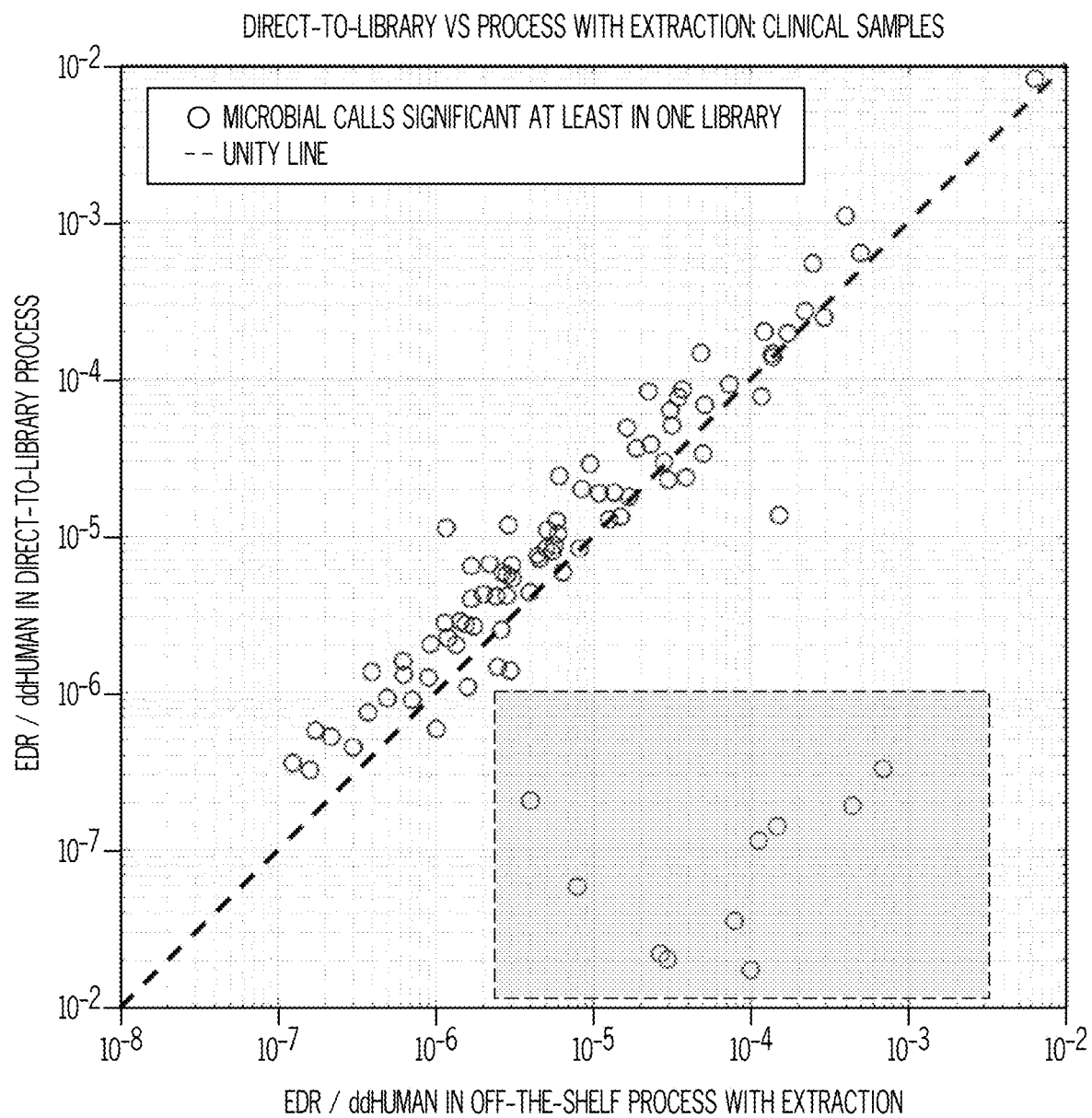
FIG. 19 depicts the ratio of the number of unique sequencing reads mapping to a microbial species (EDR) to the number of unique sequencing reads mapping to the human reference (ddHuman) for an off-the-shelf process with an extraction on x-axis and for process without extraction (direct to library process) on y-axis for a group of plasma samples. Each symbol represents one microbial species detected. The shaded area in the plot includes the microbes contributed by the environmental contamination in the process with extraction.

To compare the ability to detect microbial signal with the process starting with extraction and direct-to-library process, the ratio of the number of unique sequencing reads mapping to a microbial species (EDR) to the number of unique sequencing reads mapping to the human reference (ddHuman) was first analyzed for each sample processed (FIG. 19; each point in the figure represents a single significant microbe in any of the contrasted libraries). The median enrichment of the microbial signal in the libraries obtained with the direct-to-library process was 1.6×, suggesting direct-to-library process enriched for the microbial signal in the clinical samples. The only microbes significantly enriched in the process with extraction as compared to the direct-to-library were found within the shaded rectangular area in FIG. 19. These significant microbes were identified as *Acidovorax temperans* detected as significant in multiple libraries obtained by the process with extraction. This signal originated from the environmental contamination during generation of the libraries by the process with extraction as revealed by the accompanying EC samples that showed a highly variable *Acidovorax temperans* in different replicates of the negative control samples, which led to overestimation of the significance in the plasma samples.

Figure 20:
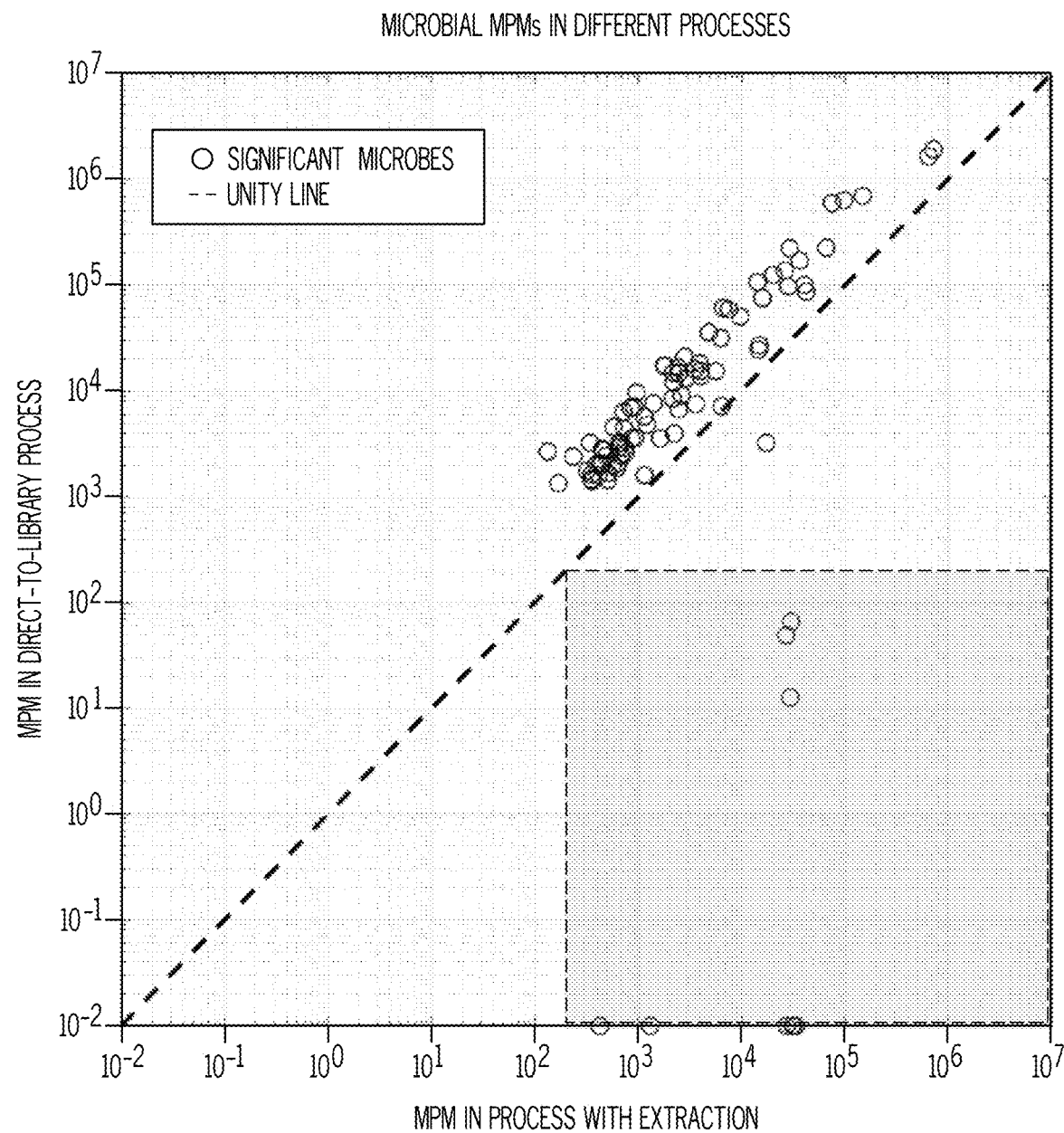
FIG. 20 depicts a comparison of the MPMs detected in the libraries obtained from plasma samples obtained with the process without extraction (direct to library process) on the y-axis and obtained with an off-the-shelf process with extraction on the x-axis. The shaded area in the plot includes the microbes contributed by the environmental contamination in the process with extraction.

The analysis of the number of molecules recovered per 1 µL of plasma by direct-to-library process vs. process with extraction (MPMs comparison in FIG. 20) showed that direct-to-library process yielded 4.5× (median increase) higher MPMs than the process with extraction. This demonstrated that the direct-to-library process recovers 4.5× higher amount of unique fragments as compared to the process with extraction. The points included in the shaded area in FIG. 20 correspond to *Acidovorax temperans* calls that were environmental contaminants as explained above.

Example 7: A Comparison of Direct-to-Library Process and a CLIA Validated Test

An additional proof-of-concept study was conducted to determine if a library made directly from plasma could detect pathogens at a similar or better level than a process that uses extraction. The Karius® Test (Karius, Inc., Redwood City, CA; see also Analytical and clinical validation of a microbial cell-free DNA sequencing test for infectious disease, Blauwkamp, et al., (2019) Nature Microbiology, 4 pp: 663-674, which is incorporated by reference herein in its entirety, including any drawings) was used as an example of a test that includes extraction prior to the start of nucleic acid library generation. Clinical, assay control, and negative control samples were processed in parallel and in an identical manner, using either the direct-to-library protocol (i.e., excluding extraction, the right side of FIG. 2A) or one that uses extraction (i.e., The Karius® Test, the left side of FIG. 2A).

Clinical samples, Positive Assay Control Samples, and Negative Control Samples were prepared as described above.

Process with Extraction

Extraction of nucleic acids from clinical samples, positive assay control samples, and negative control samples, and subsequent conversion of the extracted nucleic acids to nucleic acid libraries, and microbe nucleic acid enrichment were performed according to the CLIA-validated Karius® Test (Karius, Inc., Redwood City, CA).

Library Generation without Extraction (i.e., Direct-to-Library Process)

Sequencing libraries from the same samples were prepared without extraction and without pathogen enrichment steps using an unprocessed plasma sample by using the procedure outlined in the section "Sequencing Library Generation" in Example 1.

Sequencing and Sequencing Data Analysis

Sequencing was performed and the resulting data analyzed as described above. Furthermore, a set of libraries prepared from the respective Negative Control Buffers were processed and sequenced within each batch. Estimated taxon abundances from the negative control samples within the batch were combined to parameterize a model of read abundance arising from the environment with variations driven by counting noise. Statistical significance values were computed for each estimated taxon abundance and those within the CRR at high significance levels comprised candidate calls (i.e., significant calls). Final calls (i.e., reportable calls) were made after additional filtering was applied, accounting for read location uniformity, read percent identity, and cross-reactivity originating from higher abundance calls.

Figure 6B:
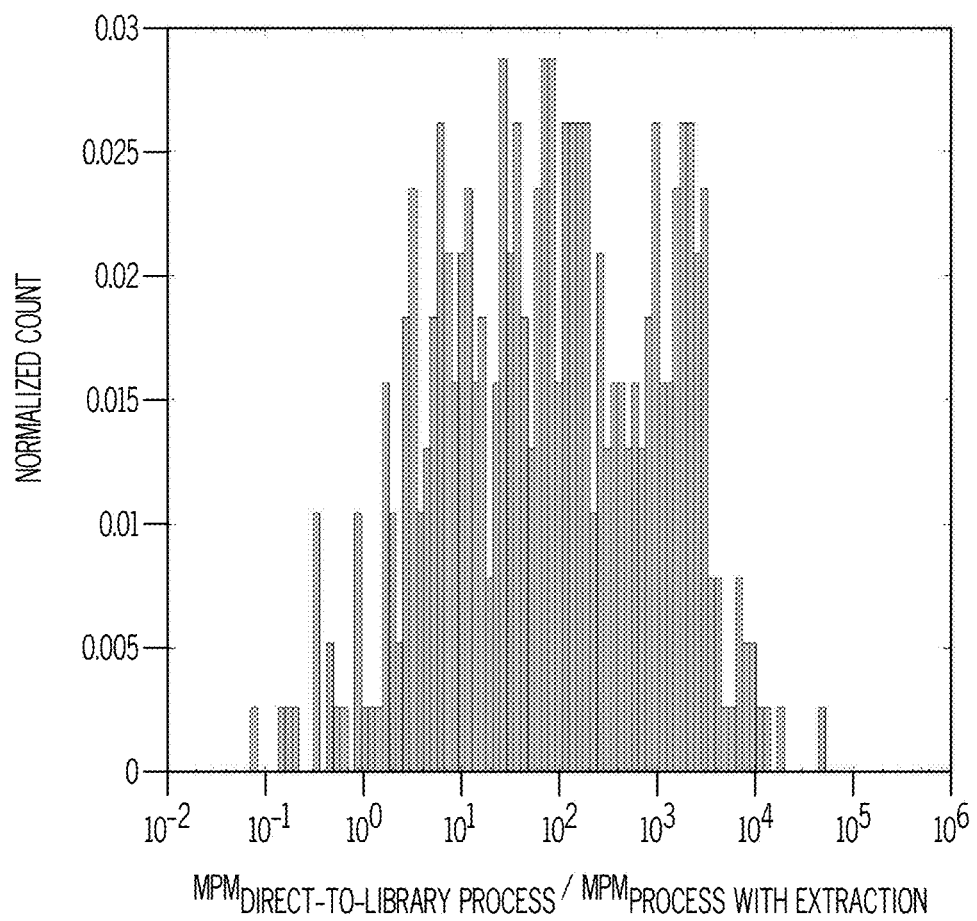
FIG. 6B depicts improved recovery of microbial signal resulting from a process without extraction.

To compare the ability to detect microbial signal with the process starting with extraction and direct-to-library process, the ratio of the number of unique sequencing reads mapping to a microbial species (EDR) to the number of unique sequencing reads mapping to the human reference (ddHuman) was first analyzed. In FIG. 6A1-6A5, the x-axis represents the EDR/ddHuman ratio measured in the libraries obtained by the process with extraction while the y-axis represents the EDR/ddHuman ratio measured in the libraries obtained with direct-to-library process for the same set of clinical samples. Considering all microbial species detected in either of the libraries, a clear shift towards higher concentration of microbial information in the libraries obtained with direct-to-library process was observed (FIG. 6A1-6A5), suggesting enrichment for the microbial signal in the direct-to-library process. In addition to the enrichment of the microbial signal resulting from the direct-to-library process, the later also enabled more efficient extraction of the information per unit of plasma sample as revealed by approximately 100× increase in MPM values when libraries were generated by the direct-to-library process as compared to the process with extraction (FIG. 6B).

Due to a reduction in GC-content, length, and secondary structure biases in the recovery of nucleic acids from the initial samples (FIG. 2C, FIG. 4A1-4D), the direct-to-library process allowed the determination of the nucleic acid fragment length distribution even in the region of short fragments. This was in contrast to the process with extraction where the more extreme GC-content, length, and secondary structure biases did not allow for accurate fragment distribution assessment. An analysis of the nucleic acid fragment length distributions of the endogenous microbial signal in the plasma samples reveals a presence of a peak (local maximum) between 30 base pairs and 70 base pairs (with a vast majority of the microbes showing a peak around 50 base pairs).

Figure 7A:
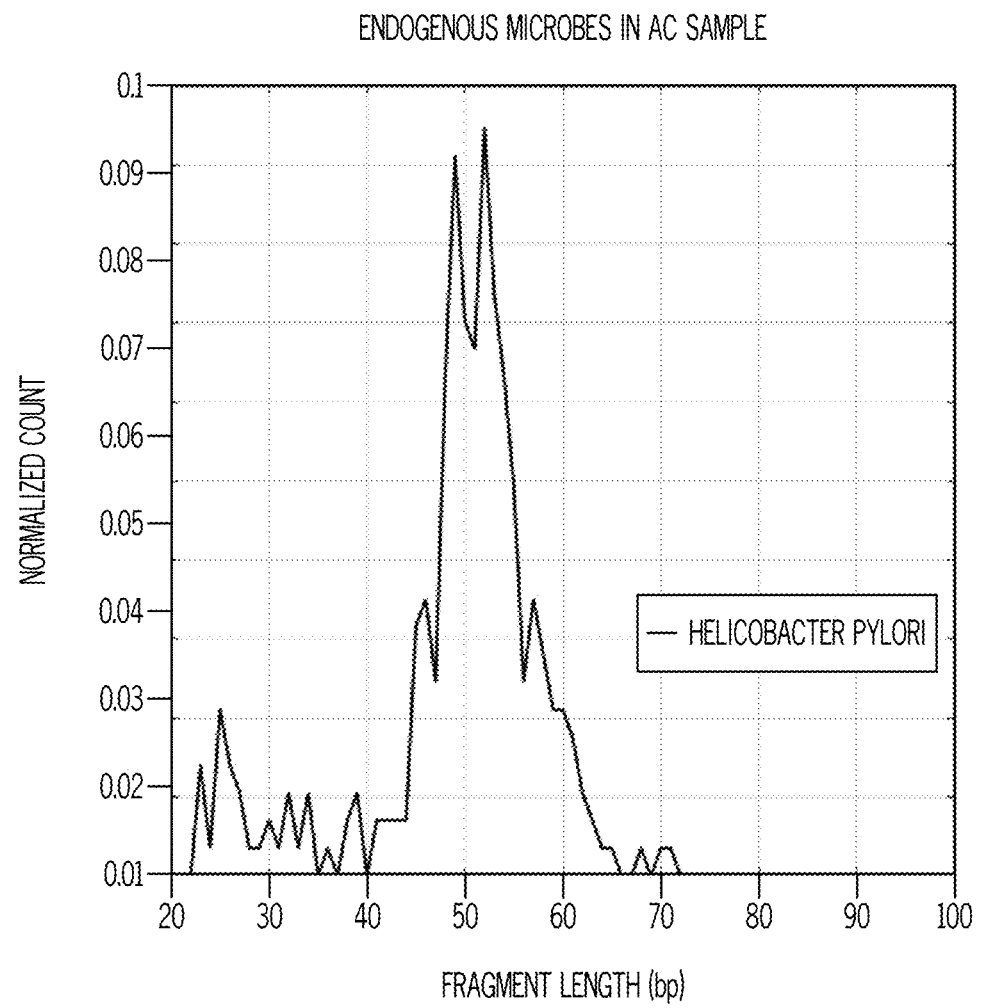
FIG. 7A depicts an example fragment length distribution of sequencing reads mapping to a reference of a microbe (*H. pylori* in this graph) that is endogenous to a sample.
Figure 7C:
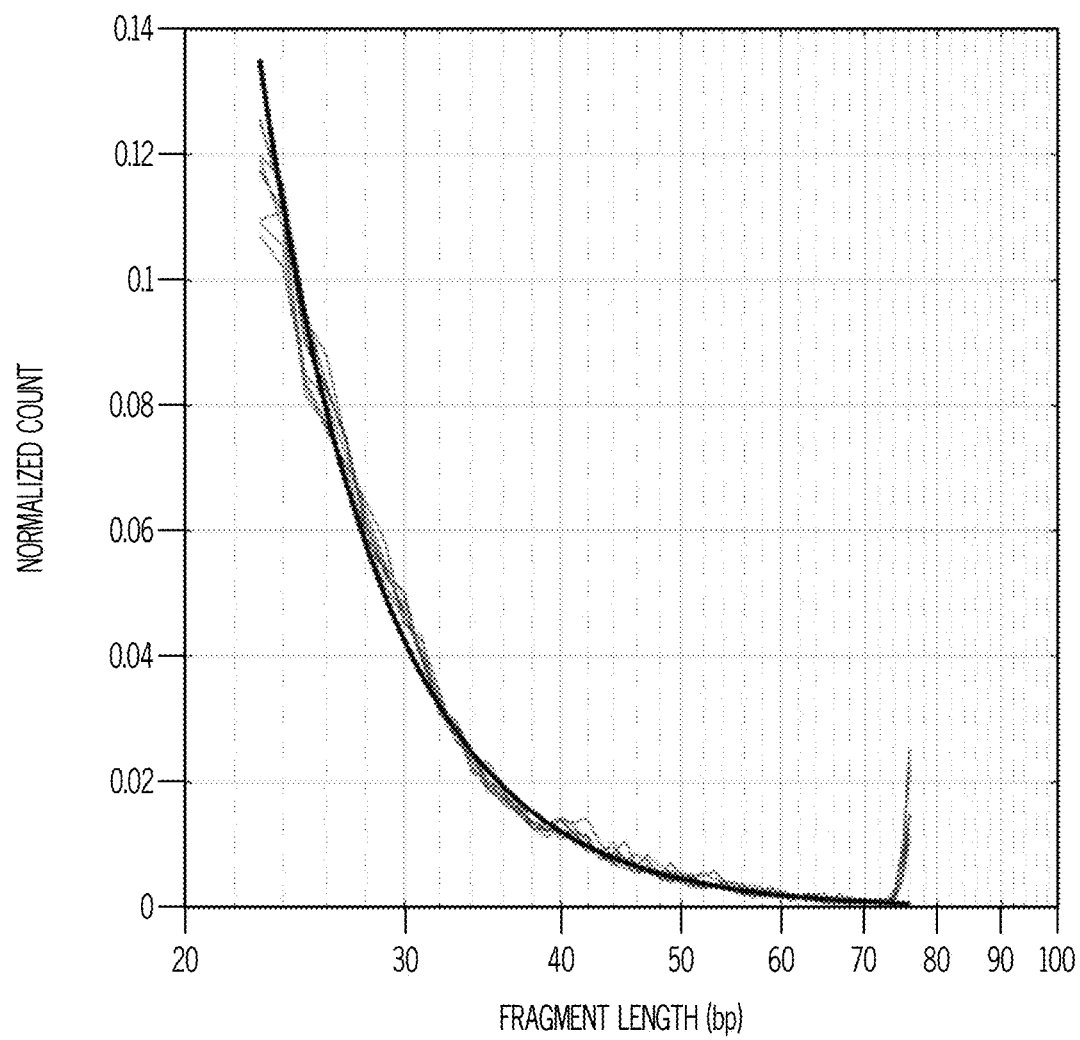
FIG. 7C depicts normalized fragment length distributions of sequencing reads obtained from several EC samples and that mapped to microbial references (thin gray lines); the exponential fit to the normalized sum of these distributions is shown as a thick black line. The data was obtained with the process without extraction.
Figure 7D:
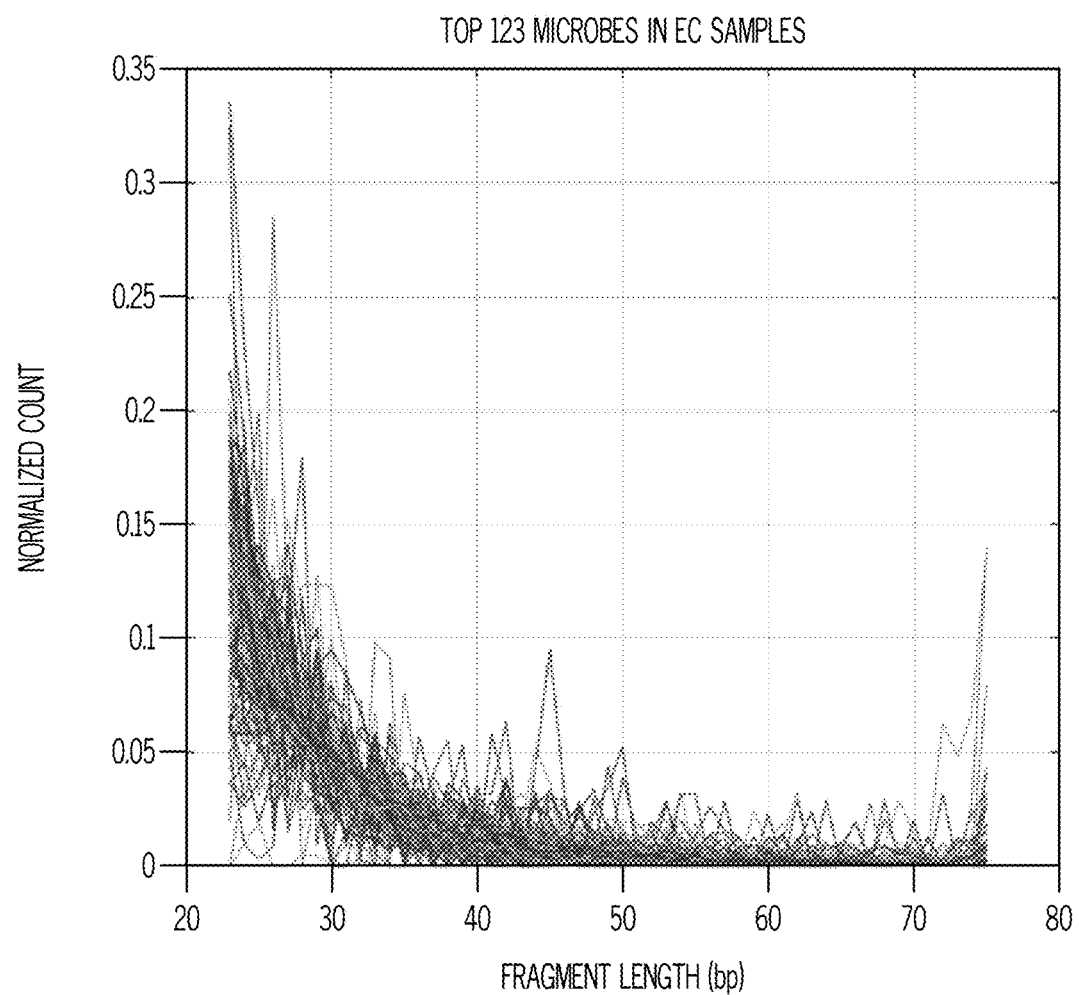
FIG. 7D depicts normalized fragment length distributions of sequencing reads mapping to 123 microbes with the highest abundance in the libraries obtained from EC samples using a process without extraction.
Figure 8A:
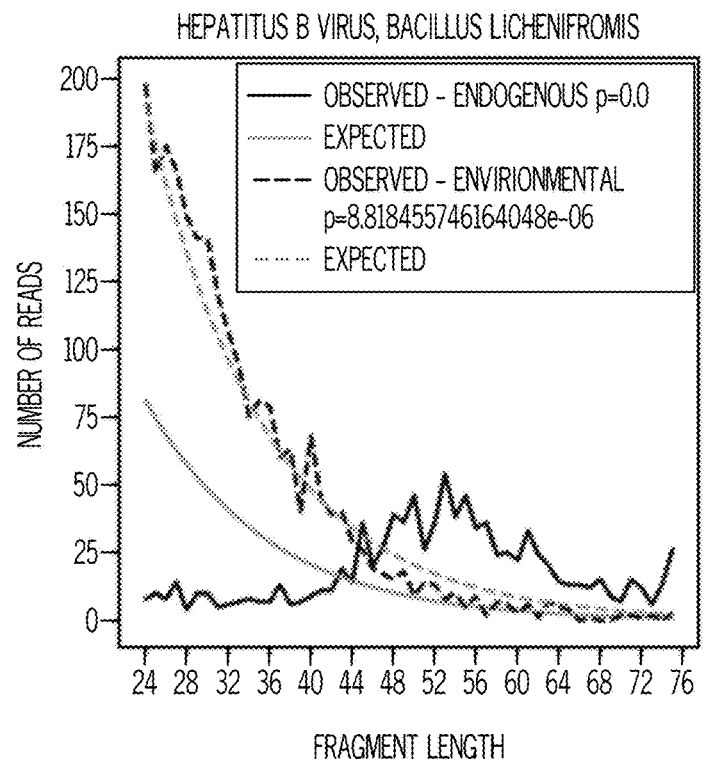
FIG. 8A-8H depict expected fragment length distributions for environmental contaminants (solid and dashed gray lines) and experimentally observed fragment length distributions for sequencing reads mapping to the references of indicated pathogens (solid and dashed black lines) as well as p-value from the chi-squared test.
Figure 8B:
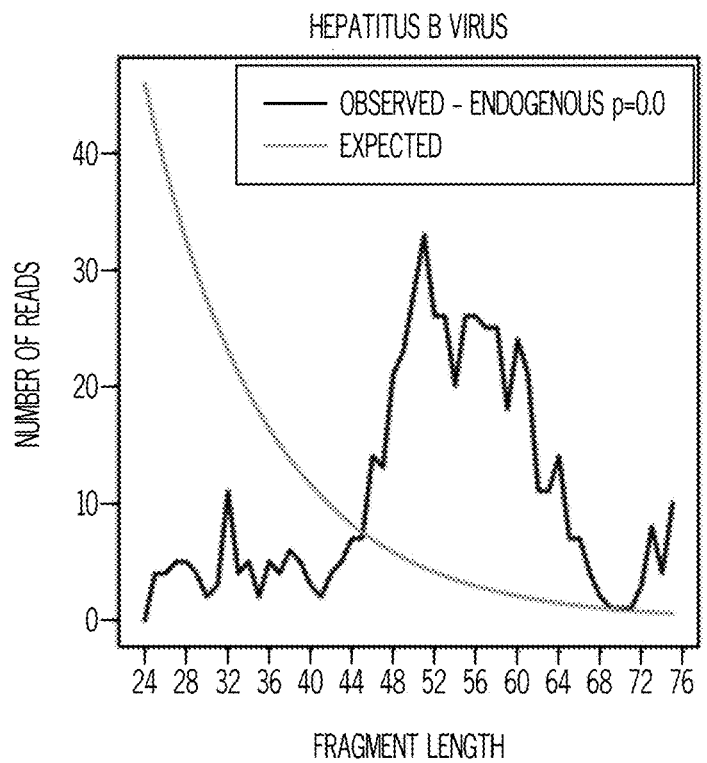
Figure 8C:
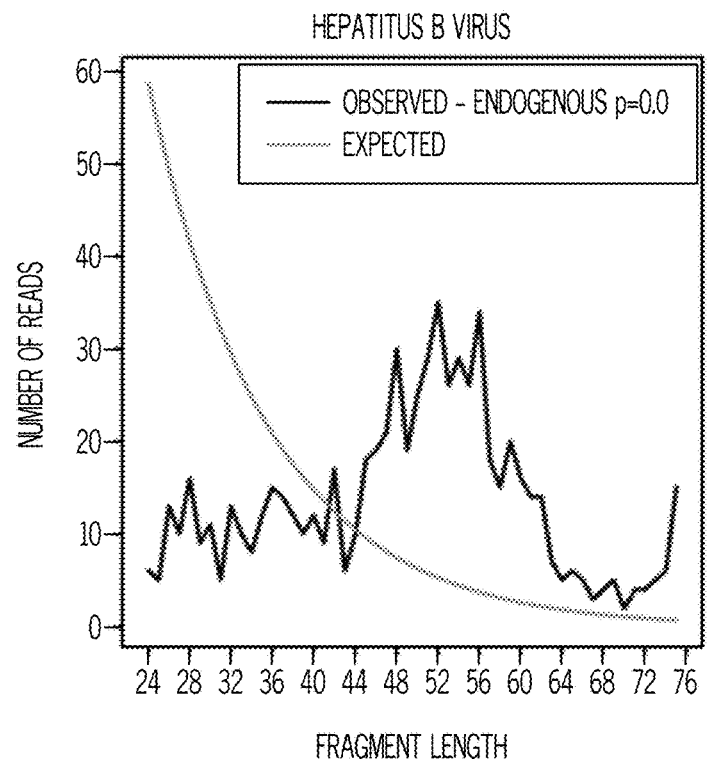
Figure 8D:
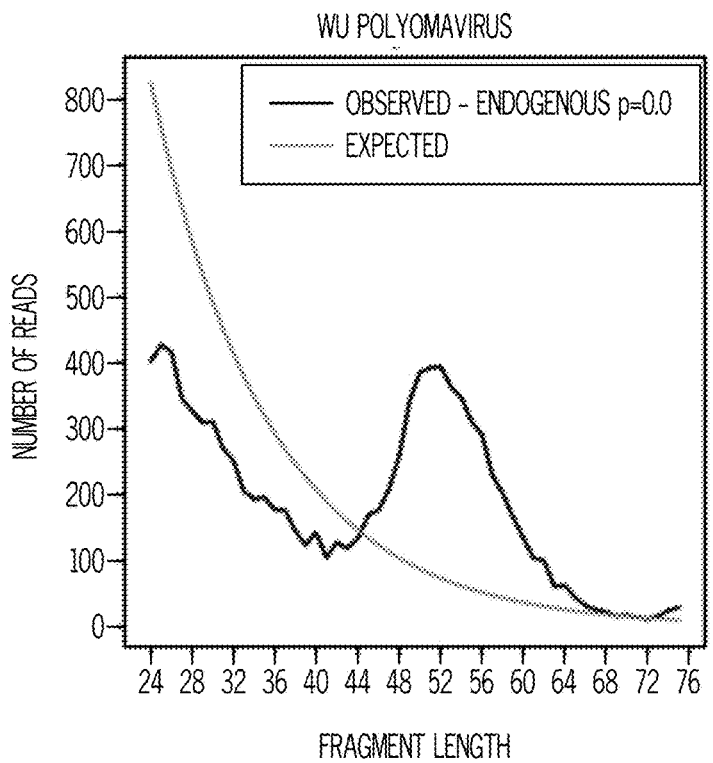
Figure 8E:
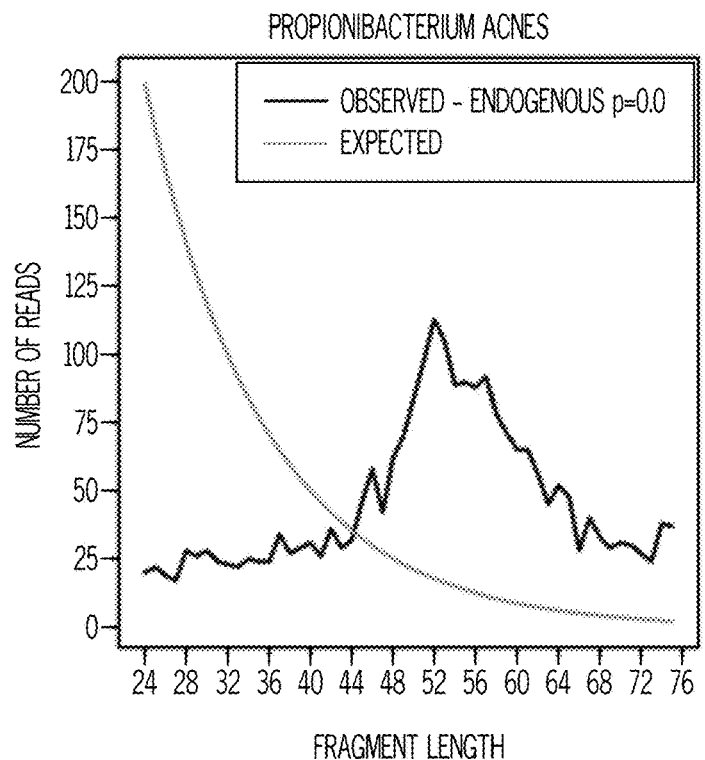
Figure 8F:
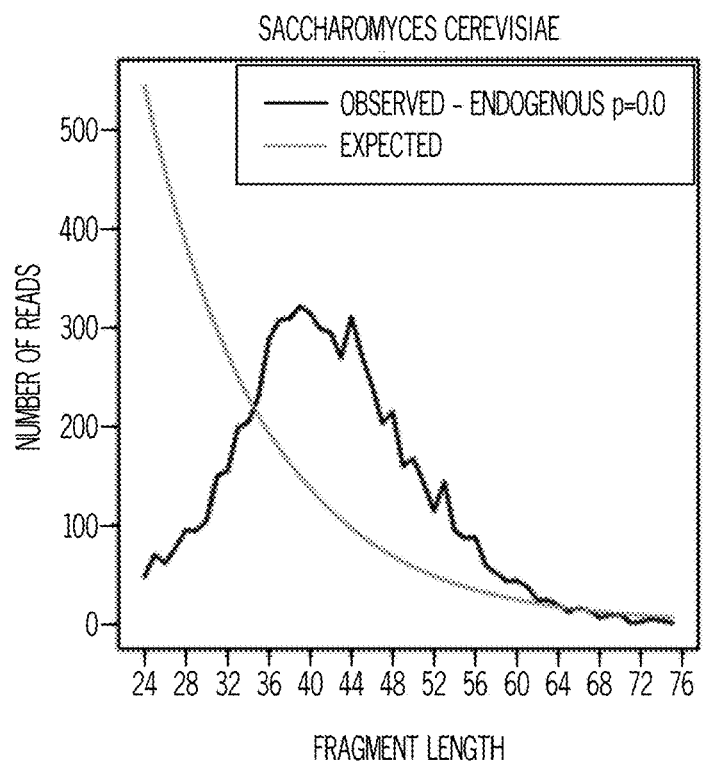
Figure 8G:
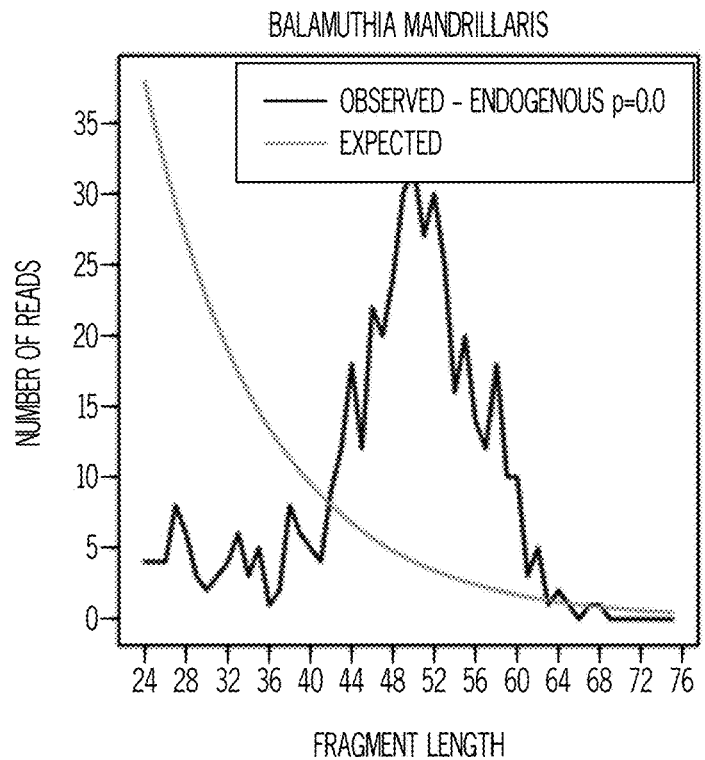
Figure 8H:
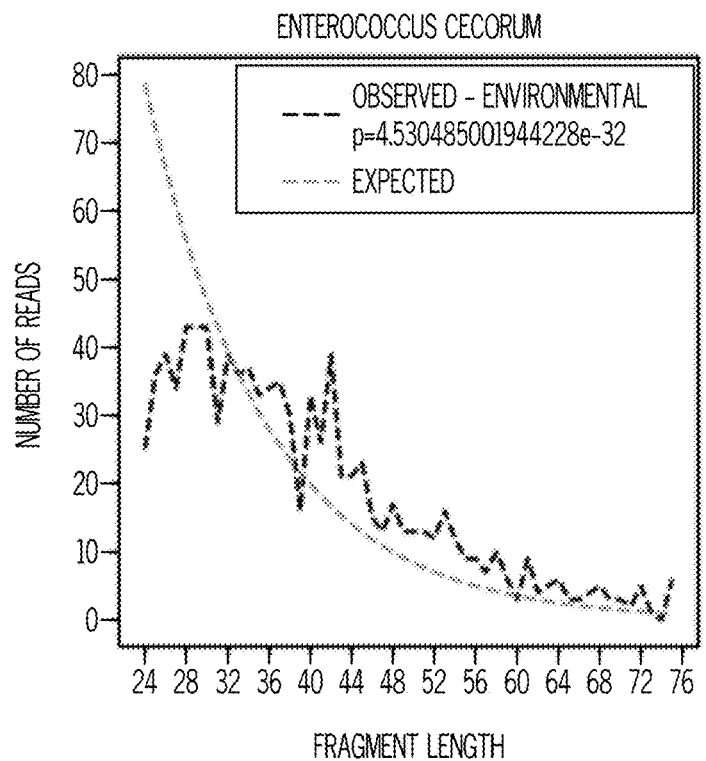
Figure 9A:
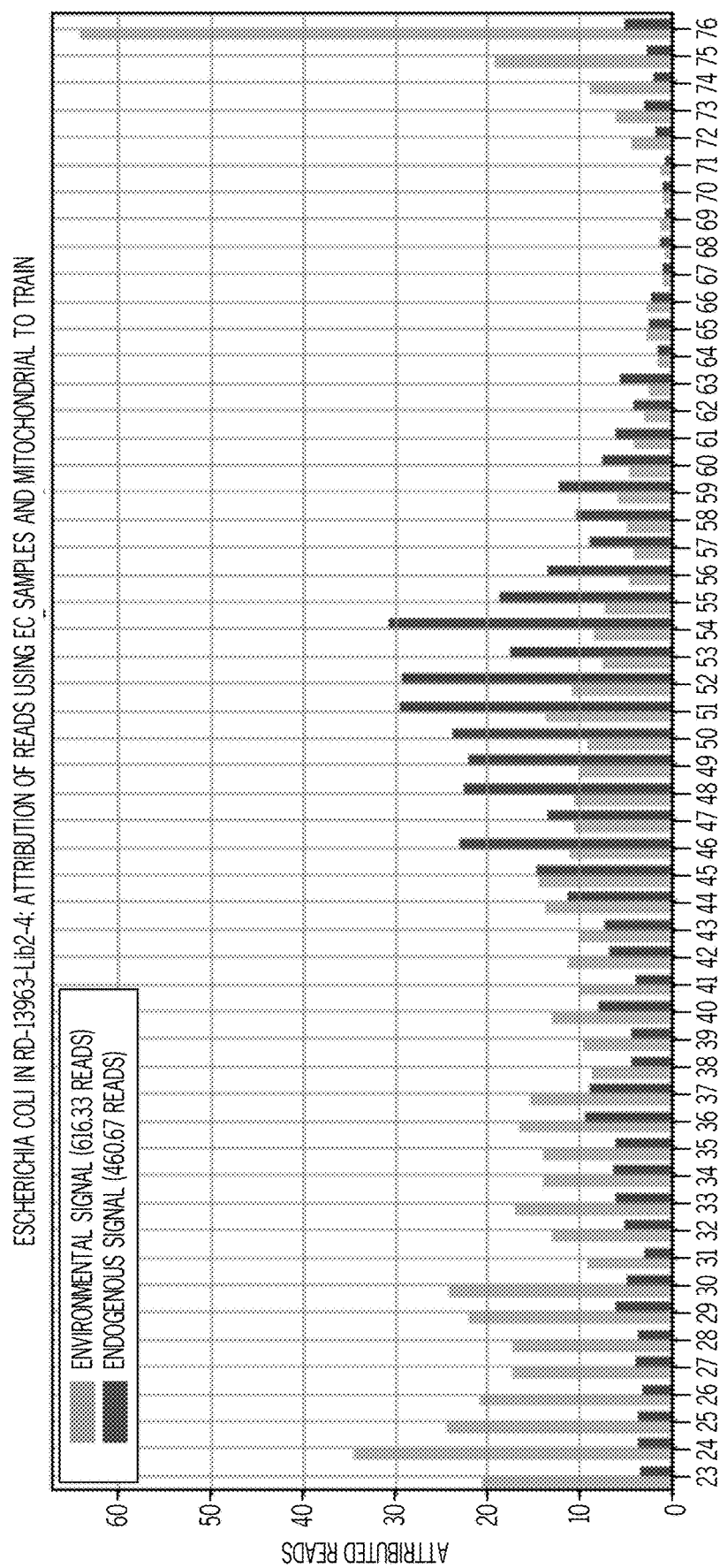
FIG. 9A depicts the distribution of fragment lengths for reads attributed to the endogenous and environmental components for a clinical sample.
Figure 9B:
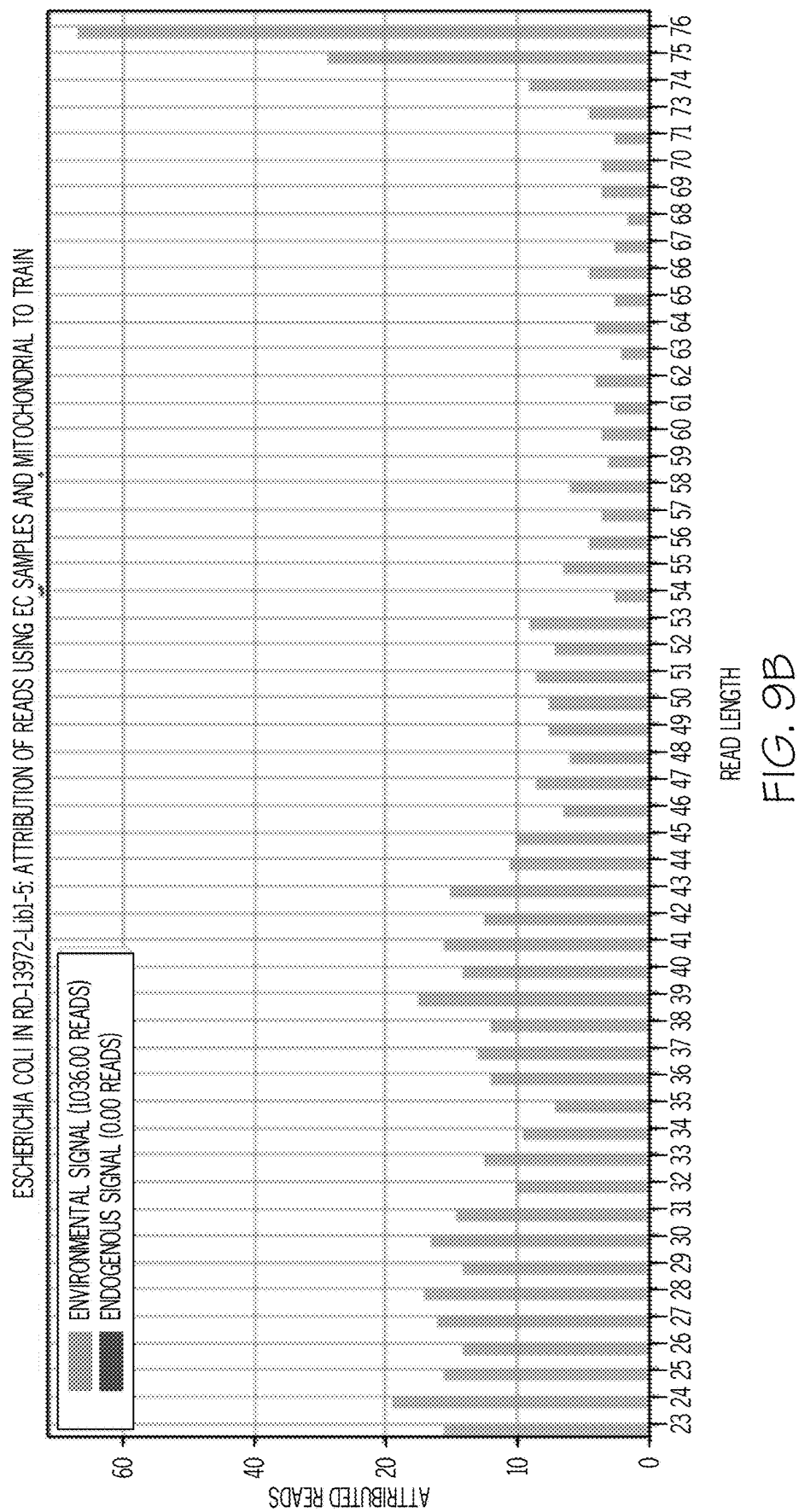
FIG. 9B-9E depict the distribution of fragment lengths for reads attributed to the endogenous and environmental components in each of the four environmental control samples on the same batch as the clinical sample in FIG. 9A.
Figure 9C:
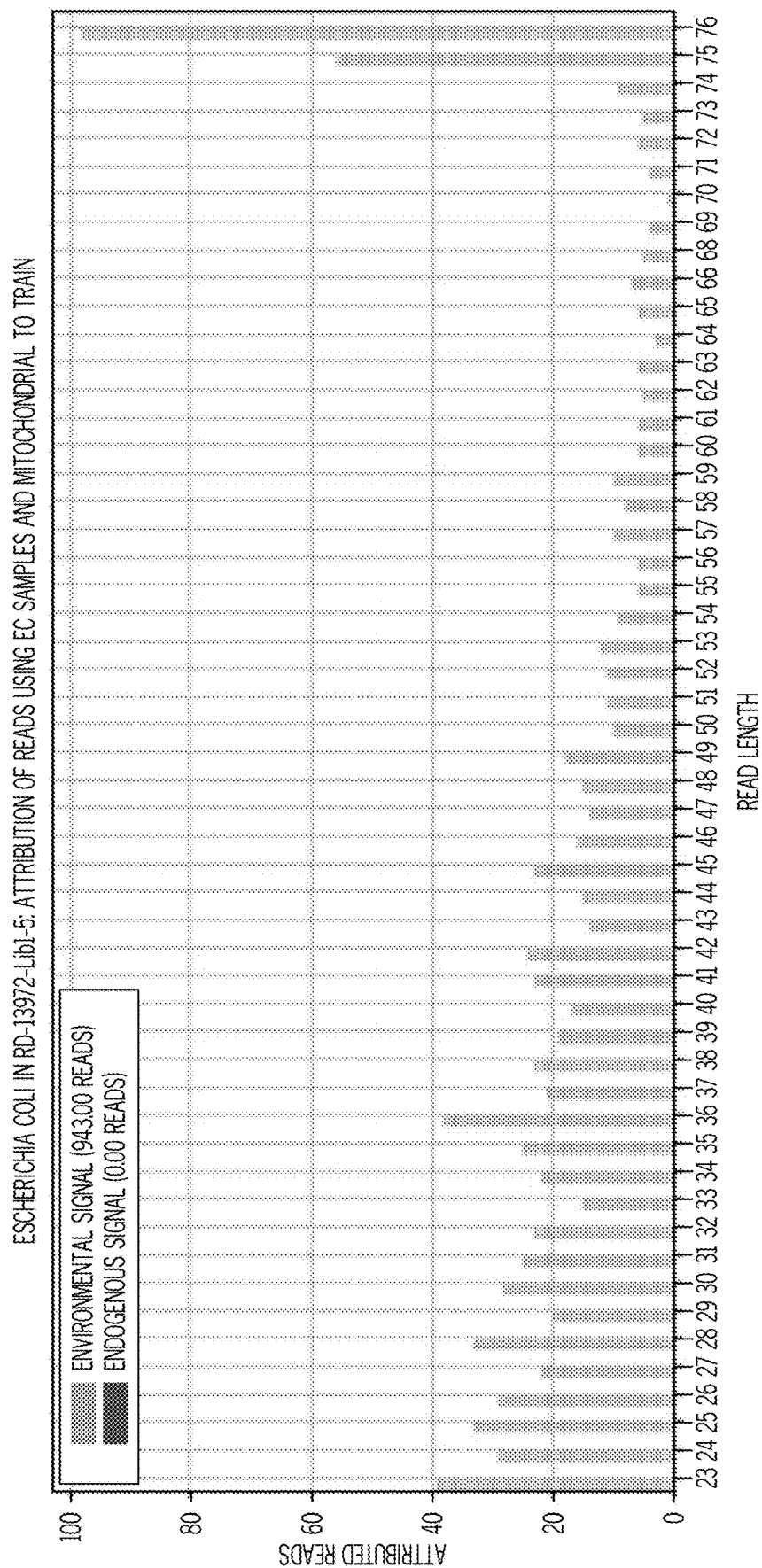
Figure 9D:
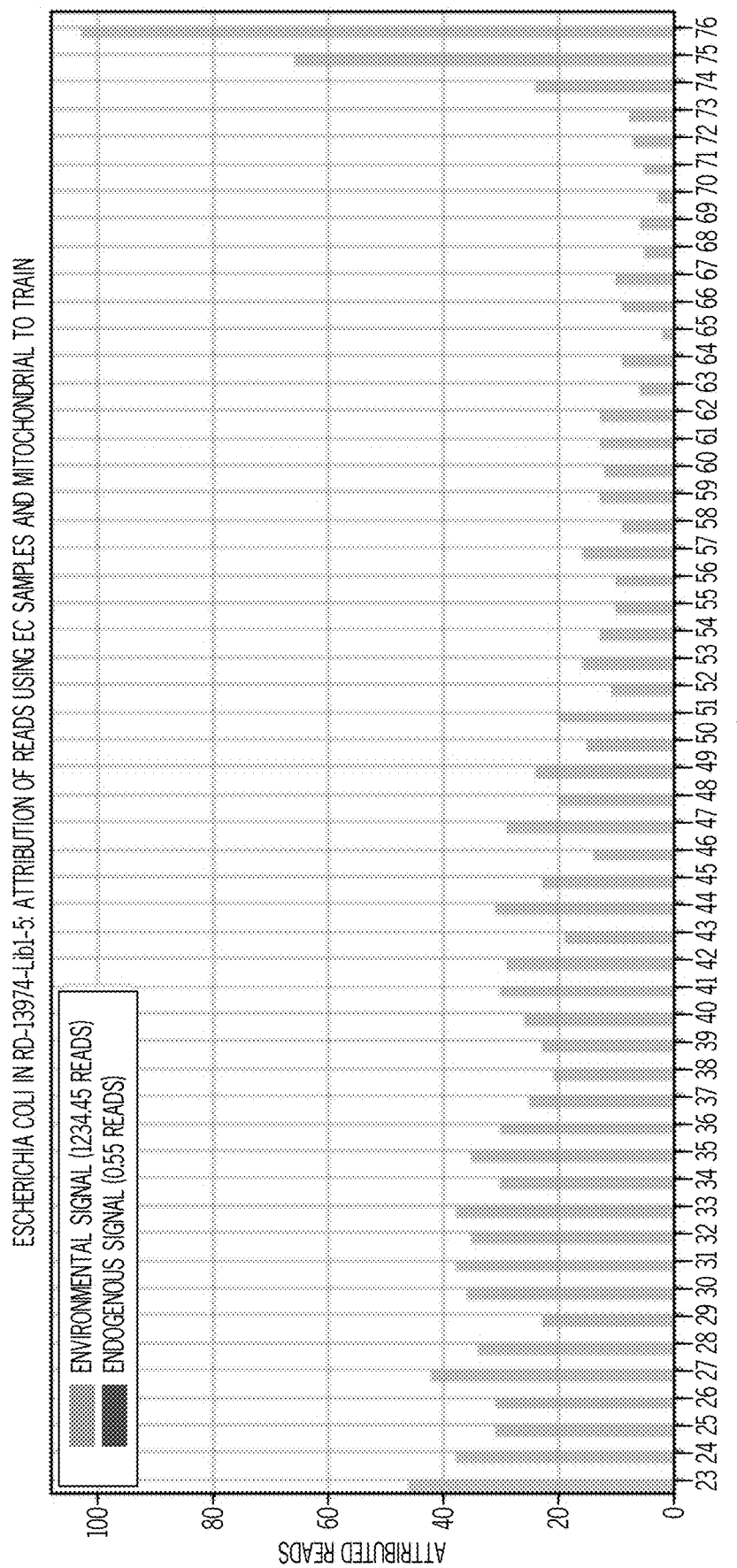
Figure 9E:
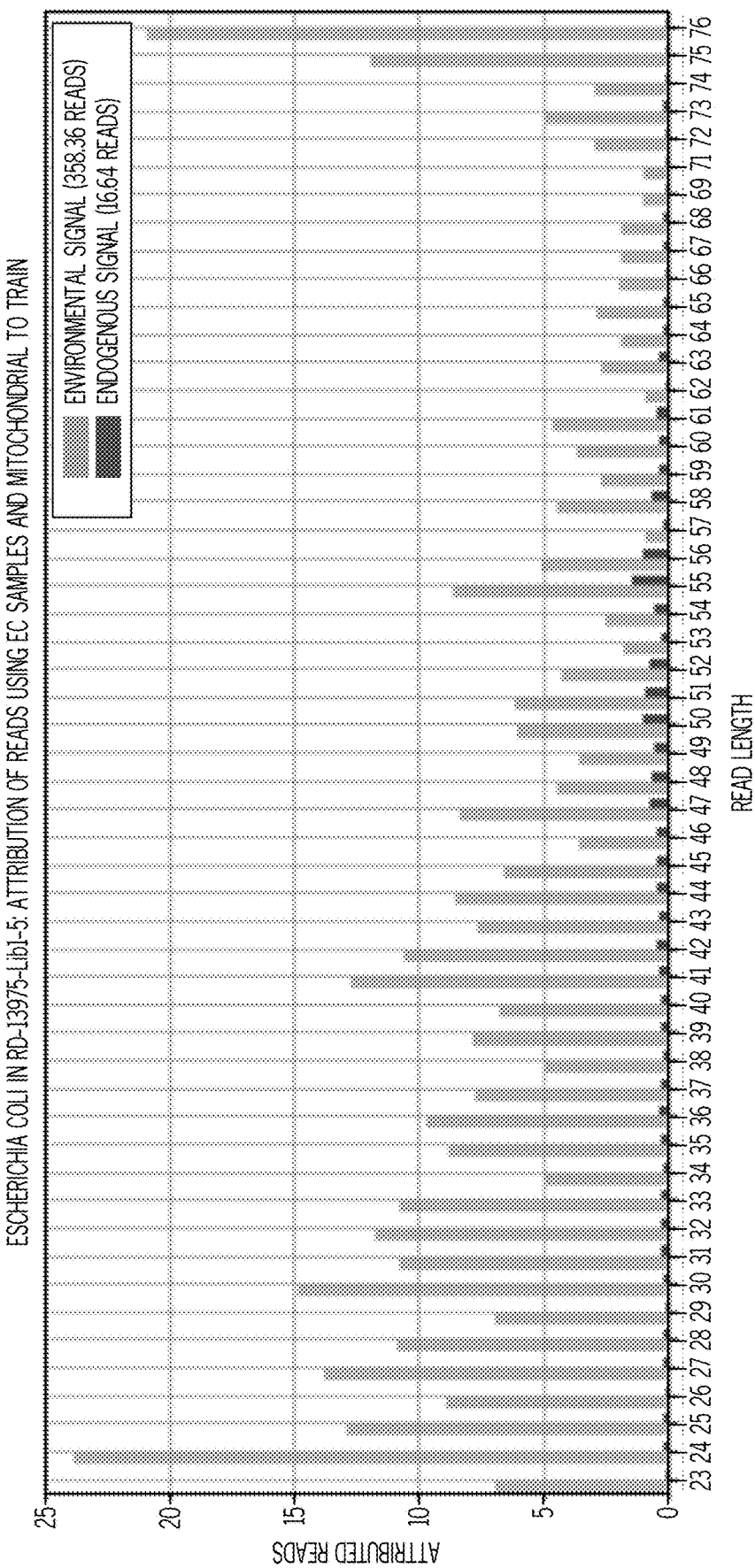

This was in sharp contrast to the microbial fragments detected in the EC sample type. For example, sequencing reads that mapped to the reference genome of *Helicobacter pylori* in the AC samples, where *Helicobacter pylori* was determined as an endogenous microbe by a dilution series showed such a typical fragment length distribution (FIG. 7A). Moreover, similar peak in the fragment length distributions of sequencing reads mapping to Hepatitis B Virus (HBV) were detected in six out of six clinical samples with orthogonally confirmed HBV infections (FIG. 7B1-7B6). Similar peaked fragment length distributions were observed for the majority of microbes present at significant levels as compared to EC, irrespective of the microbe superkingdom. In contrast, EC samples processed along these AC and clinical samples showed an overall fragment length distribution type lacking the peak that was best fit by an exponential (FIG. 7C). The per species fragment length distributions for the top 123 microbial species detected in the EC samples are shown in FIG. 7D, which demonstrates the absence of any peaks in the region where a peak is detected for the endogenous signal (i.e., region between 30 and 70 base pairs). For clarity, FIG. 7E1-7E2 shows the top two environmental contaminants of the direct-to-library process used in this example (*Saccharomyces cerevisiae* and *Yarrowia lipolytica*) and their respective distributions of fragment lengths, confirming the absence of a peak in the above mentioned region for the environmental contaminants. The difference in the observed fragment length distributions between endogenous microbes and microbial environmental contaminants in clinical and EC samples was not due to the difference in the sample matrix (i.e., plasma background vs. aqueous buffer in clinical vs. EC samples) as the fragment length distributions of environmental contaminants in clinical samples were identical to the fragment length of the same microbes in the EC samples. As an example, FIG. 7F1-7F2 shows the fragment length distributions for *Saccharomyces cerevisiae* and *Yarrowia lipolytica* environmental contaminants in the clinical samples which are the same as fragment length distributions for the same microbes in the EC samples (FIG. 7E1-7E2).

Example 8: Fragment Length Distributions to Remove Contaminants

If the nucleic acids originating from the endogenous microbes and environmental contaminants show different fragment length distributions, their fragment length distribution can be used to distinguish between contaminating and endogenous microbial signals thus reducing the false positive rate for target nucleic acids. Eight clinical samples were selected to test the filter based on the fragment length distribution, of which 6 contained an orthogonally confirmed endogenous pathogen, 1 contained a confirmed contaminant, and 1 contained both an orthogonally confirmed endogenous pathogen as well as a confirmed contaminant. The set included 6 different species.

An exponential distribution was fit to the fragment length distribution for reads that were assigned to any pathogens in the environmental control samples across 3 batches to determine an expected fragment length distribution for contamination. For each pathogen signal, the fragment length distribution observed in the sample for the taxon of interest was compared to the expected distribution, which was scaled to match the total number of reads mapping to the taxon of interest. A chi-squared test was performed to compare the fragment length distribution seen in the clinical sample to the expected distribution for contamination. Pathogens were filtered out if the p-value >=1e−50. The two confirmed environmental contaminants were removed with this filter and all 7 confirmed endogenous pathogens remained. FIG. 8A-8H shows the expected and observed fragment length distributions for each of the pathogens, as well as the p-value from the chi-squared test.

Example 9: Fragment Length Distributions to Deconvolute Endogenous and Environmental Contamination Components A statistical mixture model may be used to estimate the abundances of microbial taxa in a sample based on metagenome sequence data (Xia et al, 2011, PLoS ONE). However, if the characteristics of DNA sequences derived from environmental nucleic acids introduced during sample processing cannot be differentiated from those derived from endogenous nucleic acids in the sample, then it is possible only to estimate a combined taxon abundance for both. However, if environmental and sample nucleic acids do have different characteristics, such as their length or GC distributions, then it becomes possible to apply a mixture model approach that infers the environmental and sample abundances individually for each taxon.

A mixture model was constructed by allowing for a differential length distribution for reads derived from environmental contamination and the sample. A clinical sample that was orthogonally confirmed to have *Escherichia coli* and also contained the environmental contamination component of *Escherichia coli* that came from the reagents was analyzed. The fragment length distribution for reads that mapped to human mitochondria in that sample was used as the prior for the endogenous fragment length distribution. The fragment length distribution for reads that map to *Escherichia coli* in the 4 environmental contamination control samples in the same batch as the clinical sample was used as the prior for the environmental fragment length distribution. In the clinical sample, 460.67 reads were attributed to the endogenous signal and 616.33 were attributed to environmental contamination signal.

The process did not attribute reads to the endogenous component when the sample was an environmental control sample, the algorithm was run on the 4 environmental samples from the same batch. In all 4 samples, >95% of the reads were attributed to the environmental signal, with 100% in 3 out of 4.

FIGS. 9A-E shows the distribution of fragment lengths for reads attributed to the endogenous and environmental components for the clinical sample (A) and the 4 environmental control samples that were run on the same batch (B-E).

Example 10: Prevention of Precipitate Formation During Denaturation Step

A protocol for generating the sequencing library without extraction described above can be further modified to prevent precipitation during and after the denaturation step by fragmenting proteins with a thermosensitive protease prior to the denaturation step. This simplifies the protocol set forth above by eliminating the need for filtering or sedimenting the precipitate that occurs in the process set forth above. This modified process differs from the process set forth above only in the Dephosphorylation and denaturation step.

In order to test the performance of the direct-to-library process that included a thermosensitive protease digestion step prior to denaturation, a 500 μL aliquot of asymptomatic plasma was spiked with 10 μL of Spike-in Master Mix (see Example 1). 15 μL of spiked asymptomatic plasma was processed according to the direct-to-library process described in Example 1 as a control. The second 15 μL aliquot of spiked asymptomatic plasma was processed according to the same protocol except that the "Dephosphorylation and denaturation" step (see Example 1 above) was replaced by the "Protein K digestion and denaturation" step described below and 3'-end adapter ligation was performed as described below.

Step A: Proteinase K digestion and denaturation. 15 μL spiked plasma sample was mixed with 45 μL of Proteinase K Master Mix (6.0 μL 10× T4 RNA Ligation Buffer (NEB, Ipswich, MA), 0.6 μL 10% Tween-20 (Thermo-Fisher, Waltham, MA), 2.0 μL Proteinase K (Sigma-Aldrich, St. Louis, MO), 36.4 μL Nuclease-free water (IDT, Coralville, IA)), mixed well, and incubated at 60° C. for 20 min, followed by 10 min incubation at 95° C. to denature nucleic acid fragments, and the undigested proteins as well as deactivate the Proteinase K. While still at 95° C. the reaction mixture was transferred immediately on ice to prevent random hybridization of the nucleic acids.

Step B: 3'-end adapter ligation. 20 μL of the reaction mixture from the Proteinase K digestion and denaturation step was mixed with 6.0 μL 10× T4 RNA Ligation Buffer (NEB, Ipswich, MA), 0.2 μL 10% Tween-20 (Thermo-Fisher, Waltham, MA), 49 μL 34% PEG-8000 (prepared in-house with PEG-8000 from Sigma-Aldrich, St. Louis, MO, and Nuclease-free water from IDT, Coralville, IA), 4 μL 10 mM ATP (NEB, Ipswich, MA), 1 μL 10 μM 3'-end adapter hybrid (see Example 1) and mixed well before adding 1 μL T4 DNA Ligase (Thermo-Fisher, Waltham, MA) and 4 μL Nuclease-free water (IDT, Coralville, IA). The final mixture was mixed well, and incubated at 37° C. for 30 min, followed by denaturation step at 95° C. for 1 min.

Figure 10:
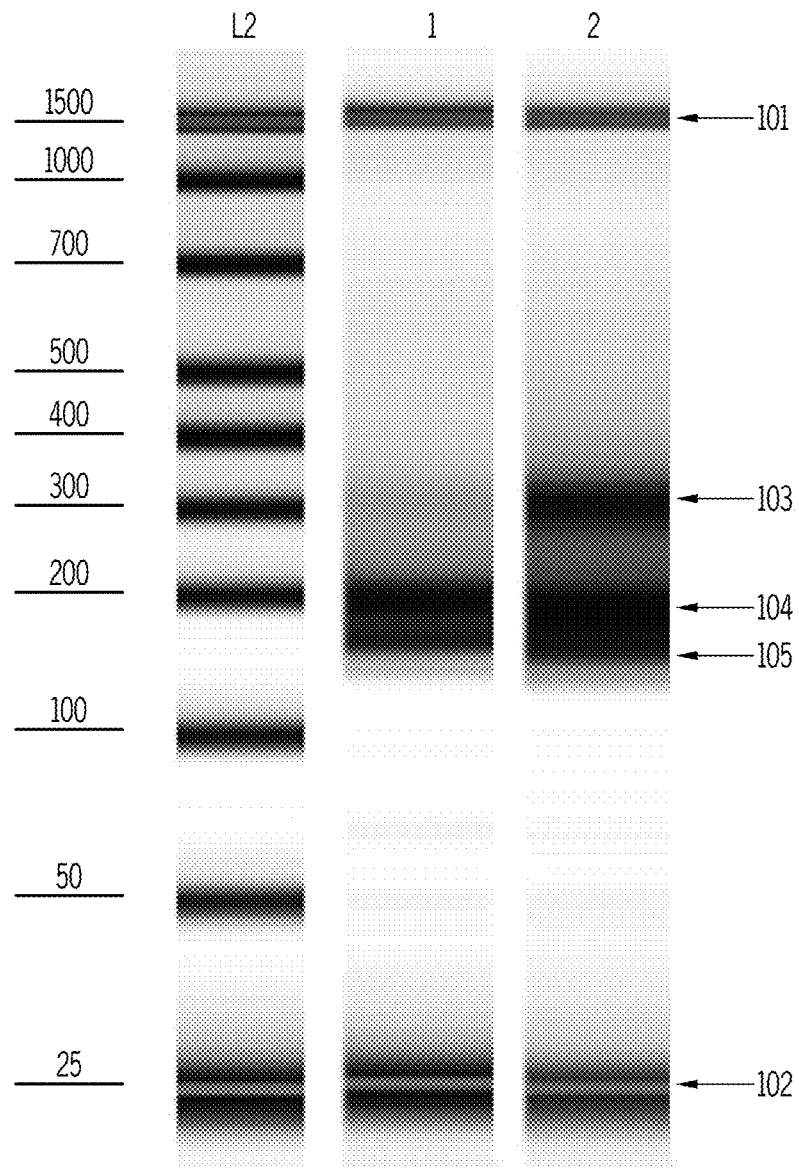
FIG. 10 depicts electropherograms of a library obtained with Proteinase K in lane 1 and a control library in lane 2.

FIG. 10 shows electropherograms of the library obtained with Proteinase K in Lane 1 and a control library in Lane 2. The direct-to-library protocol with Proteinase K digestion step showed comparable yields on the short nucleic acid fragments (e.g., fragments indicated as a band 104 in FIG. 10) while it suppressed the recovery of the longer nucleic acid fragments (e.g., nucleosomal fragments indicated as band 103 in FIG. 10). Such suppression of the recovery of longer fragments may result in an enrichment of the target nucleic acids that are primarily shorter than the nucleosomal fragments (e.g., microbial cell-free fragments).

Example 11: Comparison of Two Direct-to-Library Processes

A direct-to-library process utilizing a ligation reaction to attach the adapter sequences to the target nucleic acid was compared to the performance of a direct-to-library process utilizing a template-switching reaction to attach the adapter sequences to the target nucleic acids (Zhu et al. (2001) BioTechniques 30: 892-897). Clinical, assay control, and negative control samples were processed in parallel and in an identical manner, using either of the direct-to-library protocols.

Clinical samples, Positive Assay Control Samples, and Negative Control Samples were prepared as described above.

Direct-to-Library Process utilizing Ligation Reaction

A sequencing library can be prepared without extraction and pathogen enrichment steps using an unprocessed plasma sample by using the procedure outlined in the section "Sequencing Library Generation" in Example 1.

Direct-to-Library Process Utilizing Template-Switching Reaction 50.0 µL of spiked sample was mixed with 20.0 µL of 10× Terminal Transferase Reaction Buffer (NEB, Ipswich, MA), 5.0 µL of Proteinase K (Sigma), 2.0 µL of 10% Tween-20 (Thermo-Fisher Scientific, Waltham, MA), 2.0 µL of 10% Triton X100 (Thermo-Fisher Scientific, Waltham, MA) and 121.0 µL Nuclease-free water. The mixture was heated to 60° C. for 20 minutes and 95° C. for 10 minutes and placed on ice until cool. 2.0 µL of 10 mM dATP, 2.0 µL Terminal Transferase (20 u/µL, NEB, Ipswich, MA) and 6.0 µL Nuclease-free water was added to prepare the A-tailing reaction which was incubated at 37° C. for 40 min. 300.0 µL of Lysis/Binding Buffer (Thermo-Fisher Scientific, Waltham, MA) was added to the reaction. The entire volume was then added to 50.0 µL of Dynabeads oligo $(dT)_{25}$ (SEQ ID NO: 13) (Thermo-Fisher Scientific, Waltham, MA), which had been washed once with Lysis/Binding Buffer (Thermo-Fisher Scientific, Waltham, MA). The mixture was incubated at 25° C. and 600 RPM. The beads were then washed twice with 600.0 µL of Wash Buffer A (Thermo-Fisher Scientific, Waltham, MA) and twice with 300.0 µL of Wash Buffer B (Thermo-Fisher Scientific, Waltham, MA) before elution in 24.0 µL of elution buffer (Thermo-Fisher Scientific, Waltham, MA) at 80° C. and 600 RPM for 3 minutes. The entire eluate was transferred to a new plate.

2.0 µL 1 µM Poly dT primer (IDT) and 6 µL of SMART-Scribe 1st Strand buffer (5×) (Takara, Kusatsu, Japan) was added to the eluate and the resulting mixture incubated at 95° C. for 1 minute before placing on ice. The Extension and Template-switching mix was prepared by combining 4.5 µL SMARTScribe 1st Strand buffer (5×) (Takara, Kusatsu, Japan), 0.5 µL dNTP mix (25 mM per nucleotide, Thermo-Fisher Scientific, Waltham, MA), 2.0 µL SMARTScribe Reverse Transcriptase (100 u/µL, Takara, Kusatsu, Japan), 2.0 µL 5 µM Template-switching Oligo (TS Oligo) (IDT), 5.0 µL of DTT (20M, Takara, Kusatsu, Japan), and 4 µL Nuclease-free water. The resulting reaction mixture was incubated for 90 min at 42° C. and the reaction was heat denatured at 70° C. for 15 min.

Next, 50.0 µL of NEBNext Ultra II Q5 (NEB, Ipswich, MA), and 8.0 µL of indexing primer mixture (NEB, Ipswich, MA) were added to the reaction from the previous step. Amplification of the nucleic acids was performed then using the following temperature cycling program: 98° C. for 30 seconds, 8 cycles of 98.0 for 10 seconds, 65° C. for 75 seconds, and a final extension of 65° C. for 5 min. Final nucleic acid libraries were then pooled in groups of four ECs, two ACs, and eighteen clinical samples before using RNAclean™ Ampure beads to purify the pool as described above. After purification, the concentration of the nucleic acids in the library pools was measured with TapeStation as described above and loaded on the sequencer according to the manufacturer's recommendations.

The sequencing data obtained from the libraries generated by the ligation-based method was analyzed as described above. The sequencing data obtained from the libraries generated by the template-switching-based method were analyzed in the same way except that the primary sequencing output demultiplexing by bcl2fastq v2.17.1.14 (with default parameters) was followed by the removal of the template switching oligos using Cutadapt, and of the poly A tails with the reads quality trimmed and subsequently filtered if shorter than 20 bases by Trimmomatic v 0.32.

FIG. 11A1-11A5 shows a comparison of the relative concentration of the unique sequencing reads mapping to significant microbes (i.e., EDR/ddHuman) obtained with the direct-to-library process utilizing the ligation reaction on the x-axis, and obtained with the direct-to-library process utilizing the template-switching reaction on the y-axis. Data has been separated by microbe superkingdom for clarity. Results revealed that both processes yield similar concentrations of the microbe information within their libraries. Consequently, the direct-to-library process utilizing a template-switching reaction to attach the adapters also yields higher concentration of the microbe information as compared to the process with extraction included.

FIG. 11B1-11B5 shows a comparison of the MPMs obtained with the direct-to-library process utilizing the ligation reaction on the x-axis and obtained with the direct-to-library process utilizing the template-switching reaction on the y-axis. Data has been separated by microbe superkingdom for clarity. Results reveal that both processes yield similar MPM for the significant microbes within their libraries. Consequently, the direct-to-library process utilizing template-switching reaction to attach the adapters also yields higher MPMs as compared to the process with extraction included.

Example 12: Detection of Microbial Signal in Raw Biological Samples

A proof of concept study was conducted to determine if a library made directly from raw biological samples could detect pathogens at a similar or better level than a process that uses extraction. To this end, clinical samples of joint fluid and bronchoalveolar lavage, as well as negative control samples were processed in parallel and in an identical manner, using either the direct-to-library protocol (i.e., excluding extraction, the right side of FIG. 2A) or one that uses extraction (i.e., The Karius® Test that includes the extraction, Blauwkamp et al 2019 Nature Microbiology, herein incorporated by reference in its entirety).

Three joint fluid (JF) and five bronchoalveolar lavage (BAL) samples were purchased (Discovery Life Sciences, Los Osos, CA), and stored at −80° C. until use. Samples were thawed before use, spiked with Spike-in master mix, and processed with direct-to-library process and a commercial process with extraction as explained in Example 8. The sequence bioinformatic processing was carried out as described in Example 7.

Figure 14B:
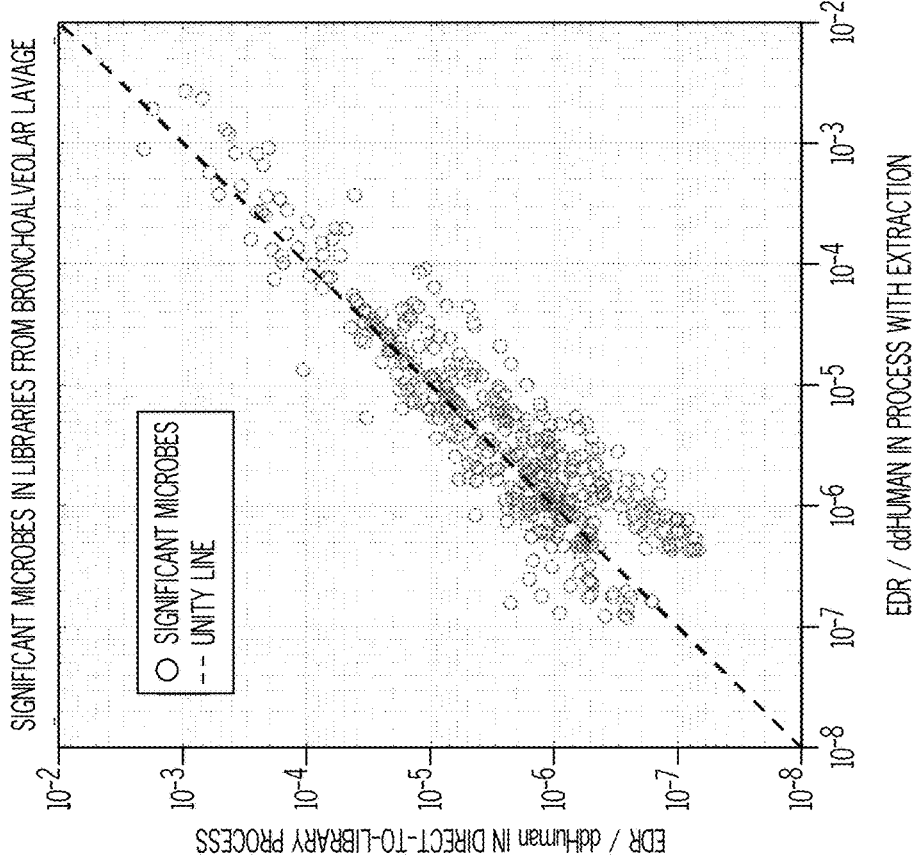
FIG. 14B depicts the ratio of the number of unique sequencing reads mapping to a microbial species (EDR) to the number of unique sequencing reads mapping to the human reference (ddHuman) for process with extraction on x-axis and for process without extraction on y-axis for samples of bronchoalveolar lavage.
Figure 14A:
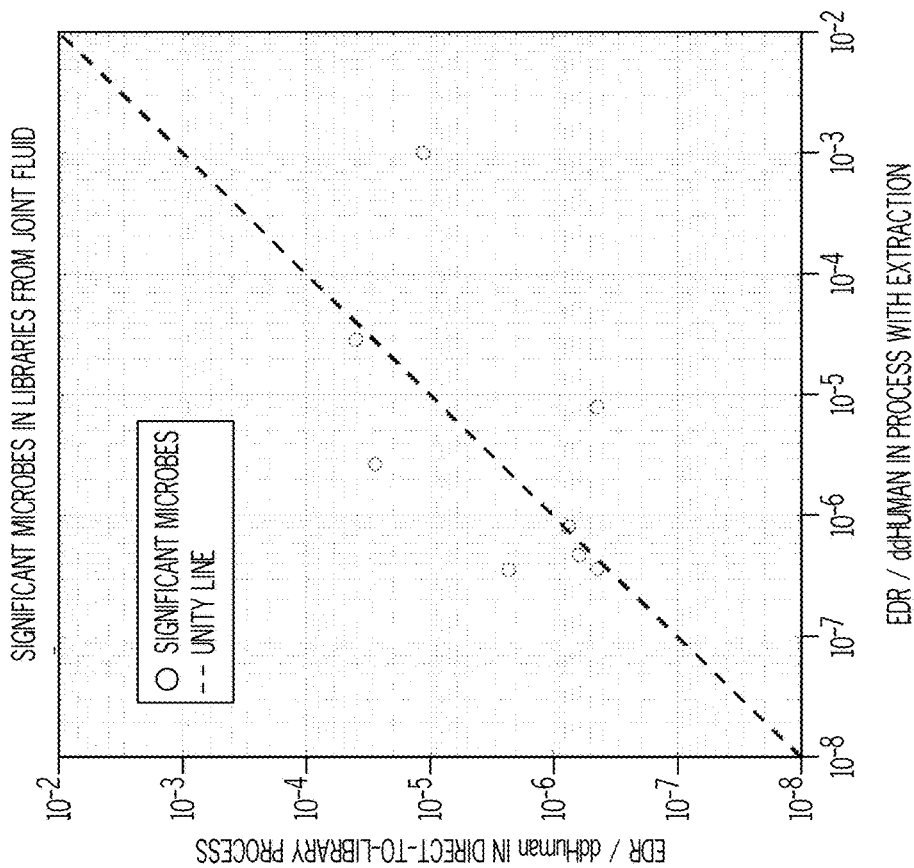
FIG. 14A depicts the ratio of the number of unique sequencing reads mapping to a microbial species (EDR) to the number of unique sequencing reads mapping to the human reference (ddHuman) for process with extraction on x-axis and for process without extraction on y-axis for samples of joint synovial fluid. Each symbol represents one microbial species detected.

To compare the ability to detect microbial signal in JF and BAL samples with the process starting with extraction and direct-to-library process, the ratio of the number of unique sequencing reads mapping to a microbial species (EDR) to the number of unique sequencing reads mapping to the human reference (ddHuman) was first analyzed for each sample processed (FIG. 14; each point in the figure represents a single significant microbe in any of the contrasted libraries). The libraries obtained from the BAL samples showed considerably higher number of significant microbes than the libraries derived from JF samples. This may be related to the fact that JF samples are sterile while BAL are typically not sterile fluids. The median enrichment of the microbial signal in the JF- and BAL-derived libraries obtained with the direct-to-library process was 1.3× and 0.8×, suggesting, on average direct-to-library process performed at least equivalently to the process with extraction.

Figure 15B:
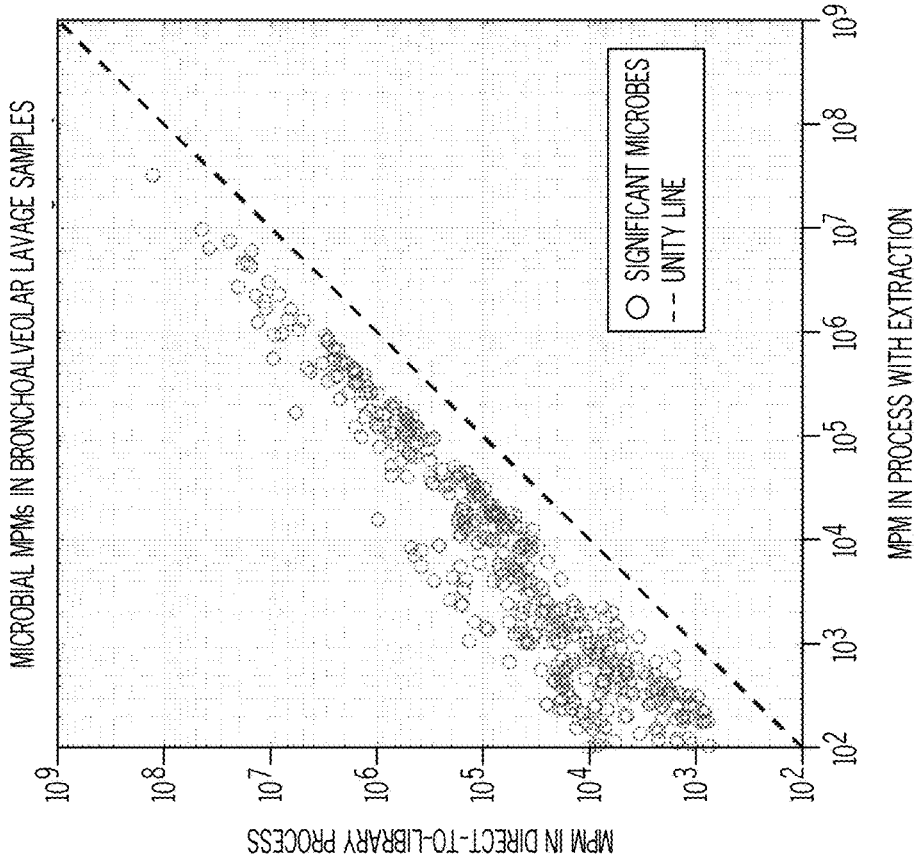
FIG. 15B depicts a comparison of the MPMs detected in the libraries obtained from bronchoalveolar lavage obtained with the process without extraction on the y-axis and obtained with the process with extraction on the x-axis.
Figure 15A:
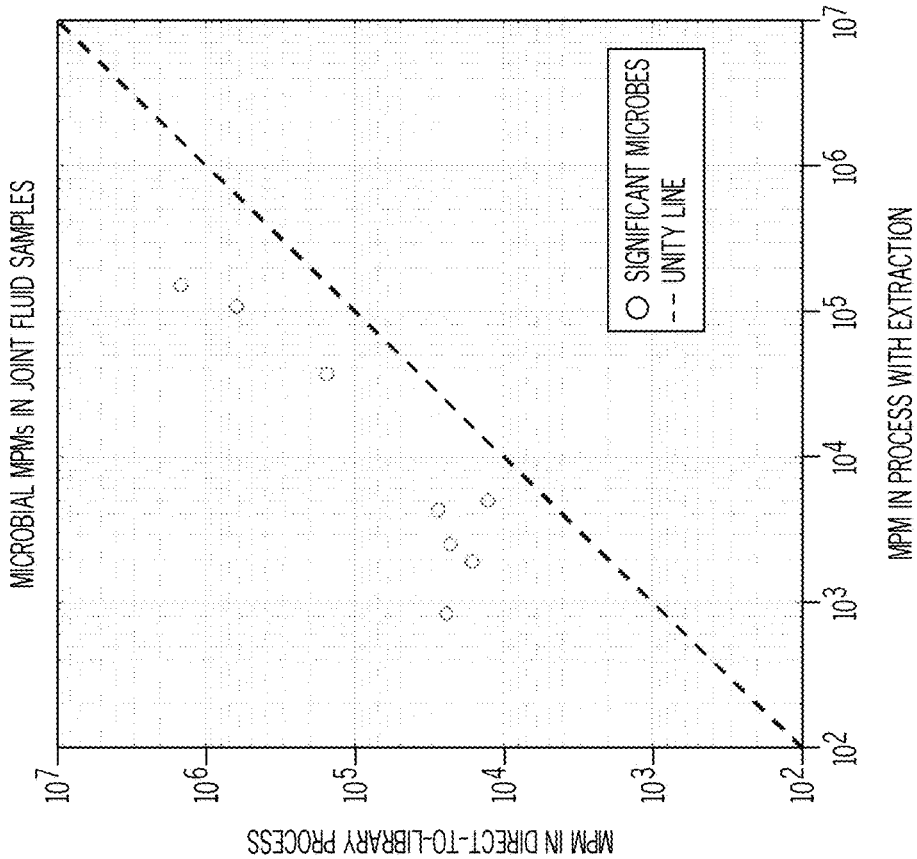
FIG. 15A depicts a comparison of the MPMs detected in the libraries obtained from joint fluid obtained with the process without extraction on the y-axis and obtained with the process with extraction on the x-axis.

The analysis of the number of molecules recovered per 1 µL of joint fluid or bronchoalveolar lavage by direct-to-library process vs. process with extraction (MPMs comparison in FIG. 15) showed that direct-to-library process yielded 7.4× or 7.9× (median increase) higher MPMs than the process with extraction, respectively. This demonstrated that the direct-to-library process recovers higher amounts of unique fragments as compared to the process with extraction.

Example 13: Comparison of a Direct-to-Library Processes with or without Beads

Human plasma is a complex matrix which can contain many inhibitors of the direct-to-library process. These interferents include but are not limited to protein, products of hemolysis, lipids, conjugated bilirubin and unconjugated bilirubin. When a sequencing library is prepared using magnetic beads to reduce the inhibitor concentration the inhibitors do not affect the yield of the library or their inhibitory effect is greatly reduced. However, when a sequencing library is prepared without the beads interferents affect the yield of the process.

Four different plasma samples were prepared. A High Hemolysis Sample (500 mg hemoglobin/dL plasma) was contrived by mixing asymptomatic plasma with an appropriate volume of hemolysis standard purchased from Sun Diagnostics (New Gloucester, ME). A Hemolysis Control Sample was prepared by mixing the asymptomatic plasma with the same volume of 1×TET buffer to dilute the asymptomatic plasma by the same factor as in the High Hemolysis Sample. A High Protein Sample (12 g/dL plasma) was contrived by mixing asymptomatic plasma with an appropriate volume of protein standard purchased from Sun Diagnostics (New Gloucester, ME). A Protein Control Sample was prepared by mixing the asymptomatic plasma with the same volume of 1×TET buffer to dilute the asymptomatic plasma by the same factor as in the High Protein Sample.

The direct-to-library process utilizing the beads (DTL w/beads) was carried out according to the template-switching-based protocol described in Example 11. The processing without the beads (DTL w/o beads) was performed as follows: Plasma was incubated with 1.6 units of Proteinase K (Sigma-Aldrich, St. Louis, MO) in 1× Terminal Transferase Reaction buffer (NEB, Ipswich, MA) at 60° C. for 20 minutes and 95° C. for 10 minutes and placed on ice until cool. One third of the solution was added to the A tailing reaction containing 0.16 mM dATP (NEB, Ipswich, MA) and 20 units Terminal Transferase (NEB, Ipswich, MA) and incubated at 37° C. for 25 minutes and heat inactivated at 75° C. for 10 minutes. Poly dT primer (62 nM) was added and incubated at 95° C. for 1 minute before placing on ice. For extension and template switching, 0.5× SMARTScribe RT buffer (Takara, Japan), 2 M DTT (Takara, Japan), 0.25 mM dNTPs (Thermo-Fisher, Waltham, MA), 200 units of SMARTScribe Reverse Transcriptase (Takara Japan) and template switching oligo (0.2 uM, IDT DNA, Coralville, IA) was added and incubated for 90 minutes at 42° C. followed by 5 cycles of 50° C. for 2 minutes and 42° C. for 2 minutes and 5 cycles of 55° C. for 30 seconds and 42° C. for 2 minutes and then heat denatured at 70° C. for 15 minutes.

This reaction was then amplified in 1× Terra Direct buffer (Takara, Japan) with 1.25 unit Terra Direct polymerase (Takara, Japan) and 200 nM PCR primers using the following conditions: 98° C. for 2 minutes, 12 cycles of 98° C. for 15 seconds, 60° C. for 30 seconds, 68° C. for 1 minute. The PCR was purified using DNA Clean and Concentrator-5 (Zymo, Irvine CA) before elution in TE (IDT, Coralville, IA).

Figure 16:
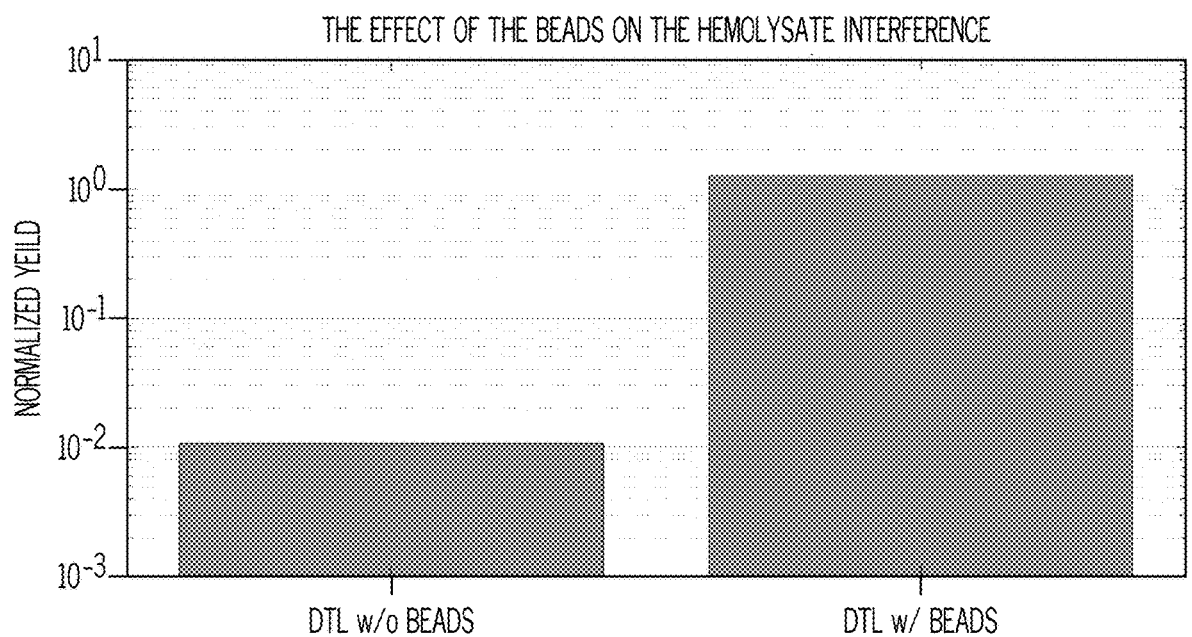
FIG. 16 shows the comparison of the normalized yield with the direct-to-library process without beads (DTL w/o beads) and the direct-to-library process with beads (DTL w/beads) in the presence of 500 mg hemoglobin/dL hemolysis interferent. Normalized yield is the number of reads resulting from the libraries made with 500 mg hemoglobin/dL hemolysis interference over the number of reads resulting from the libraries made from healthy plasma, where the same volumes of the amplified libraries were pooled, purified, and sequenced.

FIG. 16 shows the comparison of the normalized yield with the direct-to-library process without beads and the direct-to-library process with beads in the presence of 500 mg/dL hemolysis interferent. Normalized yield was defined as the number of sequencing reads resulting from the libraries derived from the High Hemolysis Sample divided by the number of sequencing reads resulting from the libraries made from the Hemolysis Control Sample when both libraries were sequenced in an unnormalized mode within a single sequencing run. Results showed that the use of the magnetic beads substantially reduced the inhibitory effects of the hemolysate as revealed by the normalized yield equal approximately 1.

Figure 17:
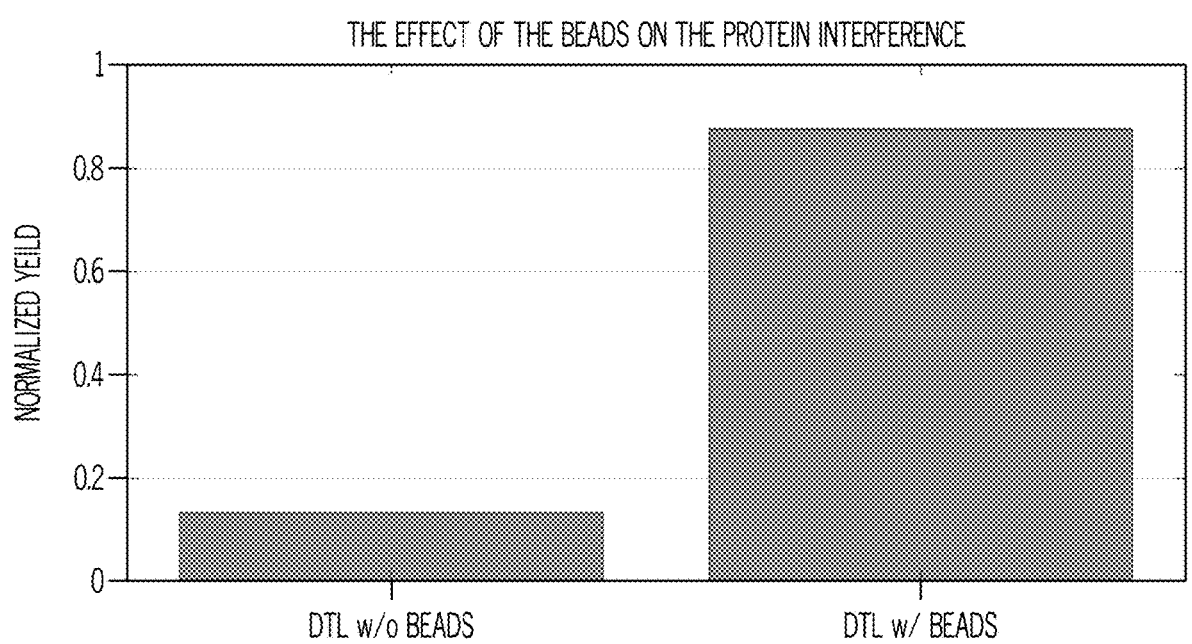
FIG. 17 shows the comparison of the normalized yield with the direct-to-library process without beads (DTL w/o beads) and the direct-to-library process with beads (DTL w/beads) in the presence of 12 g/dL blood-extracted proteins. Normalized yield is the number of reads resulting from the libraries made with 12 g/dL protein interferent over the number of reads resulting from the libraries made from healthy plasma. Results show that when magnetic beads are not used to purify the cell-free nucleic acids there is very little yield.

FIG. 17 shows the comparison of the normalized yield obtained with the direct-to-library process without beads and the direct-to-library process with beads in the presence of 12 g/dL interfering protein. Normalized yield was defined as the ratio of sequencing reads resulting from the libraries prepared from High Protein Sample divided by the number of sequencing reads obtained from the libraries derived from Protein Control Sample when both libraries were sequenced in an unnormalized mode within a single sequencing run. Results show that magnetic beads lower the inhibitory effect of the protein interferent as revealed by a higher normalized yield in the presence of the magnetic beads.

Example 14: Pathogen Enrichment by Selective Denaturation

Selective denaturation may be used in a single-stranded protocol or a double-stranded protocol. Selective denaturation may be used in the denaturation step following the initial dephosphorylation or during the thermally-induced elution of the final amplifiable strands off the magnetic beads. Thermal denaturation can be calibrated to elute fragments of certain length of GC-content by setting the correct temperature. One skilled in the art would understand how to set the correct temperature. Additionally, nucleic acid denaturizing agents (e.g., urea, guanidinium chloride, and/or DMSO, etc.) can be used instead. Also, a similar approach can be used in the context of double-stranded library protocols where initial adapter ligation includes shorter partially biotinylated subsections of the full-length adapters in order to provide better discrimination during the on-bead denaturation step.

This example applied selective denaturation principle to the template-switching based direct-to-library process in order to deplete the longer cell-free human sequences (e.g. nucleosomal fragments), and enrich for the cell-free microbial sequences that are typically present at higher molar fraction in the short length ranges (<110 bp). Selective denaturation was brought about by skipping Proteinase K (i.e. decreasing the probability of host's nucleosomal fragments to be successfully included in the final library), and lowering the temperature of denaturation to prevent dissociation of longer (e.g. nucleosomal length) nucleic acids.

Clinical and healthy plasma samples along with the control samples (see above) were processed according to the template-switching-based direct-to-library method utilizing a full denaturation described above (Example 11). The same set of samples were processed according to the selective denaturation process as follows: 50.0 µL of each spiked sample was mixed with 2.0 µL of 10% Tween-20 (Thermo-Fisher Scientific, Waltham, MA) and 104.0 µL Nuclease-free water. The mixture was heated to 60° C. for 5 minutes to bring about selective denaturation and 37° C. for 5 minutes and placed on ice until cool. 40.0 µL of 10× Terminal Transferase Reaction Buffer (NEB, Ipswich, MA), 2.0 µL of 10 mM dATP and 2.0 µL Terminal Transferase (20 u/µL, NEB, Ipswich, MA) was added to prepare the A-tailing reaction which was incubated at 37° C. for 40 min. The mixture was lysed and incubated with Dynabeads oligo $(dT)_{25}$ (SEQ ID NO: 13) following the manufacturer's recommended protocols. Eluate was collected according to the manufacturer's recommended protocol. Extension and template switching was performed with SMARTScribe Reverse Transcriptase and according to the manufacturer's recommended protocols. The mixture was amplified.

Amplification of the nucleic acids using an indexing primer mixture (NEB, Ipswich MA) was performed according to the manufacturer's recommended protocol and using the following temperature cycling program: 98° C. for 30 seconds, 8 cycles of 98° C. for 10 seconds, 65° C. for 75 seconds, and a final extension of 65° C. for 5 min. Final nucleic acid libraries were then pooled in groups of four ECs, two ACs, and eighteen clinical samples before using RNAclean™ Ampure beads to purify the pool as described above. After purification, the concentration of the nucleic acids in the library pools was measured with TapeStation as described above and loaded on the sequencer according to the manufacturer's recommendations. The same set of healthy plasma and clinical samples was processed with the template-switching-based direct-to-library process that included a Proteinase K step and thermal denaturation at 95° C. as described above.

Figure 18:
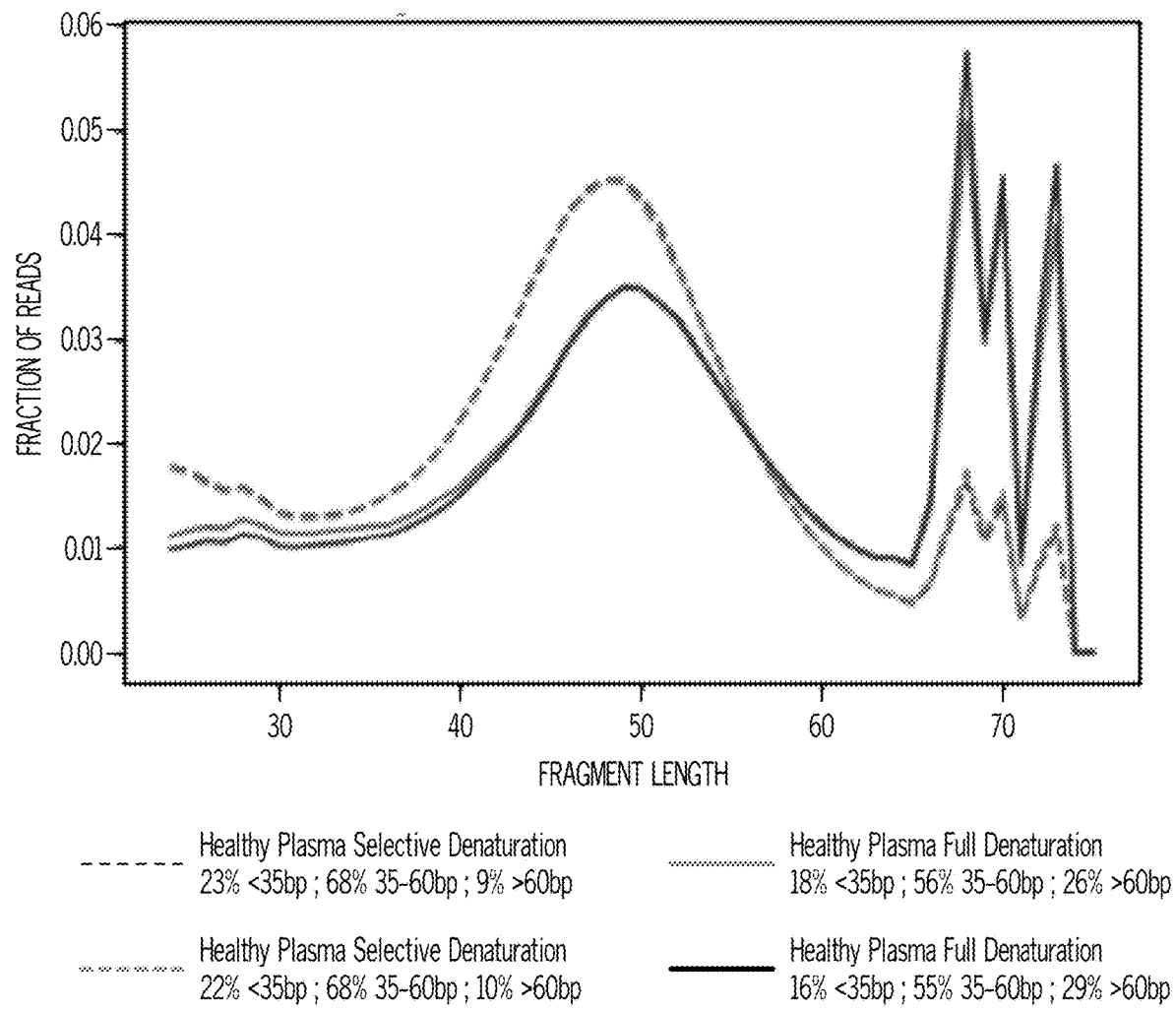
FIG. 18 shows the comparison of the length profiles in healthy plasma between the "Direct-to-Library Process utilizing Template-switching Reaction with Beads and without Proteinase K" and "Direct-to-Library Process utilizing Template-switching Reaction with Beads". When proteinase K is omitted from the direct-to-library process, a greater fraction of the reads are between 35-60 base pairs long. Fragment length on x-axis is given in units of base pair. Fraction of reads on y-axis is calculated relative to the total sequencing reads mapping to human reference.
Figure 21A:
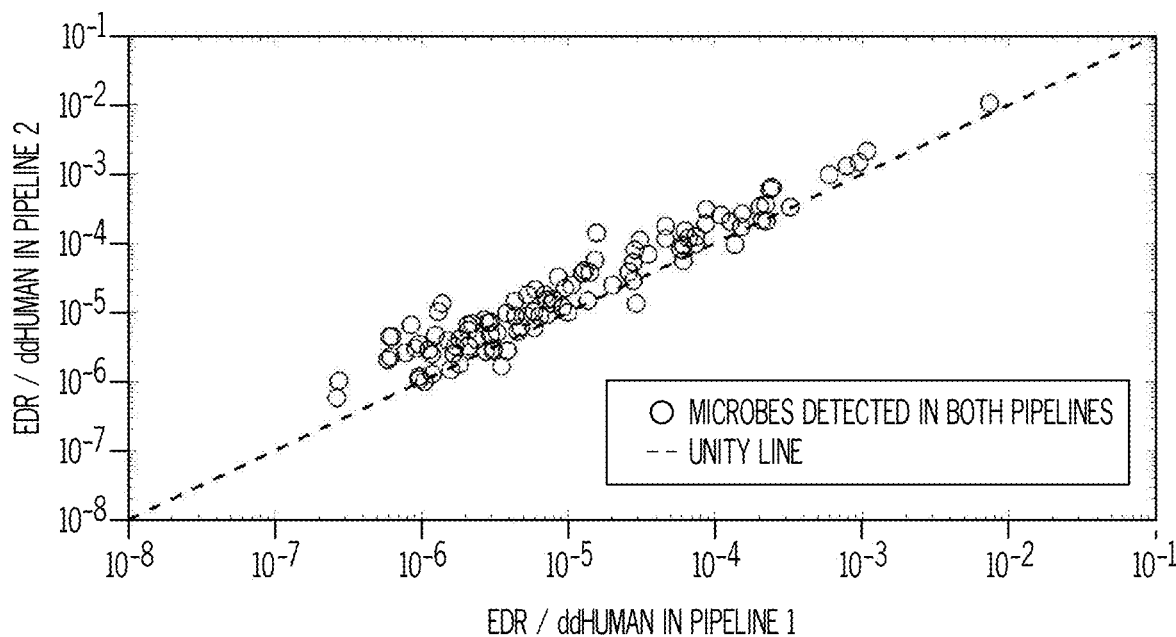
FIG. 21A depicts the ratio of the number of unique sequencing reads mapping to a microbial species (EDR) to the number of unique sequencing reads mapping to the human reference (ddHuman) for a direct-to-library process not utilizing selective denaturation (Pipeline 1) on x-axis and for direct-to-library process with selective denaturation (Pipeline 2) on y-axis for a group of plasma samples. Each symbol represents one microbial species detected.
Figure 21B:
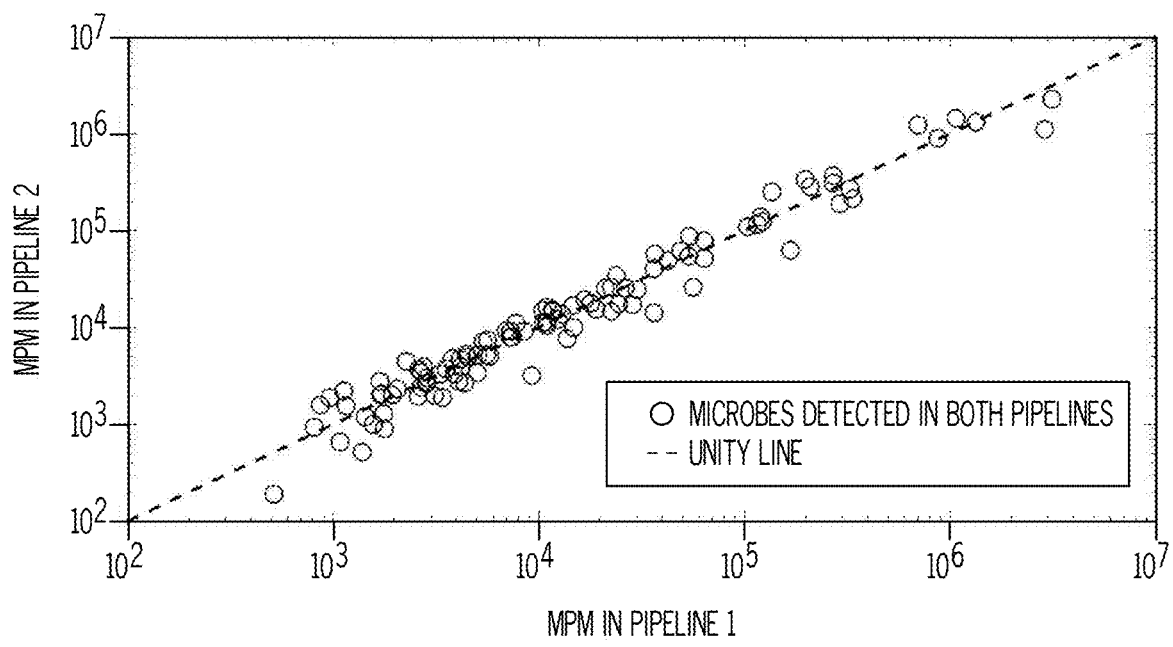
FIG. 21B depicts a comparison of the MPMs detected in the libraries obtained with a direct-to-library process not utilizing selective denaturation (Pipeline 1) on x-axis and with a direct-to-library process with selective denaturation (Pipeline 2) on y-axis for a group of plasma samples.

The analysis of the fragment length distributions recovered from healthy plasma with the pipeline utilizing selective denaturation and with a pipeline utilizing a regular full denaturation step is shown in FIG. 18. The fraction of the human fragments originating from longer human fragments is decreased in the pipeline with selective denaturation as revealed by the decrease in the fraction of reads longer than 60 bp. In addition, FIG. 21A shows the that pipeline utilizing selective denaturation (Pipeline 2) enriches for the cell-free microbial signal in the clinical samples as compared to the pipeline not utilizing selective denaturation (Pipeline 1) while measuring the same concentration of the microbial signal in the initial sample (FIG. 21B)

Example 15: RNA-Containing Sample Processing Options

Healthy plasma sample double spiked with Sendai virus, an avian parainfluenza negative strand RNA virus (Charles River Laboratory, Wilmington, MA), and synthetic DNA process control molecule (see above) were processed according to the template-switching-based direct-to-library method without denaturation with modifications described below to enable preferential RNA or DNA incorporation as well as incorporation and downstream capture of both nucleic acids. The same set of samples were processed with: (i) RNA A-tailing reaction, (ii) DNA A-tailing reaction and (ii) Combined nucleic acid A-tailing reaction as described here. The reaction conditions used were as follows: (i) RNA A-tailing reaction: 50.0 µL of each spiked sample was mixed with a mastermix comprising of 20.0 µL of 10× E. coli Poly(A) polymerase Reaction Buffer (NEB, Ipswich, MA), 6.0 µL of 10 mM ATP and 3.0 µL Poly(A) polymerase (5000 u/µL, NEB, Ipswich, MA) and 121.0 µL Nuclease-free water to prepare the A-tailing reaction which was incubated at 37° C. for 40 min. (ii) DNA A-tailing reaction: 50.0 µL of each spiked sample was mixed with a master mix comprising of 40.0 µL of 10× Terminal Transferase Reaction Buffer (NEB, Ipswich, MA), 2.0 µL of 10% Tween-20 (Thermo-Fisher Scientific, Waltham, MA), 2.0 µL of 10 mM dATP and 2.0 µL Terminal Transferase (20 u/µL, Ipswich, MA), and 104.0 Nuclease-free water to prepare the A-tailing reaction which was incubated at 37° C. for 40 min. (iii) Combined nucleic acid A-tailing reaction: 50.0 µL of each spiked sample was mixed with a master mix comprising of 40.0 µL of 10× Terminal Transferase Reaction Buffer (NEB, Ipswich, MA), 2.0 µL of 10% Tween-20 (Thermo-Fisher Scientific, Waltham, MA), 2.0 µL of 10 mM dATP, 15.0 µL of 10 mM ATP, 2.0 µL Terminal Transferase (20 u/µL, NEB, Ipswich, MA), 1.0 µL Poly(A) polymerase (5000 u/µL, NEB, Ipswich, MA) and 87.0 µL Nuclease-free water to prepare the A-tailing reaction which was incubated at 37° C. for 40 min. The mixture was lysed and incubated with Dynabeads oligo $(dT)_{25}$ (SEQ ID NO: 13) following the manufacturer's recommended protocols. Eluate was collected according to the manufacturer's recommended protocol. Extension and template switching was performed with SMARTScribe Reverse Transcriptase and according to the manufacturer's recommended protocols. The mixture was amplified using an indexing primer mixture (NEB, Ipswich MA) and was performed according to the manufacturer's recommended protocol and using the following temperature cycling program: 98° C. for 30 seconds, 8 cycles of 98° C. for 10 seconds, 65° C. for 75 seconds, and a final extension of 65° C. for 5 min. Final nucleic acid libraries were then pooled in groups before using RNAclean™ Ampure beads to purify the pool as described above. After purification, the concentration of the nucleic acids in the library pools was measured with TapeStation as described above and loaded on the sequencer according to the manufacturer's recommendations. Results from one such series of experiments are presented in FIG. 22.

Figure 23A:
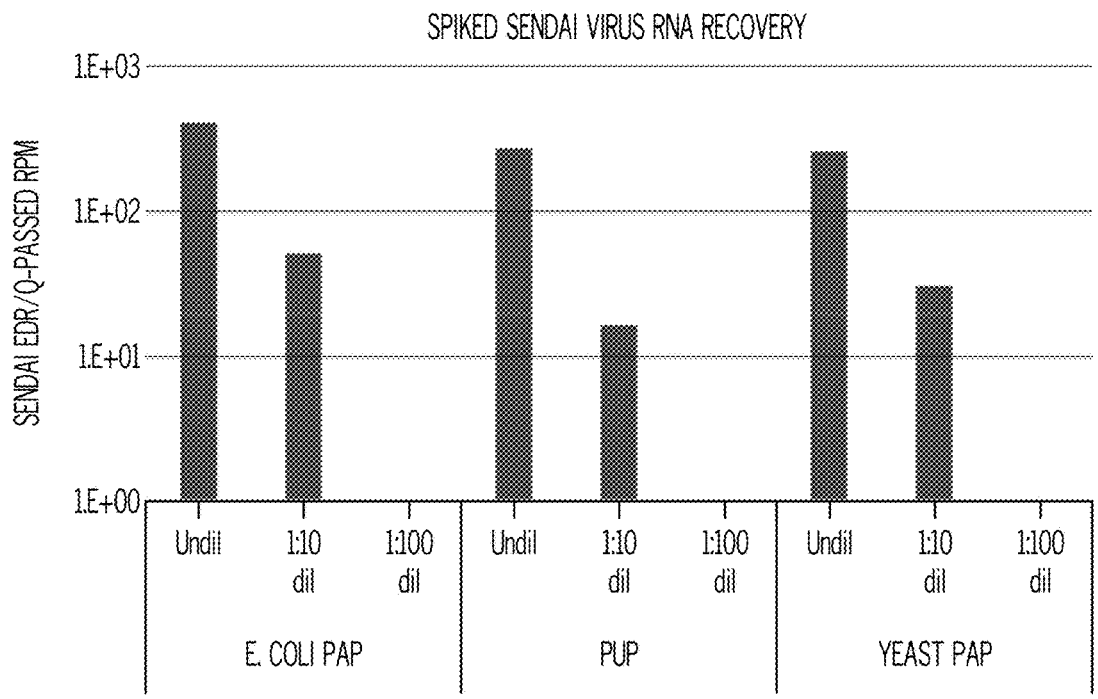
FIG. 23A depicts the relative efficiency of spiked RNA molecule capture by different polyadenylation enzymes or enzymes that are not canonical polyadenylation enzymes but can use adenosine as a substrate for polyadenylation under certain conditions.
Figure 23B:
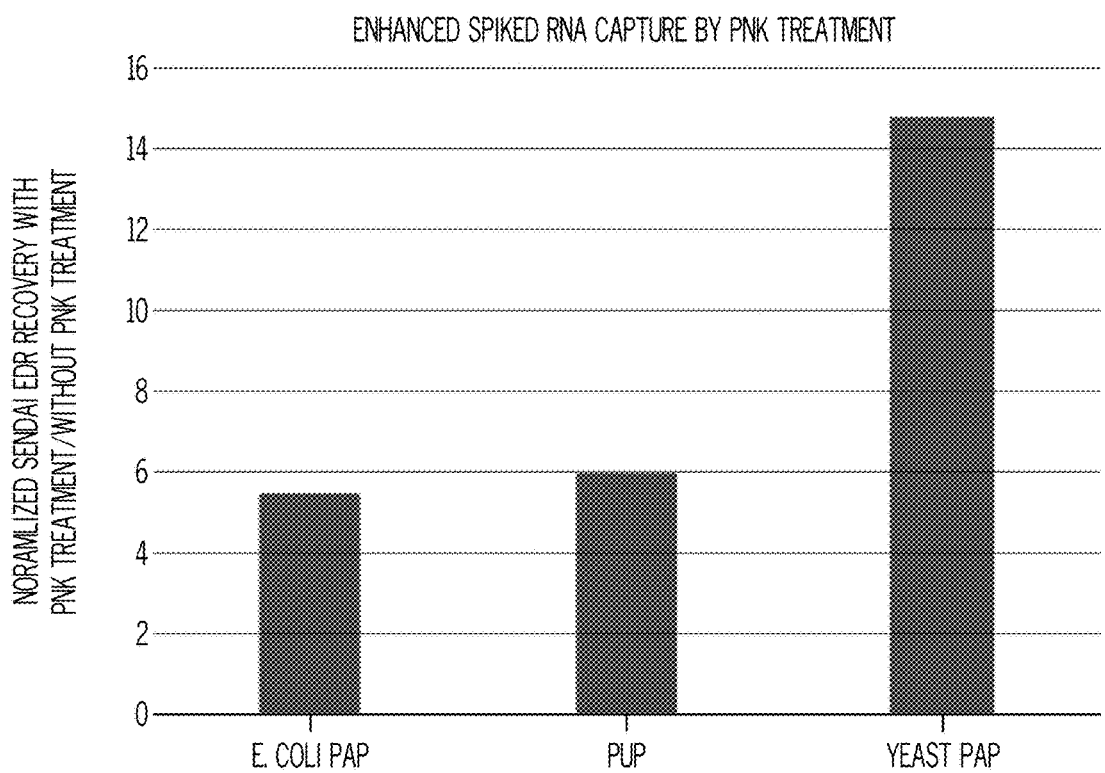
FIG. 23B depicts the enhancement of spiked RNA capture by these enzymes following dephosphorylation of RNA 3' ends.

Healthy plasma sample spiked with Sendai virus, an avian parainfluenza negative strand RNA virus was processed according to the template-switching-based direct-to-library method without denaturation conditions with modifications described below to enable RNA incorporation. The same set of samples were processed with: (i) E. coli Poly (A) polymerase (NEB, Ipswich, MA), (ii) Poly (U) polymerase ((NEB, Ipswich, MA) or (iii) Yeast Poly (A) polymerase (Thermo Fisher Scientific). The reaction conditions were as follows: (i) 50.0 µL of each spiked sample was mixed with a mastermix comprising of 20.0 of 10× E. coli Poly(A) polymerase Reaction Buffer (NEB, Ipswich, MA), 6.0 µL of 10 mM ATP and 3.0 µL Poly(A) polymerase (5 u/µL, NEB, Ipswich, MA) and 121.0 Nuclease-free water to prepare the A-tailing reaction which was incubated at 37° C. for 40 min. (ii) 50.0 µL of each spiked sample was mixed with a mastermix comprising of 20.0 of 10×NEB2 Reaction Buffer (NEB, Ipswich, MA), 6.0 µL of 10 mM ATP and 3.0 Poly(U) polymerase (2 u/uL, NEB, Ipswich, MA) and 121.0 µL Nuclease-free water to prepare the A-tailing reaction which was incubated at 37° C. for 40 min. (iii) 50.0 µL of each spiked sample was mixed with a mastermix comprising of 30.0 µL of 5× Yeast Poly(A) polymerase buffer (ThermoFisher Scientific), 6.0 µL of 10 mM ATP and 3.0 µL Yeast Poly(A) polymerase (2.5 u/uL, ThermoFisher Scientific) and 111.0 µL Nuclease-free water to prepare the A-tailing reaction which was incubated at 37° C. for 40 min. Modifications of the above reactions to include PNK treatment involved simultaneous incubation with Polynucleotide kinase (PNK, NEB, Ipswich, MA) along with the various Poly nucleotide polymerases. The reaction conditions were as follows: (i) 50.0 µL of each spiked sample was mixed with a mastermix comprising of 20.0 µL of 10× *E. coli* Poly(A) polymerase Reaction Buffer (NEB, Ipswich, MA), 6.0 µL of 10 mM ATP and 3.0 µL Poly(A) polymerase (5 u/µL, NEB, Ipswich, MA), 2.0 µl T4 Polynucleotide kinase (10 u/µL, NEB, Ipswich, MA) and 119.0 µL Nuclease-free water to prepare the A-tailing reaction which was incubated at 37° C. for 40 min. (ii) 50.0 µL of each spiked sample was mixed with a mastermix comprising of 20.0 µL of 10×NEB2 Reaction Buffer (NEB, Ipswich, MA), 6.0 µL of 10 mM ATP and 3.0 Poly(U) polymerase (2 u/uL, NEB, Ipswich, MA), 2.0 µl T4 Polynucleotide kinase (10 u/µL, NEB, Ipswich, MA) and 119.0 µL Nuclease-free water to prepare the A-tailing reaction which was incubated at 37° C. for 40 min. (iii) 50.0 µL of each spiked sample was mixed with a mastermix comprising of 30.0 µL of 5× Yeast Poly(A) polymerase buffer (ThermoFisher Scientific), 6.0 µL of 10 mM ATP and 3.0 µL Yeast Poly(A) polymerase (2.5 u/uL, ThermoFisher Scientific), 2.0 µl T4 Polynucleotide kinase (10 u/µL, NEB, Ipswich, MA) and 109.0 µL Nuclease-free water to prepare the A-tailing reaction which was incubated at 37° C. for 40 min. The individual mixtures were lysed and incubated with Dynabeads oligo (dT)$_{25}$ (SEQ ID NO: 13) following the manufacturer's recommended protocols. Eluate was collected according to the manufacturer's recommended protocol. Extension and template switching was performed with SMARTScribe Reverse Transcriptase and according to the manufacturer's recommended protocols. The mixture was amplified. Amplification of the nucleic acids using an indexing primer mixture (NEB, Ipswich MA) was performed according to the manufacturer's recommended protocol and using the following temperature cycling program: 98° C. for 30 seconds, 8 cycles of 98° C. for 10 seconds, 65° C. for 75 seconds, and a final extension of 65° C. for 5 min. Final nucleic acid libraries were then pooled in groups of four ECs, two ACs, and eighteen clinical samples before using RNAclean™ Ampure beads to purify the pool as described above. After purification, the concentration of the nucleic acids in the library pools was measured with TapeStation as described above and loaded on the sequencer according to the manufacturer's recommendations. Results from one such series of experiments are shown in FIG. 23.

FIG. 22A1-22A2 demonstrates that RNA-containing plasma samples can be processed with a direct-to-library method to generate sequencing libraries from which an RNA-based signal can be detected in sequencing data. The efficiency of conversion of the endogenous RNA molecules is higher when RNA A-tailing reaction is used. FIG. 22B1-22B2 demonstrates that the simultaneous processing of endogenous DNA and RNA molecules is feasible using a direct-to-library method. FIG. 23A demonstrates that a variety of enzymes can be used to add a not-templates extension at the 3'-end of an RNA template within the context of the a direct-to-library method. For every enzyme tested in FIG. 23A, the overall yield is enhanced by a preceding dephosphorylation of the RNA templates as indicated by the ratios >1 in all the reaction conditions tested.

What is claimed is:

1. A method of preparing a nucleic acid library from an initial sample, comprising generating a nucleic acid library from the initial sample,
wherein the initial sample comprises a plasma sample, a synovial fluid sample, a bronchoalveolar lavage sample, a cerebrospinal fluid sample or a urine sample,
wherein nucleic acids used to generate the nucleic acid library are not extracted from the initial sample before preparing the nucleic acid library and wherein generating the nucleic acid library from the initial sample comprises:
(a) dephosphorylating the nucleic acids in the initial sample to produce a group of dephosphorylated nucleic acids;
(b) denaturing the dephosphorylated nucleic acids to produce denatured nucleic acids;
(c) attaching a 3'-end adapter to the denatured nucleic acids to produce adapted nucleic acids;
(d) annealing a primer to the adapted nucleic acids and extending the primer with a polymerase to generate complementary strands;
(e) attaching a 5'-end adapter; and
(f) amplifying the complementary strands.

2. The method of claim 1, further comprising isolating the nucleic acids after (f).

3. The method of claim 1, further comprising adding one or more process control molecules to the initial sample to provide a spiked initial sample and generating the nucleic acid library from the spiked initial sample, wherein nucleic acids used to generate the nucleic acid library are not extracted from the spiked initial sample before preparing the nucleic acid library.

4. The method of claim 1, wherein the initial sample is a plasma sample.

5. The method of claim 1, wherein the initial sample is from a human subject.

6. The method of claim 5, wherein said human subject has undergone an organ transplant.

7. The method of claim 3, wherein the one or more process control molecules comprise one or more of an ID Spike, a Spank, a Spark, and a GC Spike-in Panel.

8. The method of claim 1, further comprising immobilizing the adapted nucleic acids on functionalized beads or columns.

9. The method of claim 8, wherein the immobilizing occurs on magnetic beads.

10. The method of claim 1, wherein attaching a 3'-end adapter to the denatured nucleic acids comprises attaching with a splint oligonucleotide.

11. The method of claim 10, wherein a 5'-end of the splint oligonucleotide comprises a bulky moiety, optionally wherein the bulky moiety comprises digoxigenin, and optionally further comprising contacting the digoxigenin with an anti-digoxigenin antibody.

12. The method of claim 1, wherein attaching a 3'-end adapter to the denatured nucleic acids and/or attaching an adapter to the 3'-end of the complementary strands comprises ligating with an enzyme comprising a T4 DNA ligase.

13. The method of claim 1, further comprising using a Klenow fragment in step (d).

14. The method of claim 2, wherein the nucleic acids used to generate the library comprise DNA or RNA.

15. The method of claim 1, wherein the step of attaching a 3'-end adapter to the denatured nucleic acids and/or attaching an adapter to the 3'-end of the complementary strands comprises the steps of incubating with a polymerase that has non-templated activity and, subsequently using a template switching reaction to attach a 3'-end adapter.

16. The method of claim 1, further comprising incubating with a protease prior to denaturing the nucleic acids.

17. The method of claim 16, wherein the protease comprises a Proteinase K.

18. The method of claim 1, further comprising heating the nucleic acids in the initial sample to denature the nucleic acids.

19. The method of claim 1, wherein the nucleic acids comprise cell-free nucleic acids.

20. The method of claim 1, wherein the nucleic acids comprise microbial nucleic acids from one or more microbes selected from the group consisting of a bacterium, a virus, a fungus, or a protozoan parasite.

* * * * *

SEQUENCE LISTING

```
<160> NUMBER OF SEQ ID NOS: 18

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agatcggaag                                                          10

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(16)
<223> OTHER INFORMATION: a, c, t, g, unknown or other

<400> SEQUENCE: 2
cttccgatct nnnnnn                                                   16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (11)..(16)
<223> OTHER INFORMATION: a, c, t, g, unknown or other

<400> SEQUENCE: 3
cttccgatct nnnnnn                                                            16

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(16)
<223> OTHER INFORMATION: a, c, t, g, unknown or other

<400> SEQUENCE: 4
cttccgatct nnnnnnagat cggaag                                                 26

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(16)
<223> OTHER INFORMATION: a, c, t, g, unknown or other

<400> SEQUENCE: 5
cttccgatct nnnnnn                                                            16

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggcctcgcgg aggcatgcgt catgctagcg tgcggggtac tcttgctatc                       50

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gagaattatt cgggggcagt gacaaccaac atctcgggtc ctgcccaacc                       50

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 8
ggtctacacg ctaatatagc gaatcaccga gaacccggcg ccacgcaatg          50

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gaacgtcctt aactccggca ggcaattaaa gggaacgtat gtataacgca          50

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atgacgcgct ttcaagcgtg gcgagtatgt gaaccaaggc ttcggacagg agatcggaag     60

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
actatatact taggtttgat ctcgccccga gaactgtaaa cctcaacatt          50

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tgaaatatct taggtttgat ctcgccccga gaactgtaaa cctcaacatt          50

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tttttttttt tttttttttt ttttt                                     25

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

```
cgacgctctt cc                                                        12

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggaagagcgt cgtgtaggga aagagtgta                                      29

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtgactggag ttcagacgtg tgctcttccg atct                                34

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
acactctttc cctacacgac gctcttcc                                       28

<210> SEQ ID NO 18
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(16)
<223> OTHER INFORMATION: a, c, u, g, unknown or other

<400> SEQUENCE: 18
cuuccgaucu nnnnnn                                                    16
```